(12) United States Patent
Das et al.

(10) Patent No.: US 6,979,694 B2
(45) Date of Patent: *Dec. 27, 2005

(54) CYCLIC PROTEIN TYROSINE KINASE INHIBITORS

(75) Inventors: Jagabandhu Das, Mercerville, NJ (US); Ramesh Padmanabha, Hamden, CT (US); Ping Chen, Belle Mead, NJ (US); Derek J. Norris, Trenton, NJ (US); Arthur M. P. Doweyko, Long Valley, NJ (US); Joel C. Barrish, Holland, PA (US); John Wityak, Robbinsville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/378,372

(22) Filed: Mar. 3, 2003

(65) Prior Publication Data

US 2004/0024208 A1 Feb. 5, 2004

Related U.S. Application Data

(62) Division of application No. 09/548,929, filed on Apr. 13, 2000, now Pat. No. 6,596,746.
(60) Provisional application No. 60/129,510, filed on Apr. 15, 1999.

(51) Int. Cl.[7] ............... A61K 31/426; A61K 31/44; C07D 277/20; C07D 417/12
(52) U.S. Cl. ............... 514/342; 514/371; 546/270.7; 548/195; 544/106; 544/133
(58) Field of Search ............... 548/195, 196; 546/270.7; 514/371, 342, 370; 544/106, 133

(56) References Cited

U.S. PATENT DOCUMENTS

| | | | |
|---|---|---|---|
| 3,505,055 A | 4/1970 | von Schmeling et al. | |
| 3,547,917 A | 12/1970 | Kulka et al. | |
| 3,709,992 A | 1/1973 | von Schmeling et al. | |
| 3,725,427 A | 4/1973 | Harrison et al. | |
| 3,796,800 A | 3/1974 | Ariyan et al. | |
| 3,879,531 A | 4/1975 | Ariyan et al. | |
| 3,896,223 A | 7/1975 | Ariyan et al. | |
| 3,932,633 A | 1/1976 | O'Brien et al. | |
| 4,942,143 A | 7/1990 | Ohsaki et al. | |
| 4,980,346 A | 12/1990 | Balogh et al. | |
| 5,057,142 A | 10/1991 | Baasner et al. | |
| 5,064,825 A | 11/1991 | Chakravarty et al. | |
| 5,399,674 A | 3/1995 | Dannheim et al. | |
| 5,438,070 A | 8/1995 | Eicken et al. | |
| 5,498,630 A | 3/1996 | Phillion et al. | |
| 5,514,643 A * | 5/1996 | Rew et al. | 504/266 |
| 5,527,763 A | 6/1996 | Miyazaki et al. | |
| 5,693,667 A | 12/1997 | Phillion et al. | |
| 5,705,513 A | 1/1998 | Phillion et al. | |
| 5,721,264 A | 2/1998 | Tanikawa et al. | |
| 5,728,693 A | 3/1998 | Stevenson | |
| 5,811,411 A | 9/1998 | Phillion et al. | |
| 5,811,428 A | 9/1998 | Suto et al. | |
| 5,817,828 A | 10/1998 | Tanikawa et al. | |
| 5,834,447 A | 11/1998 | Phillion et al. | |
| 5,840,909 A | 11/1998 | Tanikawa et al. | |
| 5,846,991 A | 12/1998 | Tanikawa et al. | |
| 5,849,723 A | 12/1998 | Phillion et al. | |
| 5,922,751 A | 7/1999 | Cavalla et al. | |
| 6,114,365 A | 9/2000 | Pevarello et al. | |
| 6,187,797 B1 * | 2/2001 | Pruitt et al. | 514/340 |
| 6,596,746 B1 * | 7/2003 | Das et al. | 514/370 |

FOREIGN PATENT DOCUMENTS

| | | |
|---|---|---|
| AU | 38554/93 | 11/1993 |
| DE | 3205638 A1 | 8/1983 |
| DE | 3220118 | 12/1983 |
| EP | 117082 A2 | 8/1984 |
| EP | 177287 | 4/1986 |
| EP | 275312 | 7/1988 |
| EP | 286041 A1 | 10/1988 |
| EP | 401030 A3 | 12/1990 |
| EP | 0412404 A2 | 2/1991 |
| EP | 0412404 B1 | 2/1991 |
| EP | 422470 A3 | 4/1991 |
| EP | 276177 | 1/1992 |
| EP | 538231 A1 | 4/1993 |
| EP | 315502 | 6/1993 |
| EP | 569912 A1 | 11/1993 |
| EP | 581960 A1 | 2/1994 |
| EP | 603595 A1 | 6/1994 |
| EP | 693480 A1 | 1/1996 |
| EP | 928790 A1 | 7/1999 |

(Continued)

OTHER PUBLICATIONS

Abstract—JP11080137, Nissan Chem. Ind. Ltd.
Abstract—JP11180965, Nissan Chem. Ind. Ltd.
Chem. Abstr. 71 (1969) 61232q, Sherlock et al.
Annual Reports in Medicinal Chemistry, 1996, vol. 31, pp. 151–160.
Egypt J. Chem., 1979, vol. 22, No. 3, pp. 179–188.
Abstract—JP4316559, Nissan Chem. Ind. Ltd.
Abstract—JP2129171, Nissan Chem. Ind. Ltd.
Abstract—JP2275857, Yoshitomi Pharm Ind. KK.
Abstract—JP62123180, Otsuka Seiyaku Kojy.
Abstract—JP57183768, Kanto Ishi Seiyaku KK.
Aldrich Chemical Company, 1992 Catalog, p. 51, entries 25, 301–4 and 28, 457–2, p. 98 entry A8, 980–4.
J. Heterocyclic Chem., 1970, vol. 7., No. 2, pp. 285–289.
Khim. Geterotsikl. Soedin., 1986, No. 2, pp. 277–278.
U.S. Appl. No. 10/378,461, filed Mar. 3, 2003, Das et al.
U.S. Appl. No. 10/378,373, filed Mar. 3, 2003, Das et al.

(Continued)

Primary Examiner—Golam M M Shameem

(57) ABSTRACT

Novel cyclic compounds and salts thereof, pharmaceutical compositions containing such compounds, and methods of using such compounds in the treatment of protein tyrosine kinase-associated disorders such as immunologic and oncologic disorders.

11 Claims, No Drawings

FOREIGN PATENT DOCUMENTS

| | | |
|---|---|---|
| EP | 0928793 A1 | 7/1999 |
| GB | 1437137 | 5/1976 |
| JP | 57-183768 | 11/1982 |
| JP | 62-123180 | 6/1987 |
| JP | 2-129171 | 5/1990 |
| JP | 2-275857 | 11/1990 |
| JP | 4-316559 | 11/1992 |
| JP | 11080137 | 3/1999 |
| JP | 11180965 | 7/1999 |
| JP | 2000186038 | 7/2000 |
| WO | WO98/56376 | 12/1978 |
| WO | WO 9519774 | 7/1985 |
| WO | WO91/00277 | 1/1991 |
| WO | WO93/07751 | 4/1993 |
| WO | WO93/25535 | 12/1993 |
| WO | WO94/22838 | 10/1994 |
| WO | WO95/18116 | 7/1995 |
| WO | WO96/00218 | 1/1996 |
| WO | WO97/09315 | 3/1997 |
| WO | WO97/36875 | 10/1997 |
| WO | WO98/28282 | 7/1998 |
| WO | WO98/52944 | 11/1998 |
| WO | WO98/57937 | 12/1998 |
| WO | WO99/00357 | 1/1999 |
| WO | WO99/21845 | 5/1999 |
| WO | WO99/24404 | 5/1999 |
| WO | WO99/31073 | 6/1999 |
| WO | WO99/57101 | 11/1999 |
| WO | WO99/58502 | 12/1999 |
| WO | WO99/62890 | 12/1999 |
| WO | WO00/02871 | 1/2000 |
| WO | WO00/17175 | 3/2000 |
| WO | WO00/24724 | 5/2000 |
| WO | WO00/26202 | 5/2000 |
| WO | WO00/26203 | 5/2000 |
| WO | WO00/31063 | 6/2000 |
| WO | WO00/39101 | 7/2000 |
| WO | WO00/39116 | 7/2000 |
| WO | WO00/47558 | 8/2000 |
| WO | WO 00/75120 | 12/2000 |
| WO | WO 01/10865 | 2/2001 |
| WO | WO 01/12621 | 2/2001 |
| WO | WO 01/17995 | 3/2001 |
| WO | WO 01/56567 | 8/2001 |
| ZA | 673552 | 5/1967 |
| ZA | 723936 | 6/1971 |

OTHER PUBLICATIONS

U.S. Appl. No. 10/395,503, filed Mar. 24, 2003, Das et al.
U.S. Appl. No. 10/886,955, filed Jul. 8, 2004, Lee.
PAJ vol. 0135, No. 17, 1989; JP01210949, Aug. 24, 1989.
PAJ vol. 0135, No. 01; JP01199955; Aug. 11, 1989.
Kassab, Rafika Ramadan, "Some reaction with 2–imino 4–thiazolidone", Al–Azhar Bulletin of Science, vol. 8(1), pp. 1–6, 1997.
Philips et al., "Thiazole Carboxanilide Fungicides: A New Structure–Activity Relationships for Succinate Dehydrogenase Inhibitors", Pest. Sci., vol. 38, pp. 1–7, 1993.
Oda, M., et al., "Structure–Activity Relationships of N–(1, 1,3–Trimethylindan–4–yl)carboxamide Fungicides", J. Pesticide Sci., vol. 18, pp. 245–251, 1993.
Wobig, Dieter, "Thiazole Derivatives, VI .—Synthesis of Thiazolo[4,5–d]–v–triazin–7(6H)–onen", Liebigs. Ann. Chem., pp. 1997–1997, 1984.
Abdel–Lateef, M.F.–A. et al., "Systemic and Chemotherapeutic Fungicidal Activity–Chemical Structure Relationship of Some 4–Methyl–5–thiazolecarboxylic Acid Derivatives.—Laboratory Screening Tests", Acta Phytopathologica Academiae Scientiarum Hungaricae, vol. 8 (3–4), pp. 269–282, 1973.

* cited by examiner

CYCLIC PROTEIN TYROSINE KINASE INHIBITORS

This application is a divisional of prior Application No. 09/548,929 filed on Apr. 13, 2000. This Application claims priority from provisional U.S. Application Ser. No. 60/129,510, filed Apr. 15, 1999, the entirety of which is incorporated herein by reference.

FIELD OF THE INVENTION

The present invention relates to cyclic compounds and salts thereof, to methods of using such compounds in treating protein tyrosine kinase-associated disorders such as immunologic and oncologic disorders, and to pharmaceutical compositions containing such compounds.

BACKGROUND OF THE INVENTION

Protein tyrosine kinases (PTKs) are enzymes which, in conjuction with ATP as a substrate, phosphorylate tyrosine residues in peptides and proteins. These enzymes are key elements in the regulation of cell signaling including cell proliferation and cell differentiation. PTKs comprise, inter alia, receptor tyrosine kinases (RPTKs), including members of the epidermal growth factor kinase family (e.g., HER1 and HER2), platelet derived growth factor (PDGF), and kinases that play a role in angiogenesis (Tie-2 and KDR); and, in addition, non-receptor tyrosine kinases, including members of the Syk, JAK and Src (e.g. Src, Fyn, Lyn, Lck and Blk) families (see Bolen, J. B., Rowley, R. B., Spana, C., and Tsygankov, A. Y., "The src family of tyrosine protein kinases in hemopoietic signal transduction", *FASEB J.*, 6, 3403–3409 (1992); Ullrich, A. and Schlessinger, J., "Signal transduction by receptors with tyrosine kinase activity", *Cell*, 61, 203–212 (1990); and Ihle, J. N., "The Janus protein tyrosine kinases in hematopoetic cytokine signaling", *Sem. Immunol.*, 7, 247–254 (1995)).

Enhanced activity of PTKs has been implicated in a variety of malignant and nonmalignant proliferative diseases. In addition, PTKs play a central role in the regulation of cells of the immune system. PTK inhibitors can thus impact a wide variety of oncologic and immunologic disorders. Such disorders may be ameliorated by selective inhibition of a certain receptor or non-receptor PTK, such as Lck, or due to the homology among PTK classes, by inhibition of more than one PTK by an inhibitor.

A PTK of particular interest is Lck which is found in T cells where it is involved in phosphorylating key protein substrates. It is required for productive antigen receptor signaling and cell activation. In the absence of Lck activity, the T cell receptor (TCR) zeta chain is not phosphorylated, the kinase ZAP-70 is not activated, and $Ca_{2+}$ mobilization essential for T cell activation does not occur (see Weiss, A. and Littman, D. R., "Signal transduction by lymphocyte antigen receptors", *Cell*, 76, 263–274 (1994); Iwashima, M., Irving, B. A., van Oers, N. S. C., Chan, A. C., and Weiss, A., "Sequential interactions of the TCR with two distinct cytoplasmic tyrosine kinases", *Science*, 263, 1136–1139 (1994); and Chan, A. C., Dalton, M., Johnson, R., Kong, G., Wang, T., Thoma, R., and Kurosaki, T., "Activation of ZAP-70 kinase activity by phosphorylation of tyrosine 493 is required for lymphocyte antigen receptor function", *EMBO J.*, 14, 2499–2508 (1995)). Inhibitors of Lck are thus useful in the treatment of T-cell mediated disorders such as chronic diseases with an important T cell component, for example rheumatoid arthritis, multiple sclerosis and lupus, as well as acute diseases where T cells are known to play an essential role, for example acute transplant rejection and delayed-type hypersensitivity (DTH) reactions.

SUMMARY OF THE INVENTION

The present invention provides cyclic compounds of the following formula I and salts thereof, for use as protein tyrosine kinase inhibitors:

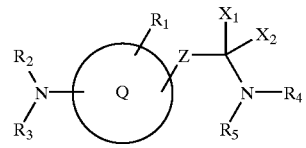

where
Q is:
(1) a 5-membered heteroaryl ring;
(2) a 6-membered heteroaryl ring; or
(3) an aryl ring;
optionally substituted with one or more groups $R_1$;
Z is:
(1) a single bond;
(2) —$R_{15}$C=CH—; or
(3) —$(CH_2)_m$—, where m is 1 to 2;
$X_1$ and $X_2$ are each hydrogen, or together form =O or =S;
$R_1$ is:
(1) hydrogen or $R_6$,
where $R_6$ is alkyl, alkenyl, alkynyl, cycloalkyl, cycloalkylalkyl, cycloalkenyl, cycloalkenylalkyl, aryl, aralkyl, heterocyclo, or heterocycloalkyl, each of which is unsubstituted or substituted with $Z_1$, $Z_2$ and one or more (preferably, one or two) groups $Z_3$;
(2) —OH or —$OR_6$;
(3) —SH or —$SR_6$;
(4) —$C(O)_2H$, —$C(O)_qR_6$, or $OC(O)_qR_6$, where q is 1 or 2;
(5) —$SO_3H$ or —$S(O)_qR_6$;
(6) halo;
(7) cyano;
(8) nitro;
(9) -$Z_4$-$NR_7R_8$;
(10) -$Z_4$-N($R_9$)-$Z_5$-$NR_{10}R_{11}$;
(11) -$Z_4$-N($R_{12}$)-$Z_5$-$R_6$;
(12) —$P(O)(OR_6)_2$;
$R_2$ and $R_3$ are each independently:
(1) hydrogen or $R_6$;
(2) -$Z_4$-$R_6$; or
(3) -$Z_{13}$-$NR_7R_8$;
$R_4$ and $R_5$:
(1) are each independently hydrogen or $R_6$;
(2) -$Z_4$-N($R_9$)-$Z_5$-$NR_{10}R_{11}$;
(3) —N($R_9$)$Z_4R_6$; or
(4) together with the nitrogen atom to which they are attached complete a 3- to 8-membered saturated or unsaturated heterocyclic ring which is unsubstituted or substituted with $Z_1$, $Z_2$ and $Z_3$, which heterocyclic ring may optionally have fused to it a benzene ring itself unsubstituted or substituted with $Z_1$, $Z_2$ and $Z_3$;
$R_7$, $R_8$, $R_9$, $R_{10}$, $R_{11}$, and $R_{12}$:
(1) are each independently hydrogen or $R_6$;

(2) $R_7$ and $R_8$ may together be alkylene, alkenylene or heteroalkyl, completing a 3- to 8-membered saturated or unsaturated ring with the nitrogen atom to which they are attached, which ring is unsubstituted or substituted with $Z_1$, $Z_2$ and $Z_3$; or (3) any two of $R_9$, $R_{10}$ and $R_{11}$ may together be alkylene or alkenylene completing a 3- to 8-membered saturated or unsaturated ring together with the nitrogen atoms to which they are attached, which ring is unsubstituted or substituted with $Z_1$, $Z_2$ and $Z_3$;

$R_{13}$ is:
(1) cyano;
(2) nitro;
(3) —$NH_2$;
(4) —NHOalkyl;
(5) —OH;
(6) —NHOaryl;
(7) —NHCOOalkyl;
(8) —NHCOOaryl;
(9) —$NHSO_2$alkyl;
(10) —$NHSO_2$aryl;
(11) aryl;
(12) heteroaryl;
(13) —Oalkyl; or
(14) —Oaryl;

$R_{14}$ is:
(1) —$NO_2$;
(2) —COOalkyl; or
(3) —COOaryl;

$R_{15}$ is:
(1) hydrogen;
(2) alkyl;
(3) aryl;
(4) arylalkyl; or
(5) cycloalkyl;

$Z_1$, $Z_2$ and $Z_3$ are each independently:
(1) hydrogen or $Z_6$, where $Z_6$ is (i) alkyl, alkenyl, alkynyl, cycloalkyl, cycloalkylalkyl, cycloalkenyl, cycloalkenylalkyl, aryl, aralkyl, alkylaryl, cycloalkylaryl, heterocyclo, or heterocycloalkyl; (ii) a group (i) which is itself substituted by one or more of the same or different groups (i); or (iii) a group (i) or (ii) which is substituted by one or more of the following groups (2) to (16) of the definition of $Z_1$, $Z_2$ and $Z_3$;
(2) —OH or —$OZ_6$;
(3) —SH or —$SZ_6$;
(4) —$C(O)_qH$, —$C(O)_qZ_6$, or —O—$C(O)_qZ_6$;
(5) —$SO_3H$, —$S(O)_qZ_6$; or $S(O)_qN(Z_9)Z_6$;
(6) halo;
(7) cyano;
(8) nitro;
(9) -$Z_4$-$NZ_7Z_8$;
(10) -$Z_4$-$N(Z_9)$-$Z_5$-$NZ_7Z_8$;
(11) -$Z_4$-$N(Z_{10})$-$Z_5$-$Z_6$;
(12) -$Z_4$-$N(Z_{10})$-$Z_5$-H;
(13) oxo;
(14) —O—$C(O)$-$Z_6$;
(15) any two of $Z_1$, $Z_2$, and $Z_3$ may together be alkylene or alkenylene completing a 3- to 8-membered saturated or unsaturated ring together with the atoms to which they are attached; or

(16) any two of $Z_1$, $Z_2$) and $Z_3$ may together be —O—$(CH_2)_r$—O—, where r is 1 to 5, completing a 4- to 8-membered saturated or unsaturated ring together with the atoms to which they are attached;

$Z_4$ and $Z_5$ are each independently:
(1) a single bond;
(2) -$Z_{11}$-$S(O)_q$-$Z_{12}$-;
(3) -$Z_{11}$-$C(O)$-$Z_{12}$-,
(4) -$Z_{11}C(S)$-$Z_{12}$-;
(5) -$Z_{11}$-O-$Z_{12}$-;
(6) -$Z_{11}$-S-$Z_{12}$-;
(7) -$Z_{11}$-O—$C(O)$-$Z_{12}$-; or
(8) -$Z_{11}$-$C(O)$—O-$Z_{12}$-;

$Z_7$, $Z_8$, $Z_9$ and $Z_{10}$;
(1) are each independently hydrogen or $Z_6$;
(2) $Z_7$ and $Z_8$, or $Z_6$ and $Z_{10}$, may together be alkylene or alkenylene, completing a 3- to 8-membered saturated or unsaturated ring together with the atoms to which they are attached, which ring is unsubstituted or substituted with $Z_1$, $Z_2$ and $Z_3$; or
(3) $Z_7$ or $Z_8$, together with $Z_9$, may be alkylene or alkenylene completing a 3- to 8-membered saturated or unsaturated ring together with the nitrogen atoms to which they are attached, which ring is unsubstituted or substituted with $Z_1$, $Z_2$ and $Z_3$;

$Z_{11}$ and $Z_{12}$ are each independently:
(1) a single bond;
(2) alkylene;
(3) alkenylene; or
(4) alkynylene; and $Z_{13}$ is:
(1) a single bond;
(2) -$Z_{11}$-$S(O)_q$-$Z_{12}$-;
(3) -$Z_{11}$-$C(O)$-$Z_{12}$-;
(4) -$Z_{11}$-$C(S)$-$Z_{12}$-;
(5) -$Z_{11}$-O-$Z_{12}$-;
(6) -$Z_{11}$-S-$Z_{12}$-;
(7) -$Z_{11}$-O—$C(O)$-$Z_{12}$-;
(8) -$Z_{11}$-$C(O)$—O-$Z_{12}$-;
(9) —$C(NR_{13})$—;
(10) —$C(CHR_{14})$—; or
(11) —$C(C(R_{14})_2)$—.

Compounds within formula I include compounds of the following formula II and salts thereof:

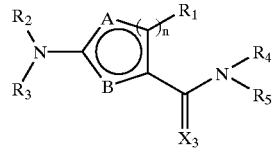

II where
n is 1 or 2
A is selected from carbon and nitrogen;
B is selected from nitrogen, oxygen and sulfur;
$X_3$ is oxygen or sulfur; and
$R_1$, $R_2$, $R_3$, $R_4$ and $R_5$ are as described above.

DETAILED DESCRIPTION OF THE INVENTION

The following are definitions of terms used in this specification. The initial definition provided for a group or term herein applies to that group or term throughout the present specification, individually or as part of another group, unless otherwise indicated.

The terms "alk" or "alkyl" refer to straight or branched chain hydrocarbon groups having 1 to 12 carbon atoms, preferably 1 to 8 carbon atoms. The expression "lower alkyl" refers to alkyl groups of 1 to 4 carbon atoms.

The term "alkenyl" refers to straight or branched chain hydrocarbon groups of 2 to 10, preferably 2 to 4, carbon atoms having at least one double bond. Where an alkenyl group is bonded to a nitrogen atom, it is preferred that such group not be bonded directly through a carbon bearing a double bond.

The term "alkynyl" refers to straight or branched chain hydrocarbon groups of 2 to 10, preferably 2 to 4, carbon atoms having at least one triple bond. Where an alkynyl group is bonded to a nitrogen atom, it is preferred that such group not be bonded directly through a carbon bearing a triple bond.

The term "alkylene" refers to a straight chain bridge of 1 to 5 carbon atoms connected by single bonds (e.g., —$(CH_2)_x$— wherein x is 1 to 5), which may be substituted with 1 to 3 lower alkyl groups.

The term "alkenylene" refers to a straight chain bridge of 2 to 5 carbon atoms having one or two double bonds that is connected by single bonds and may be substituted with 1 to 3 lower alkyl groups. Exemplary alkenylene groups are —CH=CH—CH=CH—, —$CH_2$—CH=CH—, —$CH_2$—CH=CH—$CH_2$—, —C$(CH_3)_2$CH=CH— and —CH$(C_2H_5)$—CH=CH—.

The term "alkynylene" refers to a straight chain bridge of 2 to 5 carbon atoms that has a triple bond therein, is connected by single bonds, and may be substituted with 1 to 3 lower alkyl groups. Exemplary alkynylene groups are —C≡C—, —$CH_2$—C≡C—, —CH$(CH_3)$—C≡C— and —C≡C—CH$(C_2H_5)$CH$_2$—.

The terms "ar" or "aryl" refer to aromatic cyclic groups (for example 6 membered monocyclic, 10 membered bicyclic or 14 membered tricyclic ring systems) which contain 6 to 14 carbon atoms. Exemplary aryl groups include phenyl, naphthyl, biphenyl and anthracene.

The terms "cycloalkyl" and "cycloalkenyl" refer to cyclic hydrocarbon groups of 3 to 12 carbon atoms.

The terms "halogen" and "halo" refer to fluorine, chlorine, bromine and iodine.

The term "unsaturated ring" includes partially unsaturated and aromatic rings.

The terms "heterocycle", "heterocyclic" or "heterocyclo" refer to fully saturated or unsaturated, including aromatic (i.e. "heteroaryl") cyclic groups, for example, 4 to 7 membered monocyclic, 7 to 11 membered bicyclic, or 10 to 15 membered tricyclic ring systems, which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system.

Exemplary monocyclic heterocyclic groups include pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl, triazinyl, and the like.

Exemplary bicyclic heterocyclic groups include indolyl, benzothiazolyl, benzoxazolyl, benzodioxolyl, benzothienyl, quinuclidinyl, quinolinyl, tetra-hydroisoquinolinyl, isoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl]or furo[2,3-b]pyridinyl), dihydroisoindolyl, dihydroquinazolinyl (such as 3,4-dihydro-4-oxo-quinazolinyl), tetrahydroquinolinyl and the like.

Exemplary tricyclic heterocyclic groups include carbazolyl, benzidolyl, phenanthrolinyl, acridinyl, phenanthridinyl, xanthenyl and the like.

The term "heteroaryl" refers to aromatic heterocyclic groups.

Exemplary heteroaryl groups include pyrrolyl, pyrazolyl, imidazolyl, oxazolyl, isoxazolyl, thiazolyl, thiadiazolyl, isothiazolyl, furyl, thienyl, oxadiazolyl, pyridinyl, pyrazinyl, pyrimidinyl, pyridazinyl, triazolyl, triazinyl, and the like.

Where q is 1 or 2, "—C(O)$_q$H" denotes —C(O)—H or —C(O)—OH; "C(O)$_q$R$_6$" or "C(O)$_q$Z$_6$" denote, respectively, —C(O)—R$_6$ or —C(O)—OR$_6$, or —C(O)-Z$_6$ or —C(O)—OZ$_6$; "—O—C(O)$_q$R$_6$" or "—O—C(O)$_q$Z$_6$" denote, respectively, —O—C(O)—R$_6$ or —O—C(O)—OR$_6$, or —O—C(O)-Z$_6$ or —O—C(O)—OZ$_6$; and "—S(O)$_q$R$_6$" or "S(O)$_q$Z$_6$" denote, respectively, —SO—R$_6$ or —SO$_2$—R$_6$, or —SO-Z$_6$ or —SO$_2$-Z$_6$.

Compounds of the formula I may in some cases form salts which are also within the scope of this invention. Reference to a compound of the formula I herein is understood to include reference to salts thereof, unless otherwise indicated. The term "salt(s)", as employed herein, denotes acidic and/or basic salts formed with inorganic and/or organic acids and bases. Zwitterions (internal or inner salts) are included within the term "salt(s)" as used herein (and may be formed, for example, where the R substituents comprise an acid moiety such as a carboxyl group). Also included herein are quaternary ammonium salts such as alkylammonium salts. Pharmaceutically acceptable (i.e., non-toxic, physiologically acceptable) salts are preferred, although other salts are useful, for example, in isolation or purification steps which may be employed during preparation. Salts of the compounds of the formula I may be formed, for example, by reacting a compound I with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates, undecanoates, and the like.

Exemplary basic salts (formed, for example, where the R substituents comprise an acidic moiety such as a carboxyl group) include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines, N-methyl-D-glucamines, N-methyl-D-glucamides, t-butyl amines, and salts with amino acids such as arginine, lysine and the like. The basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

Prodrugs and solvates of the compounds of the invention are also contemplated herein. The term "prodrug", as employed herein, denotes a compound which, upon administration to a subject, undergoes chemical conversion by metabolic or chemical processes to yield a compound of the formula I, or a salt and/or solvate thereof. Solvates of the compounds of formula I are preferably hydrates.

All stereoisomers of the present compounds, such as those which may exist due to asymmetric carbons on the R substituents of the compound of the formula I, including enantiomeric and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations.

Throughout the specification, groups and substituents thereof are chosen to provide stable moieties and compounds.

Preferred Compounds

Preferred compounds of the present invention are compounds of the formula I, and salts thereof, wherein Q is thiazole and wherein one or more, and especially all, of Z, $X_1$, $X_2$ $R_1$, $R_2$, $R_3$, $R_4$, and $R_6$ are selected from the following definitions:

Z is a single bond;

$R_1$ is selected from hydrogen, halo, alkyl, aryl, alkoxy, alkoxycarbonyl, or aryloxycarbonyl and is more preferably hydrogen;

$X_1$ and $X_2$ together form =O or =S and more preferably form =O;

$R_2$ is hydrogen;

$R_3$ is selected from -$Z_4$-$R_6$ or -$Z_{13}$-$NR_7R_8$ and is more preferably -$Z_4$-$R_6$ wherein $Z_4$ is a single bond and $R_6$ is aryl or heteroaryl which is unsubstituted or substituted with $Z_1$, $Z_2$ and one or more (preferably, one or two) groups $Z_3$;

$R_4$ is hydrogen; and $R_5$ is selected from aryl groups or heteroaryl groups which are substituted with $Z_1$, $Z_2$ and one or more (such as one or two) groups $Z_3$.

Methods of Preparation

The compounds of the formula I may be prepared by methods such as those illustrated in the following Schemes A through E and I through XI. Solvents, temperatures, pressures, and other reaction conditions may readily be selected by one of ordinary skill in the art. All documents cited are incorporated herein by reference in their entirety. Starting materials are commercially available or readily prepared by one of ordinary skill in the art. Constituents of compounds are as defined elsewhere in the specification or as specifically defined in a scheme.

The methods described herein may be carried out with starting materials and/or reagents in solution or alternatively, where appropriate, with one or more starting materials or reagents bound to a solid support (see (1) Thompson, L. A., Ellman, J. A., *Chemical Reviews*, 96, 555–600 (1996); (2) Terrett, N. K., Gardner, M., Gordon, D. W., Kobylecki, R. J., Steele, J., *Tetrahedron*, 51, 8135–8173 (1995); (3) Gallop, M. A., Barrett, R. W., Dower, W. J., Fodor, S. P. A., Gordon, E. M., *Journal of Medicinal Chemistry*, 37, 1233–1251 (1994); (4) Gordon, E. M., Barrett, R. W., Dower, W. J., Fodor, S. P. A., Gallop, M. A., *Journal of Medicinal Chemistry*, 37, 1385–1401 (1994); (5) Balkenhohl, F., von dem Bussche-Hünnefeld, Lansky, A., Zechel, C., *Angewandte Chemie International Edition in English*, 35, 2288–2337 (1996); (6) Balkenhohl, F., von dem Bussche-Hünnefeld, Lansky, A., Zechel, C., *Angewandte Chemie*, 108, 2436–2487 (1996); and (7) Sofia, M. J., *Drugs Discovery Today*, 1, 27–34 (1996)).

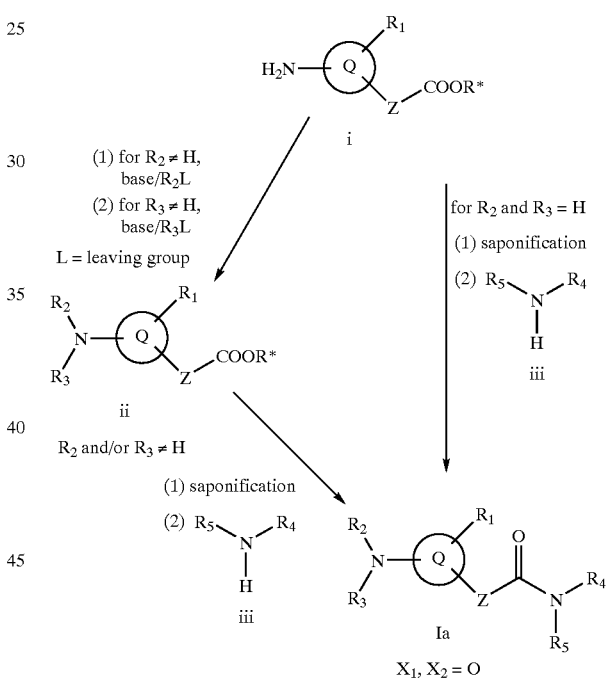

Scheme A

Scheme A illustrates a general method for forming compound Ia, which is a compound of the formula I where $X_1$ and $X_2$ together form =O. As shown in Scheme A, compound Ia where $R_2$ and $R_3$ are hydrogen may be formed by saponification of i, (R* is a carboxyl protecting group such as alkyl or arylalkyl) followed by reaction with amine iii by methods known in the art. Alternatively i may be reacted with $R_2L$, where L is a leaving group such as halogen (for example, in equimolar portions), optionally followed by reaction with $R_3L$ (for example, in equimolar portions) to form ii. Also alternatively, i may be subjected to reductive amination using the appropriate aldehyde or ketone to form ii. The compound Ii may then be saponified and reacted with amine iii, under conditions known to those skilled in the art, to form Ia where $R_2$ and/or $R_3$ are other than hydrogen.

Methods for preparing preferred substituents on the compounds I are illustrated in the following Schemes I to XI.

Scheme B

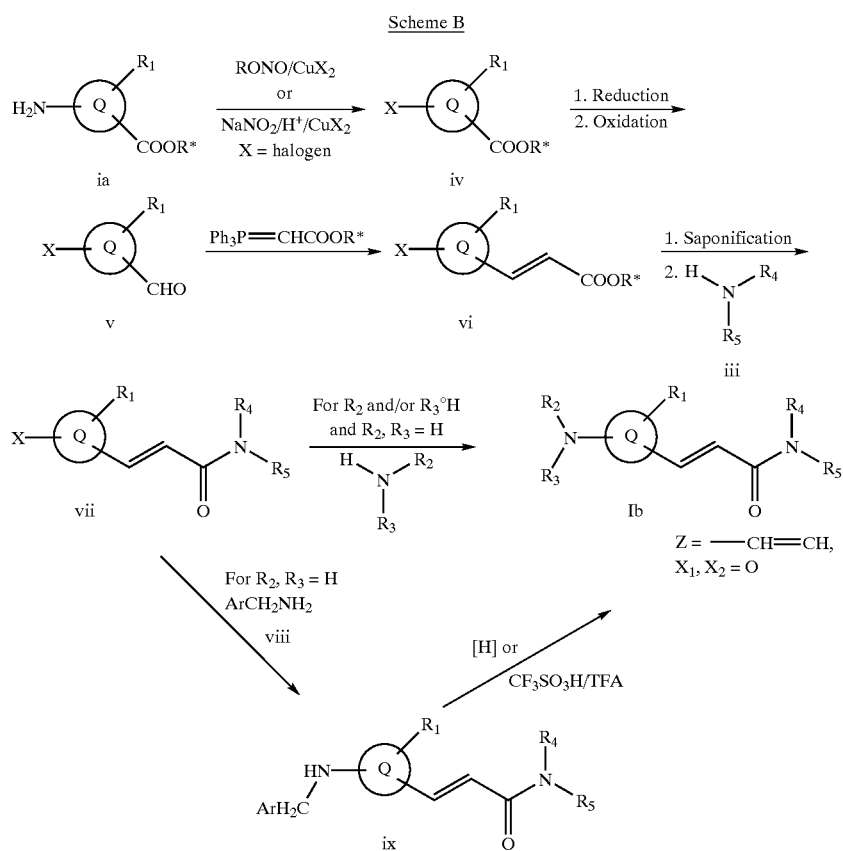

Scheme B illustrates a general method for forming compound Ib, which is a compound of formula I where Z is —CH=CH— and $X_1$ and $X_2$ together form =O. As shown in Scheme B, a 2-halo-compound vi can be prepared by reacting an appropriately substituted 2-amino-compound Ia with copper (ii) halide and an alkyl nitrite such as tert-butyl nitrite in an aprotic solvent such as acetonitrile to form 2-halo-compound Iv (see J. Het. Chem. 22, 1621 (1985)). Compound iv can be reduced with a reducing agent such as sodium borohydride in ethanol or aqueous tetrahydrofuran to form an alcohol, which can be oxidized with an oxidizing agent such as pyridinium chlorochromate or pyridinium dichromate to form aldehyde v. Compound v can be reacted with an alkyl(triphenylphosphorylidene) acetate to form carboxylate vi. Compound vi can be saponified and then reacted with an amine iii by methods known to those skilled in the art to form vii. Compound vii can be reacted with an amine $R_2R_3NH$ to form Ib where Z is —CH=CH— and $X_1$, $X_2$ together form =O. Alternatively, compounds of formula Ib where $R_2$ and $R_3$ are H, can be formed by reacting compound vii with an appropriately substituted benzyl amine such as 4-methoxybenzyl amine to form compound ix, which can be hydrogenolyzed or treated with an acid such as trifluoromethanesulfonic acid and trifluoroacetic acid in the presence of anisole to form Ib where $R_2$ and $R_3$ are hydrogen.

Methods for preparing preferred substituents on the compounds I are illustrated in the following Schemes I to XI.

Scheme C

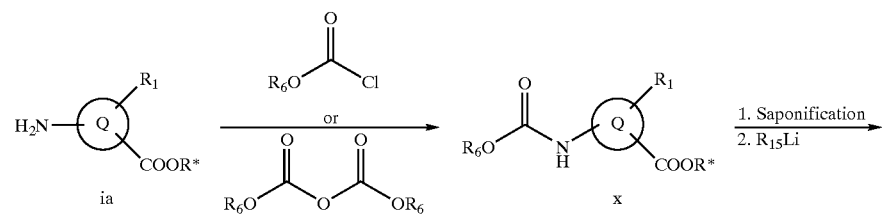

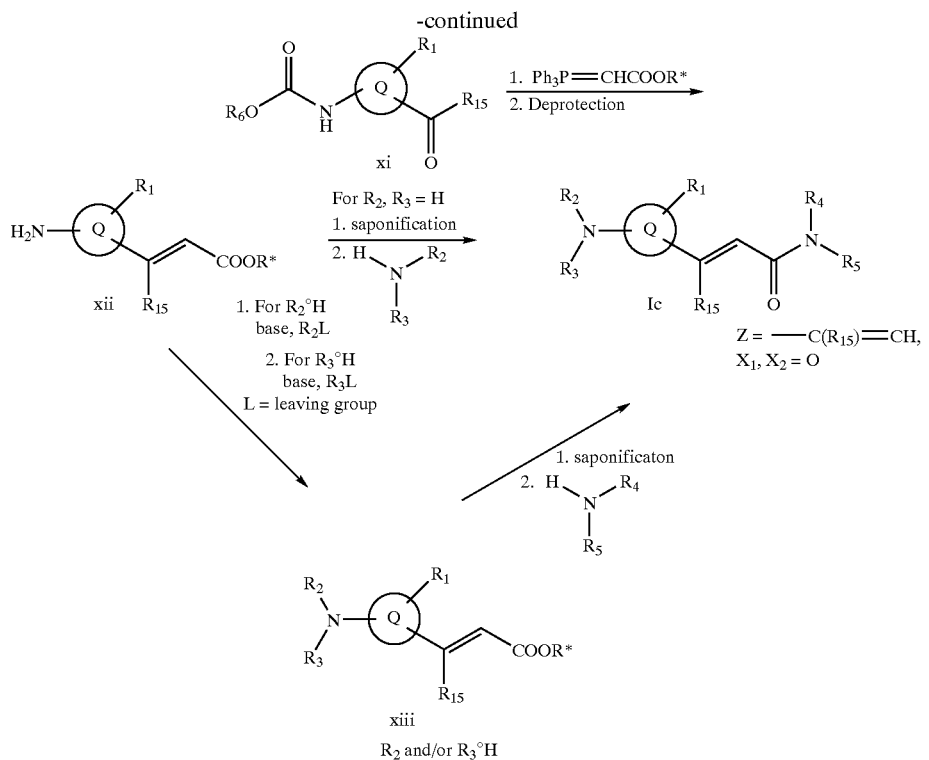

Scheme C illustrates a general method for forming compound Ic, which is a compound of formula I where Z is —$R_{15}$C═CH— and $X_1$ and $X_2$ together form ═O. As shown in Scheme C, a 2-amino-compound ia can be reacted with a chloroformate or dicarbonate to form x, which can be saponified and treated with an organolithium reagent to form compound xi. Compound xi may be reacted with an alkyl (triphenylphosphorylidene)acetate, followed by deprotection of the carbamate protecting group to form xii. Alternatively, compound Ic where $R_2$ and $R_3$ are hydrogen may be formed by saponification of xii followed by reaction with an amine $R_4R_5$NH by methods known to those skilled in the art. Alternatively, compound xii may be reacted with $R_2$L where L is a leaving group such as halogen (for example, in equimolar portions), optionally followed by reaction with $R_3$L (for example, in equimolar portions) to form xiii, which may be saponified and reacted with an amine $R_4R_5$NH by methods known to those skilled in the art to form Ia where $R_2$ and/or $R_3$ are other than hydrogen.

Methods for preparing preferred substituents on the compounds I are illustrated in the following Schemes I to XI.

Scheme D

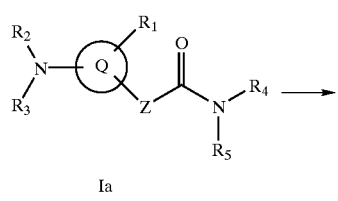

Ia

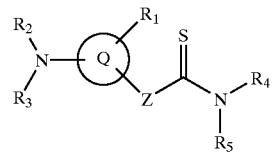

Id

Scheme D illustrates a general method for forming compound Id, which is a compound of the formula I where $X_1$ and $X_2$ together form ═S. The compounds of the formula Ia obtained in Scheme A may be converted into the corresponding thioamide Id using a reagent such as Lawesson's reagent (2,4-bis(4-methoxyphenyl)-1,3-dithia-2,4-diphosphetane-2,4-disulfide (see *Bull. Soc. Chim. Belg.*, 87, 223 (1978)).

Methods for preparing preferred substituents on the compounds I are illustrated in the following Schemes I to XI.

Scheme E

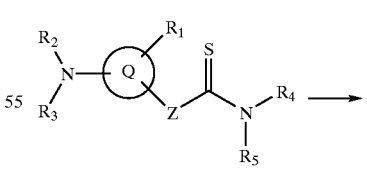

Id

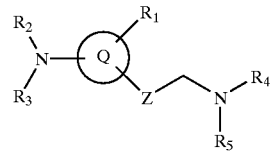

Ie

Scheme E illustrates a general method for forming compound Ie, which is a compound of the formula I where $X_1$ and $X_2$ are each hydrogen. As shown in Scheme E, the compound of the formula Id obtained in Scheme D may be converted into the corresponding amine Ie by reduction, for example, by reaction with Raney nickel.

Methods for preparing preferred substituents on the compounds I are illustrated in the following Schemes I to XI.

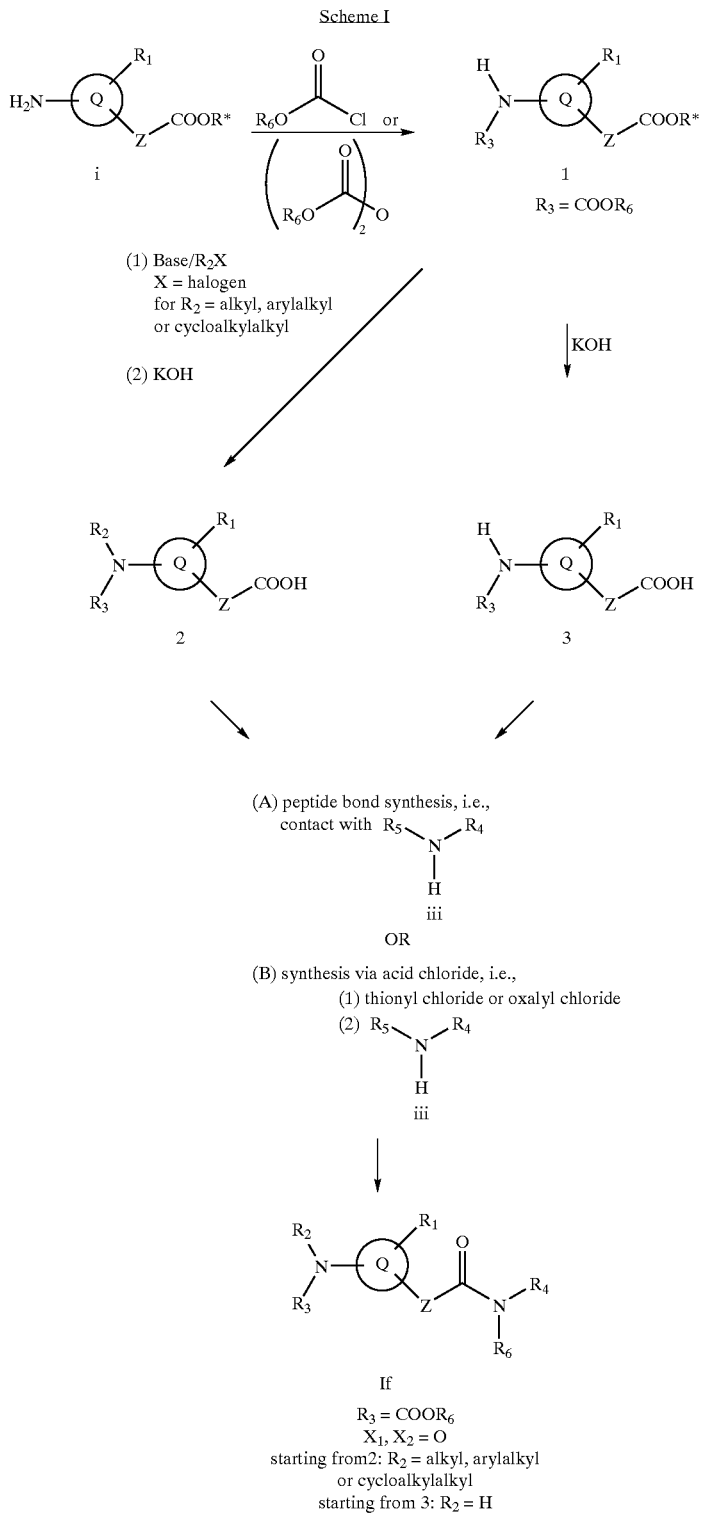

As shown in Scheme I, carboxylate i can be reacted with a chloroformate or dicarbonate to form 1. Compound 1 can be treated with a base such as sodium hydride, sodium/potassium hexamethyldisilazide, or lithium diisopropylamide (LDA), and an alkylating agent $R_2X$ where X is halogen and $R_2$ is preferably alkyl, arylalkyl, or cycloalkylalkyl, and then saponified with an aqueous base such as potassium hydroxide to give 2. Alternatively, 1 can the subjected to reductive amination using the appropriate aldehyde or ketone and saponified with an aqueous base such as potassium hydroxide to give 2. Compound 1 may, alternatively, be simply saponified with an aqueous base such as potassium hydroxide to give 3 where $R_2$ is hydrogen.

Acid 2 may be reacted with an amine iii using reaction conditions well known in the art for peptide bond synthesis (see, for example, Bodanszky and Bodanszky, The Practice of Peptide Chemistry, Springer-Verlag, 1984; Bodanszky, Principles of Peptide Synthesis, Springer-Verlag, 1984) to give the compound Id which a compound of the formula I where $X_1$ and $X_2$ together form =O, $R_3$ is $COOR_6$, and, since 2 is the starting material, $R_2$ is preferably alkyl, arylalkyl or cycloalkylalkyl. For example, reagents which activate the carboxyl group of 2 for reaction with the amine iv include bis-(2-oxo-3-oxazolidinyl)phosphinic chloride (BOP chloride), benzotriazol-1-yloxy-tris(dimethylamino)phosphonium hexafluorophosphate (BOP reagent), [O-(7-azabenzotriazol-1-yl)-1,1,3,3-tetramethyluronium] hexafluorophosphate (HATU), and carbodiimides such as dicyclohexylcarbodiimide (DCC) or 3-ethyl-3'-(dimethylamino)propylcarbodiimide (EDCI) either alone or in combination with a hydroxybenzotriazole. Alternatively, the activated ester intermediate can be isolated and then treated with the appropriate amine iv in a nonprotic solvent such as tetrahydrofuran (THF) or dimethylformamide (DMF) in the presence of a base, for example, an organic base such as sodium/potassium hexamethyldisilazide, triethylamine, diisopropylethylamine or 1,8-diazabicyclo[5.4.0]undec-7-ene (DBU), or an inorganic base such as sodium, potassium or cesium carbonate or sodium or potassium hydride. Alternatively, the acid halide of 2 may be prepared, for example, by reaction with thionyl chloride or oxalyl chloride, followed by subsequent reaction with amine iii to provide compound If, which is a compound of the formula I where $R_3$ is $COOR_6$, $X_1$ and $X_2$ together form =O, and $R_2$ is alkyl, arylalkyl or chycloalkylalkyl.

Similar reactions as employed above for the conversion of 2 to If may be used to convert 3 to If where $R_3$ is $COOR_6$, $X_1$ and $X_2$ together form =O, and $R_2$ is hydrogen.

Scheme II

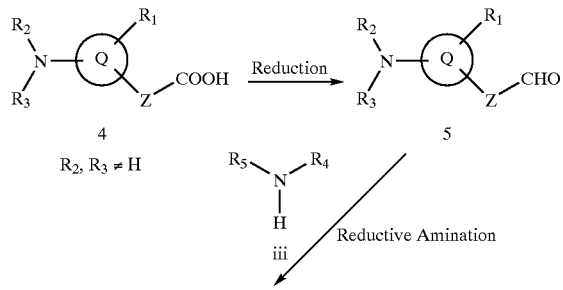

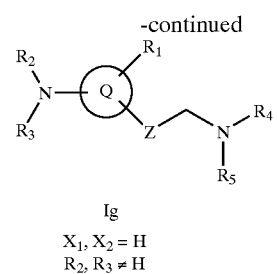

Ig
$X_1, X_2 = H$
$R_2, R_3 \neq H$

As shown in Scheme II, acid 4 where $R_2$ and $R_3$ are not hydrogen and are selected such that the nitrogen to which they are attached is non-basic, is reduced to the aldehyde 5 by methods well know in the art (see March, Advanced Organic Chemistry, Wiley, 1985). For example, the acid 4 may be converted to its corresponding ester followed by reduction with diisobutylaluminum hydride. Alternatively, the acid 4 may be reduced to the corresponding primary alcohol, for example, by treatment with borane/THF, $LiAlH_4$, or via reduction of a mixed anhydride, followed by subsequent oxidation to the aldehyde 5 using Cr(VI) (e.g., pyridinium chlorochromate, "PCC") or under Swern or Moffatt conditions (e.g., $(COCl)_2$/dimethylsulfoxide). The starting acid 4 may be obtained, for example, by saponification of ii.

Reductive amination (see Hudlicky, Reductions in Organic Chemistry, Wiley, 1984) of aldehyde 5 with amine iii in the presence of a reducing agent such as $NaBH_3CN$, $NaBH(OAc)_3$ (Ac=acetyl) or hydrogen and a palladium catalyst produces the amine compound Ig, which is a compound of the formula I where $X_1$ and $X_2$ are each hydrogen and $R_2$ and $R_3$ are each not hydrogen.

Scheme III

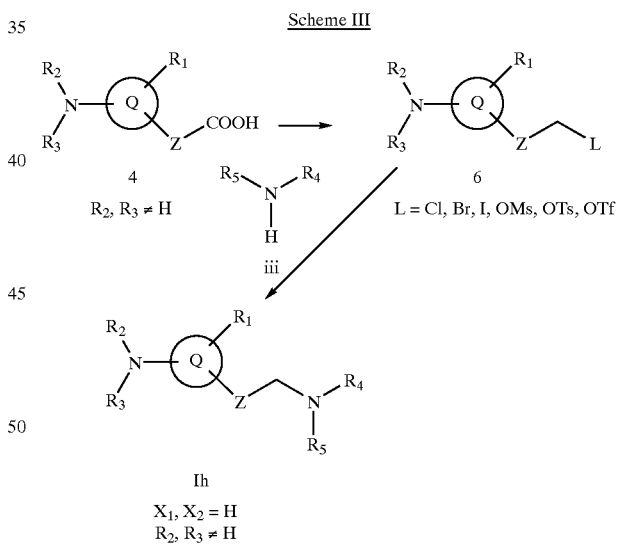

Ih
$X_1, X_2 = H$
$R_2, R_3 \neq H$

As shown in Scheme III, reduction of the acid 4 to a primary alcohol (for example, by treatment with borane/tetrahydrofuran, $LiAlH_4$, or via reduction of a mixed anhydride), followed by conversion by methods well known in the art (see March, Advanced Organic Chemistry, Wiley, 1985), provides 6 which contains a leaving group such as a halide, tosylate (OTs), mesylate (OMs) or triflate (OTf). The groups $R_2$ and $R_3$ are selected such that the resulting nitrogen to which they are attached is non-basic. Compound 6 can then be converted into compound Ih, which is a compound of the formula I where $X_1$ and $X_2$ are each hydrogen and $R_2$ and $R_3$ are each not hydrogen, by a displacement reaction with amine iii, preferably where amine iii is used in excess.

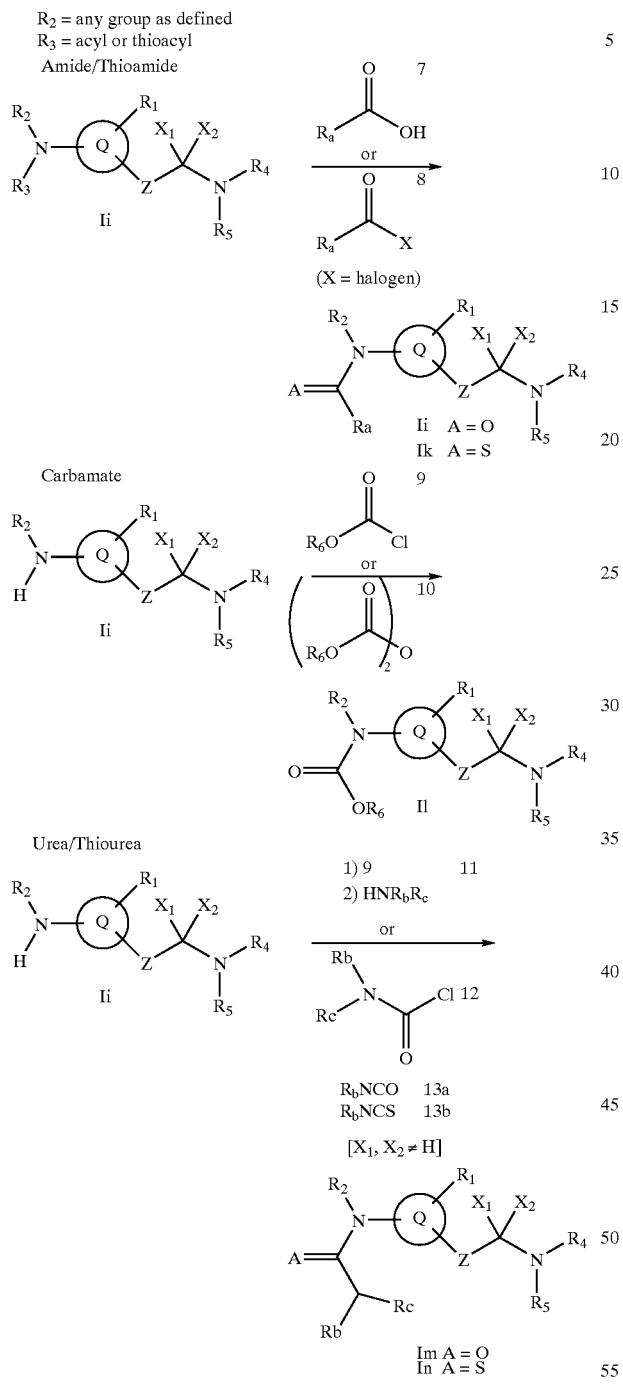

Scheme IV illustrates methods which may be used for the preparation of compounds Ij, Ik, Il, Im and In. Ij, Ik, Il, Im and In are compounds of the formula I where $R_2$ is any group as defined, $R_3$ is an acyl or thioacyl group, $X_1$ and $X_2$ are not hydrogen, and R, is not a primary or secondary amine. Ij, Ik, Il, Im and In have other particular substituents which are specified in this Scheme and below. The starting compound Ii can be prepared by suitable methods described in Schemes A and D.

Amide Ij can be prepared by treatment of amine compound Ii with a carboxylic acid 7 in the presence of reagents which activate the carboxyl group for reaction as described above, for example BOP reagent, HATU, and carbodiimides such as DCC or EDCI either alone or in combination with a hydroxybenztriazole. Alternatively, the acid halide 8 may be reacted with amine compound Ii in the presence of an acid scavenger such as diisopropylethylamine. The corresponding thioamide Ik can be prepared by the treatment of amide Ii (where $X_1$, $X_2 \neq O$) with Lawesson's reagent as described above.

Carbamate Ii can be prepared by treatment of amine compound Ii with a chloroformate 9 or dicarbonate 10 in the presence of an acid scavenger such as diisopropylethylamine.

The urea Im may be prepared by treatment of amine compound Ii with either: 1) a chloroformate 9, such as phenylchloroformate, followed by reaction with an amine 11; 2) a carbamoyl chloride 12 in the presence of an acid scavenger such as diisopropylethylamine; or 3) reaction with an isocyanate 13a (where $R_c$ in Im=H). The corresponding thiourea In may be prepared by treatment of amine compound Ii with a thioisocyanate 13b.

$R_a$ is selected from those groups included in the definition of $R_6$ such that the group $—C(=A)-R_a$ is an acyl or thioacyl group within the definition of $R_3$. $R_b$ and $R_c$ are selected from those groups included in the definitions of $R_7$ and $R_8$, such that the group $—C(=A)—N(R_b)(R_c)$ is an acyl or thioacyl group within the definition of $R_3$.

Scheme V $R_2$ = any group as defined other than acyl
$R_3$ = alkyl, cycloalkyl, cycloalkylalkyl, cycloalkenylalkyl, aralkyl or saturated heterocycle -continued

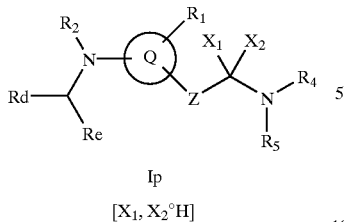

Ip

[X₁, X₂ = H]

Scheme V illustrates a method which can be used for the preparation of Ip, which is a compound of the formula I where R₂ is any group as defined other than acyl, and which is selected such that the nitrogen to which it is attached is basic, R₃ is alkyl, cycloalkyl, cycloalkylalkyl, cycloalkenylalkyl, aralkyl, or saturated heterocycle, and X₁ and X₂ are not hydrogen. The starting compounds Io and Iq can be prepared by suitable methods described in Schemes A and D.

As shown in Scheme V, amine compound Io is reacted with an aldehyde or ketone 14 under reductive amination conditions described above to give the amine Ip. Compound Ip may also be prepared by treatment of an amine compound Iq, where R₂ and R₃ are hydrogen, with t-butyl nitrite or sodium nitrite in the presence of a copper (II) halide to give the halo-substituted compound 15, followed by displacement with amine 16 in the presence of a base such as sodium or potassium hydride or the like (see Lee et al., *J. Heterocyclic Chemistry*, 22, 1621 (1985)).

R_d and R_e are independently selected from hydrogen, alkyl, aryl, cycloalkyl or cycloalkenyl, or together are alkylene or alkenylene completing a 3- to 8-membered saturated or unsaturated ring, such that the group —CH(R_d)(R_e) is a group within the definition of R₃.

Scheme VI

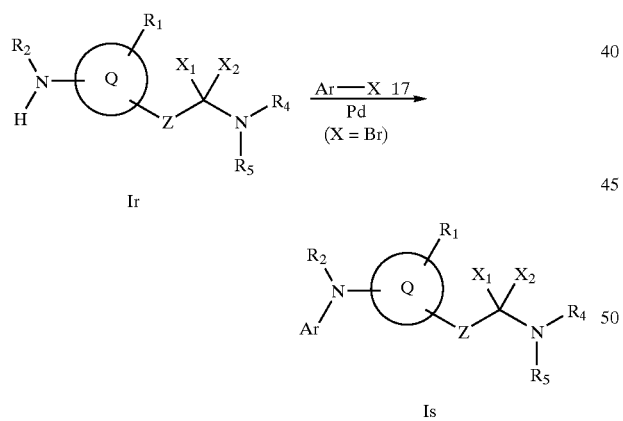

Is

R₂ = any group as defined other than acyl
R₃ = aryl, heteroaryl

As shown in Scheme VI, when R₂ is any group as defined other than acyl, and is selected such that the nitrogen to which it is attached is basic, R₃ is aryl or heteroaryl, and X₁ and X₂ are not hydrogen, amine compound Ir may be reacted with a halophenyl or haloheteroaromatic group 17 in the presence of a palladium (0) catalyst (see *J. Am. Chem. Soc.*, 118, 7215 (1996)) to give amine Is, which is a compound of the formula I having the particular substituents described in this Scheme. The starting compound Ir can be prepared by suitable methods described in Schemes A and D.

Scheme VII

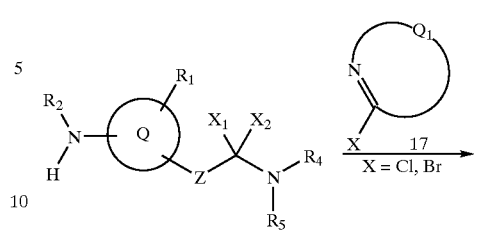

It

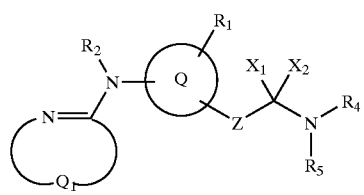

Iu

R₂ = any group as defined
R₃ = heteroaryl

As shown in Scheme VII, when R₂ is any group as defined and R₃ is a heteroaromatic group, amine compound It may be reacted, in the presence of a base if needed, with a 2-halosubstituted heteroaromatic compound 17 where Q₁, together with atoms to which is is bonded, forms a 5- or 6-membered monocyclic or 10- to 12-membered bicyclic heteroaromatic group (such as forming 2-chloropyridine or 2-chloropyrimidine) to give the amine Iu, where Iu is a compound of the formula I having the particular substituents described in this Scheme. The starting compound It can be prepared by suitable methods described in Schemes A and D.

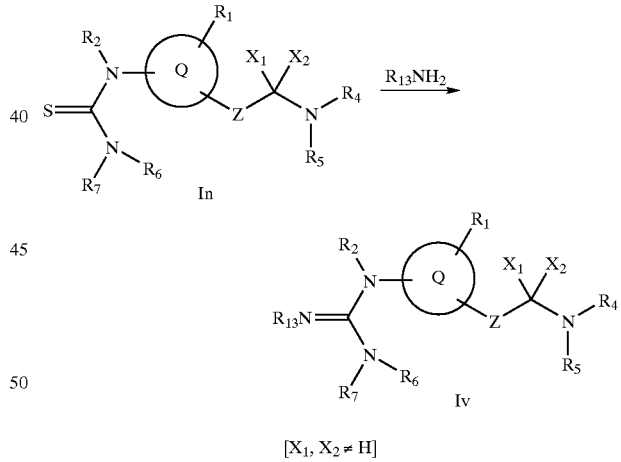

Iv

[X₁, X₂ ≠ H]

As shown in Scheme VIII, thiourea compound In (where X₁ and X₂ are not hydrogen) may be reacted with the appropriate amine in the presence of bis-(2-oxo-3-oxazolidinyl)phosphinic chloride (BOP chloride) benzotriazol-1-yloxy-tris(dimethylamino)phosphonium hexafluorophosphate (BOP-reagent), [O-(7-azabenzotriazol-1-yl)-1,1,3,3-tetramethyluroniumlhexafluorophosphate (HATU) and carbodiimide, such as dicyclohexyl carbodiimide (DCC) or 3-ethyl-3'-(dimethylamino)propyl carbodiimide (EDCI) or diisopropyl carbodiimide (DIC) in the presence of an organic base such as triethylamine, diisopropylethylamine or dimethylaminopyridine in solvents such as dimethylformamide, dichloromethane or tetrahydrofuran to form compound Iv, which is a compound of the formula I having the particular substituents described in this Scheme.

Alternatively, Compound In can be reacted with the appropriate amine in the presence of a mercury (II) salt such as mercuric chloride, or by other methods known in the literature, to form Iv.

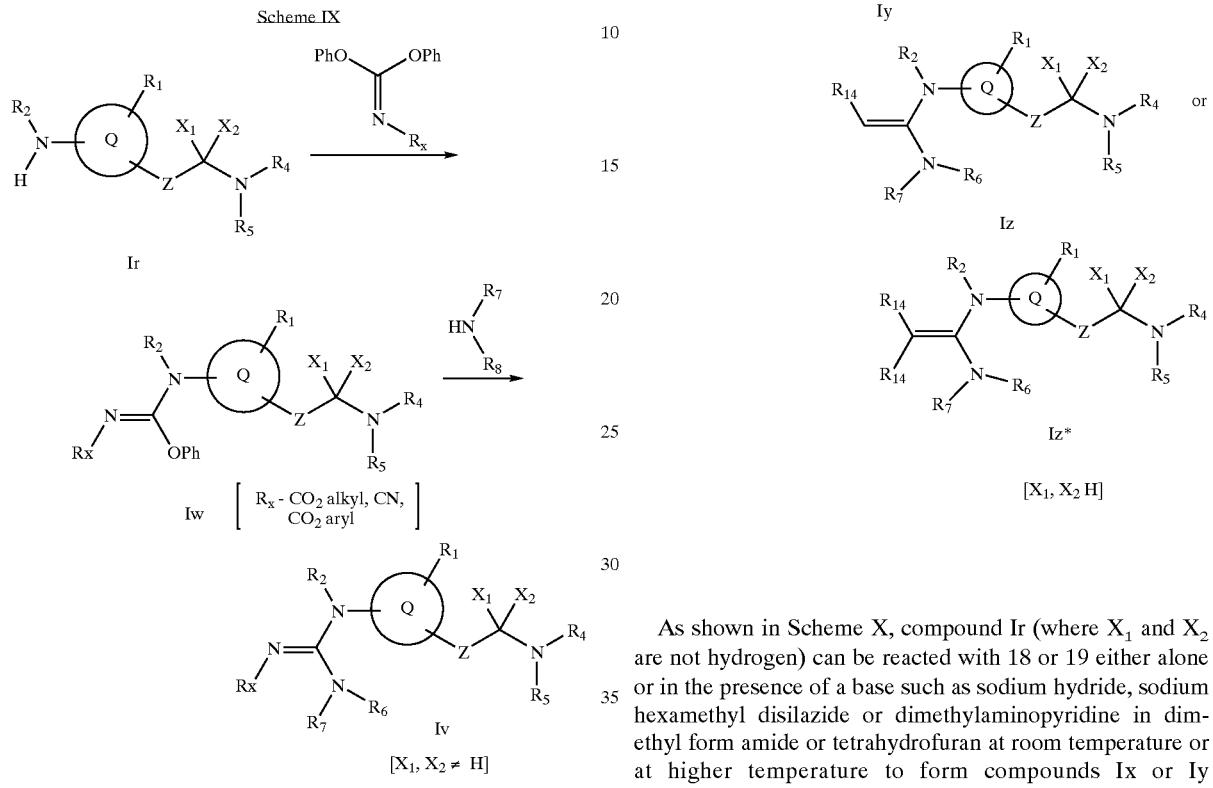

As shown in Scheme IX, amine Ir (where $X_1$ and $X_2$ are not hydrogen) can be reacted with diphenylcyanocarbonimidate either alone or in the presence of a base such as sodium hydride, sodium hexamethyldisilazide or dimethylaminopyridine in acetonitrile, tetrahydrofuran, or dimethylformamide at room temperature or elevated temperature to form intermediate compound Iw. Compound Iw can be reacted with an amine $R_7R_8NH$ to form compound Iv, which is a compound of the formula I having the particular substituents described in this Scheme.

As shown in Scheme X, compound Ir (where $X_1$ and $X_2$ are not hydrogen) can be reacted with 18 or 19 either alone or in the presence of a base such as sodium hydride, sodium hexamethyl disilazide or dimethylaminopyridine in dimethyl form amide or tetrahydrofuran at room temperature or at higher temperature to form compounds Ix or Iy respectively, which can be reacted with an amine $R_7R_8NH$ at room temperature or elevated temperature to form compounds Iz or Iz* respectively. Compound Iz is a compound of the formula I having the particular substituents described in this Scheme. Compound Iz* is a compound of the formula I having the particular substituents described in this Scheme.

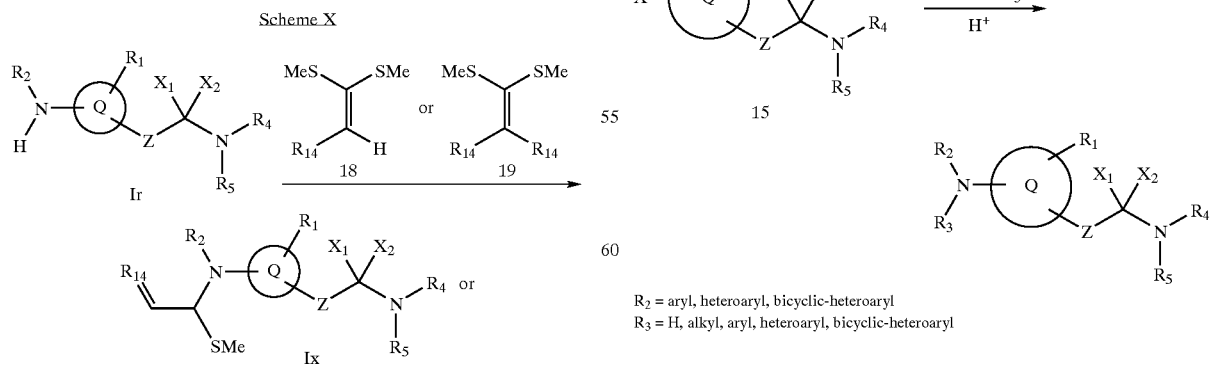

As shown in Scheme XI, compounds of formula I can also be prepared from 15 by treatment with the defined amine in the presence of an acid catalyst (for example, see: Gunzenhauser et al., *Helv. Chim. Acta,* 71, 33 (1988)).

Utility

The compounds of the present invention inhibit protein tyrosine kinases, especially Src-family kinases such as Lck, Fyn, Lyn, Src, Yes, Hck, Fgr and Blk, and are thus useful in the treatment, including prevention and therapy, of protein tyrosine kinase-associated disorders such as immunologic and oncologic disorders. The compounds inhibit also receptor tyrosine kinases including HER1 and HER2 and are therefore useful in the treatment of proliferative disorders such as psoriasis and cancer. The ability of these compounds to inhibit HER1 and other receptor kinases will also permit their use as anti-angiogenic agents to treat disorders such as cancer and diabetic retinopathy. "protein tyrosine kinase-associated disorders" are those disorders which result from aberrant tyrosine kinase activity, and/or which are alleviated by the inhibition of one or more of these enzymes. For example, Lck inhibitors are of value in the treatment of a number of such disorders (for example, the treatment of autoimmune diseases), as Lck inhibition blocks T cell activation. The treatment of T cell mediated diseases, including inhibition of T cell activation and proliferation, is a particularly preferred embodiment of the present invention. Compounds which selectively block T cell activation and proliferation are preferred. Compounds of the present invention which block the activation of endothelial cell PTK by oxidative stress, thereby limiting surface expression of adhesion molecules that induce neutrophil binding, and which inhibit PTK necessary for neutrophil activation are useful, for example, in the treatment of ischemia and reperfusion injury.

The present invention thus provides methods for the treatment of protein tyrosine kinase-associated disorders, comprising the step of administering to a subject in need thereof at least one compound of the formula I in an amount effective therefor. Other therapeutic agents such as those described below may be employed with the inventive compounds in the present methods. In the methods of the present invention, such other therapeutic agent(s) may be administered prior to, simultaneously with or following the administration of the compound(s) of the present invention.

Use of the compounds of the present invention in treating protein tyrosine kinase-associated disorders is exemplified by, but is not limited to, treating a range of disorders such as: transplant (such as organ transplant, acute transplant or heterograft or homograft (such as is employed in burn treatment)) rejection; protection from ischemic or reperfusion injury such as ischemic or reperfusion injury incurred during organ transplantation, myocardial infarction, stroke or other causes; transplantation tolerance induction; arthritis (such as rheumatoid arthritis, psoriatic arthritis or osteoarthritis); multiple sclerosis; chronic obstructive pulmonary disease (COPD), such as emphysema; inflammatory bowel disease, including ulcerative colitis and Crohn's disease; lupus (systemic lupus erythematosis); graft vs. host disease; T-cell mediated hypersensitivity diseases, including contact hypersensitivity, delayed-type hypersensitivity, and gluten-sensitive enteropathy (Celiac disease); psoriasis; contact dermatitis (including that due to poison ivy); Hashimoto's thyroiditis; Sjogren's syndrome; Autoimmune Hyperthyroidism, such as Graves' Disease; Addison's disease (autoimmune disease of the adrenal glands); Autoimmune polyglandular disease (also known as autoimmune polyglandular syndrome); autoimmune alopecia; pernicious anemia; vitiligo; autoimmune hypopituatarism; Guillain-Barre syndrome; other autoimmune diseases; cancers, including cancers where Lck or other Src-family kinases such as Src are activated or overexpressed, such as colon carcinoma and thymoma, and cancers where Src-family kinase activity facilitates tumor growth or survival; glomerulonephritis; serum sickness; uticaria; allergic diseases such as respiratory allergies (asthma, hayfever, allergic rhinitis) or skin allergies; scleracierma; mycosis fungoides; acute inflammatory responses (such as acute respiratory distress syndrome and ishchemia/reperfusion injury); dermatomyositis; alopecia areata; chronic actinic dermatitis; eczema; Behcet's disease; Pustulosis palmoplanteris; Pyoderma gangrenum; Sezary's syndrome; atopic dermatitis; systemic schlerosis; and morphea. The present invention also provides a method for treating the aforementioned disorders such as atopic dermatitis by administration of any compound capable of inhibiting protein tyrosine kinase.

Src-family kinases other than Lck, such as Hck and Fgr, are important in the Fc gamma receptor responses of monocytes and macrophages. Compounds of the present invention inhibit the Fc gamma dependent production of TNF alpha in the monocyte cell line THP-1 that does not express Lck. The ability to inhibit Fc gamma receptor dependent monocyte and macrophage responses results in additional anti-inflammatory activity for the present compounds beyond their effects on T cells. This activity is especially of value, for example, in the treatment of inflammatory diseases such as arthritis or inflammatory bowel disease. In particular, the present compounds are of value for the treatment of autoimmune glomerulonephritis and other instances of glomerulonephritis induced by deposition of immune complexes in the kidney that trigger Fc gamma receptor responses leading to kidney damage.

In addition, Src family kinases other than Lck, such as Lyn and Src, are important in the Fc epsilon receptor induced degranulation of mast cells and basophils that plays an important role in asthma, allergic rhinitis, and other allergic disease. Fc epsilon receptors are stimulated by IgE-antigen complexes. Compounds of the present invention inhibit the Fc epsilon induced degranulation responses, including in the basophil cell line RBL that does not express Lck. The ability to inhibit Fc epsilon receptor dependent mast cell and basophil responses results in additional anti-inflammatory activity for the present compounds beyond their effect on T cells. In particular, the present compounds are of value for the treatment of asthma, allergic rhinitis, and other instances of allergic disease.

The combined activity of the present compounds towards monocytes, macrophages, T cells, etc. may be of value in the treatment of any of the aforementioned disorders.

In a particular embodiment, the compounds of the present invention are useful for the treatment of the aforementioned exemplary disorders irrespective of their etiology, for example, for the treatment of transplant rejection, rheumatoid arthritis, multiple sclerosis, chronic obstructive pulmonary disease, inflammatory bowel disease, lupus, graft v. host disease, T-cell mediated hypersensitivity disease, psoriasis, Hashimoto's thyroiditis, Guillain-Barre syndrome, cancer, contact dermatitis, allergic disease such as allergic rhinitis, asthma, ischemic or reperfusion injury, or atopic dermatitis whether or not associated with PTK.

By virtue of their ability to inhibit HER1 and HER2 kinases, compounds of the present invention can also be used for the treatment of proliferative diseases, including psoriasis and cancer. The HER1 receptor kinase has been shown to be expressed and activated in many solid tumors including non-small cell lung, colorectal, and breast cancer. Similarly, the HER2 receptor kinase has been shown to be overexpressed in breast, ovarian, lung and gastric cancer. Monoclonal antibodies that downregulate the abundance of the HER2 receptor or inhibit signaling by the HER1 receptor have shown anti-tumor efficacy in preclincal and clinical studies. It is therefore expected that inhibitors of the HER1 and HER2 kinases will have efficacy in the treatment of tumors that depend on signaling from either of the two receptors. These compounds are expected to have efficacy either as single agent or in combination with other chemotherapeutic agents such as placlitaxel (Taxol), doxorubicin hydrochloride (adriamycin), and cisplatin (Platinol). See the following documents and references cited therein: Cobleigh, M. A., Vogel, C. L., Tripathy, D., Robert, N. J., Scholl, S., Fehrenbacher, L., Wolter, J. M., Paton, V., Shak, S., Lieberman, G., and Slamon, D. J., "Multinational study of the efficacy and safety of humanized anti-HER2 monoclonal antibody in women who have HER2-overexpressing metastatic breast cancer that has progressed after chemotherapy for metastatic disease", J. of Clin. Oncol. 17(9), p. 2639–2648 (1999); Baselga, J., Pfister, D., Cooper, M. R., Cohen, R., Burtness, B., Bos, M., D'Andrea, G., Seidman, A., Norton, L., Gunnett, K., Falcey, J., Anderson, V., Waksal, H., and Mendelsohn, J., "Phase I studies of anti-epidermal growth factor receptor chimeric antibody C225 alone and in combination with cisplatin", J. Clin. Oncol. 18(4), p. 904–914 (2000).

The present invention also provides pharmaceutical compositions comprising at least one of the compounds of the formula I capable of treating a protein tyrosine kinase-associated disorder in an amount effective therefor, and a pharmaceutically acceptable vehicle or diluent. The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the formula I may be administered by any suitable means, for example, orally, such as in the form of tablets, capsules, granules or powders; sublingually; buccally; parenterally, such as by subcutaneous, intravenous, intramuscular, or intrasternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The present compounds may also be administered liposomally.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The present compounds may also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

The effective amount of a compound of the present invention may be determined by one of ordinary skill in the art, and includes exemplary dosage amounts for an adult human of from about 0.1 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to protein tyrosine kinase-associated disorders.

The compounds of the present invention may be employed alone or in combination with each other and/or other suitable therapeutic agents useful in the treatment of protein tyrosine kinase-associated disorders such as PTK inhibitors other than those of the present invention, antiinflammatories, antiproliferatives, chemotherapeutic agents, immunosuppressants, anticancer agents and cytotoxic agents.

Exemplary such other therapeutic agents include the following: cyclosporins (e.g., cyclosporin A), CTLA4-Ig, antibodies such as anti-ICAM-3, anti-IL-2 receptor (Anti-Tac), anti-CD45RB, anti-CD2, anti-CD3 (OKT-3), anti-CD4, anti-CD80, anti-CD86, monoclonal antibody OKT3, agents blocking the interaction between CD40 and gp39, such as antibodies specific for CD40 and/or gp39 (i.e., CD154), fusion proteins constructed from CD40 and gp39 (CD40Ig and CD8gp39), inhibitors, such as nuclear translocation inhibitors, of NF-kappa B function, such as deoxyspergualin (DSG), non-steroidal antiinflammatory drugs (NSAIDs) such as ibuprofen, steroids such as prednisone or dexamethasone, gold compounds, antiproliferative agents such as methotrexate, FK506 (tacrolimus, Prograf), mycophenolate mofetil, cytotoxic drugs such as azathiprine and cyclophosphamide, TNF-α inhibitors such as tenidap, anti-TNF antibodies or soluble TNF receptor such as etanercept (Enbrel), rapamycin (sirolimus or Rapamune), leflunimide (Arava), and cyclooxygenase-2 (COX-2) inhibitors such as celecoxib (Celebrex) and rofecoxib (Vioxx), or derivatives thereof, and the PTK inhibitors disclosed in the following U.S. Patent Applications, incorporated herein by reference in their entirety: Ser. No. 60/056,770, filed Aug. 25, 1997 Ser. No. 60/069,159, filed Dec. 9, 1997 Ser. No. 09/097,338, filed Jun. 15, 1998 Ser. No. 60/056,797, filed Aug. 25, 1997 Ser. No. 09/094,797, filed Jun. 15, 1998 Ser. No. 60/065, 042, filed Nov. 10, 1997 Ser. No. 09/173,413, filed Oct. 15, 1998, Ser. No. 60/076,789, filed Mar. 4, 1998 and Ser. No. 09/262,525, filed Mar. 4, 1999 See the following documents and references cited therein: Hollenbaugh, D., Douthwright, J., McDonald, V., and Aruffo, A., "Cleavable CD401 g fusion proteins and the binding to sgp39", *J. Immunol. Methods* (Netherlands), 188(1), p. 1–7 (Dec. 15, 1995); Hollenbaugh, D., Grosmaire, L. S., Kullas, C. D., Chalupny, N. J., Braesch-Andersen, S., Noelle, R. J., Stamenkovic, I., Ledbetter, J. A., and Aruffo, A., "The human T cell antigen gp39, a member of the TNF gene family, is a ligand for the CD40 receptor: expression of a soluble form of gp39 with B cell co-stimulatory activity", -*EMBO J* (England), 11(12), p 4313–4321 (December 1992); and Moreland, L. W. et al., "Treatment of rheumatoid arthritis with a recombinant human tumor necrosis factor receptor (p75)-Fc fusion protein, *New England J. of Medicine*, 337(3), p. 141–147 (1997).

Exemplary classes of anti-cancer agents and cytotoxic agents include, but are not limited to: alkylating agents, such as nitrogen mustards, alkyl sulfonates, nitrosoureas, ethylenimines, and triazenes; antimetabolites, such as folate antagonists, purine analogues, and pyrimidine analogues; antibiotics, such as anthracyclines, bleomycins, mitomycin, dactinomycin, and plicamycin; enzymes, such as L-asparaginase; farnesyl-protein transferase inhibitors; hormonal agents, such as glucocorticoids, estrogens/antiestrogens, androgens/antiandrogens, progestins, and luteinizing hormone-releasing hormone anatagonists, octreotide acetate; microtubule-disruptor agents, such as ecteinascidins or their analogs and derivatives; microtubule-stabilizing agents such as paclitaxel (Taxol®), docetaxel (Taxotere®), and epothilones A-F or their analogs or derivatives; plant-derived products, such as vinca alkaloids, epipodophyllotoxins, taxanes; and topoisomerase inhibitors; prenyl-protein transferase inhibitors; and miscellaneous agents such as, hydroxyurea, procarbazine, mitotane, hexamethylmelamine, platinum coordination complexes such as cisplatin and carboplatin; and other agents used as anti-cancer and cytotoxic agents such as biological response modifiers, growth factors; immune modulators, and monoclonal antibodies. The compounds of the invention may also be used in conjunction with radiation therapy.

Representative examples of these classes of anti-cancer and cytotoxic agents include, but are not limited to, mechlorethamine hydrochlordie, cyclophosphamide, chlorambucil, melphalan, ifosfamide, busulfan, carmustin, lomustine, semustine, streptozocin, thiotepa, dacarbazine, methotrexate, thioguanine, mercaptopurine, fludarabine, pentastatin, cladribin, cytarabine, fluorouracil, doxorubicin hydrochloride, daunorubicin, idarubicin, bleomycin sulfate, mitomycin C, actinomycin D, safracins, saframycins, quinocarcins, discodermolides, vincristine, vinblastine, vinorelbine tartrate, etoposide, teniposide, paclitaxel, tamoxifen, estramustine, estramustine phosphate sodium, flutamide, buserelin, leuprolide, pteridines, diyneses, levamisole, aflacon, interferon, interleukins, aldesleukin, filgrastim, sargramostim, rituximab, BCG, tretinoin, irinotecan hydrochloride, betamethosone, gemcitabine hydrochloride, altretamine, and topoteca and any analogs or derivatives thereof.

Preferred members of these classes include, but are not limited to paclitaxel, cisplatin, carboplatin, doxorubicin, caminomycin, daunorubicin, aminopterin, methotrexate, methopterin, mitomycin C, ecteinascidin 743, porfiromycin, 5-fluorouracil, 6-mercaptopurine, gemcitabine, cytosine arabinoside, podophyllotoxin or podophyllotoxin derivatives such as etoposide, etoposide phosphate or teniposide, melphalan, vinblastine, vincristine, leurosidine, vindesine, and leurosine.

Examples of anti-cancer and other cytotoxic agents include the following: epothilone derivatives as found in U.S. Ser. No. 09/506,481 filed Feb. 17, 2000 German Patent No. 4138042.8; WO 97/19086, WO 98/22461, WO 98/25929, WO 98/38192, WO 99/01124, WO 99/02224, WO 99/02514, WO 99/03848, WO 99/07692, WO 99/27890, WO 99/28324, WO 99/43653, WO 99/54330, WO 99/54318, WO 99/54319, WO 99/65913, WO 99/67252, WO 99/67253, and WO 00/00485; cyclin dependent kinase inhibitors as found in WO 99/24416; and prenyl-protein transferase inhibitors as found in WO 97/30992 and WO 98/54966.

The above other therapeutic agents, when employed in combination with the compounds of the present invention, may be used, for example, in those amounts indicated in the Physicians' Desk Reference (PDR) or as otherwise determined by one of ordinary skill in the art.

The following assays can be employed in ascertaining the degree of activity of a compound ("test compound") as a PTK inhibitor. Compounds described in the following Examples have been tested in one or more of these assays, and have shown activity.

Enzyme Assay Using Lck, Fyn, Lyn, Hck, Fgr, Src, Blk or Yes

The following assay has been carried out using the protein tyrosine kinases Lck, Fyn, Lyn, Hck, Fgr, Src, Blk and Yes.

The protein tyrosine kinase of interest is incubated in kinase buffer (20 mM MOPS, pH 7, 10 mM $MgCl_2$) in the presence of the test compound. The reaction is initiated by the addition of substrates to the final concentration of 1 μM ATP, 3.3 μCi/ml [$_{33}$P] gamma-ATP, and 0.1 mg/ml acid denatured enolase (prepared as described in Cooper, J. A., Esch, F. S., Taylor, S. S., and Hunter, T., "Phosphorylation sites in enolase and lactate dehydrogenase utilized by tyrosine protein kinases in vivo and in vitro", *J. Biol. Chem.*, 259, 7835–7841 (1984)). The reaction is stopped after 10 minutes by the addition of 10% trichloroacetic acid, 100 mM sodium pyrophosphate followed by 2 mg/ml bovine serum albumin. The labeled enolase protein substrate is precipitated at 4 degrees, harvested onto Packard Unifilter plates and counted in a Topcount scintillation counter to ascertain the protein tyrosine kinase inhibitory activity of the test compound (activity inversely proportional to the amount of labeled enolase protein obtained). The exact concentration of reagents and the amount of label can be varied as needed.

This assay is advantageous as it employs an exogenous substrate (enolase) for more accurate enzyme kinetics, and can be conducted in a 96-well format that is readily automated. In addition, His-tagged protein tyrosine kinases (described below) offer much higher production yields and purity relative to GST-protein tyrosine kinase fusion protein.

The protein tyrosine kinase may be obtained from commercial sources or by recombinant methods described herewith. For the preparation of recombinant Lck, human Lck was prepared as a His-tagged fusion protein using the Life Technologies (Gibco) baculovirus vector pFastBac Hta (commercially available) in insect cells. A cDNA encoding human Lck isolated by PCR (polymerase chain reaction) was inserted into the vector and the protein was expressed using the methods described by the manufacturer. The Lck was purified by affinity chromatography. For the production of Lck in insect cells using baculovirus, see Spana, C., O'Rourke, E. C., Bolen, J. B., and Fargnoli, J., "Analysis of the tyrosine kinase p56lck expressed as a glutathione S-transferase protein in *Spodoptera frugiperda* cells," *Protein expression and purification*, Vol. 4, p. 390–397 (1993). Similar methods may be used for the recombinant production of other Src-family kinases.

Enzyme Assay Using HER1 or HER2

Compounds of interest were assayed in a kinase buffer that contained 20 mM Tris.HCl, pH 7.5, 10 mM $MnCl_2$, 0.5 mM dithiothreitol, bovine serum albumin at 0.1 mg/ml, poly(glu/tyr, 4:1) at 0.1 mg/ml, 1 μM ATP, and 4 μCi/ml [gamma-$_{33}$P]ATP. Poly(glu/tyr, 4:1) is a synthetic polymer that serves as a phosphoryl acceptor and is purchased from Sigma Chemicals. The kinase reaction is initiated by the addition of enzyme and the reaction mixtures were incubated at 26° C. for 1 h. The reaction is terminated by the addition of EDTA to 50 mM and proteins are precipitated by the addition of trichloroacetic acid to 5%. The precipitated proteins are recovered by filtration onto Packard Unifilter plates and the amount of radioactivity incorporated is measured in a Topcount scintillation counter.

For the preparation of recombinant HER1, the cytoplasmic sequence of the receptor were expressed in insect cells as a GST fusion protein, which was purified by affinity chromatography as described above for Lck. The cytoplasmic sequence of HER2 was subcloned into the baculovirus expression vector pBlueBac4 (Invitrogen) and was expressed as an untagged protein in insect cells. The recombinant protein was partially purified by ion-exchange chromatography.

Cell Assays (1) Cellular Tyrosine Phosohorylation

Jurkat T cells are incubated with the test compound and then stimulated by the addition of antibody to CD3 (monoclonal antibody G19-4). Cells are lysed after 4 minutes or at another desired time by the addition of a lysis buffer containing NP-40 detergent. Phosphorylation of proteins is detected by anti-phosphotyrosine immunoblotting. Detection of phosphorylation of specific proteins of interest such as ZAP-70 is detected by immunoprecipitation with anti-ZAP-70 antibody followed by anti-phosphotyrosine immunoblotting. Such procedures are described in Schieven, G. L., Mittler, R. S., Nadler, S. G., Kirihara, J. M., Bolen, J. B., Kanner, S. B., and Ledbetter, J. A., "ZAP-70 tyrosine kinase, CD45 and T cell receptor involvement in UV and $H_2O_2$ induced T cell signal transduction", *J. Biol. Chem.*, 269, 20718–20726 (1994), and the references incorporated therein. The Lck inhibitors inhibit the tyrosine phosphorylation of cellular proteins induced by anti-CD3 antibodies.

For the preparation of G19-4, see Hansen, J. A., Martin, P. J., Beatty, P. G., Clark, E. A., and Ledbetter, J. A., "Human T lymphocyte cell surface molecules defined by the workshop monoclonal antibodies," in *Leukocyte Typing I*, A. Bernard, J. Boumsell, J. Dausett, C. Milstein, and S. Schlossman, eds. (New York: Springer Verlag), p. 195–212 (1984); and Ledbetter, J. A., June, C. H., Rabinovitch, P. S., Grossman, A., Tsu, T. T., and Imboden, J. B., "Signal transduction through CD4 receptors: stimulatory vs. inhibitory activity is regulated by CD4 proximity to the CD3/T cell receptor", *Eur. J. Immunol.*, 18, 525 (1988).

(2) Calcium Assay

Lck inhibitors block calcium mobilization in T cells stimulated with anti-CD3 antibodies. Cells are loaded with the calcium indicator dye indo-1, treated with anti-CD3 antibody such as the monoclonal antibody G19-4, and calcium mobilization is measured using flow cytometry by recording changes in the blue/violet indo-1 ratio as described in Schieven, G. L., Mittler, R. S., Nadler, S. G., Kirihara, J. M., Bolen, J. B., Kanner, S. B., and Ledbetter, J. A., "ZAP-70 tyrosine kinase, CD45 and T cell receptor involvement in UV and $H_2O_2$ induced T cell signal transduction", *J. Biol. Chem.*, 269, 20718–20726 (1994), and the references incorporated therein.

(3) Proliferation Assays

Lck inhibitors inhibit the proliferation of normal human peripheral blood T cells stimulated to grow with anti-CD3 plus anti-CD28 antibodies. A 96 well plate is coated with a monoclonal antibody to CD3 (such as G19-4), the antibody is allowed to bind, and then the plate is washed. The antibody bound to the plate serves to stimulate the cells. Normal human peripheral blood T cells are added to the wells along with test compound plus anti-CD28 antibody to provide co-stimulation. After a desired period of time (e.g., 3 days), the [3H]-thymidine is added to the cells, and after further incubation to allow incorporation of the label into newly synthesized DNA, the cells are harvested and counted in a scintillation counter to measure cell proliferation.

The following Examples illustrate embodiments of the present invention, and are not intended to limit the scope of the claims. Abbreviations employed in the Examples are defined below. Compounds of the Examples are identified by the example and step in which they are prepared (for example, "1A" denotes the title compound of step A of Example 1), or by the example only where the compound is the title compound of the example (for example, "2" denotes the title compound of Example 2).

Abbreviations aq.=aqueous conc.=concentrated

DMSO=dimethylsulfoxide

EtOAc=ethyl acetate $Et_2O$=diethyl ether h=hours

HATU=N-[dimethylamino-1H-1,2,3-triazolo-[4,5-b]
  pyridin-1-yl methylene]-N-methyl methanaminium
  hexafluorophosphate N-oxide
MeOH=methanol
MOPS=4-morpholine-propanesulfonic acid
MS=mass spectrometry
Ret Time=retention time
RT=room temperature
satd.=saturated
TFA=trifluoroacetic acid
THF=tetrahydrofuran
DMF=N,N-dimethylformamide

EXAMPLE 1

Preparation of [5-[[(2,4,6-Trimethylphenyl)amino]
carbonyl]-4-methyl-2-thiazolyl]carbamic Acid, 1,1-
dimethylethyl Ester

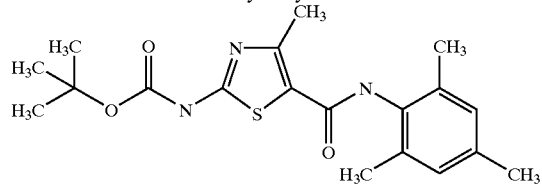

A. Ethyl-2-tert-butoxycarbonyloxyamino-4-methyl-
thiazole-5-carboxylate

A suspension of ethyl-2-amino-4-methyl-thiazole-5-carboxylate (18.6 g, 100 mmol), di-t-butyldicarbonate (26.2 g, 120 mmol) and 4-dimethylaminopyridine (800 mg, 6.55 mmol) in dry tetrahydrofuran (300 mL) was stirred under nitrogen for 18 h. The solvent was evaporated in vacuo. The residue was suspended in dichloromethane (1 L) and filtered through a pad of celite. The filtrate was washed with 1 N aqueous HCl solution (300 mL, 2×), water and brine, dried (MgSO$_4$), and concentrated in vacuo. The residue was triturated with hexanes. The solid was filtered and dried in vacuo to obtain the title compound (20 g, 72%) as a tan solid.

B. 2-tert-butoxycarbonyloxyamino-4-methyl-thiazole-5-carboxylic Acid

A stirred solution of ethyl-2-tert-butoxycarbonyloxyamino-4-methyl-thiazole-5-carboxylate (10 g, 34.95 mmol) in tetrahydrofuran-ethanol (250 mL, 2:3) was treated with a 6N KOH solution (250 mL). The mixture was heated to 55° C. overnight. The solution was cooled to 0° C. and acidified with concd. HCl to pH 1. The solvent was evaporated in vacuo. The residue was washed with water, diethyl ether, dried in vacuo over anhydrous phosphorous pentoxide to obtain the title acid (6 g, 89%) as a white solid.

C. 2-tert-butoxycarbonyloxyamino-4-methyl-thiazole-5-carboxylic Acid Chloride

A 2 M solution of oxalyl chloride in dichloromethane (22.5 mL, 45 mmol) was added dropwise to a stirred suspension of 2-tert-butoxycarbonyloxyamino-4-methyl-thiazole-5-carboxylic acid (10 g, 38.72 mmol) in dichloromethane (150 mL) and N,N-dimethyl formamide (150 μL) at 0° C. The suspension gradually became homogenous after addition was complete. The solution was allowed to warm to room temperature and stirred at rt for 1.5 h. The solvent was evaporated in vacuo and the residue was coevaporated with toluene (300 mL, 2×) and then dried in vacuo to obtain the title acid chloride (10.7 g, 99%) as a tan solid.

D. [5-[[(2,4,6-Trimethylphenyl)amino]carbonyl]-4-methyl-2-thiazolyl]carbamic Acid, 1,1-dimethylethyl Ester 2,4,6-Trimethyl aniline (6.3 mL, 38.66 mmol) was added dropwise to a stirred solution of 2-tert-butoxycarbonyloxyamino-4-methyl-thiazole-5-carboxylic acid chloride (10.7 g, 38.66 mmol) in dichloromethane (150 mL) at 0° C. After 20 min, diisopropylethylamine (8.8 mL, 44.88 mmol) was added dropwise. The solution was allowed to warm to rt and stirred for an additional 2 h. The solvent was evaporated in vacuo. The residue was suspended in EtOAc (700 mL), washed with 1 N aq. HCl solution (300 mL, 2×), water, and brine; dried (MgSO$_4$), filtered and concentrated. The residue was triturated with ether to obtain the title compound (12.5 g, 86%) as a tan solid.

EXAMPLE 2

Preparation of 2-Amino-N-(2,4,6-trimethylphenyl)-
4-methyl-5-thiazolecarboxamide

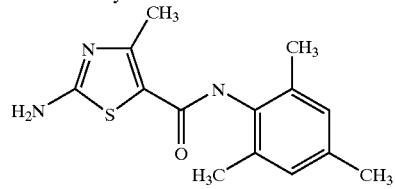

A solution of [5-[[(2,4,6-Trimethylphenyl)amino]carbonyl]-4-methyl-2-thiazolyl]carbamic acid, 1,1-dimethylethyl ester (10 g, 26.63 mmol) in trifluoroacetic acid (100 mL) was stirred at rt for 3 h. The solution was concentrated under reduced pressure and the residue was diluted with EtOAc (700 mL), washed with 5% aq. KHCO$_3$ solution (400 mL, 2×), water, and brine; dried (MgSO$_4$), filtered and concentrated. The residue was washed with ether (200 mL) and acetonitrile (100 mL) to obtain the title compound (6.7 g, 91%) as a white solid.

EXAMPLE 3

Preparation of [5-[[(2,4,6-Trimethylphenyl)amino]
carbonyl]-4-trifluoromethyl-2-thiazolyl]carbamic
Acid, 1,1-dimethylethyl Ester

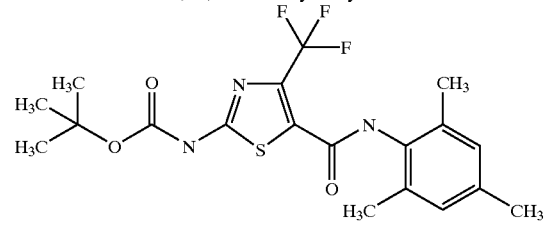

A. Ethyl-2-tert-butoxycarbonyloxyamino-4-trifluoromethyl-thiazole-5-carboxylate

A suspension of ethyl-2-amino-4-trifluoromethyl-thiazole-5-carboxylate (5.05 g, 21.02 mmol), di-t-butyldicarbonate (4.82 g, 22.07 mmol) and 4-dimethylaminopyridine (260 mg, 2.1 mmol) in dichloromethane (209 mL) was stirred under nitrogen for 1.5 h. The solvent was evaporated in vacuo. The residue was chromatographed on a silica gel column. Elution with 5% EtOAc in hexanes, followed by 15% EtOAc in hexanes afforded the title compound (6.57 g, 92%) as a white solid.

B. 2-Tert-butoxycarbonyloxyamino-4-trifluoromethyl-thiazole-5-carboxylic Acid

A stirred solution of ethyl-2-tert-butoxycarbonyloxyamino-4-trifluoromethyl-thiazole-5-carboxylate (6.5 g, 19.1 mmol) in methanol (100 mL) was treated with a 1N aq. NaOH solution (573 mL). The mixture was stirred at rt overnight. The solution was cooled to 0° C.

and acidified with a 6 M aq. HCl solution to pH 1 and extracted with chloroform (150 mL, 6×). The chloroform extracts were combined, dried (Na$_2$SO$_4$), filtered and concentrated under reduced pressure and in vacuo to obtain the title acid (5.75 g, 96%) as a white solid.

C. [5-[[(2,4,6-Trimethylphenyl)amino]carbonyl]-4-trifluoromethyl-2-thiazolyl]carbamic Acid, 1,1-dimethylethyl Ester 4-Methylmorpholine (40 μL, 0.39 mmol) was added to a mixture of 2-tert-butoxycarbonyloxyamino-4-trifluoromethyl-thiazole-5-carboxylic acid (100 mg, 0.32 mmol), 2,4,6-trimethylaniline (45 μL, 0.32 mmol), and benzotriazol-1-yloxy-tris-(dimethylamino)phosphonium hexafluorophosphate (BOP reagent, 380 mg, 0.4 mmol) in DMF (2 mL). The solution was stirred at rt for 72 h, diluted with dichloromethane and washed with 0.25 M aq. KHSO$_4$ solution followed by satd. aq. KHCO$_3$ solution. The dichloromethane extract was separated, dried (Na$_2$SO$_4$), filtered and concentrated. The residue was chromatographed on a silica gel column and eluted with 5% EtOAc in hexanes followed by 10% EtOAc in hexanes to obtain the title compound (90 mg, 65%) as a white solid.

EXAMPLE 4

Preparation of 2-Amino-N-(2,4,6-trimethylphenyl)-4-trifluoromethyl-5-thiazolecarboxamide, trifluoroacetate (1:1)

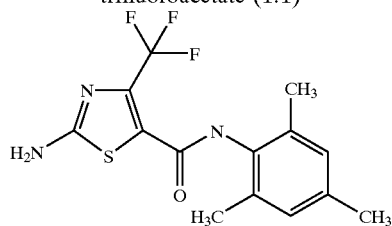

A solution of [5-[[(2,4,6-Trimethylphenyl)amino]carbonyl]-4-trifluoromethyl-2-thiazolyl]carbamic acid, 1,1-dimethylethyl ester (120 mg, 0.28 mmol) in trifluoroacetic acid (5 mL) was stirred at 0° C. for 1 h. The solution was concentrated under reduced pressure and the residue was coevaporated with ether to obtain a yellow solid which was triturated with hexanes to obtain the title compound (96 mg, 76%) as a light yellow solid.

EXAMPLE 5

Preparation of [5-[[(2,4,6-Trimethylphenyl)amino]carbonyl]-4-phenyl-2-thiazolyl]carbamic acid, 1,1-dimethylethyl ester

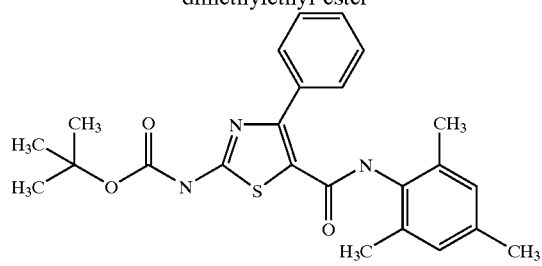

A. Ethyl-2-tert-butoxycarbonyloxyamino-4-phenyl-thiazole-5-carboxylate

Compound 5A was prepared by an analogous method as that of 3A, except using ethyl-2-amino-4-phenyl-thiazole-5-carboxylate to give the title compound 5A as a white solid (90.5%).

B. 2-Tert-butoxycarbonyloxyamino-4-phenyl-thiazole-5-carboxylic Acid

Compound 5B was prepared by an analogous method as that of 3B, except using 5A to give the title compound 5B as a white solid (99%).

C. 2-Tert-butoxycarbonyloxyamino-4-phenyl-thiazole-5-carboxylic acid chloride

Compound 5C was prepared by an analogous method as that of 1C, except using 5B to give the title compound 5C as a white solid (90%).

D. [5-[[(2,4,6-Trimethylphenyl)amino]carbonyl]-4-phenyl-2-thiazolyl]carbamic acid, 1,1-dimethylethyl ester Compound 5D was prepared by an analogous method as that of 1D, except using 5C to give the title compound 5D as a light yellow solid (93%).

EXAMPLE 6

Preparation of 2-Amino-N-(2,4,6-trimethylphenyl)-4-phenyl-5-thiazolecarboxamide, Trifluoroacetate (1:1)

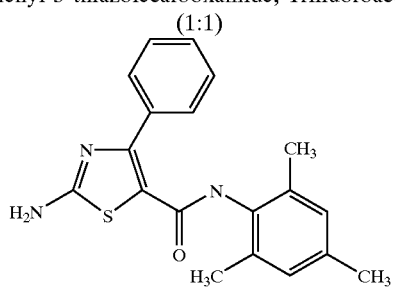

Compound 6 was prepared by an analogous method as that of 4, except using 5D to give the title compound 6 as a white solid (68%).

EXAMPLE 7

Preparation of [5-[[Phenylamino]carbonyl]-4-methyl-2-thiazolyl]carbamic acid, 1,1-dimethylethyl ester

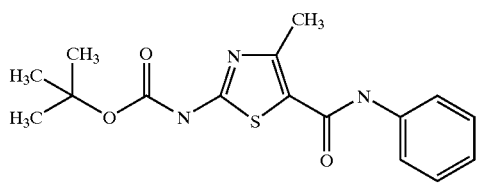

Compound was prepared by an analogous method as that of 1D, except using aniline in place of 2,4,6-trimethylaniline and triethylamine in place of diisopropylethylamine to give the title compound 7 as an off-white solid (76%).

EXAMPLE 8

Preparation of 2-Amino-N-(phenyl)-4-methyl-5-thiazolecarboxamide, trifluoroacetate (1:1)

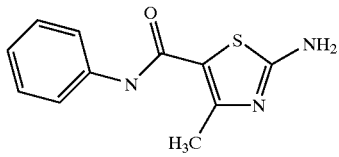

Compound 8 was prepared by an analogous method as that of 4, except using 7 to give the title compound 8 as a white solid (68%).

EXAMPLE 9

Preparation of [5-[[(2,4-Dichlorophenyl)amino]carbonyl]-4-methyl-2-thiazolyl]carbamic acid, 1,1-dimethylethyl ester

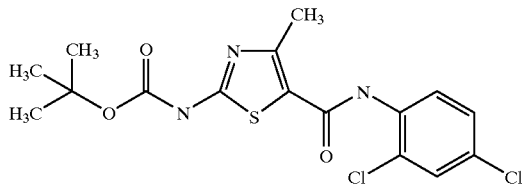

Compound 9 was prepared by an analogous method as that of 1D, except using 2,4-dichloroaniline to give the title compound 9 as a white solid (28%).

EXAMPLE 10

Preparation of 2-Amino-N-(2,4-dichlorophenyl)-4-methyl-5-thiazolecarboxamide, Trifluoroacetate (1:1)

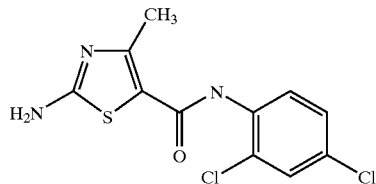

Compound 10 was prepared by an analogous method as that of 4, except using 9 to give the title compound 8 as a white solid (100%).

EXAMPLE 11

Preparation of 5-[[(2,4,6-Trimethylphenyl)amino]carbonyl]-2-thiazolyl]carbamic acid, 1,1-dimethylethyl ester

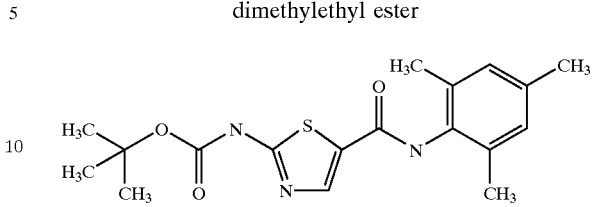

A. Ethyl-2-tert-butoxycarbonyloxyamino-thiazole-5-carboxylate

Compound 11A was prepared by an analogous method as that of 3A, except using ethyl-2-amino-thiazole-5-carboxylate to give the title compound 11A as a white solid (79.5%).

B. 2-Tert-butoxycarbonyloxyamino-thiazole-5-carboxylic acid

Compound 11B was prepared by an analogous method as that of 3B, except using 11A to give the title compound 11B as a white solid (95.5%).

C. 2-Tert-butoxycarbonyloxyamino-thiazole-5-carboxylic acid Chloride

Compound 11C was prepared by an analogous method as that of 1C, except using 11B to give the title compound 11C.

D. [5-[[(2,4,6-Trimethylphenyl)amino]carbonyl]-2-thiazolyl]carbamic acid, 1,1-dimethylethyl ester Compound 11D was prepared by an analogous method as that of 1D, except using 11C to give the title compound 11D as an off-white solid (70%).

EXAMPLE 12

Preparation of 2-Amino-N-(2,4,6-trimethylphenyl)-4-phenyl-5-thiazolecarboxamide, Trifluoroacetate (1:1)

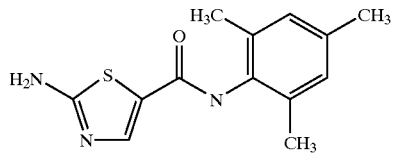

Compound 12 was prepared by an analogous method as that of 4, except using 11D to give the title compound 12 as a light yellow solid (88%).

EXAMPLES 13 TO 53

General Procedure

Compounds 13 to 53 were prepared following the procedure described below. Appropriate amines (0.40 mmol) and diisopropylethylamine (70 μL, 0.40 mmol) were added to a suspension of 1C (100 mg, 0.36 mmol) in dichloromethane (3 mL). The solution was stirred mechanically in a sealed tube at rt for 16 h. The reaction mixtures were diluted with methanol (200 μL) and loaded in Varian SCX ion exchange columns (2 g/6 cc) pretreated with methanol-dichloromethane (8 mL, 1:1) followed by dichloromethane (8 mL). SCX Column filtration were performed using a Gilson robot unit. The column was washed sequentially with dichloromethane (9 mL), dichloromethane-methanol (9 mL, 4:1), dichloromethane-methanol (9 mL, 1:1), methanol (9 mL), 0.01 M ammonium hydroxide in methanol (9 mL) and 0.05 M ammonium hydroxide in methanol (9 mL). The elutes were collected separetely by the robot and then concentrated using a speed vac. Fractions containing the products were combined.

"HPLC Ret Time" is the HPLC retention time under the following conditions: YMC S5 ODS 4.6×50 mm Ballastic Column, 4 min gradient starting from 100% solvent A (10% MeOH, 90% $H_2O$, 0.2% $H_3PO_4$) to 100% solvent B (90% MeOH, 10% $H_2O$, 0.2% $H_3PO_4$), flow rate 4 mL/min, $\lambda$=220 nM.

| EX. NO. | Compound Structure | Compound Name | HPLC Ret Time (min) |
|---|---|---|---|
| 13 | 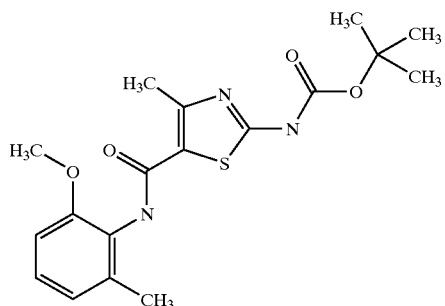 | [5-[[(2-Methoxy-6-methylphenyl)amino]-carbonyl]-4-methyl-2-thiazolyl]carbamic acid 1,1-dimethylethyl ester | 3.79 |
| 14 | 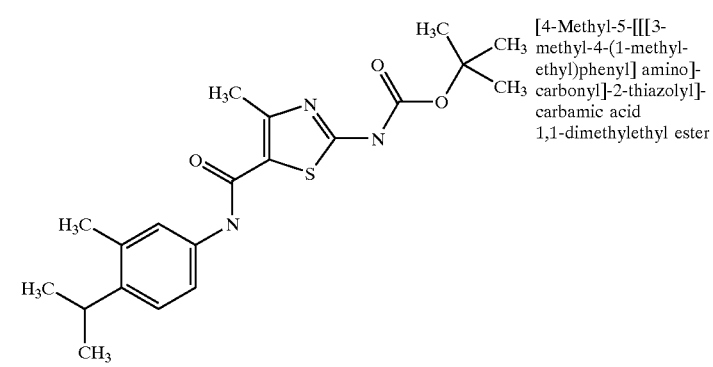 | [4-Methyl-5-[[[3-methyl-4-(1-methyl-ethyl)phenyl]amino]-carbonyl]-2-thiazolyl]-carbamic acid 1,1-dimethylethyl ester | 4.51 |
| 15 | 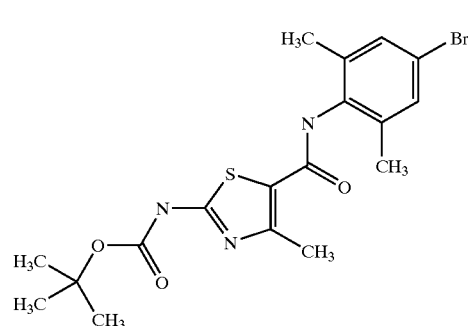 | [5-[[(4-Bromo-2,6-di-methylphenyl)amino]-carbonyl]-4-methyl-2-thiazolyl]carbamic acid 1,1-dimethylethyl ester | 4.24 |
| 16 | 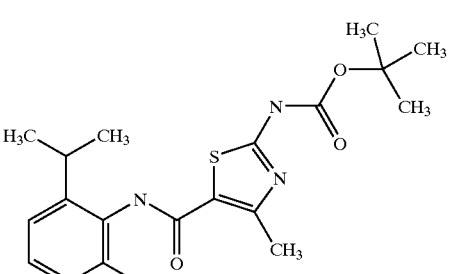 | [4-Methyl-5-[[[2-methyl-6-(1-methylethyl)-phenyl]-amino]carbonyl]-2-thiazolyl]carbamic acid 1,1-dimethylethyl ester | 4.17 |

-continued

| EX. NO. | Compound Structure | Compound Name | HPLC Ret Time (min) |
|---|---|---|---|
| 17 | 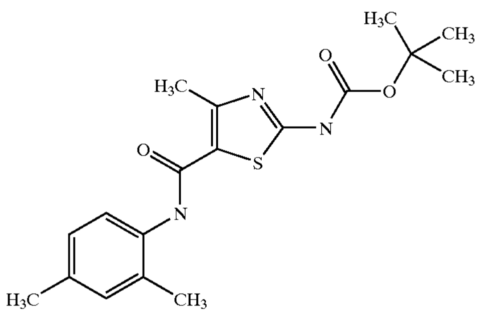 | [5-[[(2,4-Dimethylphenyl)-amino]carbonyl]-4-methyl-2-thiazolyl]carbamic acid 1,1-dimethylethyl ester | 4.05 |
| 18 | 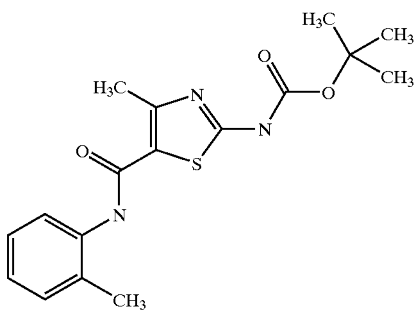 | [4-Methyl-5-[[(2-methylphenyl)amino]carbonyl]-2-thiazolyl]carbamic acid 1,1-dimethylethyl ester | 3.87 |
| 19 | 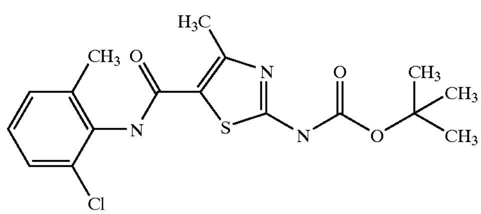 | [5-[[(2-Chloro-6-methylphenyl)amino]carbonyl]-4-methyl-2-thiazolyl]carbamic acid 1,1-dimethylethyl ester | 3.86 |
| 20 | 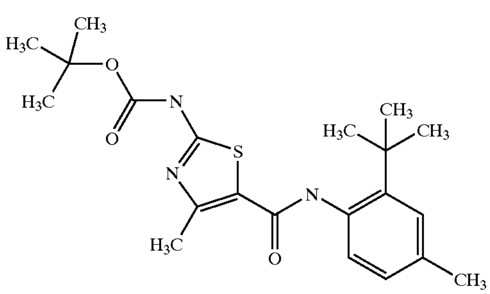 | [5-[[[2-(1,1-Dimethylethyl)-4-methylphenyl]amino]carbonyl]-4-methyl-2-thiazolyl]carbamic acid 1,1-dimethylethyl ester | 4.30 |
| 21 | 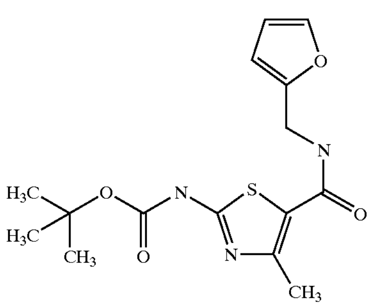 | [5-[[(2-Furanylmethyl)-amino]carbonyl]-4-methyl-2-thiazolyl]carbamic acid 1,1-dimethylethyl ester | 3.54 |

| EX. NO. | Compound Structure | Compound Name | HPLC Ret Time (min) |
|---|---|---|---|
| 22 | 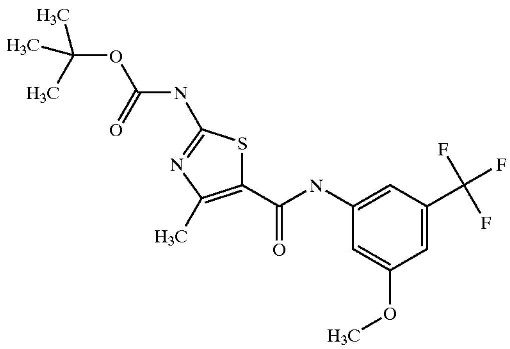 | [5-[[[3-Methoxy-5-(trifluoromethyl)phenyl]-amino]carbonyl]-4-methyl-2-thiazolyl]carbamic acid 1,1-dimethylethyl ester | 4.43 |
| 23 | 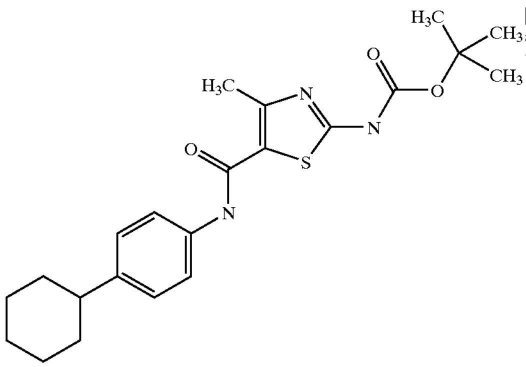 | [5-[[(4-Cyclohexylphenyl)-amino]carbonyl]-4-methyl-2-thiazolyl]carbamic acid 1,1-dimethylethyl ester | 4.78 |
| 24 | 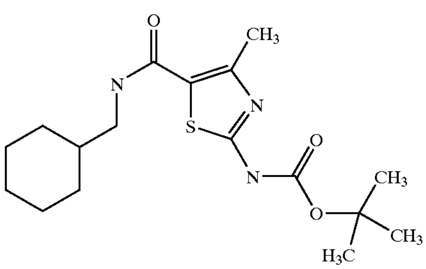 | [5-[[(Cyclohexylmethyl)-amino]carbonyl]-4-methyl-2-thiazolyl]carbamic acid 1,1-dimethyltethyl ester | 4.21 |
| 25 | 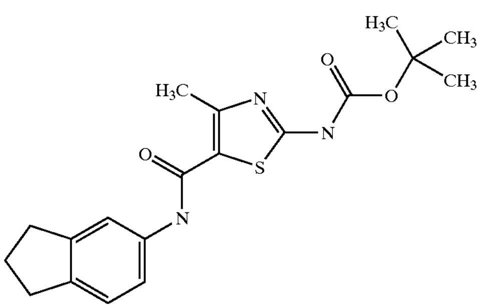 | [5-[[(2,3-Dihydro-1H-indenyl)amino]carbonyl]-4-methyl-2-thiazolyl]carbamic acid 1,1-dimethylethyl ester | 4.30 |
| 26 | 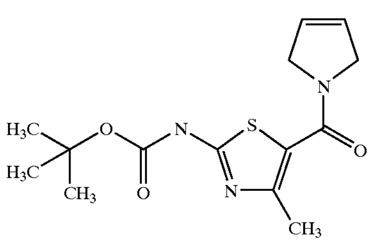 | [5-[(2,5-Dihydro-1H-pyrrol-1-yl)carbonyl]-4-methyl-2-thiazolyl]carbamic acid 1,1-dimethylethyl ester | 3.56 |

-continued

| EX. NO. | Compound Structure | Compound Name | HPLC Ret Time (min) |
|---|---|---|---|
| 27 | 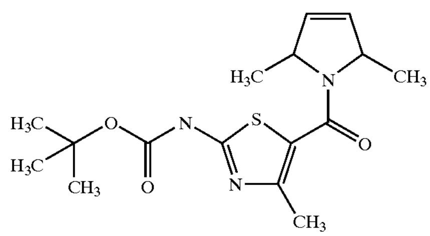 | [5-[(2,5-Dihydro-2,5-dimethyl-1H-pyrrol-1-yl)-carbonyl]-4-methyl-2-thiazolyl]carbamic acid 1,1-dimethylethyl ester | 3.86 |
| 28 | 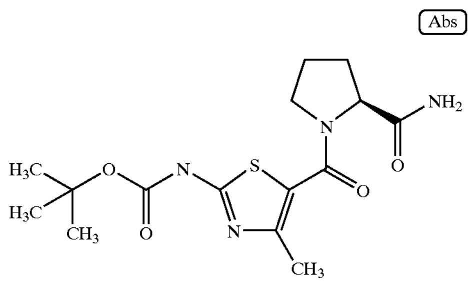 | 1-[[2-[[(1,1-Dimethyl-ethoxy)carbonyl]amino]-4-methyl-5-thiazolyl]carbonyl]-L-prolinamide | 2.96 |
| 29 | 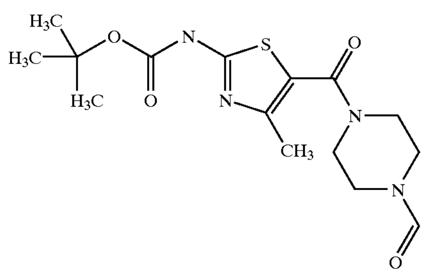 | [5-[(4-Formyl-1-piperazinyl)-carbonyl]-4-methyl-2-thiazolyl]carbamic acid 1,1-dimethylethyl ester | 2.90 |
| 30 | 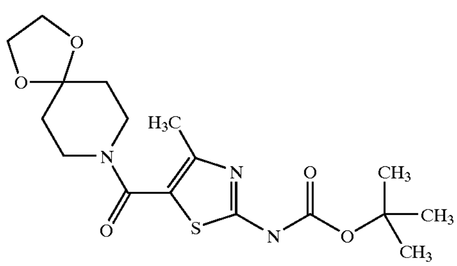 | [5-(1,4-Dioxa-8-azaspiro[4.5]-decan-8-ylcarbonyl)-4-methyl-2-thiazolyl]carbamic acid 1,1-dimethylethyl ester | 3.54 |
| 31 | 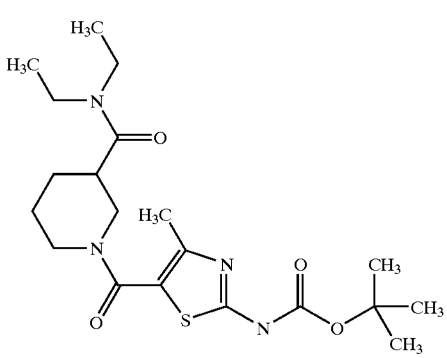 | [5-[[3-[(Diethylamino)carbonyl]-1-piperidinyl]carbonyl]-4-methyl-2-thiazolyl]carbamic acid 1,1-dimethylethyl ester | 3.66 |

-continued

| EX. NO. | Compound Structure | Compound Name | HPLC Ret Time (min) |
|---|---|---|---|
| 32 | 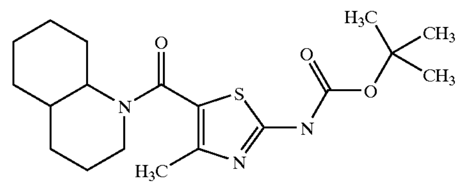 | [4-Methyl-5-[(octahydro-1-quinolinyl)carbonyl]-2-thiazolyl]carbamic acid 1,1-dimethylethyl ester | 4.37 |
| 33 | 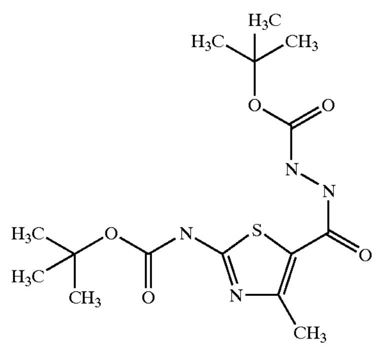 | 2-[[(1,1-Dimethylethoxy)carbonyl]amino]-4-methyl-5-thiazolecarboxylic acid 2-[(1,1-dimethylethoxy)carbonyl]hydrazide | 3.50 |
| 34 | 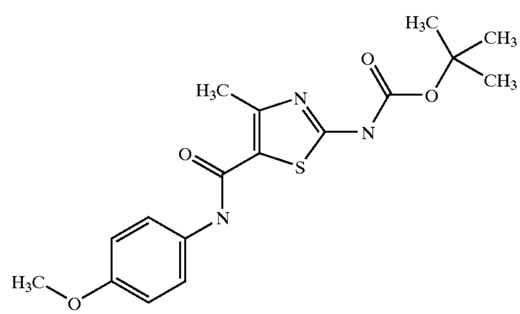 | [5-[[(4-Methoxyphenyl)amino]carbonyl]-4-methyl-2-thiazolyl]carbamic acid 1,1-dimethylethyl ester | 3.83 |
| 35 | 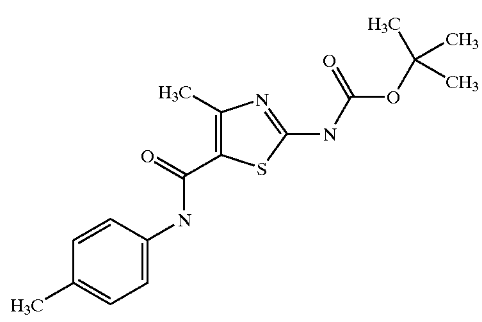 | [4-Methyl-5-[[(4-methylphenyl)amino]carbonyl]-2-thiazolyl]carbamic acid 1,1-dimethylethyl ester | 4.07 |
| 36 | 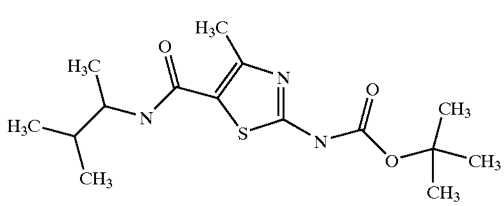 | [5-[[(1,2-Dimethylpropyl)amino]carbonyl]-4-methyl-2-thiazolyl]carbamic acid 1,1-dimethylethyl ester | 3.87 |

-continued

| EX. NO. | Compound Structure | Compound Name | HPLC Ret Time (min) |
|---|---|---|---|
| 37 | 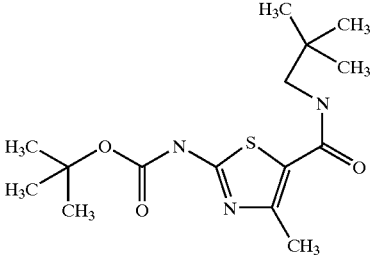 | [5-[[(2,2-Dimethylpropyl)amino]carbonyl]-4-methyl-2-thiazolyl]-carbamic acid 1,1-dimethylethyl ester | 3.97 |
| 38 | 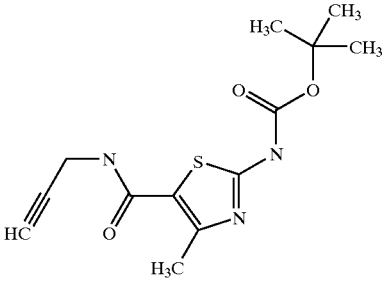 | [4-Methyl-5-[(2-propynyl-amino)carbonyl]-2-thiazolyl]-carbamic acid 1,1-dimethylethyl ester | 3.22 |
| 39 | 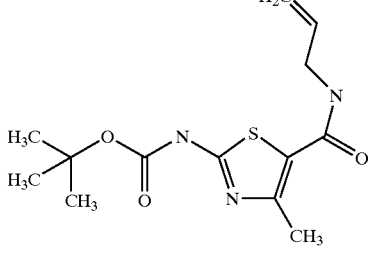 | [4-Methyl-5-[(2-propenyl-amino)carbonyl]-2-thiazolyl]-carbamic acid 1,1-dimethylethyl ester | 3.41 |
| 40 | 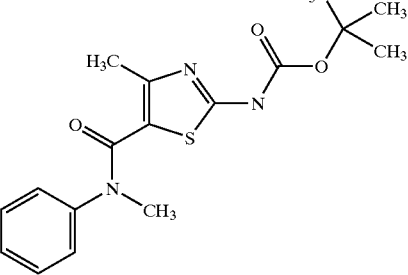 | [4-Methyl-5-[(methylphenyl-amino)carbonyl]-2-thiazolyl]-carbamic acid 1,1-dimethylethyl ester | 3.75 |
| 41 | 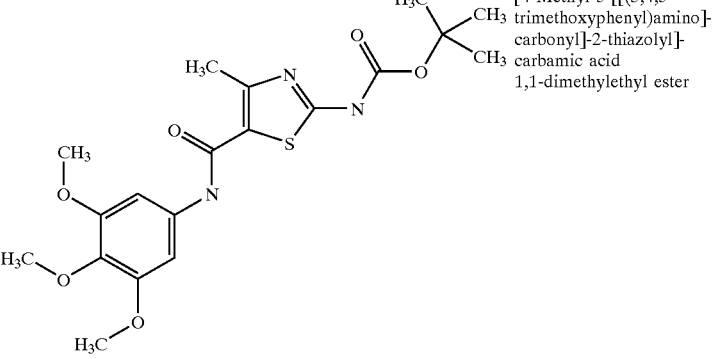 | [4-Methyl-5-[[(3,4,5-trimethoxyphenyl)amino]-carbonyl]-2-thiazolyl]-carbamic acid 1,1-dimethylethyl ester | 3.84 |

-continued

| EX. NO. | Compound Structure | Compound Name | HPLC Ret Time (min) |
|---|---|---|---|
| 42 | 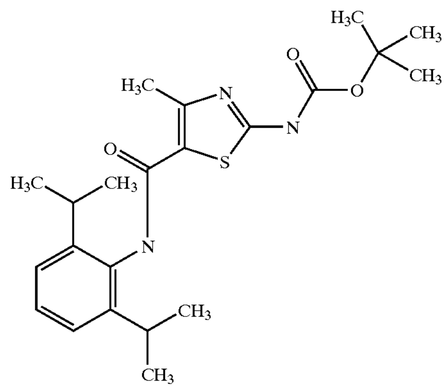 | [5-[[[2,6-Bis(1-methyl-ethyl)phenyl]amino]-carbonyl]-4-methyl-2-thiazolyl]carbamic acid 1,1-dimethylethyl ester | 4.40 |
| 43 | 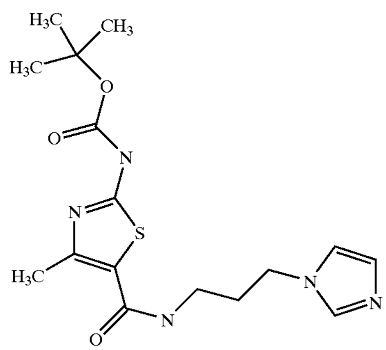 | [5-[[[3-(1H-Imidazol-1-yl)propyl]amino]carbonyl]-4-methyl-2-thiazolyl]-carbamic acid 1,1-dimethylethyl ester | 2.45 |
| 44 | 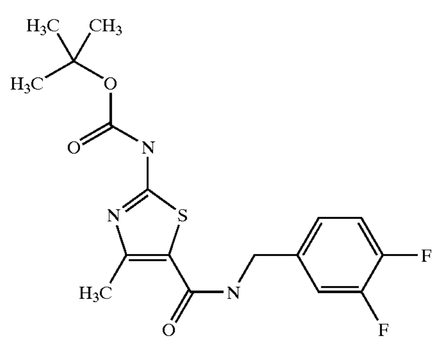 | [5-[[[(3,4-Difluorophenyl)-methyl]amino]carbonyl]-4-methyl-2-thiazolyl]-carbamic acid 1,1-dimethylethyl ester | 3.97 |
| 45 | [Abs] | N-[[2-[[(1,1-Dimethyl-ethoxy)carbonyl]amino]-4-methyl-5-thiazolyl]carbonyl]-L-leucine methyl ester | 3.99 |

-continued

| EX. NO. | Compound Structure | Compound Name | HPLC Ret Time (min) |
|---|---|---|---|
| 46 | 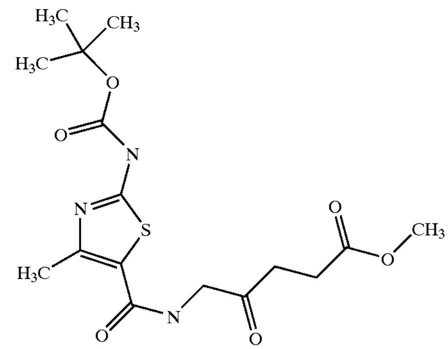 | 5-[[[2-[[(1,1-Dimethylethoxy)carbonyl]amino]-4-methyl-5-thiazolyl]carbonyl]amino]-4-oxopentanoic acid methyl ester | 3.27 |
| 47 | 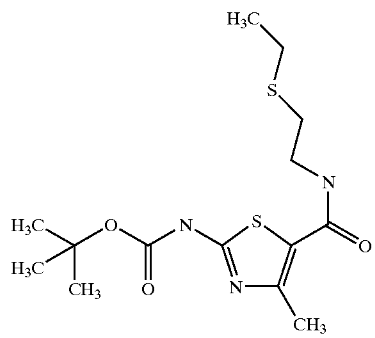 | [5-[[[2-(Ethylthio)ethyl]amino]carbonyl]-4-methyl-2-thiazolyl]carbamic acid 1,1-dimethylethyl ester | 3.75 |
| 48 | 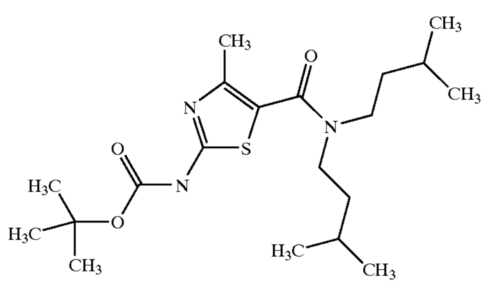 | [5-[[Bis(3-methylbutyl)amino]carbonyl]-4-methyl-2-thiazolyl]carbamic acid 1,1-dimethylethyl ester | 4.67 |
| 49 | 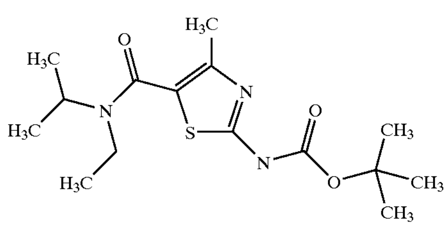 | [5-[[Ethyl(1-methylethyl)amino]carbonyl]-4-methyl-2-thiazolyl]carbamic acid 1,1-dimethylethyl ester | 3.84 |
| 50 | 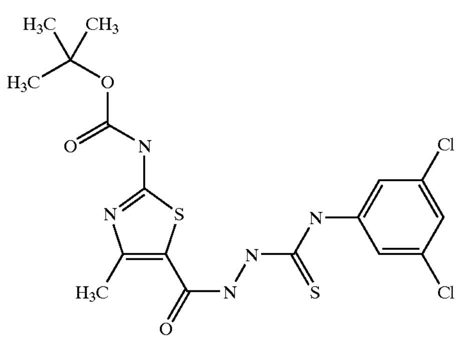 | 2-[[(1,1-Dimethylethoxy)carbonyl]amino]-4-methyl-5-thiazolecarboxylic acid 2-[[(3,5-dichlorophenyl)amino]thioxomethyl]hydrazide | 4.66 |

-continued

| EX. NO. | Compound Structure | Compound Name | HPLC Ret Time (min) |
|---|---|---|---|
| 51 | 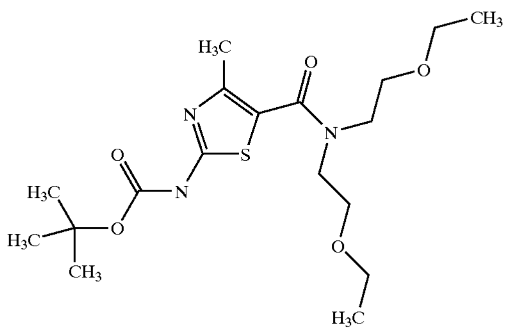 | [5-[[Bis(2-ethoxyethyl)-amino]carbonyl]-4-methyl-2-thiazolyl]carbamic acid 1,1-dimethylethyl ester | 3.83 |
| 52 | 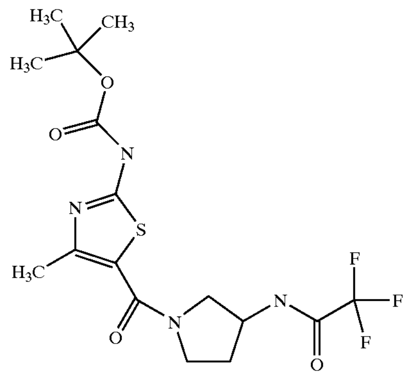 | [4-Methyl-5-[[3-[(tri-fluoroacetyl)amino]-1-pyrrolidinyl]carbonyl]-2-thiazolyl]carbamic acid 1,1-dimethylethyl ester | 3.47 |
| 53 | 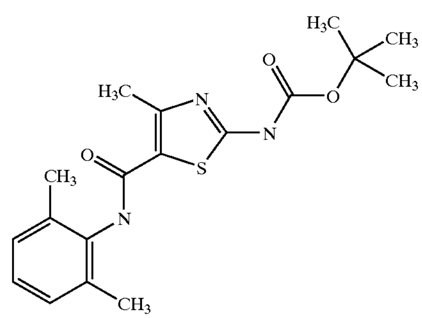 | [5-[[(2,6-Dimethyl-phenyl)amino]carbonyl]-4-methyl-2-thiazolyl]carbamic acid 1,1-dimethylethyl ester | 3.87 |

EXAMPLES 54 to 129

General Procedure

Compounds 54 to 129 were prepared following the procedure described below. Diisopropylethyl amine (60 µL, 0.34 mmol) was added to a mixture of amine 2 (30 mg, 0.11 mmol), appropriate carboxylic acid (0.13 mmol), 1-hydroxy-7-azabenzotriazole (19.5 mg, 0.14 mmol), and ethyl-3-(3-dimethylamino)-propyl carbodiimide hydrochloride (26.8 mg, 0.14 mmol) in THF (0.4 mL). The mixture was heated in a sealed tube under argon at 45° C. for 24 h. The reaction mixture was diluted with dichloromethane (4 mL) and washed with 2 N aq. HCl solution (2 mL, 3×). The dichloromethane solution was passed through a Varian SCX cation exchange column (2 g, 6 cc) on a Gilson robot. The column was eluted sequentially with acetonitrile-methanol (10 mL, 4:1), methanol-2M methanolic ammonia (3 mL, 4:1), and 2 M methanolic ammonia solution (3 mL, 4×). The fractions were collected separately using the Gilson robot. Fraction containing the product was concentrated and dried in vacuo. "HPLC Ret Time" is the HPLC retention time under the following conditions: YMC S5 ODS 4.6×50 mm Ballastic Column, 4 min gradient starting from 100% solvent A (10% MeOH, 90% $H_2O$, 0.2% $H_3PO_4$) to 100% solvent B (90% MeOH, 10% $H_2O$, 0.2% $H_3PO_4$), flow rate 4 mL/min, λ=220 nM for compounds 54–127. For compounds 128–129 HPLC conditions are: Zorbax S8-C18 4.5 mm×7.5 cm short column, 8 min gradient starting from 100% solvent A (10% MeOH, 90% $H_2O$, 0.2% $H_3PO_4$) to 100% solvent B (90% MeOH, 10% $H_2O$, 0.2% $H_3PO_4$), flow rate 2.5 mL/min, λ=217 nM.

| EX. NO. | Compound Name | HPLC Ret Time (min) |
|---|---|---|
| 54 | 2-[[(2,2-Dichloro-1-methylcyclopropyl)carbonyl]-amino]-4-methyl-N-(2,4,6-trimethylphenyl)-5-thiazolecarboxamide | 4.22 |
| 55 | 2-[(Cyclohexylacetyl)amino]-4-methyl-N-(2,4,6-trimethylphenyl)-5-thiazolecarboxamide | 4.47 |
| 56 | 2-[(2,5-Difluoro-benzoyl)amino]-4-methyl-N-(2,4,6-trimethylphenyl)-5-thiazolecarboxamide | 4.15 |
| 57 | 2-[(5-Bromo-2-chloro-benzoyl)amino]-4-methyl-N-(2,4,6-trimethylphenyl)-5-thiazolecarboxamide | 4.37 |
| 58 | 2-[(3-Cyanobenzoyl)-amino]-4-methyl-N-(2,4,6-trimethylphenyl)-5-thiazolecarboxamide | 4.06 |

-continued

| EX. NO. | Compound Structure | Compound Name | HPLC Ret Time (min) |
|---|---|---|---|
| 59 | 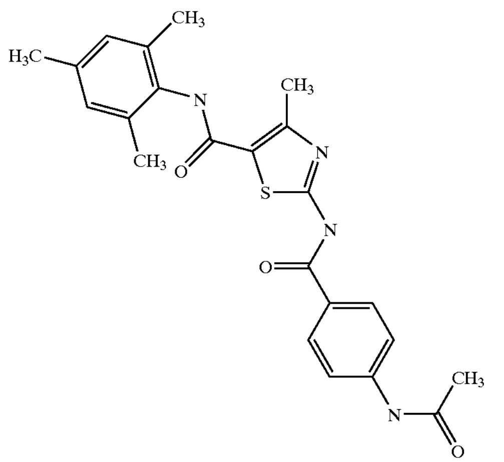 | 2-[[4-(Acetylamino)-benzoyl]amino]-4-methyl-N-(2,4,6-trimethylphenyl)-5-thiazolecarboxamide | 4.60 |
| 60 | 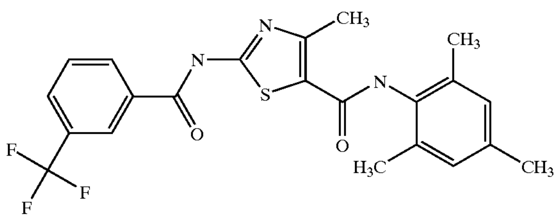 | 4-Methyl-2-[[3-(trifluoromethyl)benzoyl]-amino]-N-(2,4,6-trimethylphenyl)-5-thiazolecarboxamide | 4.45 |
| 61 | 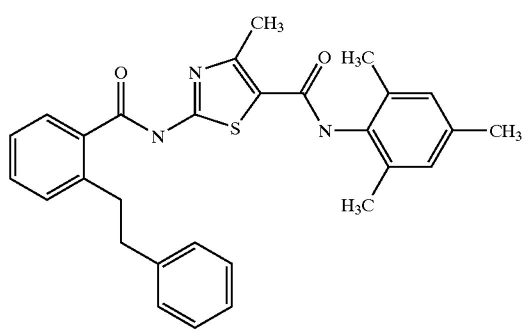 | 4-Methyl-2-[[2-(2-phenylethyl)benzoyl]-amino]-N-(2,4,6-tri-methylphenyl)-5-thiazolecarboxamide | 4.64 |
| 62 | 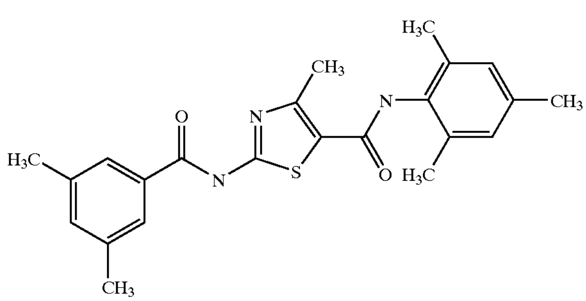 | 2-[(3,5-Dimethylbenzoyl)-amino]-4-methyl-N-(2,4,6-trimethylphenyl)-5-thiazolecarboxamide | 4.49 |
| 63 | 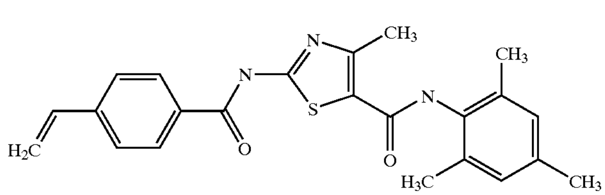 | 2-[(4-Ethenylbenzoyl)-amino]-4-methyl-N-(2,4,6-trimethylphenyl)-5-thiazolecarboxamide | |

-continued
| EX. NO. | Compound Structure | Compound Name | HPLC Ret Time (min) |
|---|---|---|---|
| 64 | 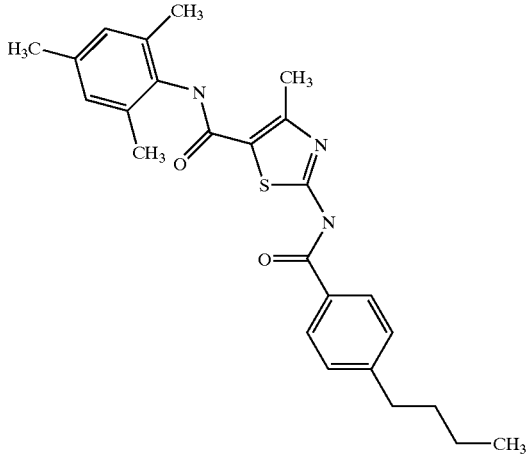 | 2-[(4-Butylbenzoyl)-amino]-4-methyl-N-(2,4,6-trimethylphenyl)-5-thiazolecarboxamide | 4.58 |
| 65 | 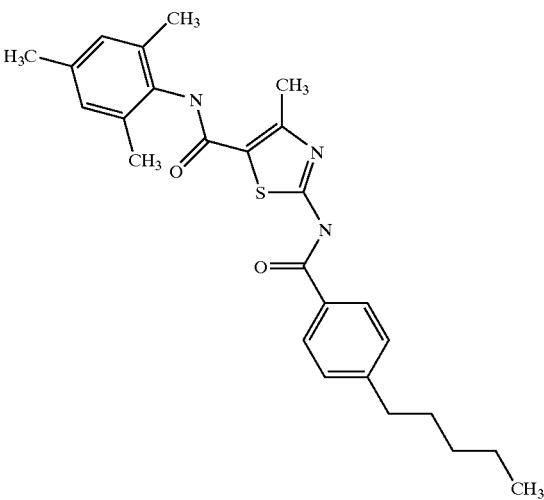 | 4-Methyl-2-[(4-pentyl-benzoyl)amino]-N-(2,4,6-trimethylphenyl)-5-thiazolecarboxamide | 4.76 |
| 66 | 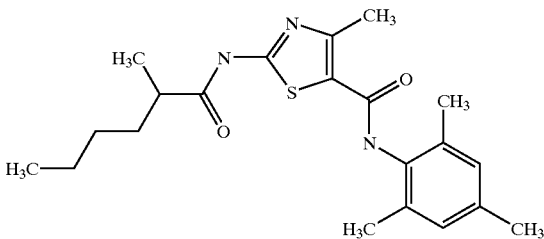 | 4-Methyl-2-[(2-methyl-1-oxohexyl)amino]-N-(2,4,6-trimethylphenyl)-5-thiazolecarboxamide | 4.41 |
| 67 | 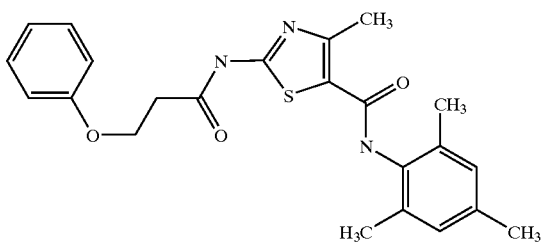 | 4-Methyl-2-[(1-oxo-3-phenoxypropyl)amino]-N-(2,4,6-trimethylphenyl)-5-thiazolecarboxamide | 4.21 |

-continued

| EX. NO. | Compound Structure | Compound Name | HPLC Ret Time (min) |
|---|---|---|---|
| 68 | 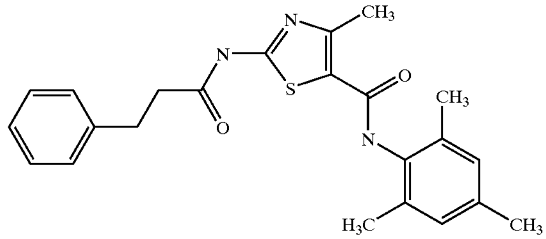 | 4-Methyl-2-[(1-oxo-3-phenylpropyl)amino]-N-(2,4,6-trimethylphenyl)-5-thiazolecarboxamide | 4.26 |
| 69 | 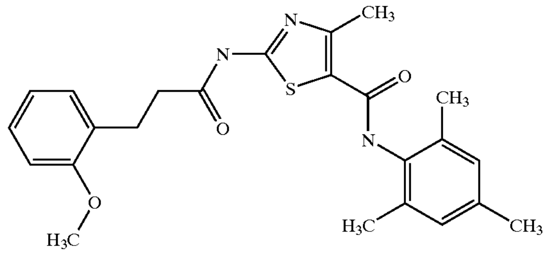 | 2-[[3-(2-Methoxyphenyl)-1-oxopropyl]-amino]-4-methyl-N-(2,4,6-trimethylphenyl)-5-thiazolecarboxamide | 4.31 |
| 70 | 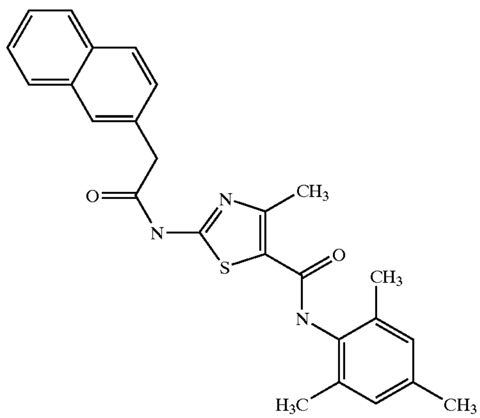 | 4-Methyl-2-[(2-naphthalenylacetyl)-amino]-N-(2,4,6-trimethylphenyl)-5-thiazolecarboxamide | 4.43 |
| 71 | 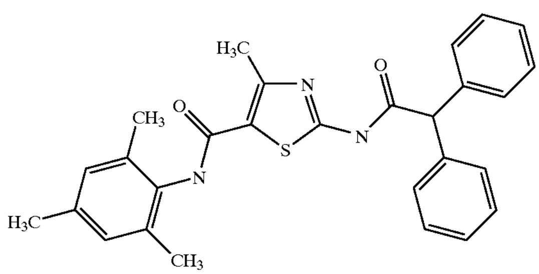 | 2-[(Diphenylacetyl)-amino]-4-methyl-N-(2,4,6-trimethylphenyl)-5-thiazolecarboxamide | 4.13 |
| 72 | 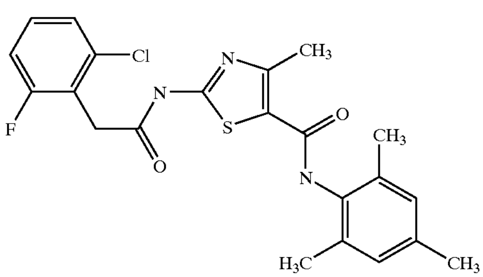 | 2-[[(2-Chloro-6-fluorophenyl)acetyl]-amino]-4-methyl-N-(2,4,6-trimethylphenyl)-5-thiazolecarboxamide | 4.17 |

-continued

| EX. NO. | Compound Structure | Compound Name | HPLC Ret Time (min) |
|---|---|---|---|
| 73 | 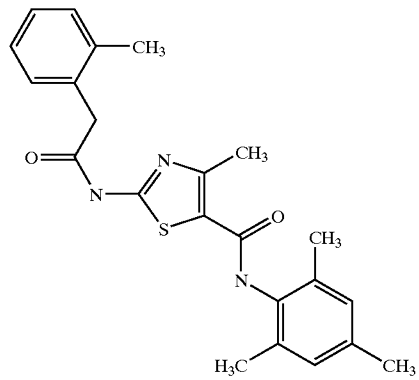 | 4-Methyl-2-[[(2-methyl-phenyl)acetyl]amino]-N-(2,4,6-trimethylphenyl)-5-thiazolecarboxamide | 3.95 |
| 74 | 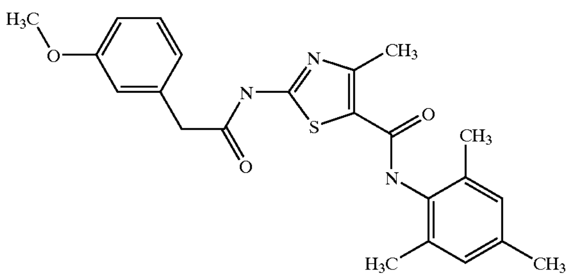 | 2-[[(3-Methoxyphenyl)-acetyl]amino]-4-methyl-N-(2,4,6-trimethylphenyl)-5-thiazolecarboxamide | 4.11 |
| 75 | 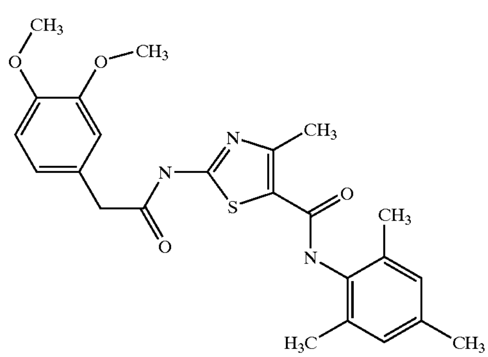 | 2-[[(3,4-Dimethoxy-phenyl)acetyl]amino]-4-methyl-N-(2,4,6-trimethylphenyl)-5-thiazolecarboxamide | 3.90 |
| 76 | 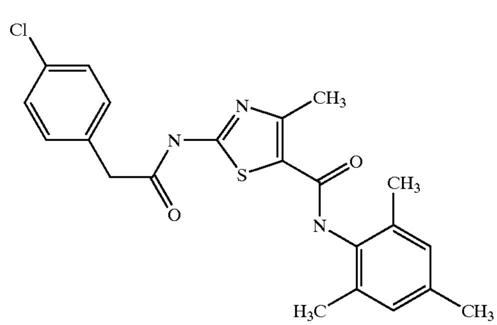 | 2-[[(4-Chlorophenyl)-acetyl]amino]-4-methyl-N-(2,4,6-tri-methylphenyl)-5-thiazolecarboxamide | 4.34 |

-continued

| EX. NO. | Compound Structure | Compound Name | HPLC Ret Time (min) |
|---|---|---|---|
| 77 | 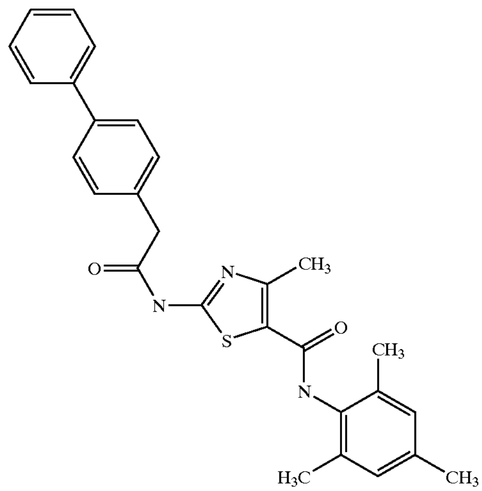 | 2-[([1,1'-Biphenyl]-4-ylacetyl)amino]-4-methyl-N-(2,4,6-trimethylphenyl)-5-thiazolecarboxamide | 4.60 |
| 78 | 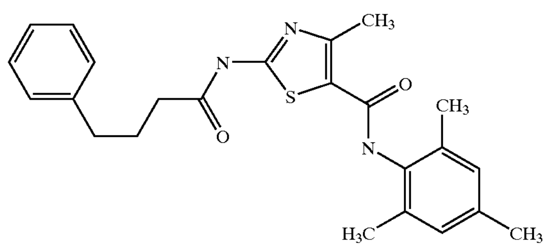 | 4-Methyl-2-[(1-oxo-4-phenylbutyl)amino]-N-(2,4,6-trimethylphenyl)-5-thiazolecarboxamide | 4.40 |
| 79 | 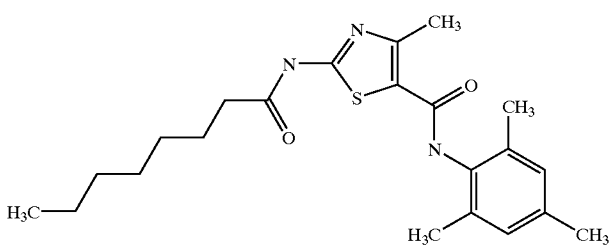 | 4-Methyl-2-[(1-oxooctyl)amino]-N-(2,4,6-trimethylphenyl)-5-thiazolecarboxamide | 4.65 |
| 80 | 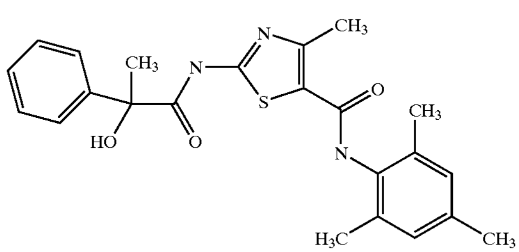 | 2-[(2-Hydroxy-2-phenyl-1-oxopropyl)amino]-4-methyl-N-(2,4,6-trimethylphenyl)-5-thiazolecarboxamide | 4.13 |
| 81 | 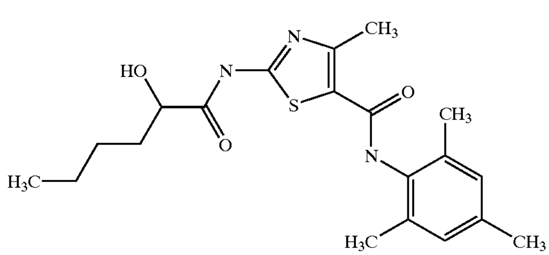 | 2-[(2-Hydroxy-1-oxohexyl)amino]-4-methyl-N-(2,4,6-trimethylphenyl)-5-thiazolecarboxamide | 4.14 |

-continued

| EX. NO. | Compound Structure | Compound Name | HPLC Ret Time (min) |
|---|---|---|---|
| 82 | 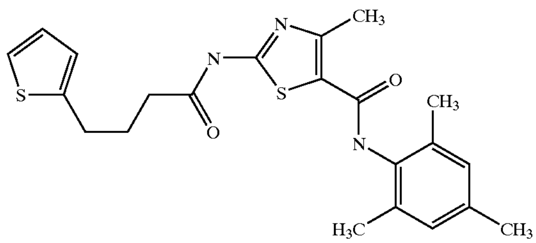 | 4-Methyl-2-[[1-oxo-4-(2-thienyl)butyl]amino]-N-(2,4,6-trimethylphenyl)-5-thiazolecarboxamide | 4.32 |
| 83 | 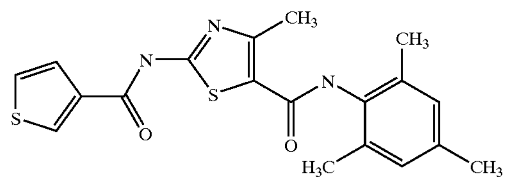 | 4-Methyl-2-[(3-thienyl-carbonyl)amino]-N-(2,4,6-trimethylphenyl)-5-thiazolecarboxamide | 4.04 |
| 84 | 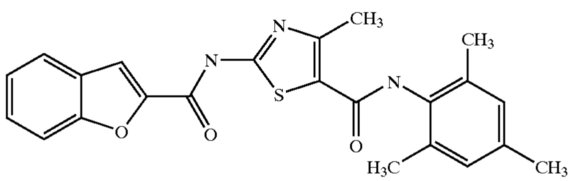 | 2-[(2-Benzofuranyl-carbonyl)amino]-4-methyl-N-(2,4,6-trimethylphenyl)-5-thiazolecarboxamide | 4.37 |
| 85 | 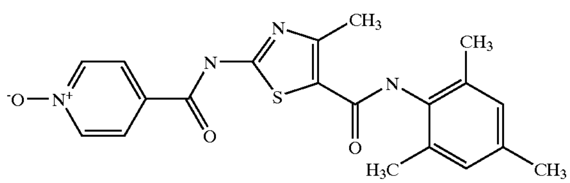 | N-[4-Methyl-5-[[(2,4,6-trimethylphenyl)amino]carbonyl]-2-thiazolyl]-4-pyridinecarboxamide, N-oxide | 3.50 |
| 86 | 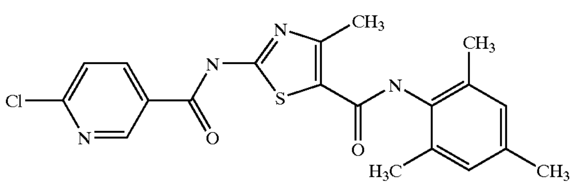 | 6-Chloro-N-[4-methyl-5-[[(2,4,6-trimethyl-phenyl)amino]carbonyl]-2-thiazolyl]-3-pyridinecarboxamide | 4.08 |
| 87 | 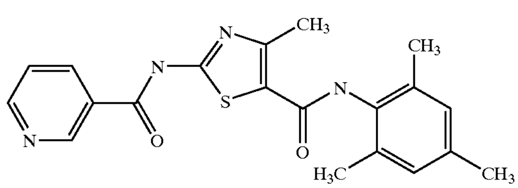 | N-[4-Methyl-5-[[(2,4,6-trimethyl-phenyl)amino]carbonyl]-2-thiazolyl]-3-pyridinecarboxamide | 3.56 |
| 88 | 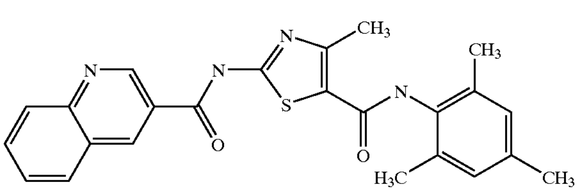 | N-[4-Methyl-5-[[(2,4,6-trimethyl-phenyl)amino]carbonyl]-2-thiazolyl]-3-quinolinecarboxamide | 4.11 |

-continued

| EX. NO. | Compound Structure | Compound Name | HPLC Ret Time (min) |
|---|---|---|---|
| 89 | 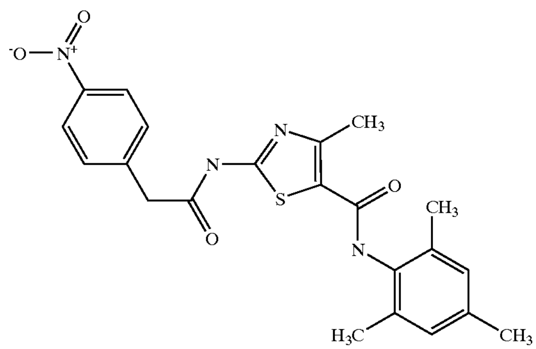 | 4-Methyl-2-[[(4-nitrophenyl)acetyl]-amino]-N-(2,4,6-trimethylphenyl)-5-thiazolecarboxamide | 4.08 |
| 90 | 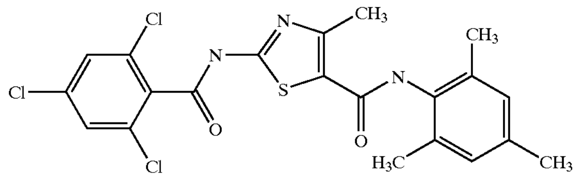 | 4-Methyl-2-[(2,4,6-trichlorobenzoyl)amino]-N-(2,4,6-trimethylphenyl)-5-thiazolecarboxamide | 4.45 |
| 91 | 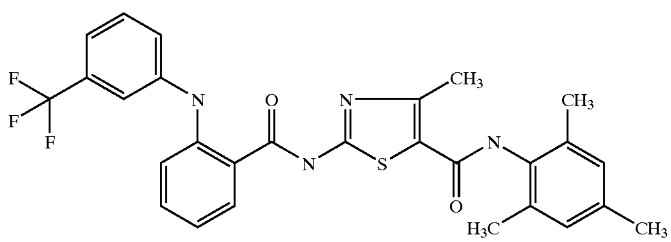 | 4-Methyl-2-[[2-[[3-(trifluoromethyl)-phenyl]amino]benzoyl]-amino]-N-(2,4,6-tri-methylphenyl)-5-thiazolecarboxamide | 4.86 |
| 92 | 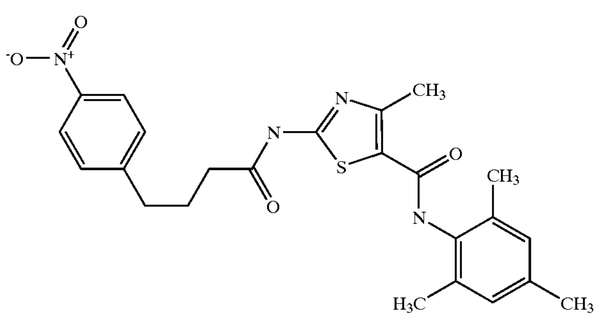 | 4-Methyl-2-[[4-(4-nitrophenyl)-1-oxobutyl]-amino]-N-(2,4,6-trimethyl-phenyl)-5-thiazolecarboxamide | 4.28 |
| 93 | 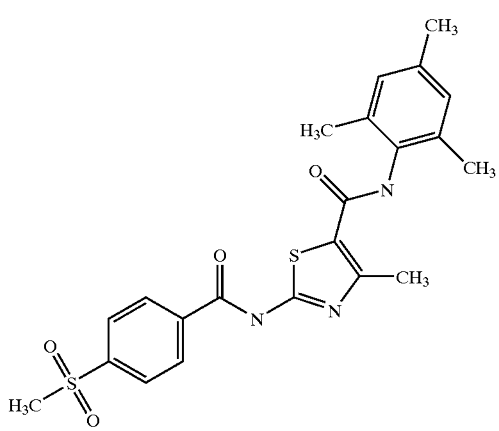 | 4-Methyl-2-[[4-(methyl-sulfonyl)benzoyl]-amino]-N-(2,4,6-trimethylphenyl)-5-thiazolecarboxamide | 3.79 |

| EX. NO. | Compound Structure | Compound Name | HPLC Ret Time (min) |
|---|---|---|---|
| 94 | 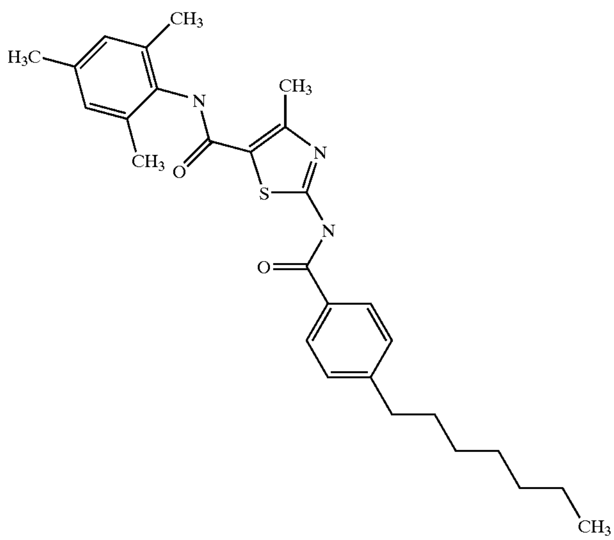 | 2-[(4-Heptylbenzoyl)amino]-4-methyl-N-(2,4,6-trimethylphenyl)-5-thiazolecarboxamide | |
| 95 | 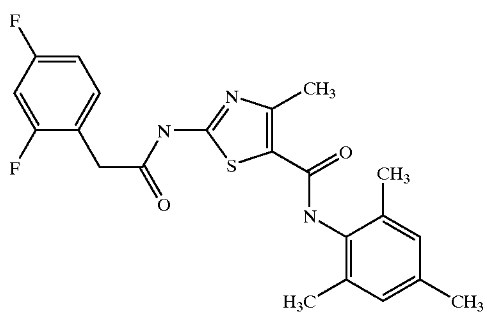 | 2-[[(2,4-Difluorophenyl)acetyl]amino]-4-methyl-N-(2,4,6-trimethylphenyl)-5-thiazolecarboxamide | 4.15 |
| 96 | 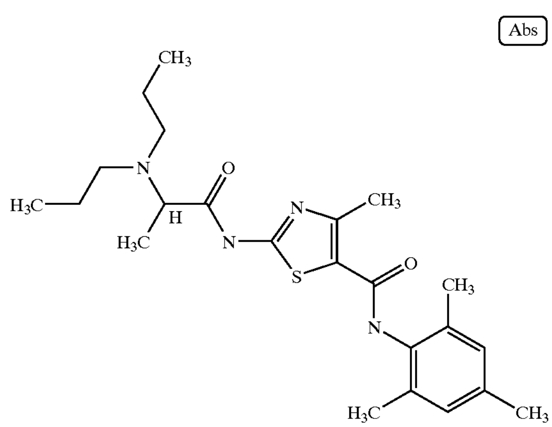 | (S)-2-[[2-(Dipropylamino)-1-oxopropyl]amino]-4-methyl-N-(2,4,6-trimethylphenyl)-5-thiazolecarboxamide | 3.20 |

-continued

| EX. NO. | Compound Structure | Compound Name | HPLC Ret Time (min) |
|---|---|---|---|
| 97 | 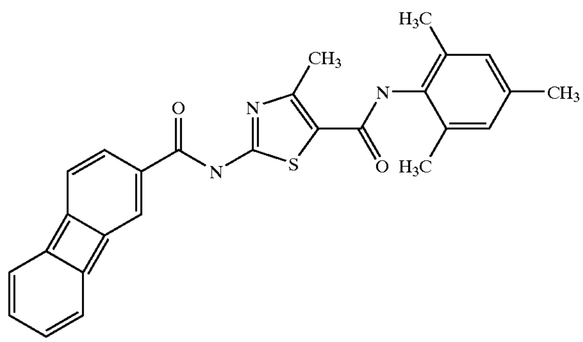 | 2-[(2-Biphenyl-enecarbonyl)amino]-4-methyl-N-(2,4,6-trimethylphenyl)-5-thiazolecarboxamide | 4.64 |
| 98 | 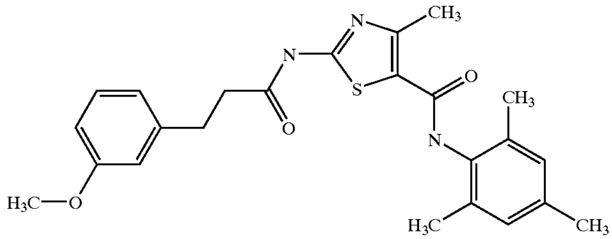 | 2-[[3-(3-Methoxyphenyl)-1-oxopropyl]amino]-4-methyl-N-(2,4,6-trimethylphenyl)-5-thiazolecarboxamide | 4.26 |
| 99 | 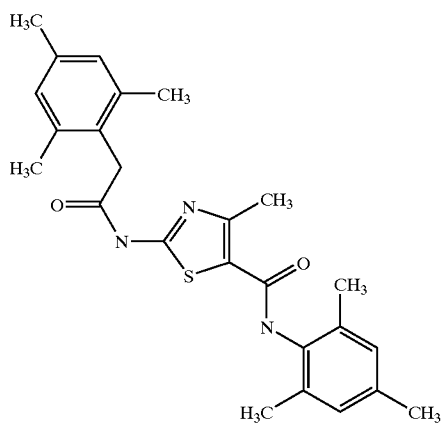 | 4-Methyl-N-(2,4,6-trimethylphenyl)-2-[[(2,4,6-trimethyl-phenyl)acetyl]amino]-5-thiazolecarboxamide | 4.52 |
| 100 | 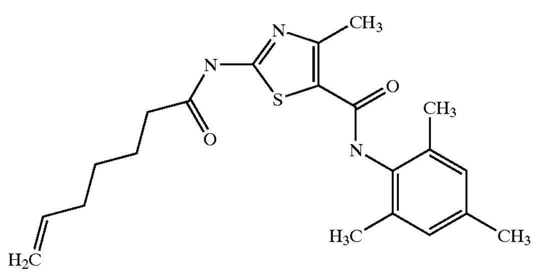 | 4-Methyl-2-[(1-oxo-6-heptenyl)amino]-N-(2,4,6-trimethylphenyl)-5-thiazolecarboxamide | 4.47 |

-continued

| EX. NO. | Compound Structure | Compound Name | HPLC Ret Time (min) |
|---|---|---|---|
| 101 | 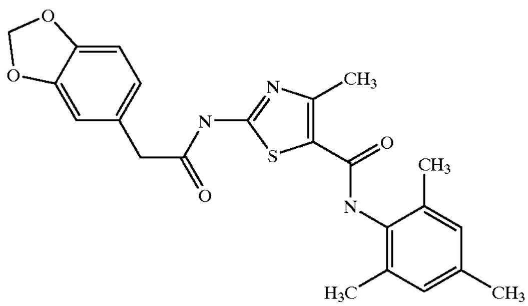 | 2-[[(1,3-Benzodioxol-5-yl)acetyl]amino]-4-methyl-N-(2,4,6-trimethylphenyl)-5-thiazolecarboxamide | 4.07 |
| 102 | 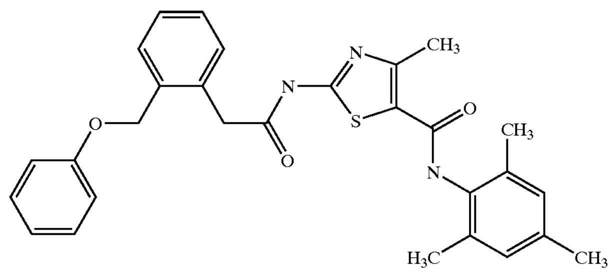 | 4-Methyl-2-[[[2-(phenylmethoxy)phenyl]acetyl]amino]-N-(2,4,6-trimethylphenyl)-5-thiazolecarboxamide | 4.46 |
| 103 | 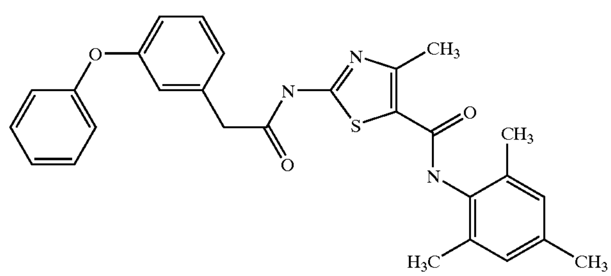 | 4-Methyl-2-[[(3-phenoxyphenyl)acetyl]amino]-N-(2,4,6-trimethylphenyl)-5-thiazolecarboxamide | 4.56 |
| 104 | 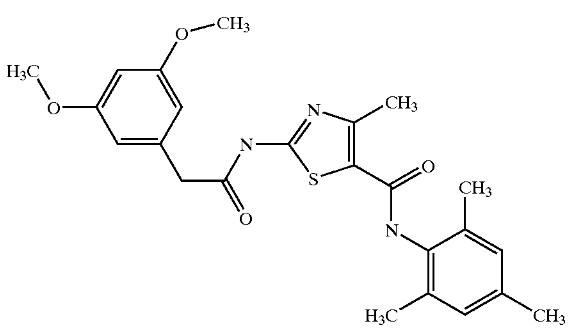 | 2-[(3,5-Dimethoxyphenyl)acetyl]amino]-4-methyl-N-(2,4,6-trimethylphenyl)-5-thiazolecarboxamide | 4.13 |
| 105 | 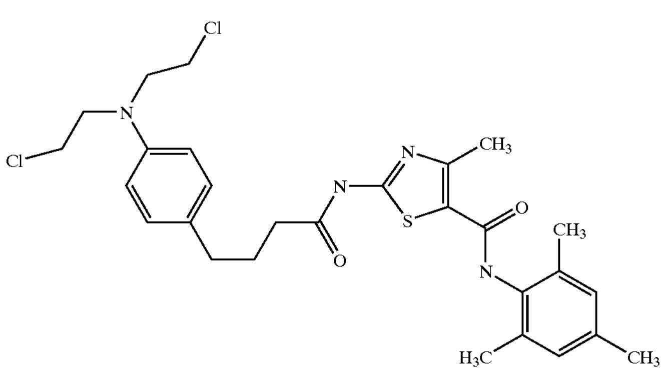 | 2-[[4-[4-[Bis(2-chloroethyl)amino]phenyl]-1-oxobutyl]amino]-4-methyl-N-(2,4,6-trimethylphenyl)-5-thiazolecarboxamide | 4.75 |

-continued
| EX. NO. | Compound Structure | Compound Name | HPLC Ret Time (min) |
|---|---|---|---|
| 106 | 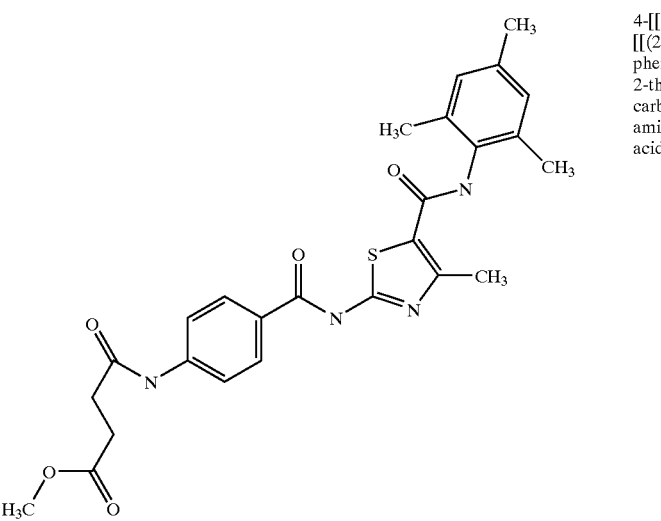 | 4-[[4-[[[4-methyl-5-[[(2,4,6-trimethyl-phenyl)amino]carbonyl]-2-thiazolyl]-amino]-carbonyl]phenyl]-amino]-4-oxobutanoic acid methyl ester | 4.03 |
| 107 | 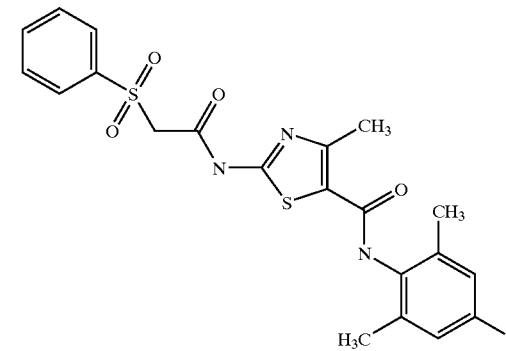 | 4-Methyl-2-[[(phenyl-sulfonyl)acetyl]amino]-N-(2,4,6-trimethylphenyl)-5-thiazolecarboxamide | 3.77 |
| 108 | 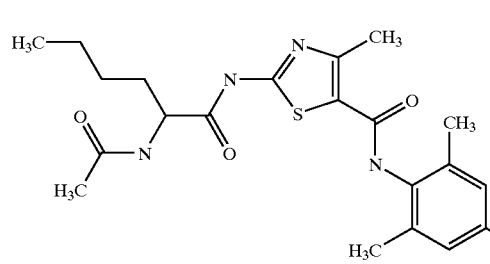 | 2-[[2-(Acetylamino)-1-oxohexyl]amino]-4-methyl-N-(2,4,6-trimethyl-phenyl)-5-thiazolecarboxamide | 3.99 |

-continued

| EX. NO. | Compound Structure | Compound Name | HPLC Ret Time (min) |
|---|---|---|---|
| 109 | 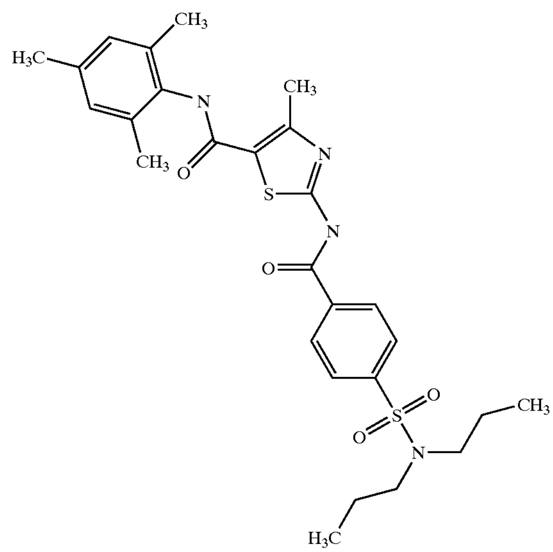 | 2-[[4-[(Dipropyl-amino)sulfonyl]benzoyl]-amino]-4-methyl-N-(2,4,6-trimethylphenyl)-5-thiazolecarboxamide | 4.51 |
| 110 | 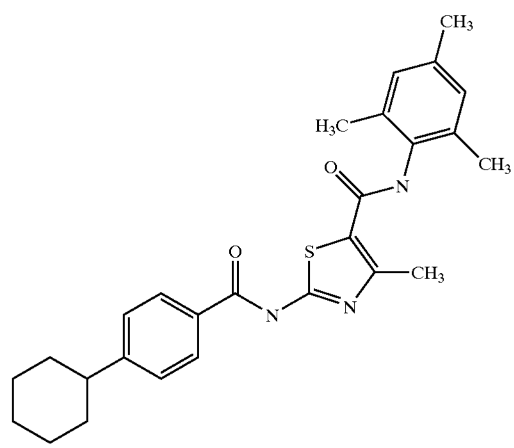 | 2-[(4-Cyclohexylbenzoyl)-amino]-4-methyl-N-(2,4,6-trimethylphenyl)-5-thiazolecarboxamide | 4.94 |
| 111 | 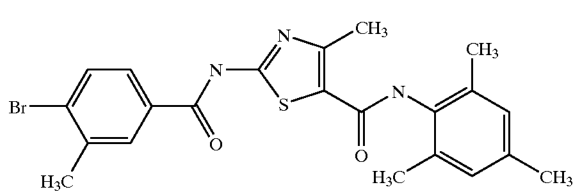 | 2-[(4-Bromo-3-methyl-benzoyl)amino]-4-methyl-N-(2,4,6-trimethylphenyl)-5-thiazolecarboxamide | 4.80 |
| 112 | 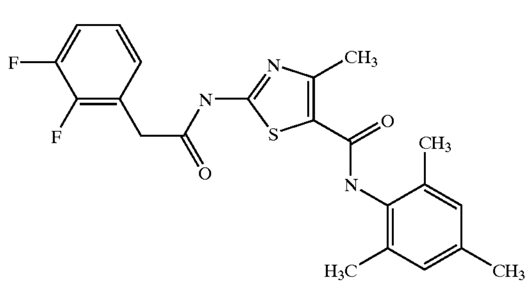 | 2-[[(2,3-Difluorophenyl)-acetyl]amino]-4-methyl-N-(2,4,6-trimethylphenyl)-5-thiazolecarboxamide | 4.14 |

-continued

| EX. NO. | Compound Structure | Compound Name | HPLC Ret Time (min) |
|---|---|---|---|
| 113 | 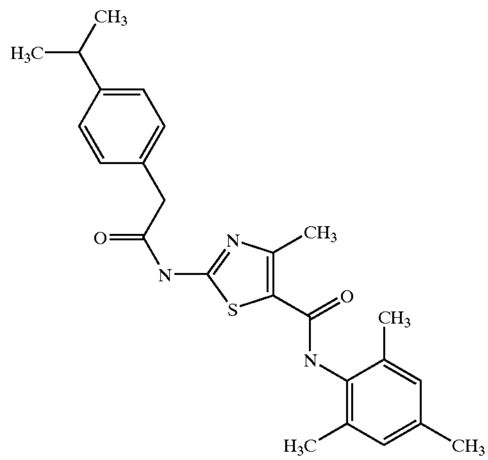 | 4-Methyl-2-[[[4-(1-methyl-ethyl)phenyl]acetyl]-amino]-N-(2,4,6-trimethylphenyl)-5-thiazolecarboxamide | 4.56 |
| 114 | 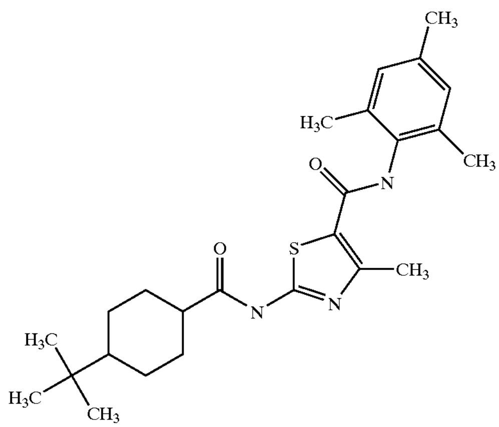 | 2-[[[4-(1,1-Dimethyl-ethyl)cyclohexyl]carbonyl]-amino]-4-methyl-N-(2,4,6-trimethylphenyl)-5-thiazolecarboxamide | 4.85 |
| 115 | 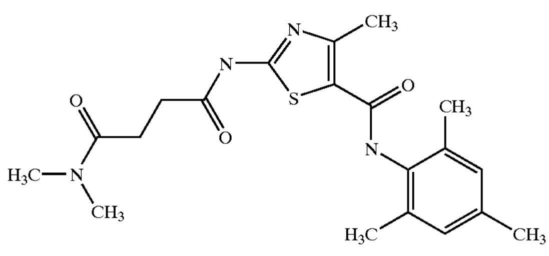 | N,N-Dimethyl-N'-[4-methyl-5-[[(2,4,6-trimethylphenyl)-amino]carbonyl]-2-thiazolyl]butanediamide | 3.50 |
| 116 | 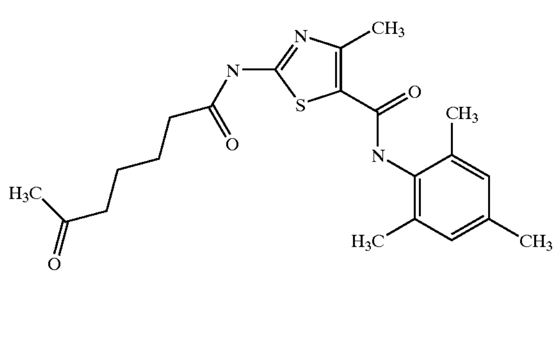 | 2-[(1,6-Dioxohexyl)amino]-4-methyl-N-(2,4,6-trimethylphenyl)-5-thiazolecarboxamide | 4.40 |

-continued

| EX. NO. | Compound Structure | Compound Name | HPLC Ret Time (min) |
|---|---|---|---|
| 117 | 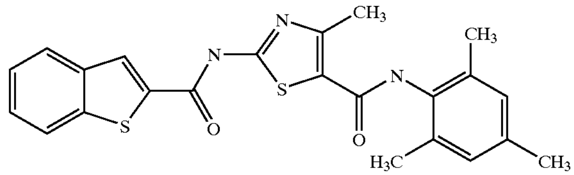 | 2-[(Benzo[b]thiophen-2-ylcarbonyl)amino]-4-methyl-N-(2,4,6-trimethylphenyl)-5-thiazolecarboxamide | 4.53 |
| 118 | 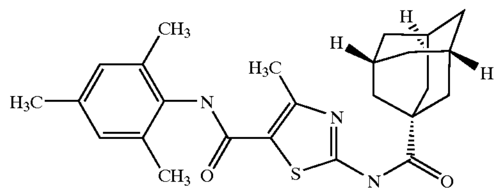 | 2-[(1-Adamantylcarbonyl)amino]-4-methyl-N-(2,4,6-trimethylphenyl)-5-thiazolecarboxamide | 4.66 |
| 119 | 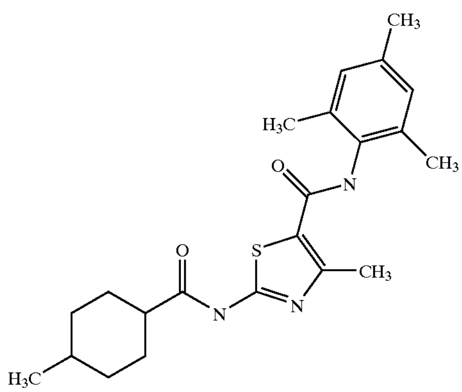 | 4-Methyl-2-[[(4-methylcyclohexyl)carbonyl]amino]-N-(2,4,6-trimethylphenyl-5-thiazolecarboxamide | 4.48 |
| 120 | 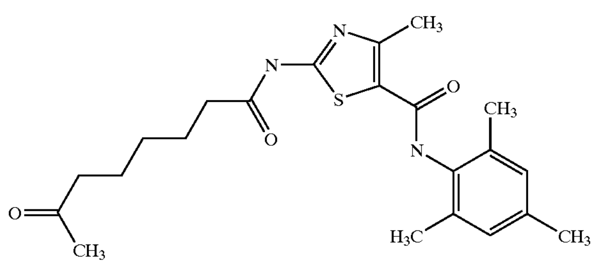 | 2-[(1,7-Dioxooctyl)amino]-4-methyl-N-(2,4,6-trimethylphenyl)-5-thiazolecarboxamide | 3.88 |
| 121 | 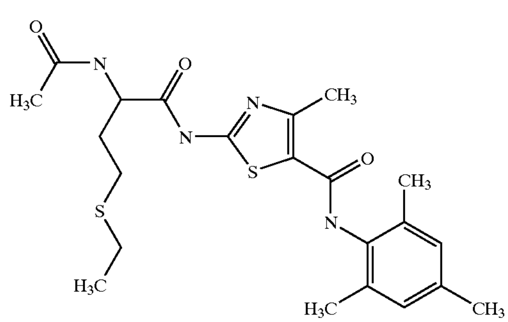 | 2-[[2-(Acetylamino)-4-(ethylthio)-1-oxobutyl]amino]-4-methyl-N-(2,4,6-trimethylphenyl)-5-thiazolecarboxamide | 3.93 |
| 122 | 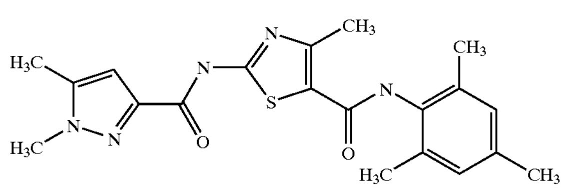 | 1,5-Dimethyl-N-[4-methyl-5-[[(2,4,6-trimethylphenyl)amino]carbonyl]-2-thiazolyl]-1H-pyrazole-3-carboxamide | 3.91 |

-continued

| EX. NO. | Compound Structure | Compound Name | HPLC Ret Time (min) |
|---|---|---|---|
| 123 | 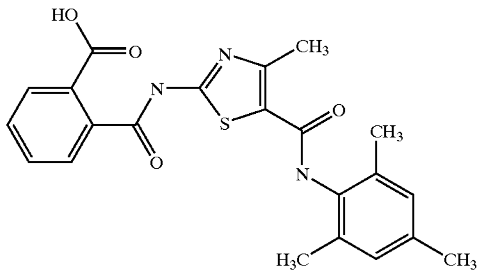 | 2-[[[4-methyl-5-[[(2,4,6-trimethylphenyl)-amino]carbonyl]-2-thiazolyl]amino]-carbonyl]benzoic acid | 3.70 |
| 124 | 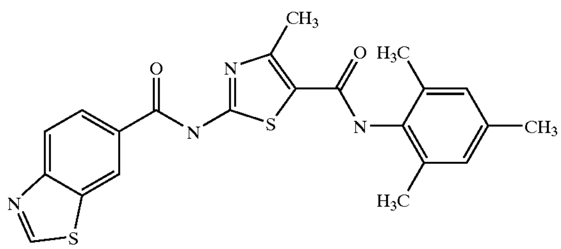 | N-[4-Methyl-5-[[(2,4,6-trimethylphenyl)amino]-carbonyl]-2-thiazolyl]-6-benzothiazolecarboxamide | 4.18 |
| 125 | 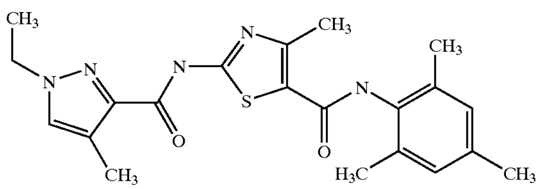 | 1-Ethyl-4-methyl-N-[4-methyl-5-[[(2,4,6-tri-methylphenyl)amino]-carbonyl]-2-thiazolyl]-1H-pyrazole-3-carboxamide | 4.09 |
| 126 | 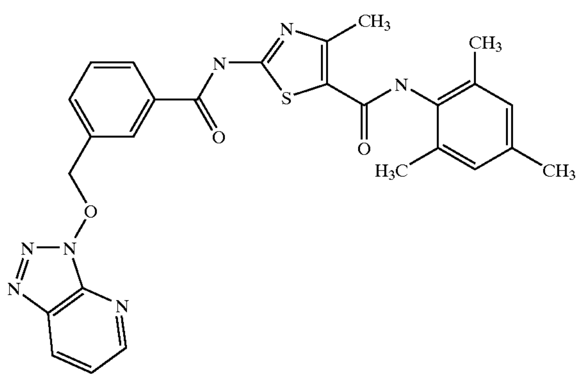 | 4-Methyl-2-[[3-[(3H-1,2,3-triazolo[4,5-b]-pyridin-3-yloxy)methyl]-benzoyl]amino]-N-(2,4,6-trimethylphenyl)-5-thiazolecarboxamide | 4.15 |
| 127 | 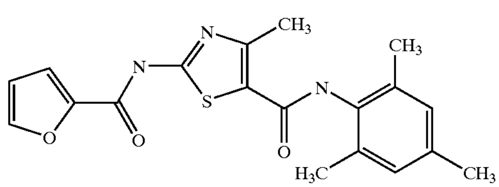 | 2-[(2-Furanylcarbonyl)-amino]-4-methyl-N-(2,4,6-trimethylphenyl)-5-thiazolecarboxamide | 4.45 |
| 128 | 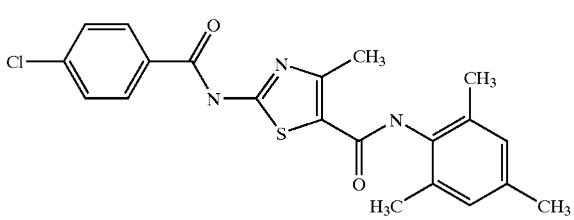 | 2-[(4-Chlorobenzoyl)-amino]-4-methyl-N-(2,4,6-trimethylphenyl)-5-thiazolecarboxamide | 8.85 |

-continued

| EX. NO. | Compound Structure | Compound Name | HPLC Ret Time (min) |
|---|---|---|---|
| 129 | 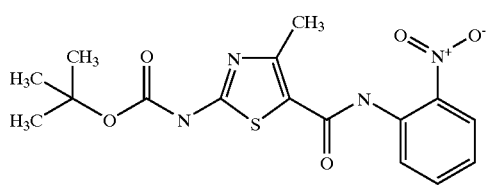 | 2-[(2,2-Dimethyl-1-oxopropyl)amino]-4-methyl-N-(2,4,6-trimethyl-phenyl)-5-thiazolecarboxamide | 8.30 |

EXAMPLE 130

Preparation of [4-Methyl-5 [[(2-nitrophenyl)amino]carbonyl]-2-thiazolyl]carbamic acid, 1,1-dimethylethyl ester 2-Nitroaniline (55 mg, 0.4 mmol) and diisopropylethylamine (70 μL, 0.4 mmol) were added dropwise to a a stirred solution of 2-tert-butoxycarbonyloxyamino-4-methyl-thiazole-5-carboxylic acid chloride 1C (100 mg, 0.36 mmol) in dichloromethane (3 mL). After 16 h at rt, 4-N,N-dimethylaminopyridine (22 mg, 0.18 mmol) was added and the mixture was stirred for additional 3.5 h. The solvent was evaporated in vacuo. The residue was chromatographed on a silica gel column. Elution with 5% EtOAc in hexanes followed by 20% EtOAc in hexanes afforded the title compound (15 mg, 11%) as a yellow solid.

EXAMPLE 131

Preparation of [4-Methyl-5[[(2,4,6-trimethylphenyl)amino]carbonyl]-2-thiazolyl]carbamic acid phenylmethyl ester

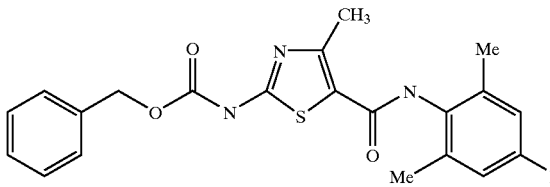

A. Ethyl-2-benzyloxycarbonyloxyamino-4-methyl-thiazole-5-carboxulate

A 3 M aq. NaHCO₃ solution (10 mL, 30 mmol) was added to a stirred solution of ethyl-2-amino-4-methyl-thiazole-5-carboxylate (372 mg, 2 mmol) in THF (20 mL) at 0–5° C. Benzyl chloroformate (500 μL) was added. After 2 h, additional benzyl chloroformate (500 μL) and the biphasic solution was stirred for an additional 2 h at 0–5° C. The mixture was diluted with dichloromethane (50 mL) and water (30 mL). The organic layer was separated, dried (MgSO₄), filtered and concentrated. The residue was chromatographed on a silica gel column. Elution with 10% EtOAc in hexanes followed by 20% and 30% EtOAc in hexanes afforded the title compound (310 mg, 48%) as a white solid.

B. 2-Benzyloxycarbonyloxyamino-4-methyl-thiazole-5-carboxylic acid

Compound 131B was prepared by an analogous method as that of 3B, except using 131A to give the title compound 131B as a white powder (77%).

C. [4-Methyl-5-[[(2,4,6-Trimethylphenyl)amino]carbonyl]-2-thiazolyl]carbamic acid, phenylmethyl ester Diisopropylethylamine (70 μL, 0.41 mmol) was added to a solution of 131B (100 mg, 0.34 mmol), 2,4,6-trimethylaniline (60 μL, 0.41 mmol), and [O-(7-azabenzotriazol-1-yl)-1,1,3,3-tetramethyluronium] hexafluorophosphate (HATU, 160 mg, 0.41 mmol). The mixture was stirred at rt for 24 h, diluted with EtOAc (20 mL) and washed with 2 N Aq. HCl solution (3×), brine, dried (Na₂SO₄), filtered and concentrated. The residue was triturated with ether (40 mL) to obtain the title compound (100 mg, 77%) as an off-white solid.

EXAMPLE 132

Preparation of Methyl[4-methyl-5-[[(2,4,6-trimethylphenyl)amino]carbonyl]-2-thiazolyl]carbamic acid, 1,1-dimethylethyl ester

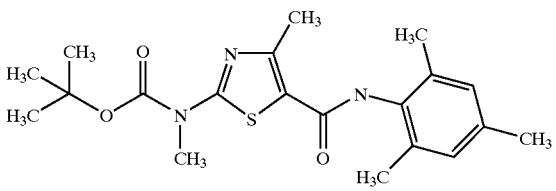

Compound 132 was prepared by an analogous method as that of 1, except using ethyl-2-tert-butoxycarbonyloxyaminomethyl-4-methyl-thiazole-5-carboxylate to give the title compound 132 as a tan solid.

EXAMPLE 133

Preparation of 4-Methyl-2-(methylamino)-N-(2,4,6-trimethylphenyl)-5-thiazolecarboxamide, trifluoroacetate (1:1)

Compound 133 was prepared by an analogous method as that of 4, except using 132 to give the title compound 133 as a white solid (91%).

EXAMPLE 134

Preparation of [4-Methyl-5-[[methyl(2,4,6-trimethylphenyl)amino]carbonyl]-2-thiazolyl] carbamic acid, 1,1-dimethylethyl ester

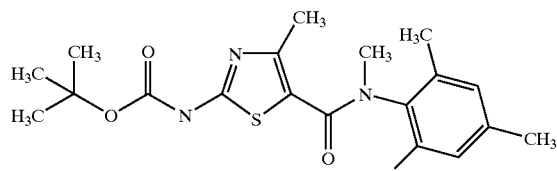

Compound 134 was prepared by an analogous method as that of 1, except using N-methyl-2,4,6-trimethylaniline to give the title compound 134 as a white solid (60%).

EXAMPLE 135

Preparation of 2-Amino-N,4-dimethyl-N-(2,4,6-trimethylphenyl)-5-thiazolecarboxamide Trifluoroacetate (1:1)

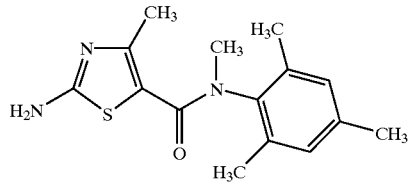

Compound 135 was prepared by an analogous method as that of 4, except using 134 to give the title compound 135 as a white solid (97%).

EXAMPLE 136

Preparation of [4-Methyl-5 [[(2,4,6-trimethylphenyl)amino]carbonyl]-2-thiazolyl] carbamic acid, methyl ester

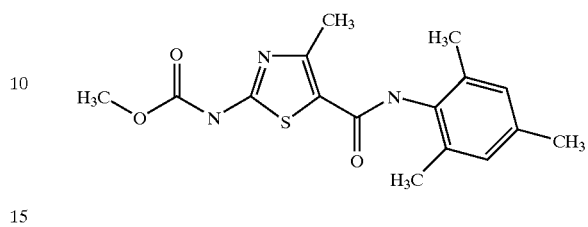

A mixture of 2 (100 mg, 0.36 mmol), pyridine (87 µL, 1.08 mmol), methyl chloroformate (111 µL, 1.44 mmol) in dichloromethane (3 mL) was stirred at rt for 1.5 h. The solution was diluted with dichloromethane and washed with aq. $NaHCO_3$ solution (20 mL, 2×), brine; dried ($MgSO_4$), filtered and concentrated. The residue was triturated with ether to obtain the title compound (88 mg, 82%) as a white solid.

EXAMPLE 137

Preparation of [4-Ethyl-5[[(2,4,6-trimethylohenyl)amino]carbonyl]-2-thiazolyl]carbamic acid, 1,1-dimethylethyl ester

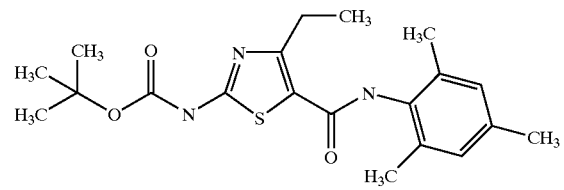

Compound 137 was prepared by an analogous method as that of 1, except using methyl-2-amino-4-ethyl-thiazole-5-carboxylate to give the title compound 137 as a white solid (70%).

EXAMPLE 138

Preparation of 2-Amino-4-ethyl-N-(2,4,6-trimethylphenyl)-5-thiazolecarboxamide, trifluoroacetate

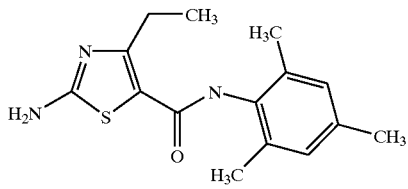

Compound 138 was prepared by an analogous method as that of 4, except using 137 to give the title compound 138 as a white solid (89%).

EXAMPLE 139

Preparation of [5-[[(2,6-Dichlorophenyl)amino]carbonyl]-4-methyl-2-thiazolyl]carbamic acid, 1,1-dimethylethyl ester

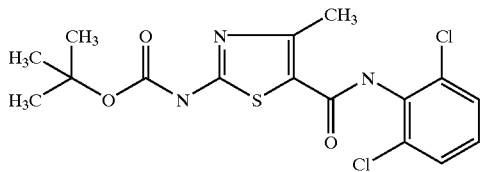

A 1 M solution of sodium bis-trimethylsilyl amide (290 µL, 0.29 mmol) was added to a stirred solution of 2,6-dichloroaniline (13.4 mg, 0.08 mmol) in THF (1 mL). After 30 min, the mixture was cooled to 0° C. and 1C (30 mg, 0.11 mmol) was added in one portion. The mixture was allowed to warm to rt and stirred for 16 h. The solution was diluted with dichloromethane and washed with 2 N aq. HCl solution (2 mL, 3×), dried (MgSO$_4$), filtered and concentrated. The residue was chromatographed on a silica gel column and eluted with 30% EtOAc in hexanes to obtain the title compound (20 mg, 45%) as a light yellow solid.

EXAMPLE 140

Preparation of 2-Amino-N-(2,6-dimethylphenyl)-4-methyl-5-thiazolecarboxamide, trifluoroacetate (1:1)

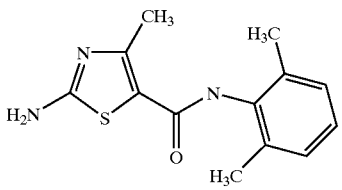

Compound 140 was prepared by an analogous method as that of 4, except using 53 to give the title compound 140 as a light tan solid (100%).

EXAMPLE 141

Preparation of 2-Amino-N-(2-methoxy-6-methylphenyl)-4-methyl-5-thiazolecarboxamide, trifluoroacetate (1:1)

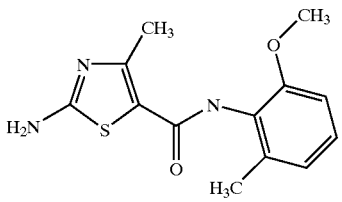

Compound 141 was prepared by an analogous method as that of 4, except using 13 to give the title compound 141 as an off-white solid (100%).

EXAMPLE 142

Preparation of 2-Amino-N-(2-methylphenyl)-4-methyl-5-thiazolecarboxamide, trifluoroacetate (1:1)

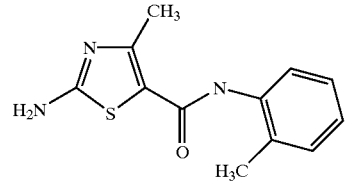

Compound 142 was prepared by an analogous method as that of 4, except using 18 to give the title compound 142 as a light tan solid (90%).

EXAMPLE 143

Preparation of 2-Amino-N-(2,6-dimethyl-4-bromophenyl)-4-methyl-5-thiazolecarboxamide, trifluoroacetate (1:1)

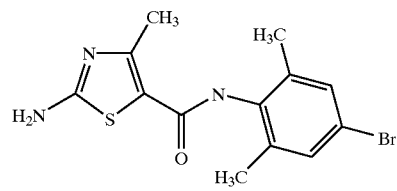

Compound 143 was prepared by an analogous method as that of 4, except using 15 to give the title compound 143 as a light tan solid (70%).

EXAMPLE 144

Preparation of 2-Amino-N-(2-chloro-6-methylphenyl)-4-methyl-5-thiazolecarboxamide, trifluoroacetate (1:1)

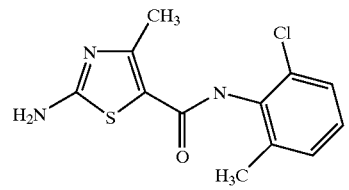

Compound 144 was prepared by an analogous method as that of 4, except using 19 to give the title compound 144 as a light tan solid (81%).

EXAMPLE 145

Preparation of 2-Amino-N-(2,4-dimethylphenyl)-4-methyl-5-thiazolecarboxamide, trifluoroacetate (1:1)

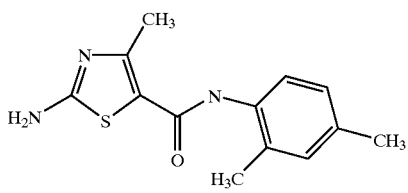

Compound 145 was prepared by an analogous method as that of 4, except using 17 to give the title compound 145 as a light tan solid (68%).

EXAMPLE 146

Preparation of 2-Amino-N-(2-methyl-6-isopropylphenyl)-4-methyl-5-thiazolecarboxamide, trifluoroacetate (1:1)

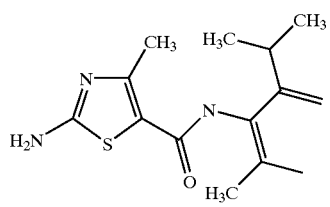

Compound 146 was prepared by an analogous method as that of 4, except using 16 to give the title compound 146 as a light tan solid (100%).

EXAMPLE 147

Preparation of 2-(Acetylamino)-4-methyl-N-(2,4,6-trimethylphenyl)-5-thiazolecarboxamide

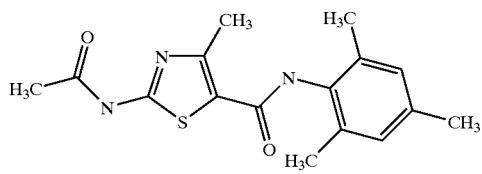

A mixture of 2 (54 mg, 0.2 mmol), acetic anhydride (22 µL, 0.23 mmol), dimethylaminopyridine (3 mg) in dichloromethane (4.5 mL) was stirred at rt for 4.5 h. The mixture was diluted with dichloromethane (65 mL) and washed with 1 N aq. HCl solution (20 mL), water; dried (MgSO$_4$), filtered and concentrated. The residue was chromatographed on a silica gel column and eluted with 35% EtOAc in hexanes to obtain the title compound (43 mg, 69%) as a white solid.

EXAMPLE 148

Preparation of 2-(Benzoylamino)-4-methyl-N-(2,4,6-trimethylphenyl)-5-thiazolecarboxamide

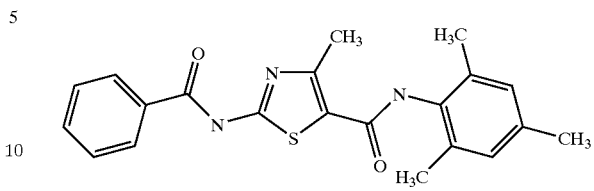

A solution of 2 (100 mg, 0.36 mmol) and benzoic anhydride (226 mg, 1 mmol) in dichloromethane (10 mL) and pyridine (2 mL) was stirred at rt overnight. The mixture was diluted with dichloromethane (50 mL) and washed with 2 N aq. HCl solution (15 mL, 2×), 10% aq. NaHCO$_3$ solution (20 mL, 2×); dried (MgSO$_4$), filtered and concentrated. The residue was chromatographed on a silica gel column and eluted with 30% EtOAc in hexanes followed by 50% EtOAc in hexanes to obtain the title compound contaminated with benzoic acid. The solid was dissolved in EtOAc (40 mL) and washed with satd. KHCO$_3$ solution (15 mL, 4×), dried (MgSO$_4$), filtered and concentrated to obtain the title compound (110 mg, 80%) as a white solid.

EXAMPLE 149

Preparation of 4-methyl-2-[(1-oxopropyl)amino]-N-(2,4,6-trimethylphenyl)-5-thiazolecarboxamide

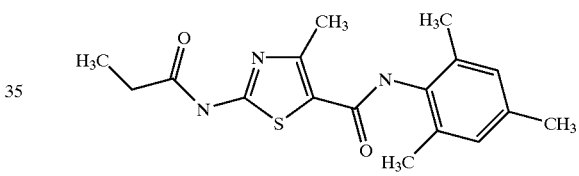

A mixture of 2 (100 mg, 0.36 mmol), propionic anhydride (332 µL, 2.58 mmol) in dichloromethane (10 mL) and pyridine (4 mL) was stirred at rt for 3 h. Dimethylaminopyridine (122 mg, 1 mmol) was added and the mixture was stirred for additional 1.5 h. The mixture was diluted with dichloromethane and washed with 1 N aq. HCl solution (25 mL, 3×), aq. NaHCO3 solution (20 mL, 2×), water(20 mL), brine; dried (MgSO$_4$), filtered and concentrated. The residue was chromatographed on a silica gel column and eluted with 20% EtOAc in hexanes to obtain the title compound (81 mg, 68%) as a white solid.

EXAMPLE 150

Preparation of 4-methyl-2-[(1-oxobutyll)amino]-N-(2,4,6-trimethylphenyl)-5-thiazolecarboxamide

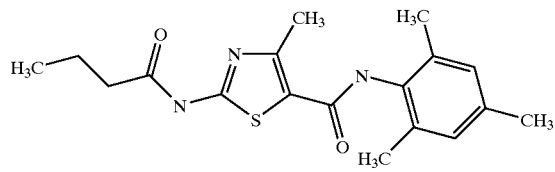

Compound 150 was prepared by an analogous method as that of 149, except using butyric anhydride to give the title compound 150 as a white solid (76%).

EXAMPLE 151

Preparation of 4-methyl-2-[(1-oxopentyl)amino]-N-(2,4,6-trimethylphenyl)-5-thiazolecarboxamide

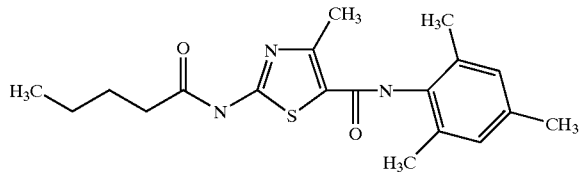

Compound 151 was prepared by an analogous method as that of 149, except using valeric anhydride to give the title compound 151 as a white solid (77%).

EXAMPLE 152

Preparation of 4-methyl-2-[(1-oxohexyl)amino]-N-(2,4,6-trimethylphenyl)-5-thiazolecarboxamide

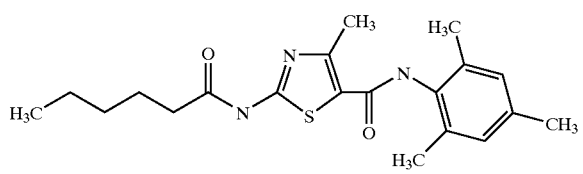

Compound 152 was prepared by an analogous method as that of 149, except using hexanoic anhydride to give the title compound 152 as a white solid (75%).

EXAMPLE 153

Preparation of 4-Methyl-2-[(phenylcetyl)amino]-N-(2,46-trimethylphenyl)-5-thiazolecarboxamide

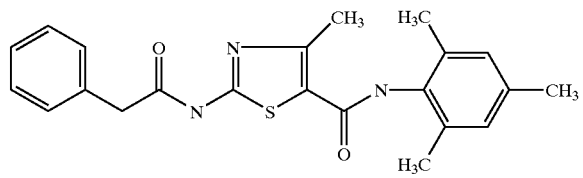

A solution of amine 2 (50 mg, 0.18 mmol), diisopropylethylamine (101 µL, 0.58 mmol), phenylacetic acid (27.2 mg, 0.20 mmol), 1-hydroxy-7-azabenzotriazole (29.4 mg, 0.22 mmol), and ethyl-3-(3-dimethylamino)-propyl carbodiimide hydrochloride (42.2 mg, 0.22 mmol) in dichloromethane (0.62 mL) was mechanically stirred in a sealed vial for 16 h. The reaction mixture was passed through a Varian SCX ion exchange column (2 g/6 cc) and eluted with acetonitrile-methanol (10 mL, 4:1) followed by 2 M methanolic ammonia solution (9 mL). Fractions containing the product were combined and then concentrated. The residue was dissolved in dichloromethane and washed with 2 N aq. HCl solution (3x), dried ($Na_2SO_4$), filtered and concentrated to obtain the title compound (39 mg, 55%) as a tan solid.

EXAMPLE 154

Preparation of 2-[[(Acetylamino)acetyl]amino]-4-methyl-N-(2,4,6-trimethylphenyl)-6-thiazolecarboxamide

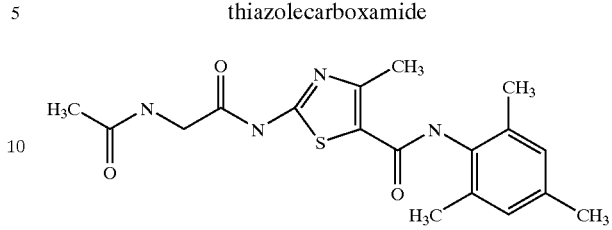

A solution of amine 2 (50 mg, 0.18 mmol), diisopropylethylamine (400 µL, 2.3 mmol), N-acetylglycine (42 mg, 0.36 mmol), 1-hydroxy-7-azabenzotriazole (49 mg, 0.36 mmol), and ethyl-3-(3-dimethylamino)-propyl carbodiimide hydrochloride (72 mg, 0.36 mmol) in THF (5 mL) was heated to 50° C. overnight. The mixture was cooled, diluted with dichloromethane (60 mL) and washed with 2 N aq. HCl solution (20 mL), satd. aq. $KHCO_3$ solution (20 mL), dried ($MgSO_4$), filtered and concentrated. The crude solid was triturated with ether (10 mL), filtered, and washed with ether (5 mL, 3x) to obtain the title compound (40 mg, 59%) as an off-white solid.

EXAMPLE 155

Preparation of 2-Amino-4-methyl-N-(2,4,6-trimethylphenyl)-5-thiazolecarbothioamide

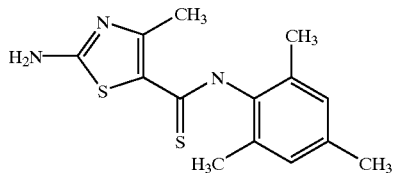

A suspension of 2 (50 mg, 0.18 mmol) and Lawesson reagent (44 mg, 0.11 mmol) in toluene (0.23 mL) was heated to 100° C. for 4 h. Additional Lawesson reagent (44 mg, 0.11 mmol) was added and the mixture was heated for additional 3.5 h. The crude mixture was chromatographed on a silica gel column and eluted with 50% EtOAc in hexanes followed by 70% EtOAc in hexanes to obtain a a yellow solid which was triturated with hexanes (6 mL) to obtain the title compound (11 mg, 21%) as a yellow solid.

EXAMPLES 156 TO 170

General Procedure

Compounds 156 to 170 were prepared following the procedure described below. Diisopropylethyl amine (60 µL, 0.34 mmol) was added to a mixture of amine 2 (30 mg, 0.11 mmol), appropriate carboxylic acid (0.13 mmol), 1-hydroxy-7-azabenzotriazole (19.5 mg, 0.14 mmol), and ethyl-3-(3-dimethylamino)-propyl carbodiumide hydrochloride (26.8 mg, 0.14 mmol) in THF (1 mL). The mixture was heated in a sealed tube under argon at 45° C. for 24 h. The reaction mixture was diluted with dichloromethane (4 mL) and washed with 2 N aq. HCl solution (2 mL, 3x), dried ($Na_2SO_4$) and concentrated using a speedvac. The crude products were either triturated with dichloromethane-ether (5 mL, 1:1) or purified by silica gel chromatography (elution solvent: 50% EtOAC in hexanes and EtOAc). "HPLC Ret Time" is the HPLC retention time under the following conditions: YMC S5 ODS 4.6×50 mm Ballastic Column, 4 min gradient starting from 100% solvent A (10% MeOH, 90% H$_2$O, 0.2% H$_3$PO$_4$) to 100% solvent B (90% MeOH, 10% H$_2$O, 0.2% H$_3$PO$_4$), flow rate 4 mL/min, λ=220 nM.

| EX. NO. | Compound Structure | Compound Name | HPLC Ret Time (min) |
|---|---|---|---|
| 156 | 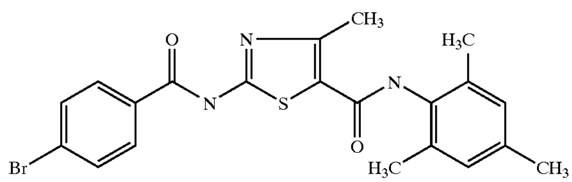 | 2-[(4-Bromobenzoyl)-amino]-4-methyl-N-(2,4,6-trimethylphenyl)-5-thiazolecarboxamide | 5.03 |
| 157 | 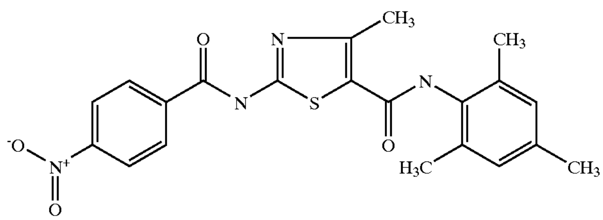 | 4-Methyl-2-[(4-nitro-benzoyl)amino]-N-(2,4,6-trimethylphenyl)-5-thiazolecarboxamide | 4.87 |
| 158 | 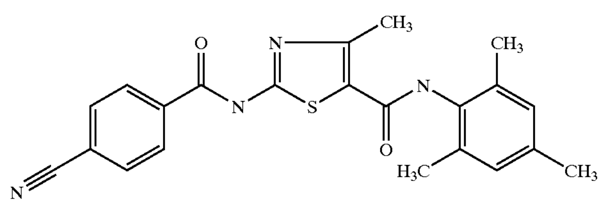 | 2-[(4-Cyanobenzoyl)-amino]-4-methyl-N-(2,4,6-trimethylphenyl)-5-thiazolecarboxamide | 4.70 |
| 159 | 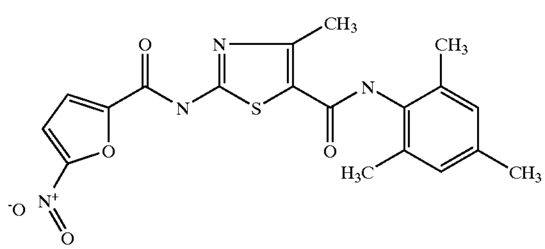 | 4-Methyl-2-[[(5-nitro-2-furanyl)carbonyl]amino]-N-(2,4,6-trimethylphenyl-5-thiazolecarboxamide | 4.63 |
| 160 | 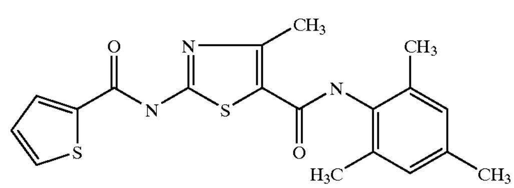 | 4-Methyl-2-[(2-thienyl-carbonyl)amino]-N-(2,4,6-trimethylphenyl)-5-thiazolecarboxamide | 4.60 |
| 161 | 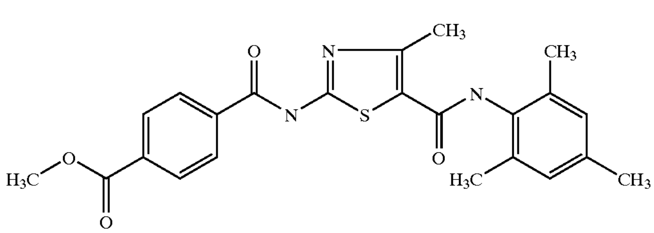 | 4-[[[4-Methyl-5-[[(2,4,6-trimethylphenyl)-amino]carbonyl]-2-thiazolyl]amino]carbonyl]benzoic acid methyl ester | 4.99 |

-continued

| EX. NO. | Compound Structure | Compound Name | HPLC Ret Time (min) |
|---|---|---|---|
| 162 | 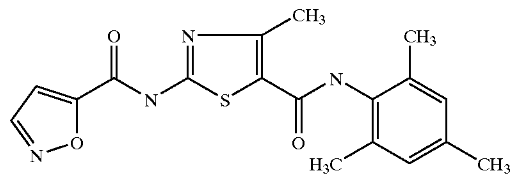 | 2-[(5-Isoxazolyl-carbonyl)amino]-4-methyl-N-(2,4,6-trimethylphenyl)-5-thiazolecarboxamide | 4.87 |
| 163 | 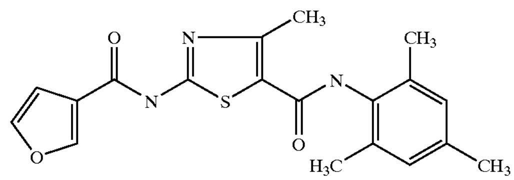 | 2-[(3-Furanylcarbonyl)amino]-4-methyl-N-(2,4,6-trimethylphenyl)-5-thiazolecarboxamide | 4.54 |
| 164 | 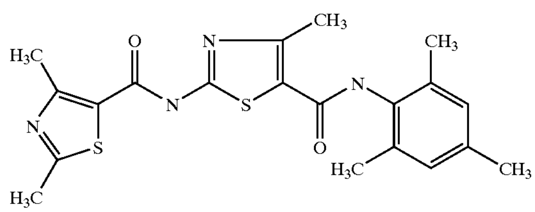 | 2-[[(2,4-Dimethyl-5-thiazolyl)carbonyl]amino]-4-methyl-N-(2,4,6-trimethylphenyl-5-thiazolecarboxamide | 4.74 |
| 165 | 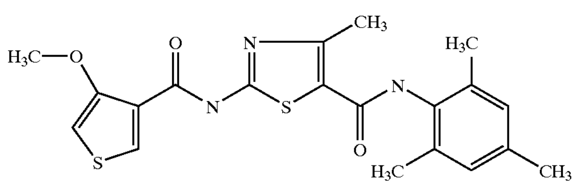 | 2-[[(4-Methoxy-3-thienyl)carbonyl]amino]-4-methyl-N-(2,4,6-trimethylphenyl)-5-thiazolecarboxamide | 4.75 |
| 166 | 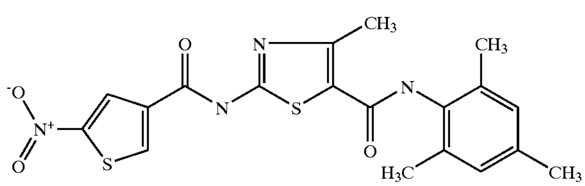 | 4-Methyl-2-[[(5-nitro-3-thienyl)carbonyl]amino]-N-(2,4,6-trimethylphenyl)-5-thiazolecarboxamide | 4.78 |
| 167 | 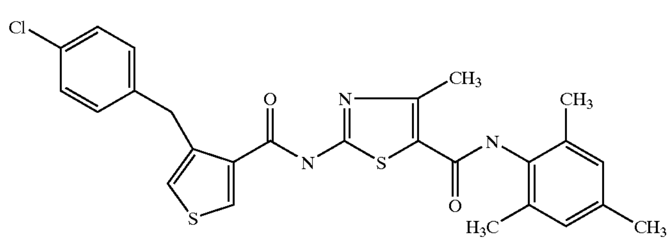 | 2-[[[4-[(4-Chloro-phenyl)thio]-3-thienyl]-carbonyl]amino]-4-methyl-N-(2,4,6-trimethylphenyl)-5-thiazolecarboxamide | 5.27 |
| 168 | 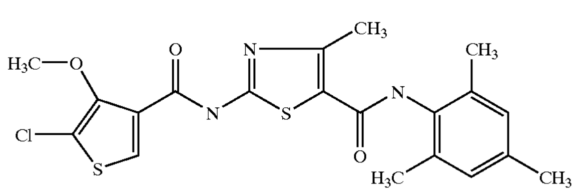 | 2-[[(5-Chloro-4-methoxy-3-thienyl)carbonyl]amino]-4-methyl-N-(2,4,6-trimethylphenyl)-5-thiazolecarboxamide | 5.04 |

| EX. NO. | Compound Structure | Compound Name | HPLC Ret Time (min) |
|---|---|---|---|
| 169 | 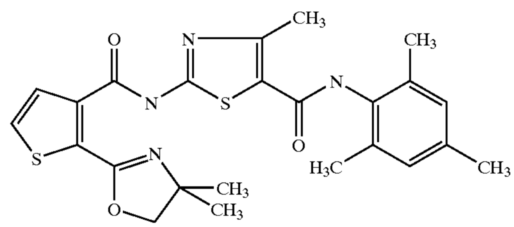 | 2-[[[2-(4,5-Dihydro-4,4-dimethyl-2-oxazolyl)-3-thienyl]carbonyl]amino]-4-methyl-N-(2,4,6-trimethylphenyl)-5-thiazolecarboxamide | 5.13 |
| 170 | 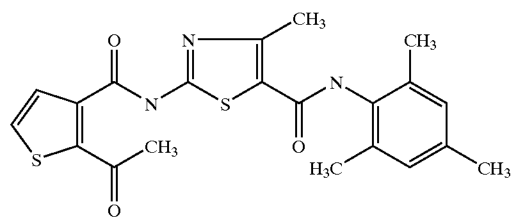 | 2-[[(2-Acetyl-3-thienyl)-carbonyl]amino]-4-methyl-N-(2,4,6-trimethylphenyl)-5-thiazolecarboxamide | 4.54 |

EXAMPLES 171 TO 180

General Procedure

Compounds 171 to 180 were prepared following the procedure described below.

A mixture of 2 (80 mg, 0.29 mmol), appropriate isocyanate (0.87 mmol) and pyridine (2 mL) in THF (3.5 mL) was stirred at rt overnight. In some cases the reaction mixture was heated to 60–70° C. for 5 h. Some of these reactions were carried out at rt overnight in the presence of catalytic N,N-dimethylaminopyridine. The reaction mixture was diluted with dichloromethane and washed with 1 N aq. HCl solution (3×), water, brine; dried (MgSO$_4$), filtered and concentrated. The crude product was purified either by trituration with ether or ether-hexanes mixture, or by chromatography on a silica gel column (elution solvent 20–40% EtOAc in hexanes) followed by trituration or by passing through Varian cation exchange SCX cartridge and sequentially eluted with methanol (5 mL), dichloromethane (5 mL), acetonitrile-methanol (10 mL, 4:1) and methanol-2 M methanolic ammonia (10 mL, 4:1) to obtain the title compound. "HPLC Ret Time" is the HPLC retention time under the following conditions: For compounds 171–172, 175, and 177 HPLC conditions are: Zorbax S8-C18 4.5 mm×7.5 cm short column, 30 min gradient starting from 100% solvent A (10% MeOH, 90% H$_2$O, 0.2% H$_3$PO$_4$) to 100% solvent B (90% MeOH, 10% H$_2$O, 0.2% H$_3$PO$_4$), flow rate 2.5 mL/min, λ=217 nM. For the other compounds HPLC conditions are: Zorbax S8-C18 4.5 mm×7.5 cm short column, 8 min gradient starting from 100% solvent A (10% MeOH, 90% H$_2$O, 0.2% H$_3$PO$_4$) to 100% solvent B (90% MeOH, 10% H$_2$O, 0.2% H$_3$PO$_4$), flow rate 2.5 mL/min, λ=217 nM.

| EX. NO. | Compound Structure | Compound Name | HPLC Ret Time (min) |
|---|---|---|---|
| 171 | 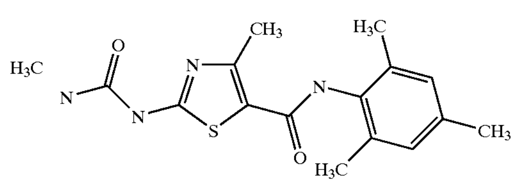 | 4-Methyl-2-[[(methyl-amino)carbonyl]amino]-N-(2,4,6-trimethylphenyl)-5-thiazolecarboxamide | 24.48 |
| 172 | 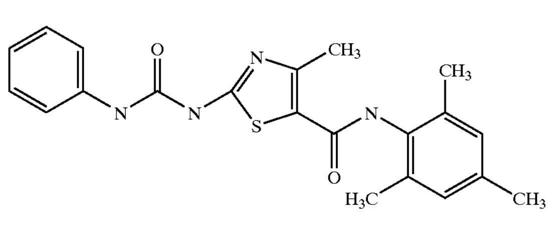 | 4-Methyl-2-[[(phenyl-amino)carbonyl]amino]-N-(2,4,6-trimethylphenyl)-5-thiazolecarboxamide | 30.45 |

-continued

| EX. NO. | Compound Structure | Compound Name | HPLC Ret Time (min) |
|---|---|---|---|
| 173 | 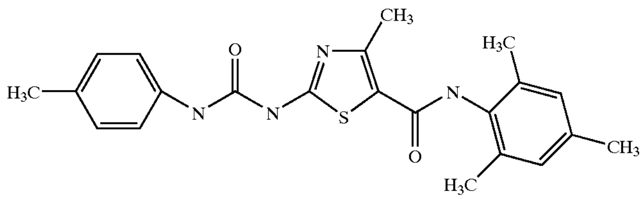 | 4-Methyl-2-[[[(4-methyl-phenyl)amino]carbonyl]amino]-N-(2,4,6-trimethylphenyl)-5-thiazolecarboxamide | 8.81 |
| 174 | 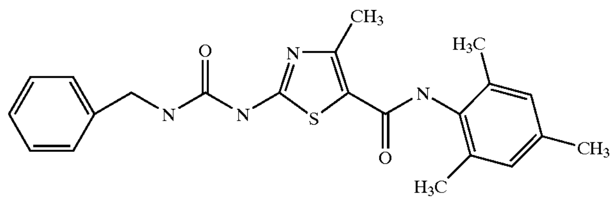 | 4-Methyl-2-[[[(phenyl-methyl)amino]carbonyl]amino]-N-(2,4,6-trimethyl-phenyl)-5-thiazolecarboxamide | 8.52 |
| 175 | 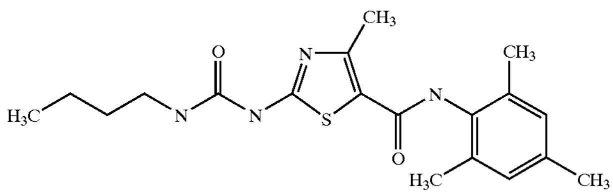 | 2-[[(Butylamino)carbonyl]amino]-4-methyl-N-(2,4,6-trimethylphenyl)-5-thiazolecarboxamide | 30.49 |
| 176 | 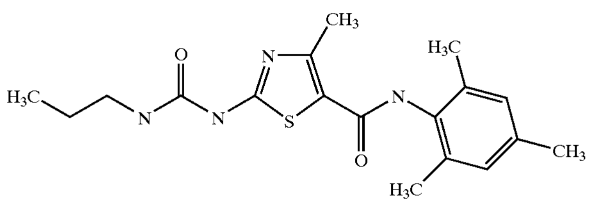 | 4-Methyl-2-[[(propyl-amino)carbonyl]amino]-N-(2,4,6-trimethylphenyl)-5-thiazolecarboxamide | 7.41 |
| 177 | 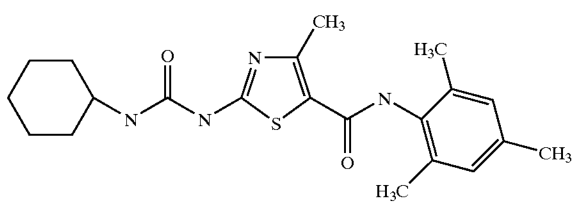 | 2-[[(Cyclohexylamino)carbonyl]amino]-4-methyl-N-(2,4,6-trimethylphenyl)-5-thiazolecarboxamide | 27.21 |
| 178 | 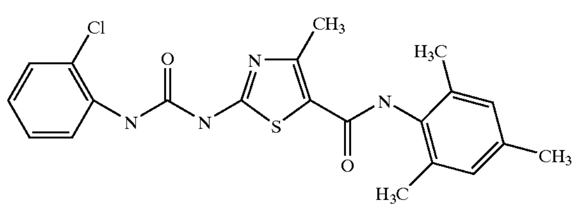 | 2-[[[(2-Chloro-phenyl)amino]carbonyl]amino]-4-methyl-N-(2,4,6-trimethylphenyl)-5-thiazolecarboxamide | 8.99 |
| 179 | 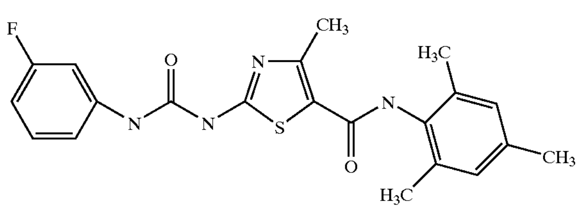 | 2-[[[(3-Fluorophenyl)-amino]carbonyl]amino]-4-methyl-N-(2,4,6-trimethyl-phenyl)-5-thiazolecarboxamide | 8.87 |

-continued

| EX. NO. | Compound Structure | Compound Name | HPLC Ret Time (min) |
|---|---|---|---|
| 180 | 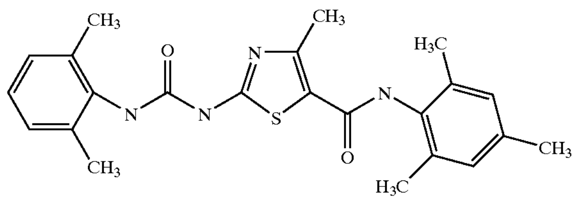 | 2-[[[(2,6-Dimethyl-phenyl)amino]carbonyl]amino]-4-methyl-N-(2,4,6-trimethylphenyl)-5-thiazolecarboxamide | 8.92 |

EXAMPLE 181

Preparation of [5-[[(2,4,6-Trimethylphenyl)amino]carbonyl]-4-methyl-2-thiazolyl]carbamic acid, phenyl ester

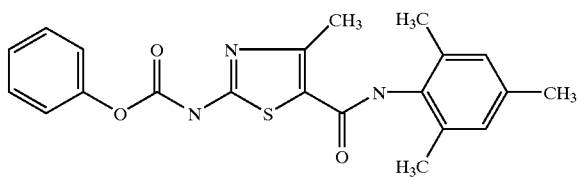

A 10% aq. KHCO$_3$ solution (170 mL) was added to a stirred solution of 2 (1.02 g, 3.7 mmol) in THF (130 mL). Phenylchloroformate (1.39 mL, 11.1 mmol) was added dropwise. The biphasic mixture was stirred at rt overnight, diluted with dichloromethane (200 mL) and washed with water (50 mL, 2×) and brine. The organic extract was separated, dried (MgSO$_4$), filtered and concentrated. The residue was chromatographed on a silica gel column and eluted with 10% EtOAc in hexanes to obtain the title compound (980 mg, 69%) as a solid.

EXAMPLES 182 TO 236

General Procedure

Compounds 182 to 236 were prepared following the procedure described below.

A solution of phenylcarbamate 181 (20 mg, 0.054 mmol) and the appropriate amine (0.08 mmol) in THF-acetonitrile (3 mL, 1:1) was stirred at rt overnight. Some of the reactions required heating to 60° C. for 4 h to overnight. The mixture was diluted with dichloromethane (4 mL) and washed with 1 N aq. HCl solution (1.5 mL, 2×), 1 N aq. NaOH solution (1.5 mL, 2×). The dichloromethane extract was separated, dried (MgSO$_4$), filtered and concentrated to obtain the title product.

"HPLC Ret Time" is the HPLC retention time under the following conditions: For compounds 182–192 HPLC conditions are: Zorbax SB-C18 4.5 mm×7.5 cm short column, 8 min gradient starting from 100% solvent A (10% MeOH, 90% H$_2$O, 0.2% H$_3$PO$_4$) to 100% solvent B (90% MeOH, 10% H$_2$O, 0.2% H$_3$PO$_4$), flow rate 2.5 mL/min, λ=217 nM. For compounds 193–236 HPLC conditions are: YMC S5 ODS 4.6×50 mm Ballastic Column, 4 min gradient starting from 100% solvent A (10% MeOH, 90% H$_2$O, 0.2% H$_3$PO$_4$) to 100% solvent B (90% MeOH, 10% H$_2$O, 0.2% H$_3$PO$_4$), flow rate 4 mL/min, λ=220 nM.

| EX. NO. | Compound Structure | Compound Name | HPLC Ret Time (min) |
|---|---|---|---|
| 182 | 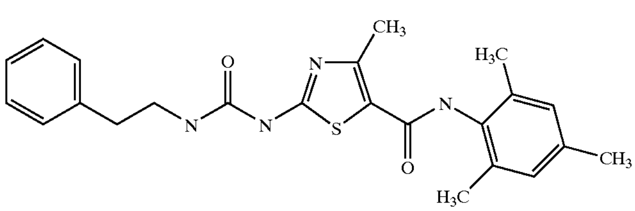 | 4-Methyl-2-[[[(2-phenylethyl)amino]carbonyl]amino]-N-(2,4,6-trimethyl-phenyl)-5-thiazole-carboxamide | 8.83 |
| 183 | 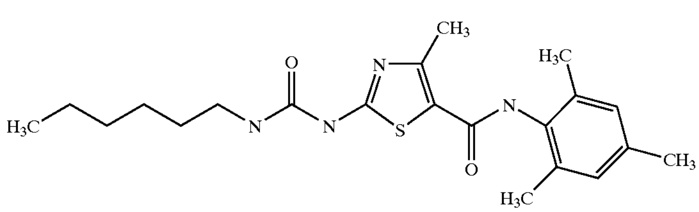 | 2-[[(Hexylamino)carbonyl]amino]-4-methyl-N-(2,4,6-trimethylphenyl)-5-thiazolecarboxamide | 9.01 |

-continued

| EX. NO. | Compound Structure | Compound Name | HPLC Ret Time (min) |
|---|---|---|---|
| 184 | 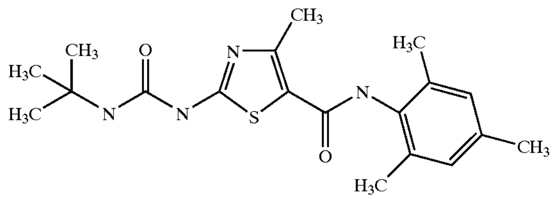 | 2-[[[(1,1-Dimethyl-ethyl)amino]carbonyl]amino]-4-methyl-N-(2,4,6-trimethyl-phenyl)-5-thiazole-carboxamide | 8.48 |
| 185 | 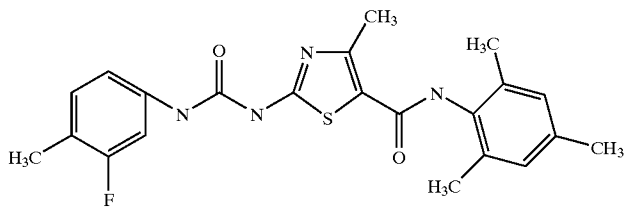 | 2-[[[(3-Fluoro-4-methylphenyl)amino]-carbonyl]amino]-4-methyl-N-(2,4,6-trimethylphenyl)-5-thiazolecarboxamide | 8.92 |
| 186 | 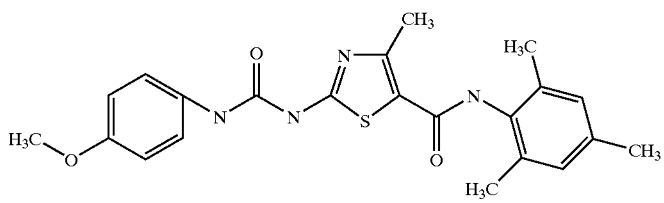 | 2-[[[(4-Methoxyphenyl)amino]carbonyl]amino]-4-methyl-N-(2,4,6-trimethylphenyl)-5-thiazolecarboxamide | 8.57 |
| 187 | 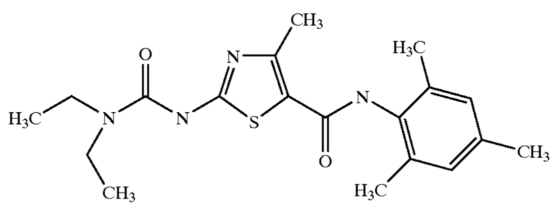 | 2-[[(Diethylamino)carbonyl]amino]-4-methyl-N-(2,4,6-trimethylphenyl)-5-thiazolecarboxamide | 8.19 |
| 188 | 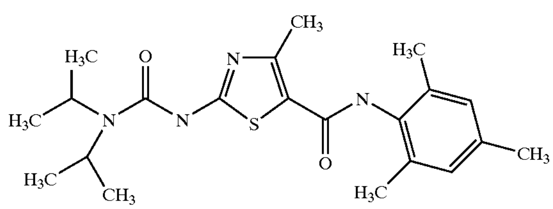 | 2-[[[Bis(1-methyl-ethyl)amino]carbonyl]amino]-4-methyl-N-(2,4,6-trimethyl-phenyl)-5-thiazole-carboxamide | 8.90 |
| 189 | 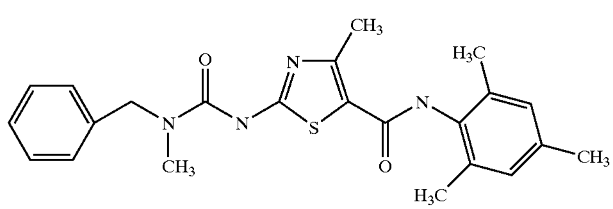 | 4-Methyl-2-[[[methyl-(phenylmethyl)amino]-carbonyl]amino]-N-(2,4,6-trimethyl-phenyl)-5-thiazole-carboxamide | 8.56 |
| 190 | 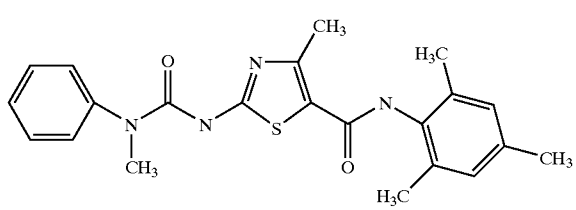 | 4-Methyl-2-[[(methyl-phenylamino)carbonyl]amino]-N-(2,4,6-trimethylphenyl)-5-thiazolecarboxamide | 8.39 |

-continued

| EX. NO. | Compound Structure | Compound Name | HPLC Ret Time (min) |
|---|---|---|---|
| 191 | 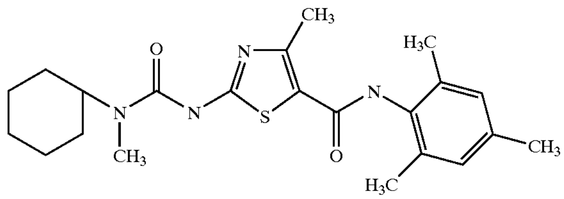 | 2-[[(Cyclohexylmethyl amino)carbonyl]amino]-4-methyl-N-(2,4,6-trimethylphenyl)-5-thiazolecarboxamide | 8.84 |
| 192 | 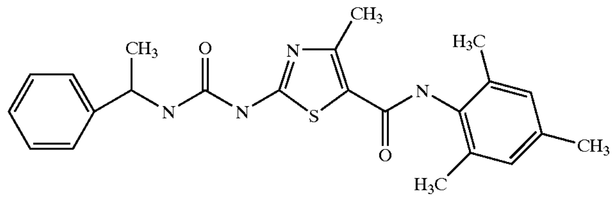 | 4-Methyl-2-[[[(1-phenylethyl) amino]-carbonyl]amino]-N-(2,4,6-trimethyl-phenyl)-5-thiazole-carboxamide | 8.47 |
| 193 | 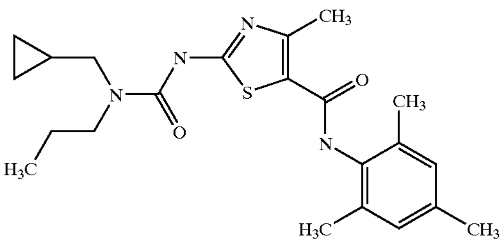 | 2-[[[(Cyclopropyl-methyl) propylamino]-carbonyl]amino]-4-methyl-N-(2,4,6-trimethylphenyl)-5-thiazolecarboxamide | 4.36 |
| 194 | 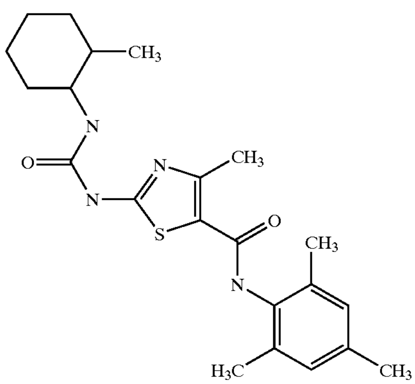 | 4-Methyl-2-[[[(2-methylcyclohexyl)amino] carbonyl]amino]-N-(2,4,6-trimethyl-phenyl)-5-thiazole-carboxamide | 4.42 |
| 195 | 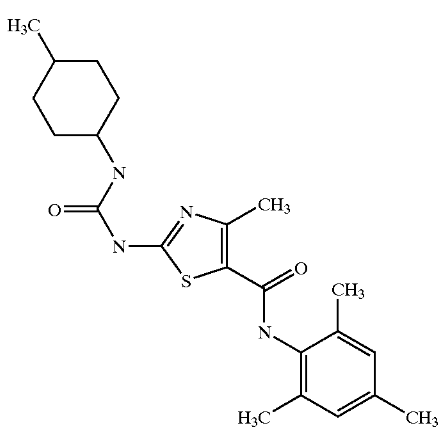 | 4-Methyl-2-[[[(4-methylcyclohexyl)-amino] carbonyl]amino]-N-(2,4,6-trimethyl-phenyl)-5-thiazole-carboxamide | 4.49 |

-continued

| EX. NO. | Compound Structure | Compound Name | HPLC Ret Time (min) |
|---|---|---|---|
| 196 | 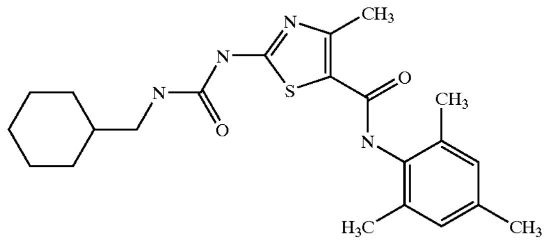 | 2-[[[(Cyclohexyl-methyl)amino]-carbonyl]amino]-4-methyl-N-(2,4,6-trimethylphenyl)-5-thiazolecarboxamide | 4.49 |
| 197 | 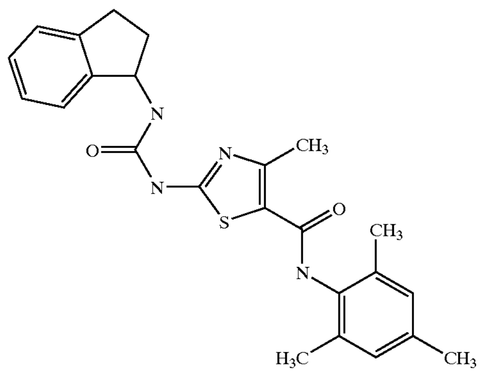 | 2-[[[(2,3-Dihydro-1H-inden-1-yl)amino]carbonyl]amino]-4-methyl-N-(2,4,6-trimethylphenyl)-5-thiazolecarboxamide | 4.35 |
| 198 | 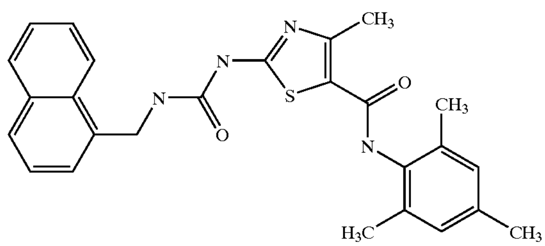 | 4-Methyl-2-[[[(1-naphthalenylmethyl)amino]carbonyl]amino]-N-(2,4,6-trimethyl-phenyl)-5-thiazole-carboxamide | 4.43 |
| 199 | 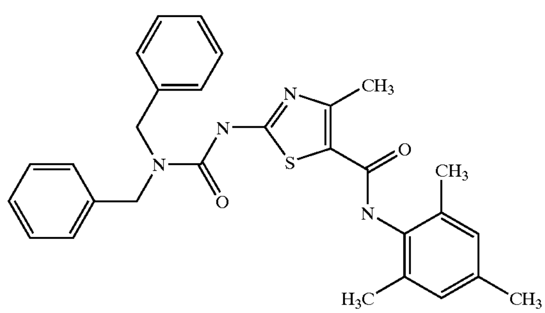 | 2-[[[Bis(phenylmethyl)amino]carbonyl]amino]-4-methyl-N-(2,4,6-trimethylphenyl)-5-thiazolecarboxamide | 4.66 |
| 200 | 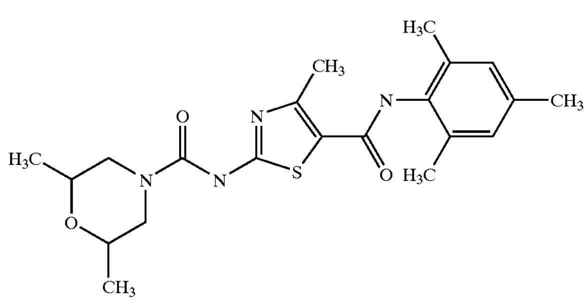 | 2,6-Dimethyl-N-[4-methyl-5-[[(2,4,6-trimethylphenyl)-amino]carbonyl]-2-thiazolyl]-4-morpholinecarboxamide | 3.97 |

-continued

| EX. NO. | Compound Structure | Compound Name | HPLC Ret Time (min) |
|---|---|---|---|
| 201 | 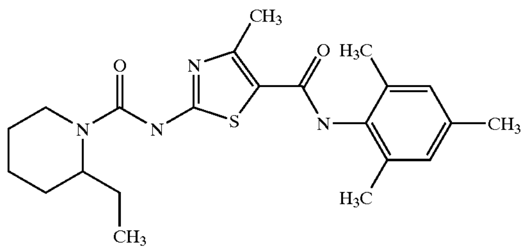 | 2-Ethyl-N-[4-methyl-5-[[(2,4,6-trimethyl-phenyl)amino]carbonyl]-2-thiazolyl]-1-piperidinecarboxamide | 4.29 |
| 202 | 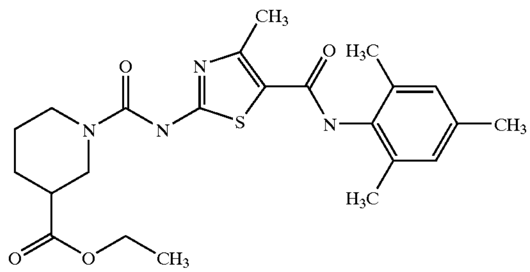 | 1-[[[4-Methyl-5-[[(2,4,6-trimethyl-phenyl)amino]carbonyl]-2-thiazolyl]-amino]carbonyl]-3-piperidinecarboxylic acid ethyl ester | 4.10 |
| 203 | 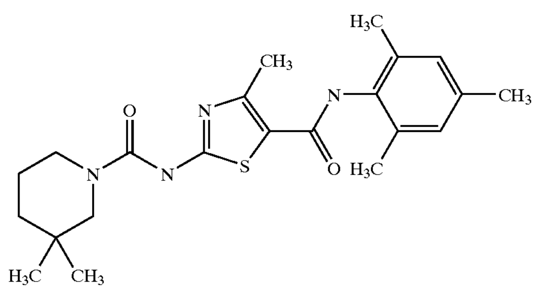 | 3,3-Dimethyl-N-[4-methyl-5-[[(2,4,6-trimethylphenyl)amino]carbonyl]-2-thiazolyl]-1-piperidinecarboxamide | 4.32 |
| 204 | 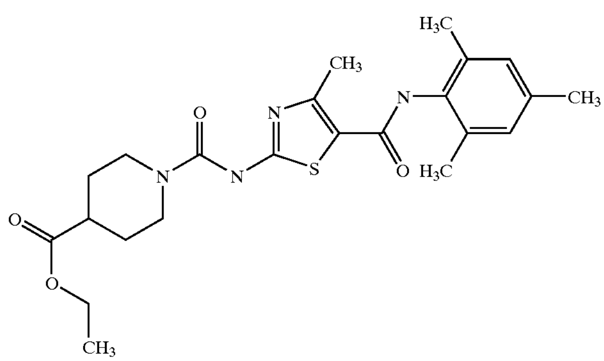 | 1-[[[4-Methyl-5-[[(2,4,6-trimethyl-phenyl)amino]carbonyl]-2-thiazolyl]-amino]carbonyl]-4-piperidinecarboxylic acid ethyl ester | 4.06 |
| 205 | 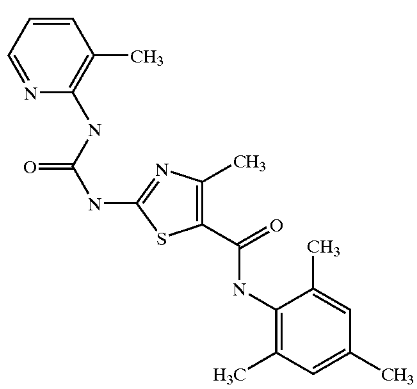 | 4-Methyl-2-[[[(3-methyl-2-pyridinyl)-amino]carbonyl]-amino]-N-(2,4,6-trimethyl-phenyl)-5-thiazolecarboxamide | 3.51 |

-continued

| EX. NO. | Compound Structure | Compound Name | HPLC Ret Time (min) |
|---|---|---|---|
| 206 | 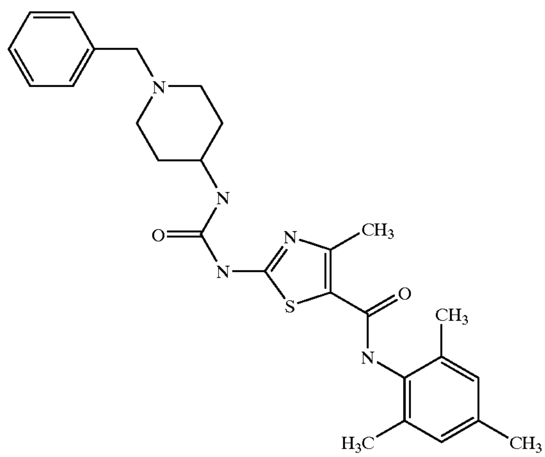 | 4-Methyl-2-[[[1-(phenylmethyl)-4-piperidinyl]amino]-carbonyl]amino]-N-(2,4,6-trimethyl-phenyl)-5-thiazole-carboxamide | 3.28 |
| 207 | 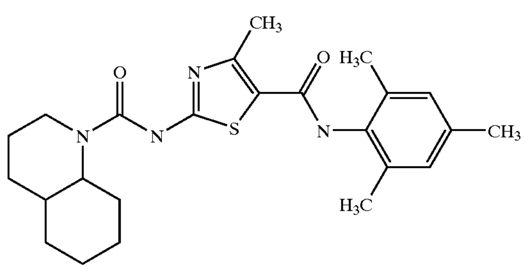 | Octahydro-N-[4-methyl-5-[[2,4,6-trimethyl-phenyl)amino]carbonyl]-2-thiazolyl]-1(2H)-quinolinecarboxamide | 4.55 |
| 208 | 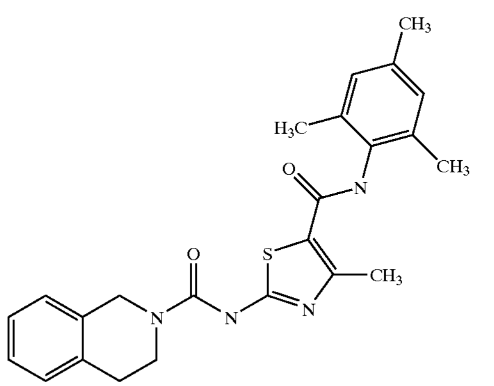 | 3,4-Dihydro-N-[4-methyl-5-[[(2,4,6-trimethylphenyl)-amino]carbonyl]-2-thiazolyl]-2(1H)-isoquinoline carboxamide | 4.35 |
| 209 | 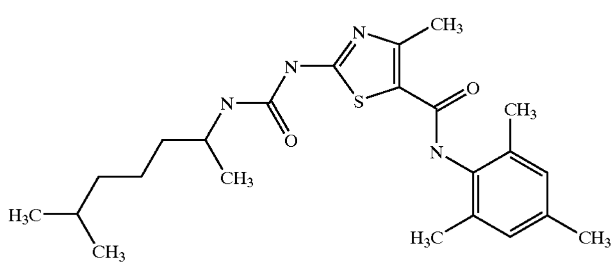 | 2-[[[(1,5-Dimethyl-hexyl)amino]carbonyl]-amino]-4-methyl-N-(2,4,6-trimethyl-phenyl)-5-thiazole-carboxamide | 4.72 |

-continued

| EX. NO. | Compound Structure | Compound Name | HPLC Ret Time (min) |
|---|---|---|---|
| 210 | 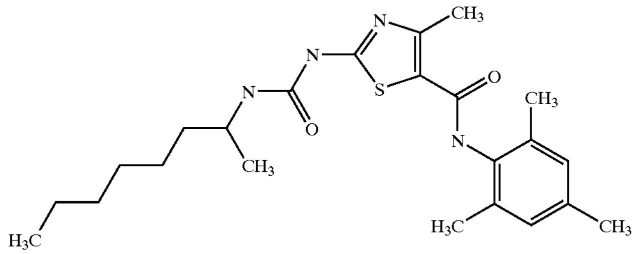 | 4-Methyl-2-[[[(1-methylheptyl)amino]-carbonyl]amino]-N-(2,4,6-trimethyl-phenyl)-5-thiazole-carboxamide | 4.74 |
| 211 | 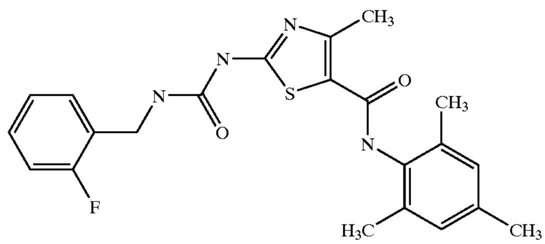 | 2-[[[[(2-Fluoro-phenyl)methyl]amino]-carbonyl]amino]-4-methyl-N-(2,4,6-trimethylphenyl)-5-thiazolecarboxamide | 4.17 |
| 212 | 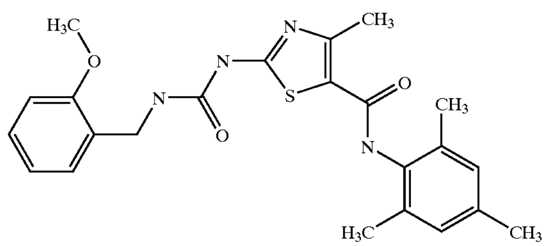 | 2-[[[[(2-Methoxy-phenyl)methyl]amino]-carbonyl]amino]-4-methyl-N-(2,4,6-trimethylphenyl)-5-thiazolecarboxamide | 4.22 |
| 213 | 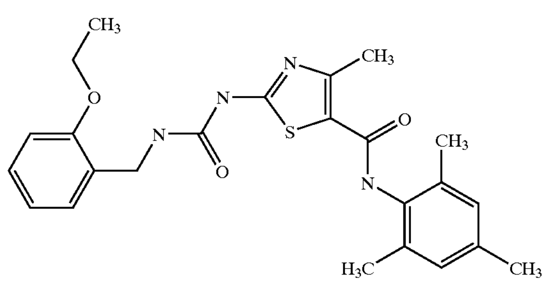 | 2-[[[[(2-Ethoxy-phenyl)methyl]amino]carbonyl]amino]-4-methyl-N-(2,4,6-trimethylphenyl)-5-thiazolecarboxamide | 4.36 |
| 214 | 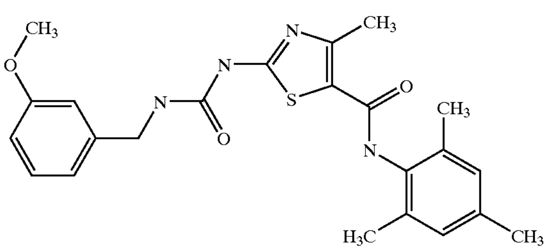 | 2-[[[[(3-Methoxy-phenyl)methyl]amino]-carbonyl]amino]-4-methyl-N-(2,4,6-trimethylphenyl)-5-thiazolecarboxamide | 4.13 |
| 215 | 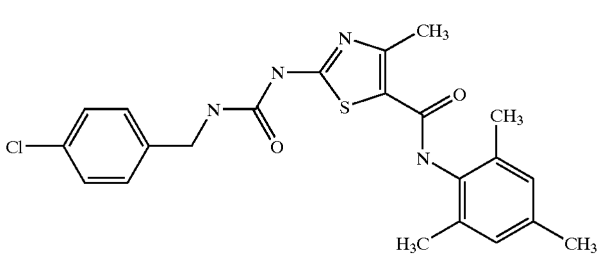 | 2-[[[[(4-Chloro-phenyl)methyl]amino]-carbonyl]amino]-4-methyl-N-(2,4,6-trimethylphenyl)-5-thiazolecarboxamide | 4.36 |

-continued

| EX. NO. | Compound Structure | Compound Name | HPLC Ret Time (min) |
|---|---|---|---|
| 216 | 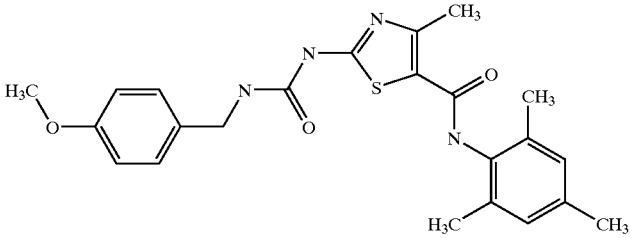 | 2-[[[[(4-Methoxy-phenyl) methyl]amino]carbonyl] amino]-4-methyl-N-(2,4,6-trimethylphenyl)-5-thiazolecarboxamide | 4.12 |
| 217 | 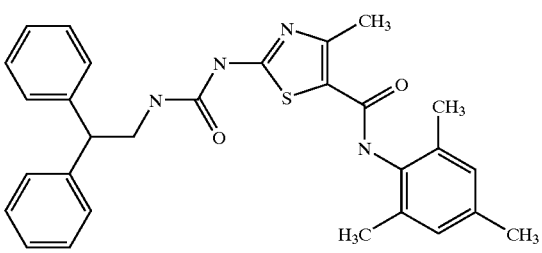 | 2-[[[(2,2-Diphenyl-ethyl) amino]carbonyl]-amino]-4-methyl-N-phenyl)-5-thiazole-carboxamide | 4.57 |
| 218 | 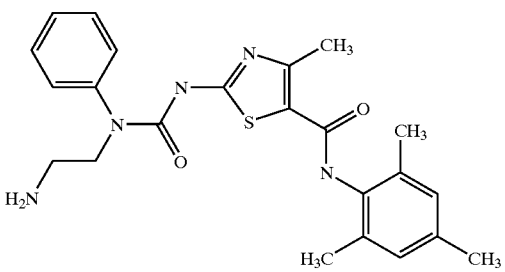 | 2-[[[(2-Aminoethyl) phenylamino]carbonyl]-amino]-4-methyl-N-(2,4,6-trimethyl-phenyl)-5-thiazole-carboxamide | 3.70 |
| 219 | 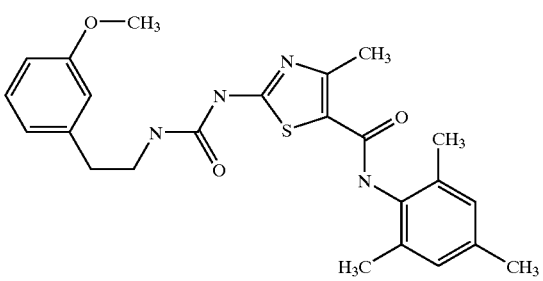 | 2-[[[[2-(3-Methoxy-phenyl)ethyl]amino]-carbonyl]amino]-4-methyl-N-(2,4,6-trimethylphenyl)-5-thiazolecarboxamide | 4.26 |
| 220 | 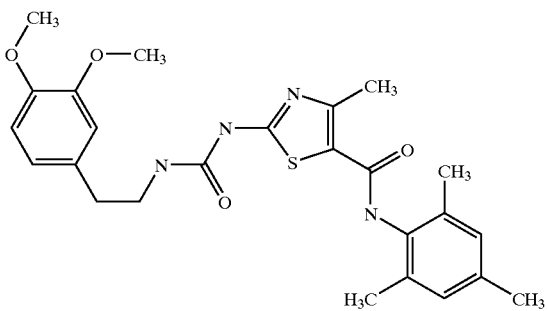 | 2-[[[[2-(3,4-Dimethoxyphenyl)ethyl] amino]carbonyl]amino]-4-methyl-N-(2,4,6-trimethylphenyl)-5-thiazolecarboxamide | 4.05 |

-continued

| EX. NO. | Compound Structure | Compound Name | HPLC Ret Time (min) |
|---|---|---|---|
| 221 | 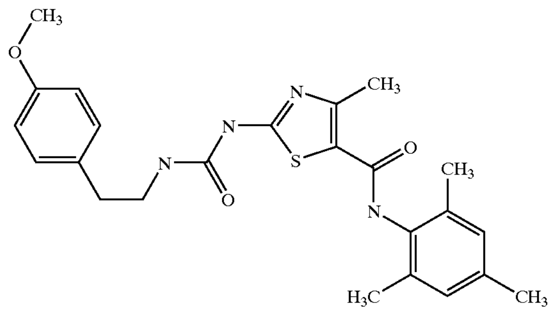 | 2-[[[[2-(4-Methoxy-phenyl)ethyl]amino]-carbonyl]amino]-4-methyl-N-(2,4,6-trimethylphenyl)-5-thiazolecarboxamide | 4.25 |
| 222 | 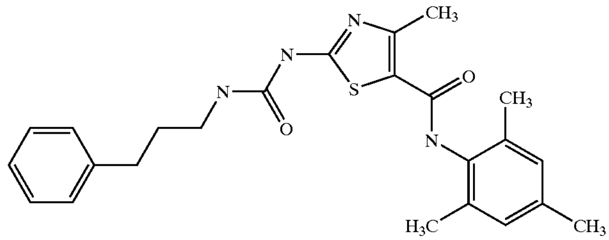 | 4-Methyl-2-[[[(3-phenylpropyl)amino]-carbonyl]amino]-N-(2,4,6-trimethyl-phenyl)-5-thiazole-carboxamide | 4.40 |
| 223 | 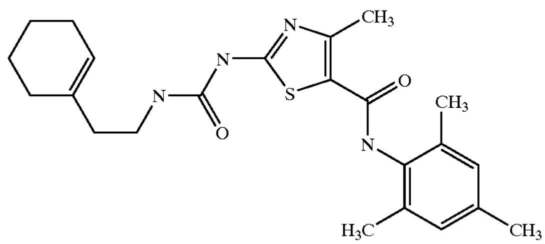 | 2-[[[[2-(CycloheX-1-en-1-yl)ethyl]-amino]carbonyl]amino]-4-methyl-N-(2,4,6-trimethylphenyl)-5-thiazolecarboxamide | 4.11 |
| 224 | 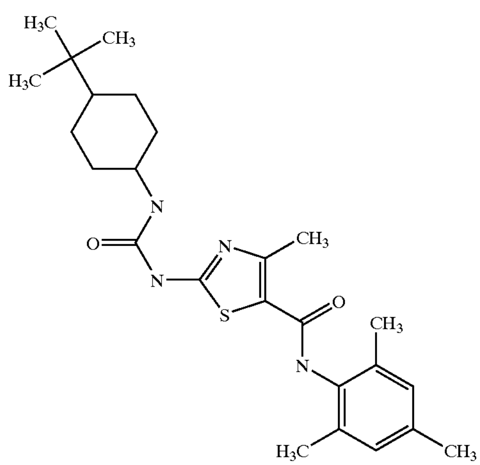 | 2-[[[[4-(1,1-Dimethylethyl)cyclo-hexyl]amino]carbonyl]-amino]-4-methyl-N-(2,4,6-trimethyl-phenyl)-5-thiazole-carboxamide | 4.85 |
| 225 | 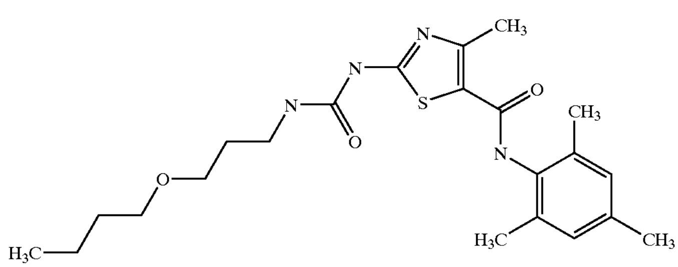 | 2-[[[(3-Butoxypropyl)amino]carbonyl]amino]-4-methyl-N-(2,4,6-trimethylphenyl)-5-thiazolecarboxamide | 4.33 |

-continued

| EX. NO. | Compound Structure | Compound Name | HPLC Ret Time (min) |
|---|---|---|---|
| 226 | 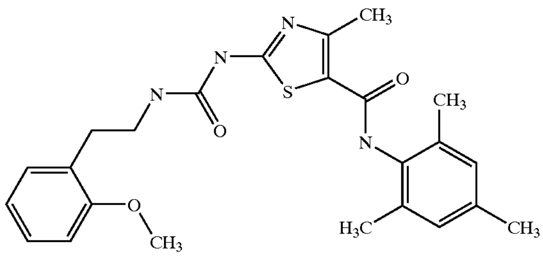 | 2-[[[[2-(2-Methoxy-phenyl)ethyl]amino]-carbonyl]amino]-4-methyl-N-(2,4,6-trimethylphenyl)-5-thiazolecarboxamide | 4.46 |
| 227 | 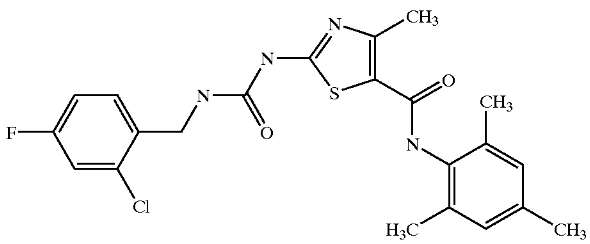 | 2-[[[[(2-Chloro-4-fluorophenyl)methyl]-amino]carbonyl]amino]-4-methyl-N-(2,4,6-trimethylphenyl)-5-thiazolecarboxamide | 4.39 |
| 228 | 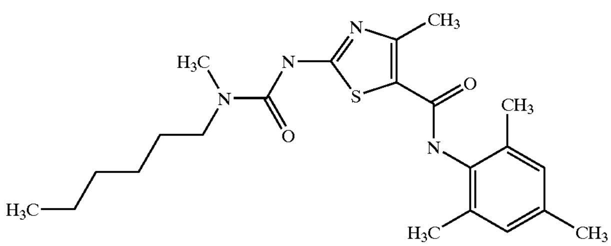 | 2-[[(Hexylmethylamino)carbonyl]amino]-4-methyl-N-(2,4,6-trimethylphenyl)-5-thiazolecarboxamide | 4.65 |
| 229 | 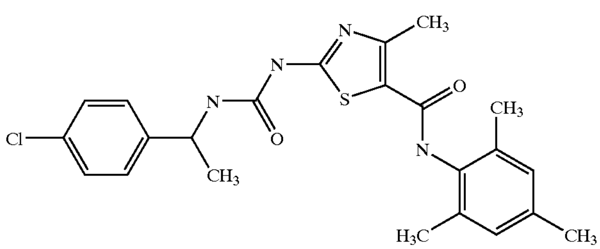 | 2-[[[[1-(4-Chloro-phenyl)ethyl]amino]-carbonyl]amino]-4-methyl-N-(2,4,6-trimethylphenyl)-5-thiazolecarboxamide | 4.42 |
| 230 | 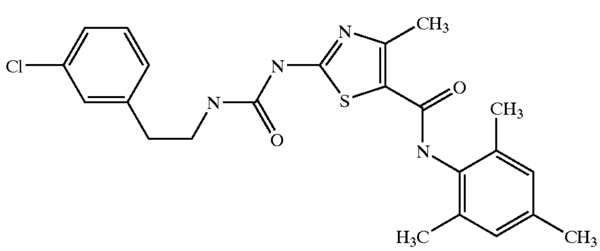 | 2-[[[[2-(3-Chloro-phenyl)ethyl]amino]carbonyl]amino]-4-methyl-N-(2,4,6-trimethyl-phenyl)-5-thiazole-carboxamide | 4.44 |
| 231 | 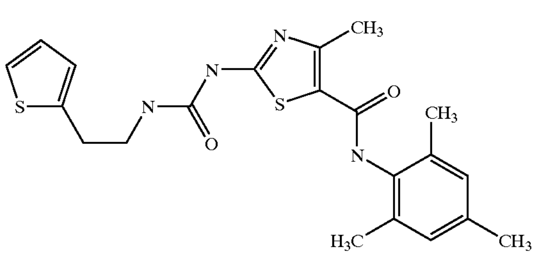 | 4-Methyl-2-[[[[2-(2-thienyl)ethyl]amino]-carbonyl]amino]-N-(2,4,6-trimethyl-phenyl)-5-thiazole-carboxamide | 4.18 |

| EX. NO. | Compound Structure | Compound Name | HPLC Ret Time (min) |
|---|---|---|---|
| 232 | 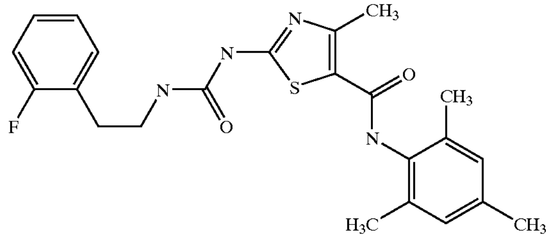 | 2-[[[[2-(2-Fluoro-phenyl)ethyl]amino]-carbonyl]amino]-4-methyl-N-(2,4,6-trimethylphenyl)-5-thiazolecarboxamide | 5.85 |
| 233 | 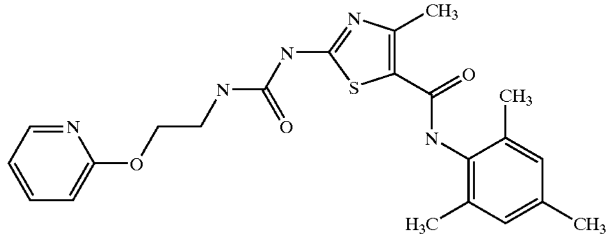 | 4-Methyl-2-[[[[2-(2-pyridinyloxy)ethyl]-amino]carbonyl]amino]-N-(2,4,6-trimethyl-phenyl)-5-thiazole-carboxamide | 4.28 |
| 234 | 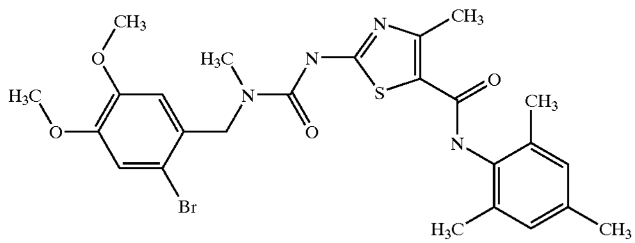 | 2-[[[[(2-Bromo-4,5-dimethoxyphenyl)methyl methylamino]carbonyl]amino]-4-methyl-N-(2,4,6-trimethylphenyl)-5-thiazolecarboxamide | 3.87 |
| 235 | 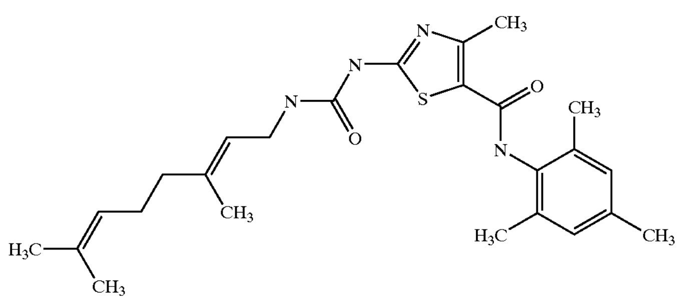 | (E)-2-[[[(3,7-Dimethyl-2,6-octadienyl)amino]-carbonyl]aminol-4-methyl-N-(2,4,6-trimethyl-phenyl)-5-thiazole-carboxamide | 4.34 |
| 236 | 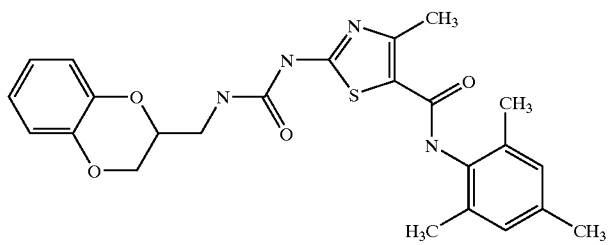 | 2-[[[[(2,3-Dihydro-1,4-benzodioxin-2-yl)methyl]amino]carbonyl]amino]-4-methyl-N-(2,4,6-trimethyl-phenyl)-5-thiazole-carboxamide | 4.27 |

EXAMPLES 237 TO 285

General Procedure

Compounds 237 to 285 were prepared following the procedure described below.

A solution of phenylcarbamate 181 (20 mg, 0.054 mmol) and the appropriate amine (0.08 mmol) in THF-acetonitrile (3 mL, 1:1) was stirred at rt overnight. The mixture was diluted with dichloromethane (4 mL) and washed with 1 N aq. HCl solution (1.5 mL, 2×), 1 N aq. NaOH solution (1.5 mL, 2×). The dichloromethane extract was separated, dried ($MgSO_4$), filtered and concentrated to obtain the title product.

"HPLC Ret Time" is the HPLC retention time under the following conditions: For compounds 237–278 HPLC conditions are: YMC S5 ODS 4.6×50 mm Ballastic Column, 4 min gradient starting from 100% solvent A (10% MeOH, 90% $H_2O$, 0.2% $H_3PO_4$) to 100% solvent B (90% MeOH, 10% $H_2O$, 0.2% $H_3PO_4$), flow rate 4 mL/min, λ=220 nM. For compounds 279–285 HPLC conditions are: Zorbax S8-C18 4.5 mm×7.5 cm short column, 8 min gradient starting from 100% solvent A (10% MeOH, 90% $H_2O$, 0.2% $H_3PO_4$) to 100% solvent B (90% MeOH, 10% $H_2O$, 0.2% $H_3PO_4$), flow rate 2.5 mL/min, λ=217 nM.

| EX. NO. | Compound Structure | Compound Name | HPLC Ret Time (min) |
|---|---|---|---|
| 237 | 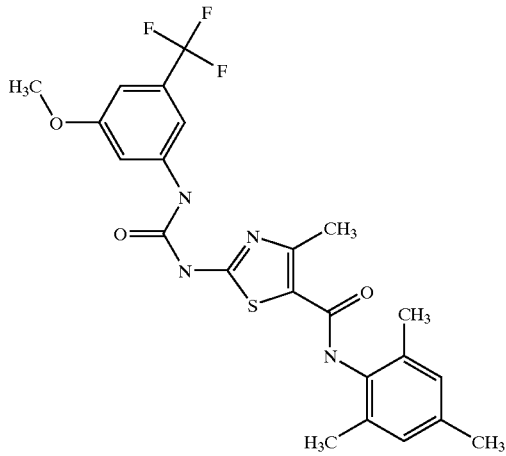 | 2-[[[[3-Methoxy-5-(trifluoromethyl)phenyl]amino]carbonyl]amino]-4-methyl-N-(2,4,6-trimethylphenyl)-5-thiazolecarboxamide | 5.36 |
| 238 | 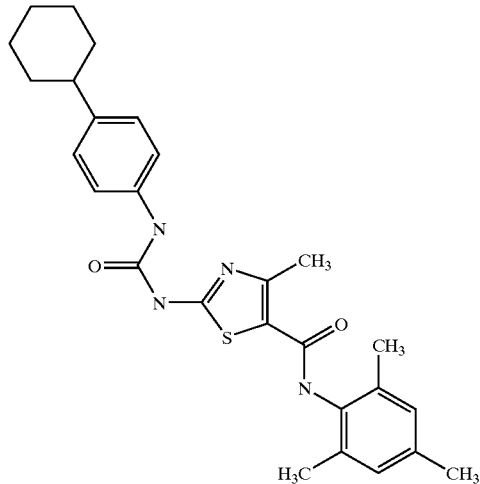 | 2-[[[(4-Cyclohexyl-phenyl)amino]carbonyl]-amino]-4-methyl-N-(2,4,6-trimethylphenyl)-5-thiazolecarboxamide | 4.73 |
| 239 | 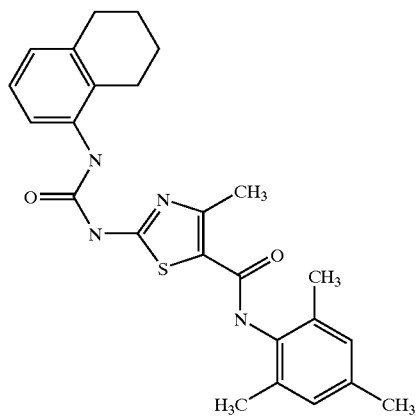 | 4-Methyl-2-[[[(5,6,7,8-tetrahydro-1-naphthalenyl)amino]-carbonyl]amino]-N-(2,4,6-trimethylphenyl)-5-thiazolecarboxamide | 5.38 |

-continued

| EX. NO. | Compound Structure | Compound Name | HPLC Ret Time (min) |
|---|---|---|---|
| 240 | 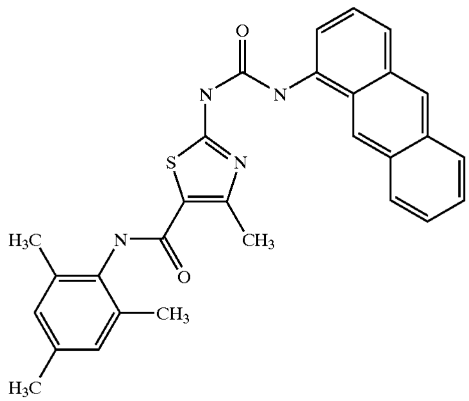 | 2-[[(1-Anthracenylamino)carbonyl]amino]-4-methyl-N-(2,4,6-trimethylphenyl)-5-thiazolecarboxamide | 4.82 |
| 241 | 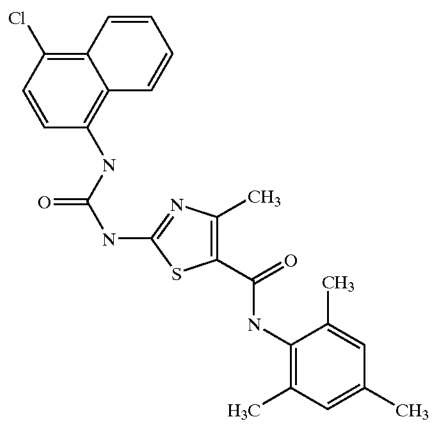 | 2-[[[(4-Chloro-1-naphthalenyl)amino]-carbonyl]amino]-4-methyl-N-(2,4,6-trimethylphenyl)-5-thiazolecarboxamide | 4.76 |
| 242 | 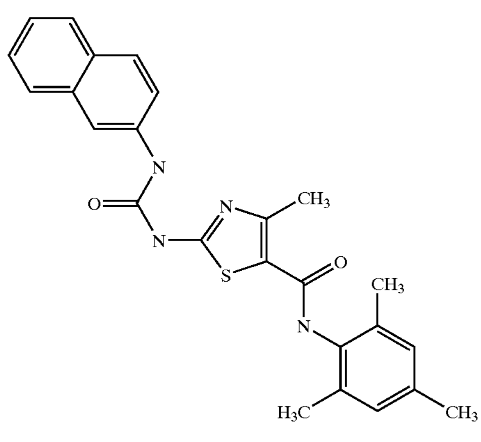 | 4-Methyl-2-[[(2-naphthalenylamino)-carbonyl]amino]-N-(2,4,6-trimethylphenyl)-5-thiazolecarboxamide | 5.28 |

| EX. NO. | Compound Structure | Compound Name | HPLC Ret Time (min) |
|---|---|---|---|
| 243 | 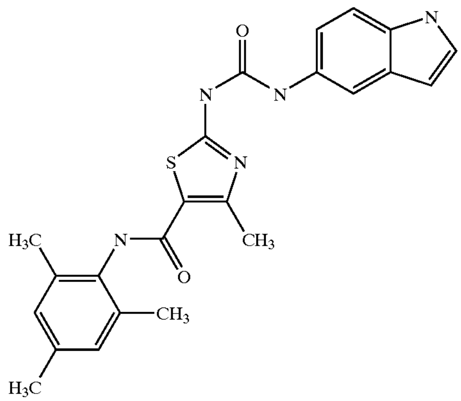 | 2-[[(1H-Indol-5-ylamino)carbonyl]amino]-4-methyl-N-(2,4,6-trimethylphenyl)-5-thiazolecarboxamide | 5.00 |
| 244 | 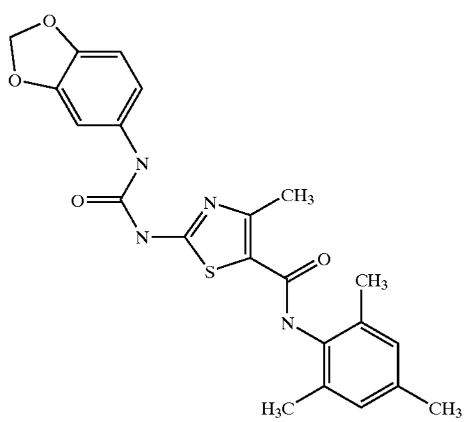 | 2-[[(1,3-Benzodioxol-5-ylamino)carbonyl]amino]-4-methyl-N-(2,4,6-trimethylphenyl)-5-thiazolecarboxamide | 4.76 |
| 245 | 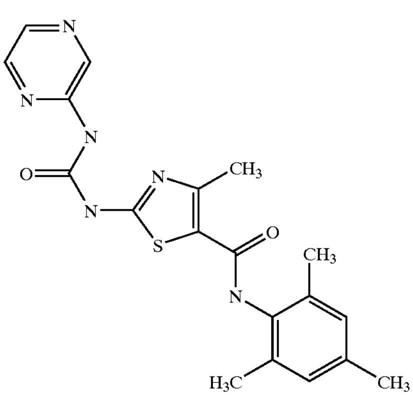 | 4-Methyl-2-[[(2-pyrazinylamino)carbonyl]amino]-N-(2,4,6-trimethyl-phenyl)-5-thiazole-carboxamide | 3.84 |

-continued
| EX. NO. | Compound Structure | Compound Name | HPLC Ret Time (min) |
|---|---|---|---|
| 246 | 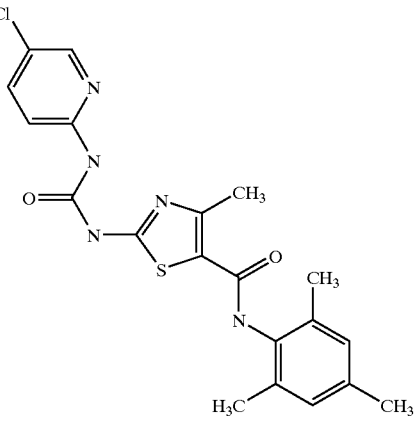 | 2-[[[(5-Chloro-2-pyridinyl)amino]carbonyl]amino]-4-methyl-N-(2,4,6-trimethylphenyl)-5-thiazolecarboxamide | 4.38 |
| 247 | 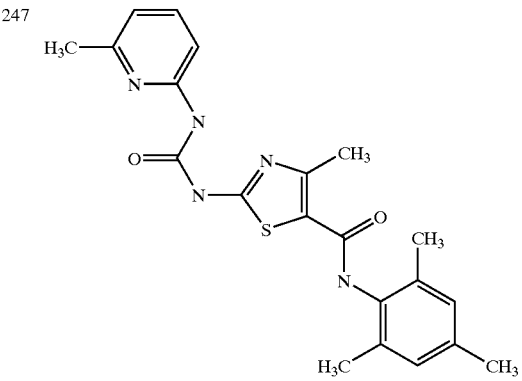 | 4-Methyl-2-[[[(6-methyl-2-pyridinyl)amino]-carbonyl]amino]-N-(2,4,6-trimethylphenyl)-5-thiazolecarboxamide | 4.44 |
| 248 | 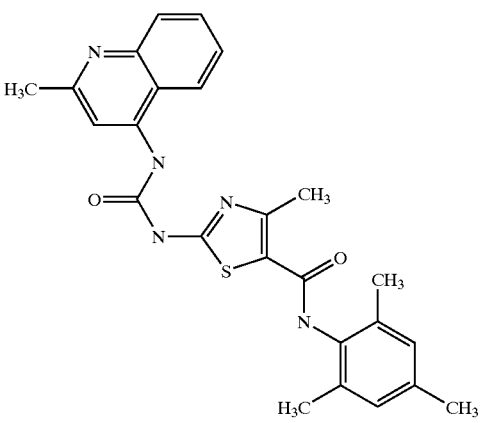 | 4-Methyl-2-[[[(2-methyl-4-quinolinyl)amino]carbonyl]amino]-N-(2,4,6-trimethylphenyl)-5-thiazolecarboxamide | 5.23 |

| EX. NO. | Compound Structure | Compound Name | HPLC Ret Time (min) |
|---|---|---|---|
| 249 | 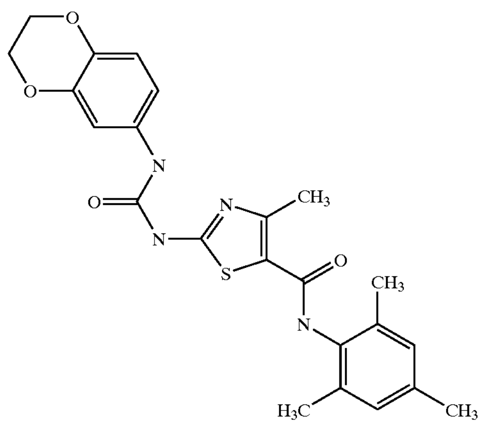 | 2-[[[(2,3-Dihydro-1,4-benzodioxin-6-yl)amino]carbonyl]amino]-4-methyl-N-(2,4,6-trimethylphenyl)-5-thiazolecarboxamide | 4.72 |
| 250 | 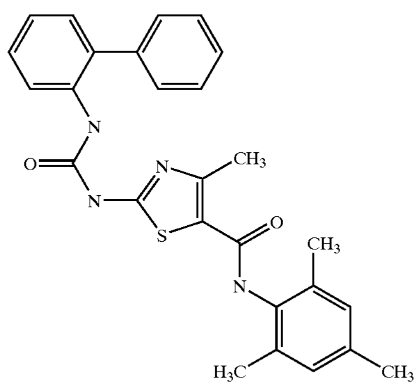 | 2-[[[([1,1'-Biphenyl]-2-ylamino)carbonyl]amino]-4-methyl-N-(2,4,6-trimethylphenyl)-5-thiazolecarboxamide | 5.29 |
| 251 | 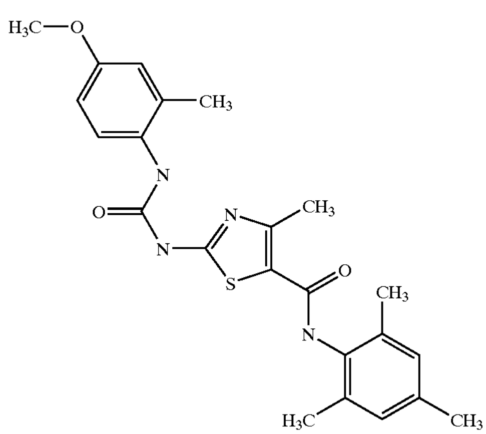 | 2-[[[(4-Methoxy-2-methylphenyl)amino]carbonyl]amino]-4-methyl-N-(2,4,6-trimethylphenyl)-5-thiazolecarboxamide | 4.80 |

-continued

| EX. NO. | Compound Structure | Compound Name | HPLC Ret Time (min) |
|---|---|---|---|
| 252 | 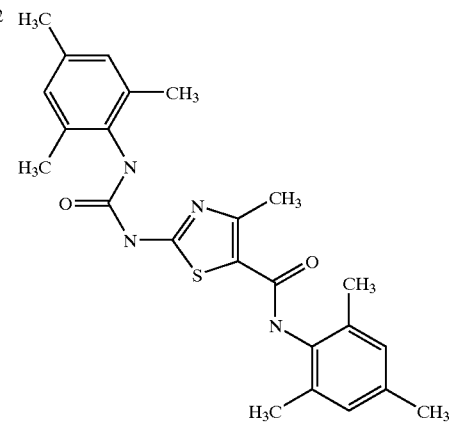 | 4-Methyl-N-(2,4,6-trimethylphenyl)-2-[[[(2,4,6-trimethylphenyl)amino]-carbonyl]amino]-5-thiazolecarboxamide | 5.06 |
| 253 | 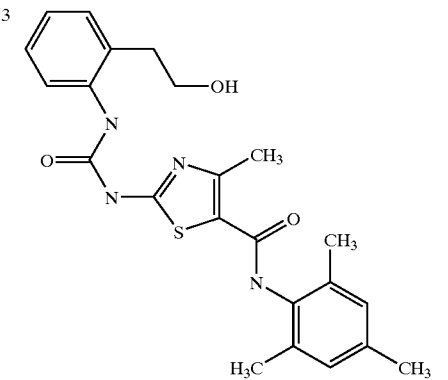 | 2-[[[[2-(2-Hydroxy-ethyl)phenyl]amino]car-bonyl]amino]-4-methyl-N-(2,4,6-trimethylphenyl)-5-thiazolecarboxamide | 4.02 |
| 254 | 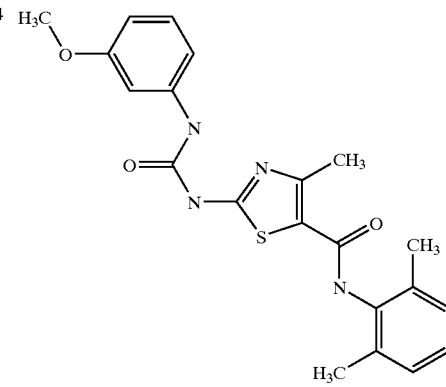 | 2-[[[(3-Methoxyphenyl)amino]carbonyl]amino]-4-methyl-N-(2,4,6-trimethylphenyl)-5-thiazolecarboxamide | 4.86 |
| 255 | 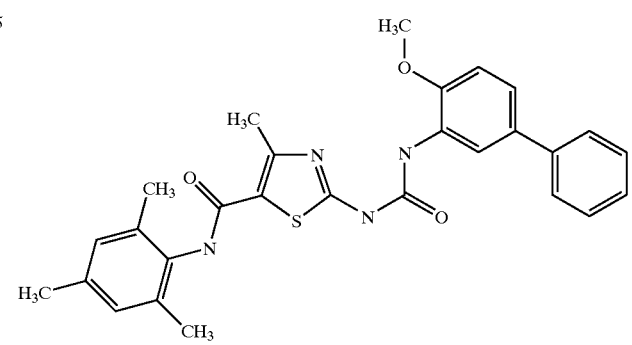 | 2-[[[(4-Methoxy[1,1'-biphenyl]-3-yl)amino]carbonyl]-amino]-4-methyl-N-(2,4,6-trimethylphenyl)-5-thiazolecarboxamide | 4.81 |

| EX. NO. | Compound Structure | Compound Name | HPLC Ret Time (min) |
|---|---|---|---|
| 256 | 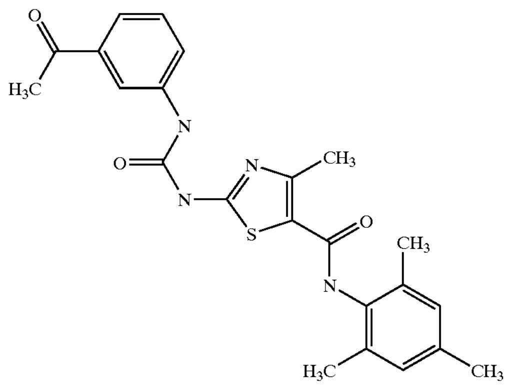 | 2-[[[(3-Acetylphenyl)amino]carbonyl]amino]-4-methyl-N-(2,4,6-trimethylphenyl)-5-thiazolecarboxamide | 4.12 |
| 257 | 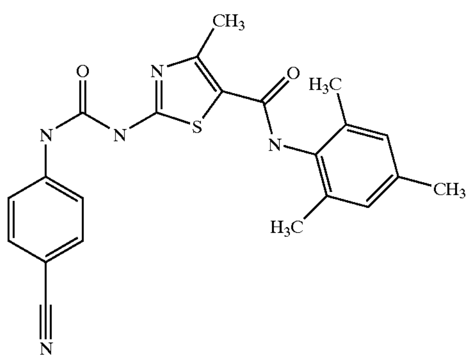 | 2-[[[(4-Cyanophenyl)amino]carbonyl]amino]-4-methyl-N-(2,4,6-trimethylphenyl)-5-thiazolecarboxamide | 4.15 |
| 258 | 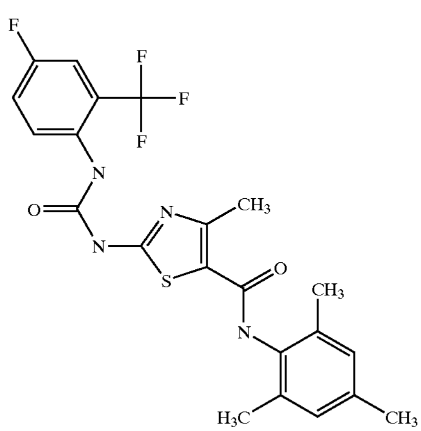 | 2-[[[[4-Fluoro-2-(trifluoromethyl)phenyl]amino]carbonyl]amino]-4-methyl-N-(2,4,6-trimethylphenyl)-5-thiazolecarboxamide | 4.99 |

-continued

| EX. NO. | Compound Structure | Compound Name | HPLC Ret Time (min) |
|---|---|---|---|
| 259 | 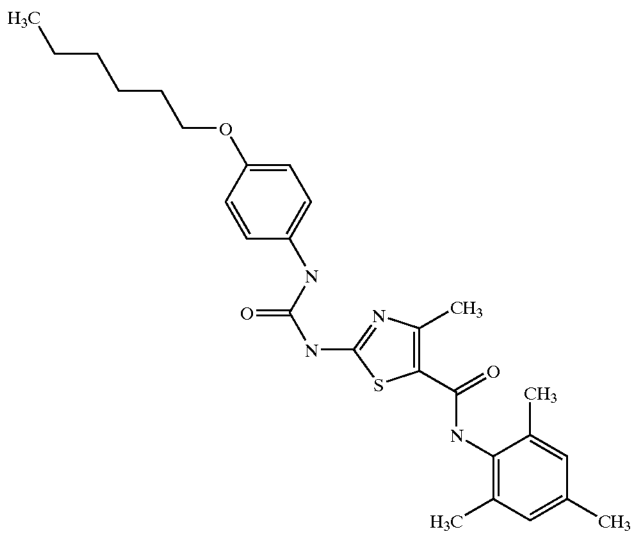 | 2-[[[(4-Hexyloxyphenyl)amino]carbonyl]amino]-4-methyl-N-(2,4,6-trimethylphenyl)-5-thiazolecarboxamide | 4.42 |
| 260 | 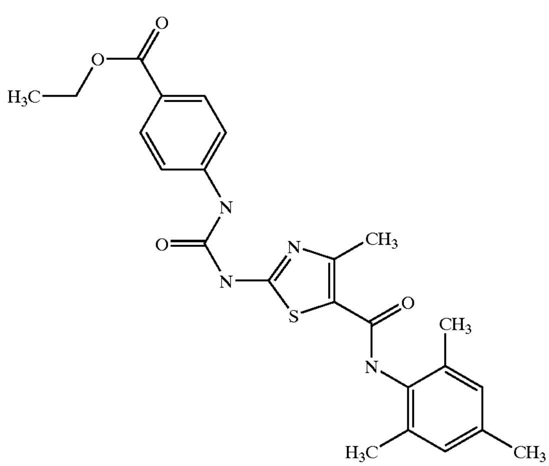 | 4-[[[[4-Methyl-5-[[(2,4,6-trimethyl-phenyl)amino]carbonyl]-2-thiazolyl]-amino]-carbonyl]amino]benzoic acid ethyl ester | 4.26 |

-continued

| EX. NO. | Compound Structure | Compound Name | HPLC Ret Time (min) |
|---|---|---|---|
| 261 | 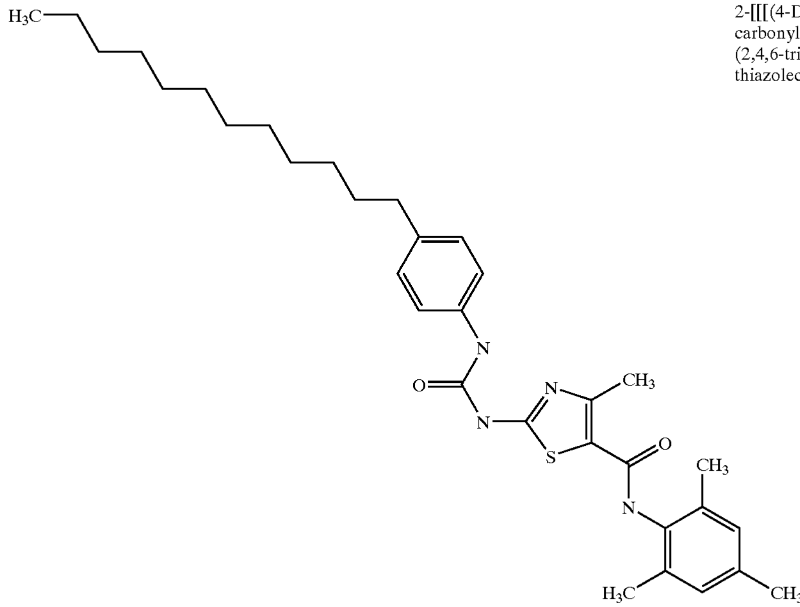 | 2-[[[(4-Decylphenyl)-amino]carbonyl]amino]-4-methyl-N-(2,4,6-trimethylphenyl)-5-thiazolecarboxamide | |
| 262 | 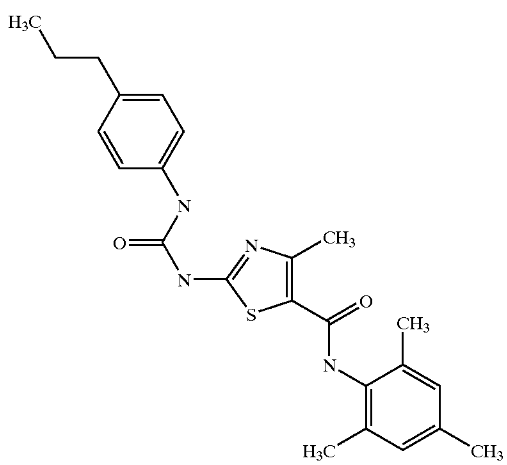 | 4-Methyl-2-[[[(4-propylphenyl)amino]-carbonyl]amino]-N-(2,4,6-trimethylphenyl)-5-thiazolecarboxamide | 4.71 |
| 263 | 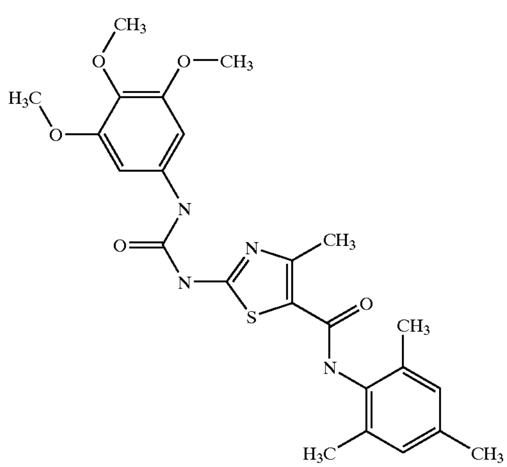 | 4-Methyl-2-[[[(3,4,5-trimethoxyphenyl)amino]-carbonyl]amino]-N-(2,4,6-trimethylphenyl)-5-thiazolecarboxamide | 4.67 |

-continued

| EX. NO. | Compound Structure | Compound Name | HPLC Ret Time (min) |
|---|---|---|---|
| 264 | 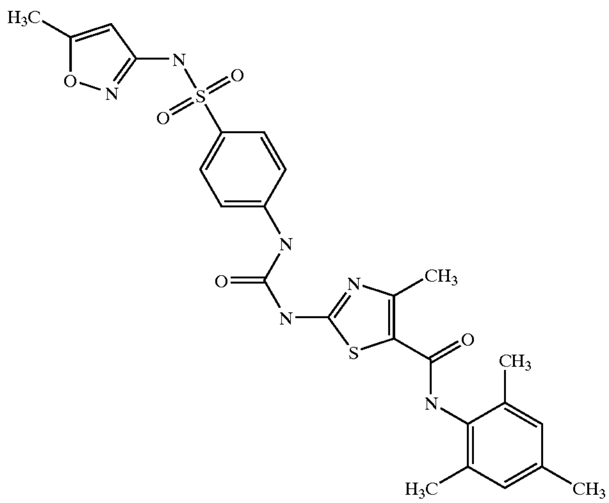 | 4-Methyl-2-[[[[4-[[(5-methyl-3-isoxazolyl)amino]sulfonyl]phenyl]-amino]carbonyl]amino]-N-(2,4,6-trimethylphenyl)-5-thiazolecarboxamide | 4.27 |
| 265 | 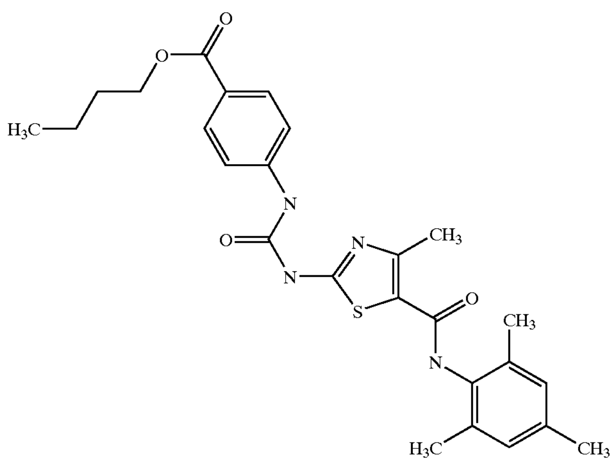 | 4-[[[[4-Methyl-5-[[(2,4,6-trimethyl phenyl)amino]carbonyl]-2-thiazolyl]-amino]carbonyl]-amino]-benzoic acid butyl ester | 4.75 |
| 266 | 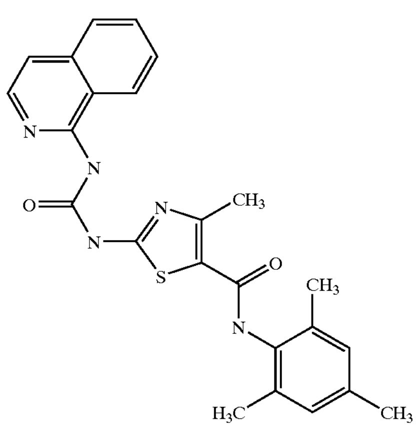 | 2-[[(1-Isoquinolinyl amino)carbonyl]amino]-4-methyl-N-(2,4,6-trimethylphenyl)-5-thiazolecarboxamide | 3.81 |

-continued

| EX. NO. | Compound Structure | Compound Name | HPLC Ret Time (min) |
|---|---|---|---|
| 267 | 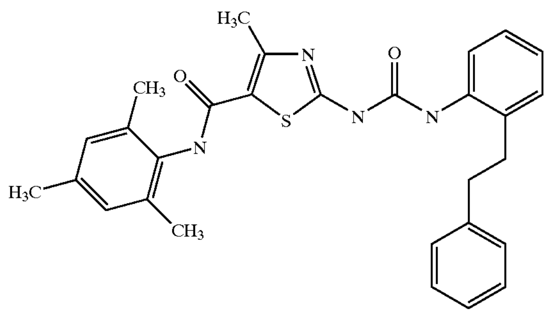 | 4-Methyl-2-[[[[2-[(phenyl-methyl)thio]-phenyl]amino]carbonyl]-amino]-N-(2,4,6-(trimethylphenyl)-5-thiazolecarboxamide | 4.42 |
| 268 | 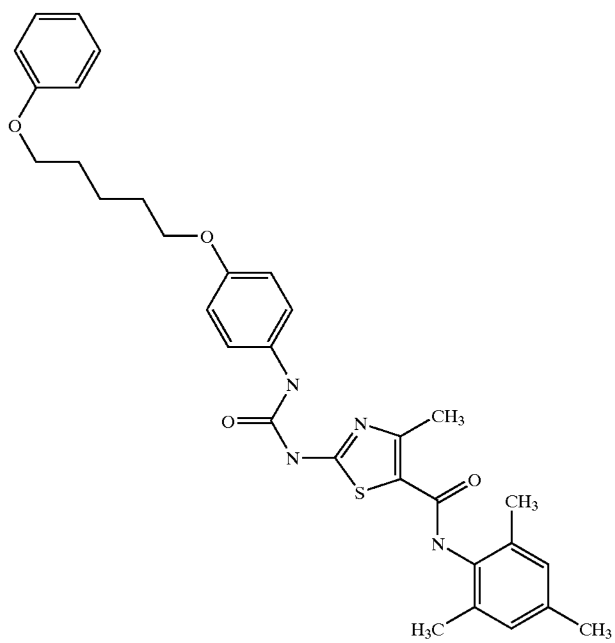 | 4-Methyl-2-[[[[4-[(5-phenoxypentyl)oxy]phenyl]amino]carbonyl]amino]-N-(2,4,6-trimethyl-phenyl)-5-thiazole-carboxamide | 4.96 |
| 269 | 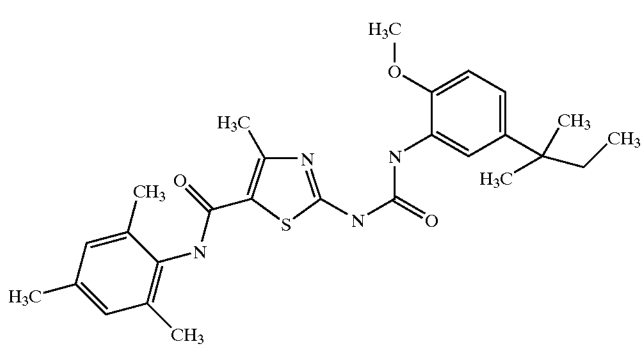 | 2-[[[[5-(1,1-Dimethyl-propyl)-2-methoxy-phenyl]amino]carbonyl]-amino]-4-methyl-N-(2,4,6-trimethylphenyl)-5-thiazolecarboxamide | 5.76 |

-continued

| EX. NO. | Compound Structure | Compound Name | HPLC Ret Time (min) |
|---|---|---|---|
| 270 | 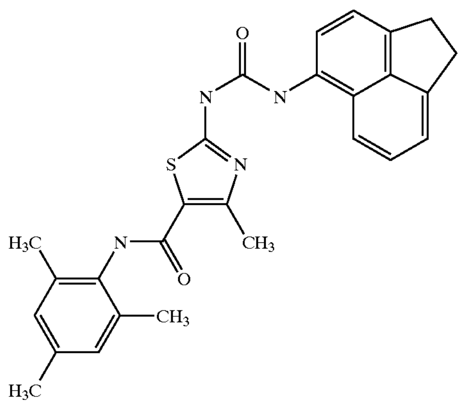 | 2-[[[(1,2-Dihydro-5-acenaphthylenyl)amino]carbonyl]amino]-4-methyl-N-(2,4,6-trimethyl-phenyl)-5-thiazole-carboxamide | 4.70 |
| 271 | 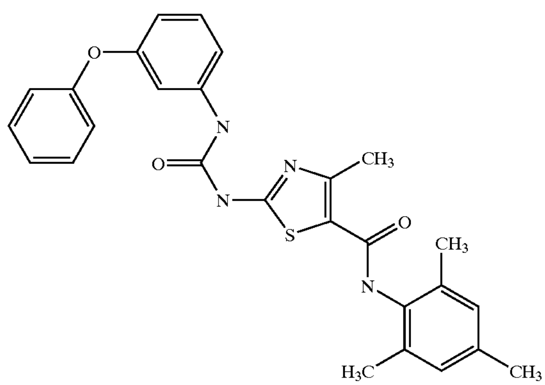 | 4-Methyl-2-[[[(3-phenoxyphenyl)amino]-carbonyl]amino]-N-(2,4,6-trimethylphenyl)-5-thiazolecarboxamide | 4.70 |
| 272 | 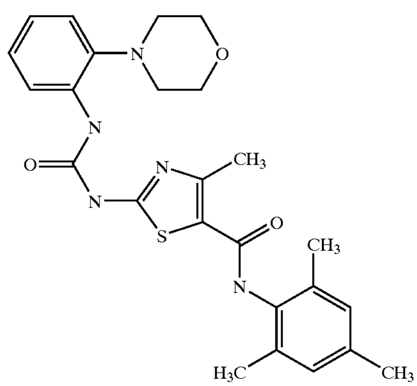 | 4-Methyl-2-[[[[2-(4-morpholinyl)phenyl]-amino]carbonyl]amino]-N-(2,4,6-trimethylphenyl)-5-thiazolecarboxamide | 5.01 |
| 273 | 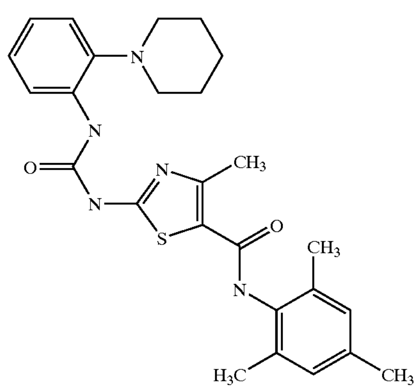 | 4-Methyl-2-[[[[2-(1-piperidinyl)phenyl]amino]carbonyl]amino]-N-(2,4,6-trimethylphenyl)-5-thiazolecarboxamide | 5.55 |

-continued

| EX. NO. | Compound Structure | Compound Name | HPLC Ret Time (min) |
|---|---|---|---|
| 274 | 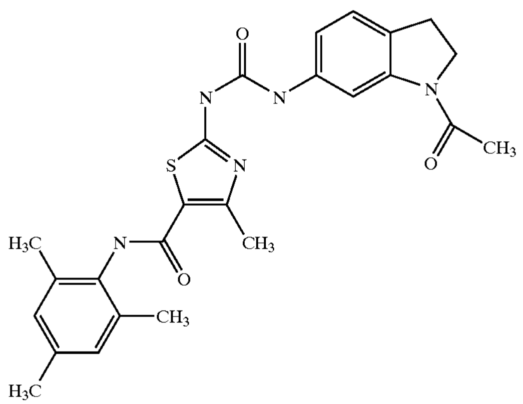 | 2-[[[(1-Acetyl-2,3-dihydro-1H-indol-6-yl)amino]carbonyl]amino]-4-methyl-N-(2,4,6-trimethylphenyl)-5-thiazolecarboxamide | 4.08 |
| 275 | 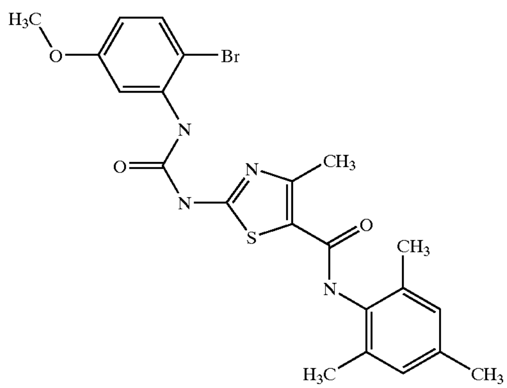 | 2-[[[(2-Bromo-5-methoxyphenyl)amino]carbonyl]amino]-4-methyl-N-(2,4,6-trimethylphenyl)-5-thiazolecarboxamide | 4.55 |
| 276 | 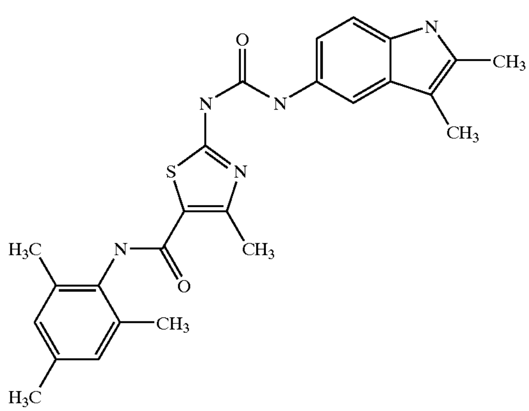 | 2-[[[(2,3-Dimethyl-1H-indol-5-yl)amino]carbonyl]amino]-4-methyl-N-(2,4,6-trimethyl phenyl)-5-thiazolecarboxamide | 4.30 |

-continued

| EX. NO. | Compound Structure | Compound Name | HPLC Ret Time (min) |
|---|---|---|---|
| 277 | 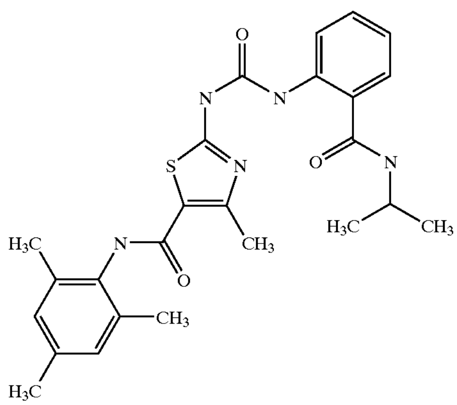 | 4-Methyl-2-[[[[2-[[(1-methylethyl)amino]carbonyl]phenyl]amino]carbonyl]amino]-N-(2,4,6-trimethylphenyl)-5-thiazolecarboxamide | 4.82 |
| 278 | 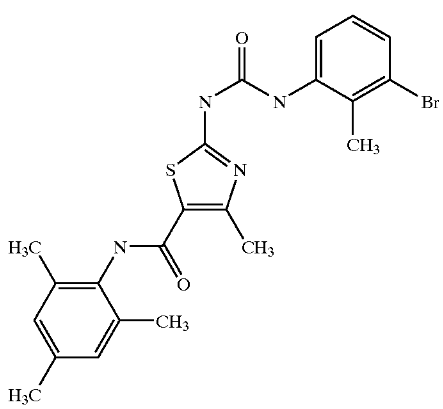 | 2-[[[(3-Bromo-2-methyl-phenyl)amino]carbonyl]-amino]-4-methyl-N-(2,4,6-trimethylphenyl)-5-thiazolecarboxamide | 4.60 |
| 279 | 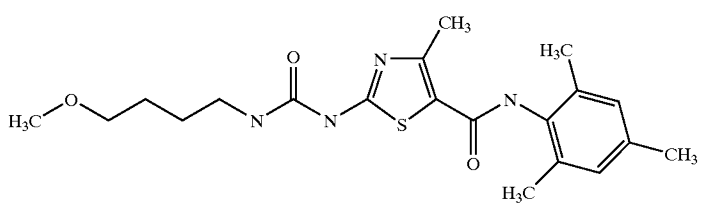 | 2-[[[(4-Methoxybutyl)amino]carbonyl]amino]-4-methyl-N-(2,4,6-trimethylphenyl)-5-thiazolecarboxamide | 7.62 |
| 280 | 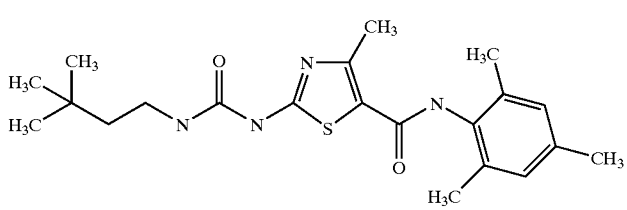 | 2-[[[(3,3-Dimethyl-butyl)amino]carbonyl]-amino]-4-methyl-N-(2,4,6-trimethylphenyl)-5-thiazolecarboxamide | 9.13 |
| 281 | 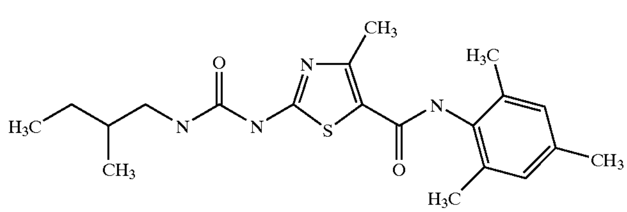 | 4-Methyl-2-[[[(2-methylbutyl)amino]-carbonyl]amino]-N-(2,4,6-trimethylphenyl)-5-thiazolecarboxamide | 8.90 |

-continued

| EX. NO. | Compound Structure | Compound Name | HPLC Ret Time (min) |
|---|---|---|---|
| 282 | 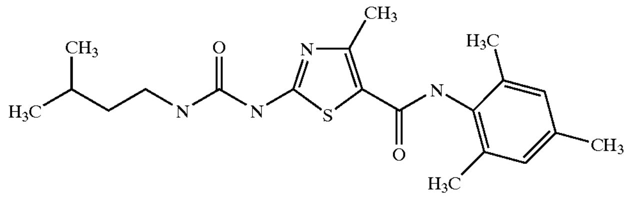 | 4-Methyl-2-[[[(3-methylbutyl)amino]carbonyl]amino]-N-(2,4,6-trimethylphenyl)-5-thiazolecarboxamide | 8.98 |
| 283 | 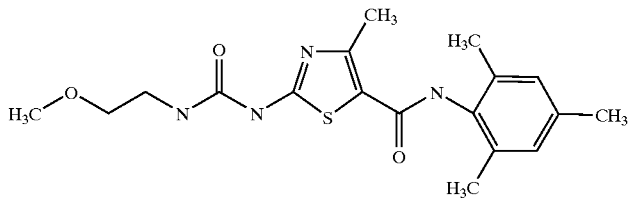 | 2-[[[(2-Methoxyethyl)-amino]carbonyl]amino]-4-methyl-N-(2,4,6-trimethylphenyl)-5-thiazolecarboxamide | 7.30 |
| 284 | 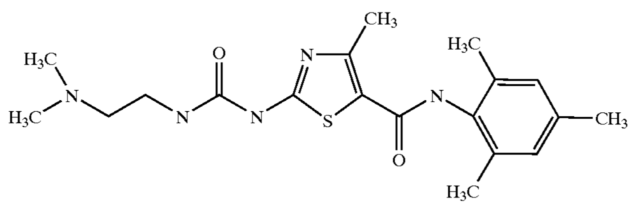 | 2-[[[[2-(Dimethyl-amino)ethyl]amino]-carbonyl]amino]-4-methyl-N-(2,4,6-trimethylphenyl)-5-thiazolecarboxamide | 5.73 |
| 285 | 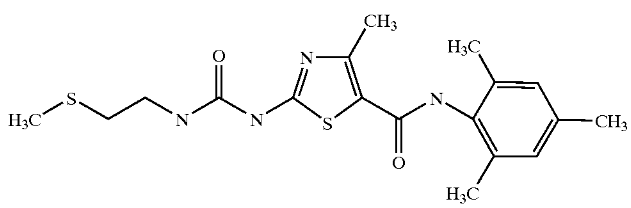 | 4-Methyl-2-[[[[2-(methylthio)ethyl]amino]carbonyl]amino]-N-(2,4,6-trimethylphenyl)-5-thiazolecarboxamide | 8.19 |

EXAMPLES 286 TO 311

General Procedure

Compounds 286 to 311 with the exception of compound 307 were prepared following the procedure described below.

A solution of 2-[[(Butylamino)carbonyl]amino]-4-methyl-5-thiazole carboxylic acid chloride (30 mg, 0.11 mmol), appropriate amine (0.12 mmol) in THF (1 mL) was treated with diisopropylethyl amine (22.6 µL, 0.13 mmol). The mixture was purged with argon and stirred mechanically in a vial for 22 h, diluted with dichloromethane (4 mL) and washed with 2 N aq. HCl solution (3×). The organic extract was separated, dried (Na$_2$SO$_4$), filtered and concentrated. The crude products were purified either by truturation with dichloromethane-ether (1:1) or by silica gel chromatography (elution solvent: 80% EtOAc in hexanes followed by EtOAc) or by automatic preparative HPLC (conditions: YMC S5 ODS A 20×100 mm Column, 10 min gradient starting from 30% solvent B (90% MeOH, 10% H$_2$O, 0.1% TFA) and 70% solvent A (10% MeOH, 90% H$_2$O, 0.1% TFA) to 100% solvent B, flow rate 20 mL/min, λ=220 nM. Compound 307 was prepared following the procedure described below. A suspension solution of 2-[[(Butylamino)carbonyl]amino]-4-methyl-5-thiazole carboxylic acid (100 mg, 0.36 mmol), and HATU (170 mg, 0.44 mmol) in DMF (3 mL) was treated with diisopropylethyl amine (62 mL, 0.44 mmol). The mixture was heated to 60° C. for 2 h, cooled, diluted with dichloromethane (12 mL), washed with 8M aq. Urea solution in 2 N aq. HCl (6 mL, 3×), 5% aq. KHCO$_3$ solution (6 mL, 3×), dried (Na$_2$SO$_4$), filtered and concentrated. The residue was triturated with EtOAc-ether to obtain the mixed anhydride intermediate (102 mg, 74%) as a white solid. A 1 M solution of sodium bis(trimethylsilylamide) in THF (170 µL, 0.17 mmol) was added dropwise to a stirred solution of 2,6-dichloroaniline (19.4 mg, 0.12 mmol) in THF (1 mL). After 15 min, the mixed anhydride intermediate (41.3 mg, 0.11 mmol) was added in one portion. A few drops of DMF was added and the solution was stirred for 16 h. Additional 1 M solution of sodium bis(trimethylsilylamide) (110 µL) was added and the mixture was stirred for additional 2 h. The mixture was diluted with dichloromethane (4 mL) and washed with 2 N aq. HCl solution (2 mL, 3×), satd. aq. KHCO$_3$ solution (3×), dried (Na$_2$SO$_4$), filtered and concentrated. The solid was washed with hexanes (2×) and the residue was chromatographed on a silica gel column. Elution with 80% EtOAc in hexanes followed by EtOAc afforded 307 (12 mg, 27%) as a light tan solid. "HPLC Ret Time" is the HPLC retention time under the following conditions: YMC S5 ODS 4.6×50 mm Ballastic Column, 4 min gradient starting from 100% solvent A (10% MeOH, 90% H$_2$O, 0.2% H$_3$PO$_4$) to 100% solvent B (90% MeOH, 10% H$_2$O, 0.2% H$_3$PO$_4$), flow rate 4 mL/min, λ=220 nM.

| EX. NO. | Compound Structure | Compound Name | HPLC Ret Time (min) |
|---|---|---|---|
| 286 | 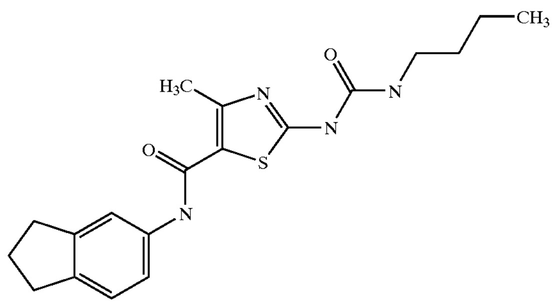 | 2-[[(Butylamino)carbonyl]amino]-N-(2,3-dihydro-1H-inden-5-yl)-4-methyl-5-thiazolecarboxamide | 4.20 |
| 287 | 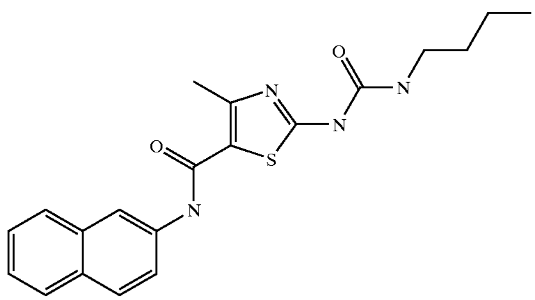 | 2-[[(Butylamino)carbonyl]amino]-N-2-naphthalenyl-4-methyl-5-thiazolecarboxamide | 4.20 |
| 288 | 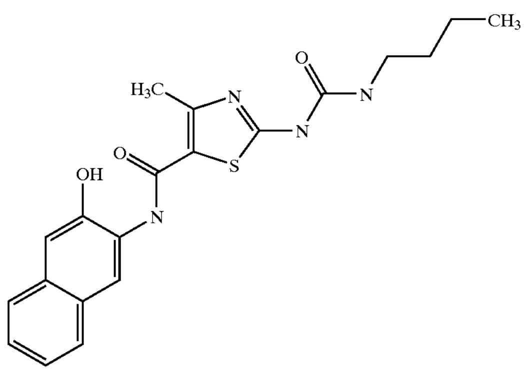 | 2-[[(Butylamino)carbonyl]amino]-N-(3-hydroxy-2-naphthalenyl)-4-methyl-5-thiazolecarboxamide | 4.24 |
| 289 | 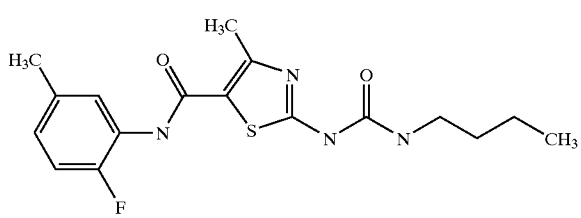 | 2-[[(Butylamino)carbonyl]amino]-N-(2-fluoro-5-methylphenyl)-4-methyl-5-thiazolecarboxamide | 3.95 |
| 290 | 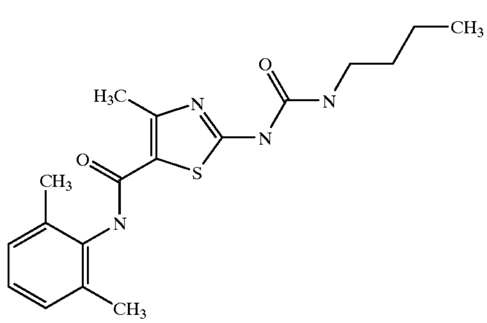 | 2-[[(Butylamino)carbonyl]amino]-N-(2,6-dimethylphenyl)-4-methyl-5-thiazolecarboxamide | 3.78 |

-continued

| EX. NO. | Compound Structure | Compound Name | HPLC Ret Time (min) |
|---|---|---|---|
| 291 | 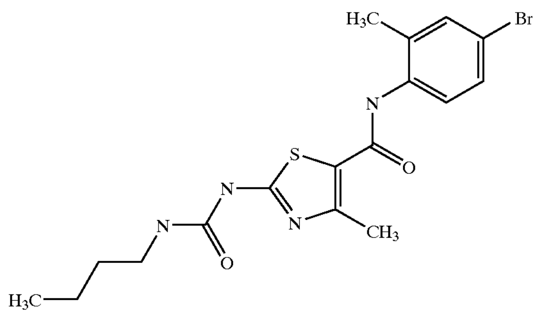 | N-(4-Bromo-2-methylphenyl)-2-[[(butylamino)carbonyl]amino]-4-methyl-5-thiazolecarboxamide | 4.12 |
| 292 | 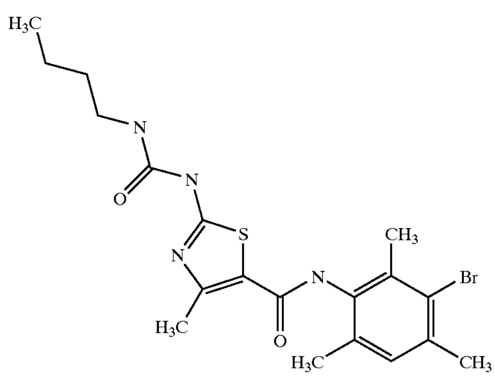 | N-(3-Bromo-2,4,6-trimethylphenyl)-2-[[(butylamino)carbonyl]amino]-4-methyl-5-thiazolecarboxamide | 4.28 |
| 293 | 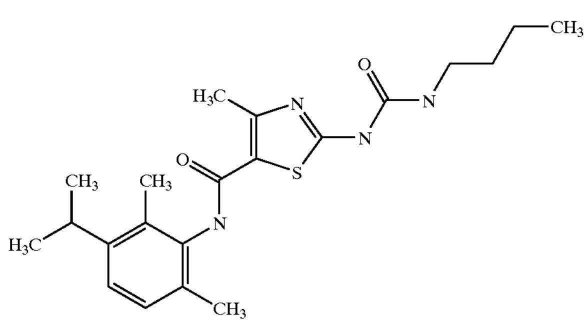 | 2-[[(Butylamino)carbonyl]amino]-N-[2,6-dimethyl-3-(1-methylethyl)phenyl]-4-methyl-5-thiazolecarboxamide | 4.28 |
| 294 | 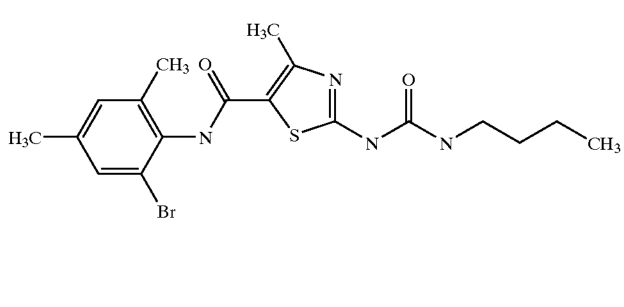 | N-(2-Bromo-4,6-dimethylphenyl)-2-[[(butylamino)carbonyl]amino]-4-methyl-5-thiazolecarboxamide | 4.00 |

-continued

| EX. NO. | Compound Structure | Compound Name | HPLC Ret Time (min) |
|---|---|---|---|
| 295 | 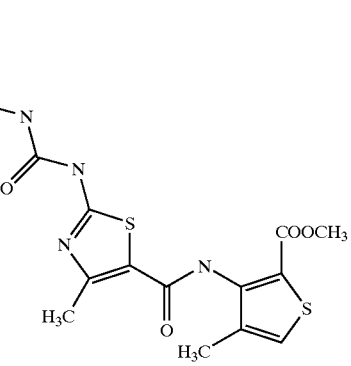 | 3-[[[2-[[(Butylamino) carbonyl]amino]- 4-methyl-5-thia- zolyl]-carbonyl] amino]-4- methyl-2-thiophene- carboxylic acid methyl ester | 3.83 |
| 296 | 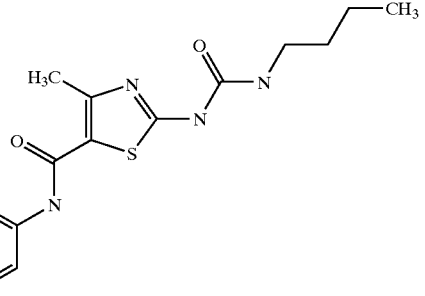 | 2-[[(Butylamino) carbonyl]amino]-4- methyl-N-(2-methyl- 6-quinolinyl)-5- thiazolecarboxamide | 2.98 |
| 297 | 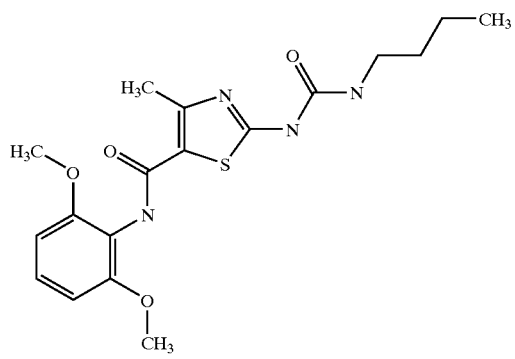 | 2-[[(Butylamino) carbonyl]amino]-N- (2,6- dimethoxyphenyl)-4- methyl-5- thiazolecarboxamide | 3.39 |
| 298 | 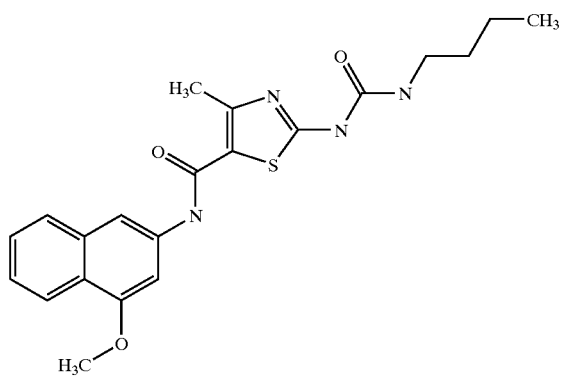 | 2-[[(Butylamino) carbonyl]amino]-N- (4- methoxy-2- naphthalenyl)-4- methyl-5- thiazolecarboxamide | 4.31 |

| EX. NO. | Compound Structure | Compound Name | HPLC Ret Time (min) |
|---|---|---|---|
| 299 | 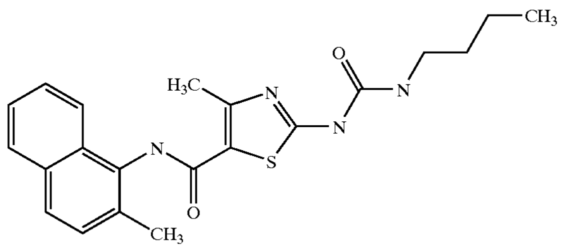 | 2-[[(Butylamino)carbonyl]amino]-N-(2-methyl-1-naphthalenyl)-4-methyl-5-thiazolecarboxamide | 3.92 |
| 300 | 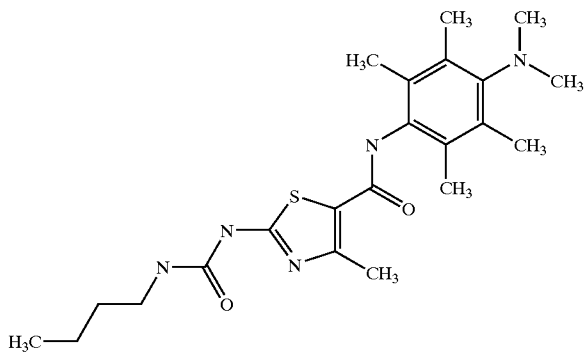 | 2-[[(Butylamino)carbonyl]amino]-N-[4-(dimethylamino)-2,3,5,6-tetramethylphenyl]-4-methyl-5-thiazolecarboxamide | 3.14 |
| 301 | 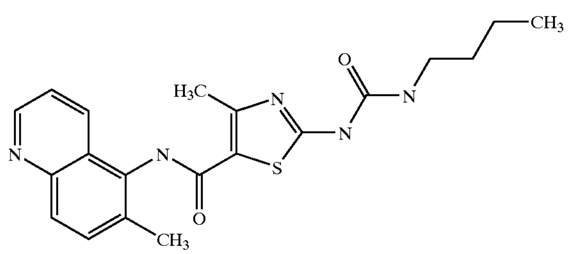 | 2-[[(Butylamino)carbonyl]amino]-N-(6-methyl-5-quinolinyl)-4-methyl-5-thiazolecarboxamide | 3.13 |
| 302 | 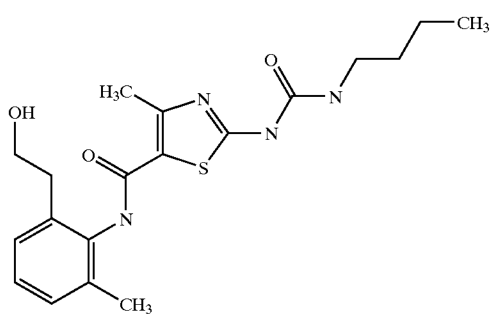 | 2-[[(Butylamino)carbonyl]amino]-N-[2-(2-hydroxyethyl)-6-methylphenyl]-4-methyl-5-thiazolecarboxamide | 3.50 |
| 303 | 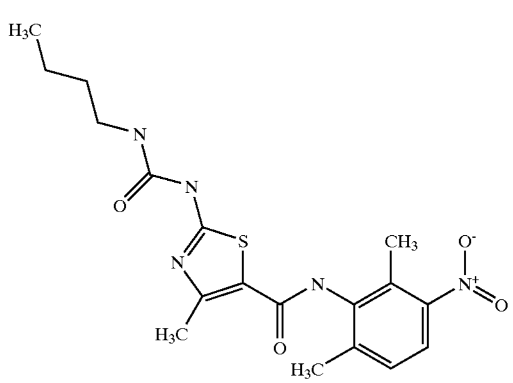 | 2-[[(Butylamino)carbonyl]amino]-N-(2,6-dimethyl-3-nitrophenyl)-4-methyl-5-thiazolecarboxamide | 3.75 |

-continued

| EX. NO. | Compound Structure | Compound Name | HPLC Ret Time (min) |
|---|---|---|---|
| 304 | 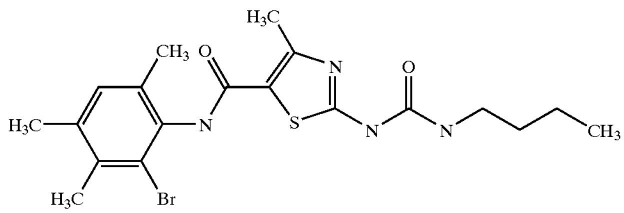 | N-(2-Bromo-3,4,6-trimethylphenyl)-2-[[(butylamino)carbonyl]amino]-4-methyl-5-thiazolecarboxamide | 4.12 |
| 305 | 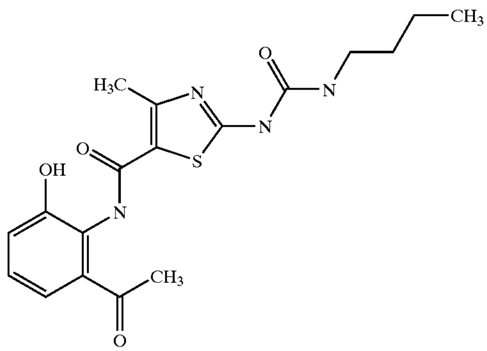 | N-(2-Acetyl-6-hydroxyphenyl)-2-[[(butylamino)carbonyl]amino]-4-methyl-5-thiazolecarboxamide | 3.75 |
| 306 | 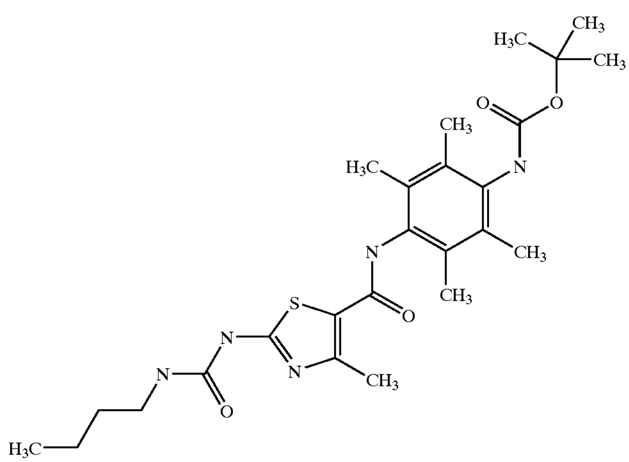 | [4-[[[2-[[(Butylamino)carbonyl]amino]-4-methyl-5-thiazolyl]carbonyl]amino]-2,3,5,6-tetramethylphenyl]carbamic acid 1,1-dimethylethyl ester | 4.10 |
| 307 | 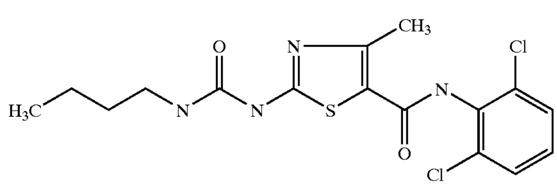 | 2-[[(Butylamino)carbonyl]amino]-N-(2,6-dichlorophenyl)-4-methyl-5-thiazolecarboxamide | 4.42 |
| 308 | 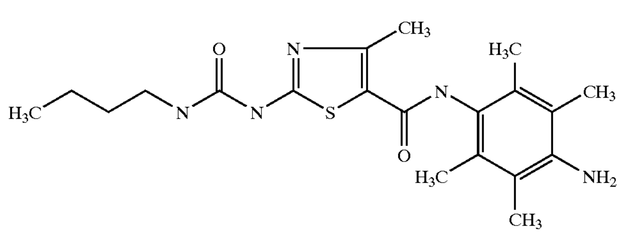 | N-(4-Amino-2,3,5,6-tetramethylphenyl)-2-[[(butylamino)carbonyl]amino]-4-methyl-5-thiazolecarboxamide | 3.15 |

-continued

| EX. NO. | Compound Structure | Compound Name | HPLC Ret Time (min) |
|---|---|---|---|
| 309 | 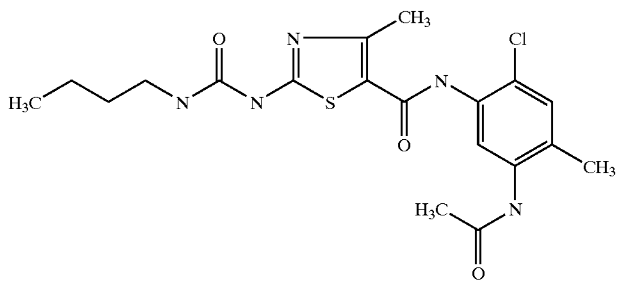 | N-[5-(Acetylamino)-2,4-dimethylphenyl]-2-[[(butylamino)carbonyl]amino]-4-methyl-5-thiazolecarboxamide | 3.52 |
| 310 | 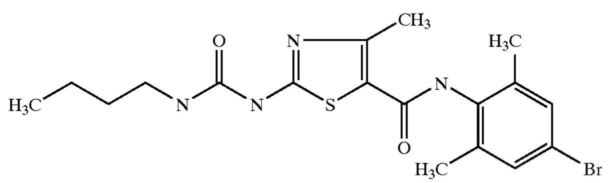 | N-(4-Bromo-2,6-dimethylphenyl)-2-[[(butylamino)carbonyl]amino]-4-methyl-5-thiazolecarboxamide | 4.93 |
| 311 | 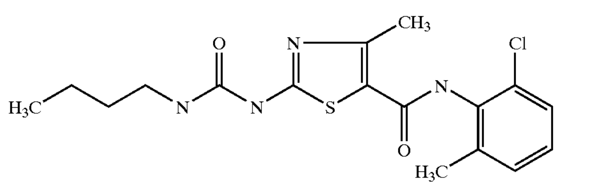 | 2-[[(Butylamino)carbonyl]amino]-N-(2-chloro-6-methylphenyl)-4-methyl-5-thiazolecarboxamide | 4.51 |

EXAMPLE 312

Preparation of 4-Methyl-2-[(methylsulfonyl)amino]-N-(2,4,6-trimethylphenyl)-5-thiazolecarboxamide

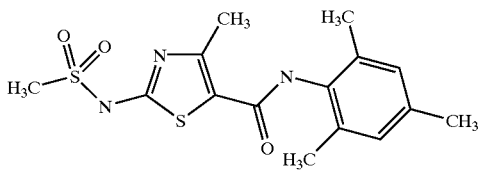

A. Ethyl-2-[(methylsulfonyl)amino]-4-methyl-thiazole-5-carboxylate

A stirred solution of ethyl-2-amino-4-methyl-thiazole-5-carboxylate (558 mg, 3 mmol) in dichloromethane (15 mL) and pyridine (5 mL) was treated with methanesulfonyl chloride (687 mg, 6 mmol) at rt overnight. The solution was diluted with dichloromethane (50 mL) and washed with 2N aq. HCl solution (15 mL, 3×), dried (MgSO₄), filtered and concentrated. The crude residue was diluted with ether (25 mL) and the solid was filtered, washed with 1:1 ether:hexane mixture (10 mL, 3×), and dried in vacuo to obtain the title compound (687 mg, 87%) as an off-white solid.

B. 2-[(Methylsulfonyl)amino]-4-methyl-thiazole-5-carboxylic acid

A stirred solution of Ethyl-2-[(methylsulfonyl)amino]-4-methyl-thiazole-5-carboxylate (300 mg, 1.14 mmol) in methanol (9 mL) was treated with a 1N NaOH solution (28.4 mL, 28.4 mmol). The mixture was stirred at rt overnight. The solution was cooled to 0° C. and acidified with 6N aq. HCl solution to pH 1. The solution was extracted with dichloromethane-chloroform mixture. The organic extract was dried (MgSO4), filtered and concentrated in vacuo to obtain the title acid (148 mg, 55%).

C. 4-Methyl-2-[(methylsulfonyl)amino]-N-(2,4,6-trimethylphenyl)-5-thiazolecarboxamide Diisopropylethylamine (87 µL, 0.5 mmol) was added to a solution of 312 B (99 mg, 0.42 mmol), 2,4,6-trimethylaniline (68 µL, 0.5 mmol), and [O-(7-azabenzotriazol-1-yl)-1,1,3,3-tetramethyluronium] hexafluorophosphate (HATU, 191 mg, 0.5 mmol) in DMF (3 mL). The mixture was stirred at rt overnight, diluted with EtOAc and washed with 0.5 N aq. HCl solution (15 mL), 10% aq. LiCl solution (25 mL, 3×), water (930 mL, 2×), brine, dried (MgSO₄), filtered and concentrated. The residue was chromatographed on a silica gel column and eluted with 50% EtOAc in hexanes, followed by 75% EtOAc in hexanes and 2% MeOH in EtOAc to obtain the title compound (19 mg, 13%) as a white solid.

EXAMPLE 313

Preparation of 4-Methyl-2-[[(phenylamino)thiocarbonyliamino)-N-(2,4,6-trimethylphenyl)-5-thiazolecarboxamide

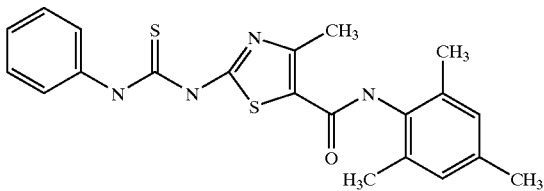

A solution of 2 (45 mg, 0.16 mmol) and phenylisothiocyanate (43 mg, 0.32 mmol) in pyridine (2 mL) was heated to 80° C. for 20 h. The mixture was cooled, diluted with dichloromethane-THF mixture (80 mL, 3:1) and washed with 2 N aq. HCl solution (15 mL, 2×). The organic extract was dried (MgSO$_4$), filtered and concentrated. The residue was diluted with EtOAc (20 mL) and the solid was filtered, washed with ether (10 mL, 3×), and dried in vacuo to obtain the title compound (35 mg, 52%) as an off-white solid.

EXAMPLE 314

Preparation of 2-[[(Ethylamino)carbonyl]amino]-4-methyl-N-(2,4,6-trimethylphenyl)-5-thiazolecarboxamide

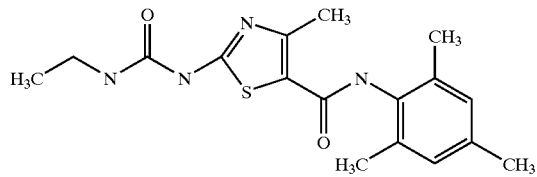

Compound 314 was prepared by an analogous method as that of compounds 171–180, using ethylisocyanate to give the title compound 314 as a white solid (65%).

EXAMPLE 315

Preparation of N-(2-Chloro-6-methylphenyl)-2-[(cyclopropylcarbonyl)amino]-5-thiazolecarboxamide

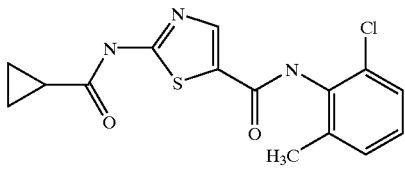

A. Ethyl-2-tert-butoxycarbonyloxyamino-4-methyl-thiazole-5-carboxylate

A suspension of ethyl-2-amino-thiazole-5-carboxylate (972 mg, 6 mmol, B. Plouvler, C. Bailly, R. Houssin, j-P. Henlchart Heterocyles 32(4), 693–701, 1991 and H. J. Becker, J. de Jonge Rec. Trav. Chim, 61, 463, 1942), di-t-butyldicarbonate (1.94 g, 9 mmol) and 4-dimethylaminopyridine (73 mg, 0.6 mmol) in dry tetrahydrofuran (75 mL) was stirred under nitrogen for 24 h. The solvent was evaporated in vacuo. The residue was suspended in ether (50 mL). The solid was washed with ether (10 mL, 3×), and dried in vacuo to obtain the title compound (1.1 g, 70%).

B. 2-tert-butoxycarbonyloxyamino-thiazole-5-carboxylic acid

A stirred solution of ethyl-2-tert-butoxycarbonyloxyamino-4-methyl-thiazole-5-carboxylate (1.1 g, 4.2 mmol) in tetrahydrofuran-methanol (80 mL, 1:1) was treated with a 6N aq. NaOH solution (20 mL, 120 mmol). The mixture was stirred at rt for 24 h. Most of THF and methanol were removed by distillation under reduced pressure and the aq. Solution was acidified with 6 N aq. HCl solution (22 mL). The precipitated solid was filtered, washed with water and ether, air dried followed by drying in vacuo to obtain the title acid (940 mg, 96%) as an off-white solid.

C. [5-[[(2-chloro-6-methylphenyl)amino]carbonyl]-2-thiazolyl]carbamic acid, 1,1-dimethylethyl ester A 2 M solution of oxalyl chloride in dichloromethane (1 mL, 2 mmol) was added dropwise to a stirred solution of 2-tert-butoxycarbonyloxyamino-thiazole-5-carboxylic acid (234 mg, 1 mmol) in THF (10 mL) and N,N-dimethyl formamide (few drops). The solution was stirred at rt for 4 h. The solvent was evaporated under reduced pressure, and in vacuo to obtain the crude acid chloride.

2-Chloro-6-methyl aniline (212 mg, 1.5 mmol) was added dropwise to a stirred solution of crude 2-tert-butoxycarbonyloxyamino-thiazole-5-carboxylic acid chloride (1 mmol) in dichloromethane (10 mL) at 0° C. Diisopropylethylamine (516 mg, 4 mmol) was added. The solution was allowed to warm to rt and stirred for 24 h, diluted with dichloromethane (60 mL) and washed with 2 N aq. HCl solution (15 mL). The organic extract was dried (MgSO$_4$), filtered and concentrated. The residue was diluted with EtOAc-ether (25 mL, 1:4) and the solid was filtered and washed with ether (5 mL, 4×), and dried in vacuo to obtain the title compound (175 mg, 48%) as a tan solid.

D. 2-Amino-N-(2-chloro-6-methylphenyl)-5-thiazolecarboxamide

Compound 315D was prepared by an analogous method as that of 2, except using compound 315C to give the title compound 315D as a tan solid.

E. 2-[(Cyclopropylcarbonyl)amino]-N-(2-chloro-6-methylphenyl)-5-thiazolecarboxamide A solution of 315D (50.6 mg, 0.19 mmol) and cyclopropanecarboxylic acid anhydride (302 mg, 1.96 mmol) in dioxane (2 mL) was heated to 93° C. overnight. The mixture was concentrated in vacuo, diluted with EtOAc and washed with satd. aq. KHCO$_3$ solution (2×). The organic extract was dried (Na$_2$SO$_4$), filtered and concentrated. The residue was triturated with ether to obtain the title compound (11 mg, 17%) as a white solid.

EXAMPLE 316

Preparation of 2-[[[(1,1-Dimethylethyl)amino]carbonyl]amino]-N-(2-chloro-6-methylphenyl)-5-thiazolecarboxamide

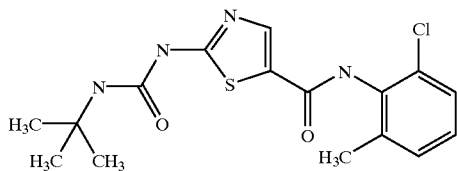

Sodium hydride (19.2 mg, 0.8 mmol) was added to a solution of 315D (48.3 mg, 0.18 mmol) and t-butylisocyanate (41 μL, 0.36 mmol) in THF (5 mL) at 0° C. After 1 h, the mixture was diluted with EtOAc and washed with cold satd. aq. ammonium chloride solution. The aqueous layer was separated and extracted with EtOAc. The EtOAc extracts were combined, dried (Na$_2$SO$_4$), filtered and concentrated. The residue was purified by automatic preparative HPLC (conditions: YMC S5 ODS A 20×100 mm Column, 10 min gradient starting from 10% solvent B (90% MeOH, 10% H2O, 0.1% TFA) and 90% solvent A (10% MeOH, 90% H$_2$O, 0.1% TFA) to 100% solvent B, flow rate 20 mL/min, λ=220 nM to obtain the title compound (18 mg, 28%) as an off-white solid.

EXAMPLE 317

Preparation of 2-[[(1,1-Dimethylethoxy)carbonyl]amino]-4-methyl-N-(2,4,6-trimethylphenyl)-5-thiazoleacetamide

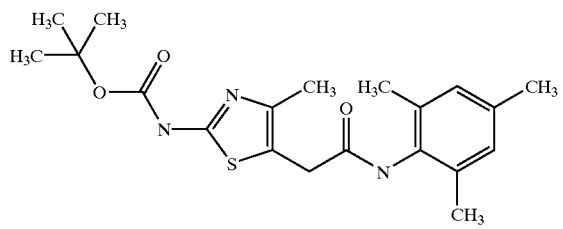

Compound 317 was prepared by an analogous method as that of 1, except using methyl-2-amino-4-methyl-thiazole-5-acetate to give the title compound 317 as an off-white solid.

EXAMPLE 318

Preparation of 2-Amino-4-methyl-N-(2,4,6-trimethylphenyl)-5-thiazoleacetamide

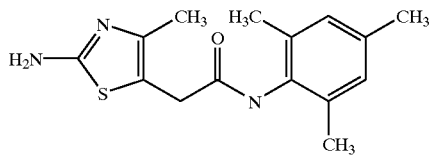

Compound 318 was prepared by an analogous method as that of 2, except using 317 to give the title compound 318 as a light brown solid.

EXAMPLE 319

Preparation of N-(2-Chloro-6-methylphenyl)-2-[(4,6-dimethyl-2-pyridinyl)amino]-5-thiazolecarboxamide

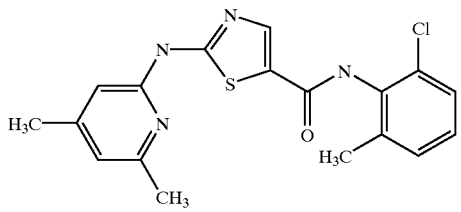

A. 2-Bromo-N-(2-chloro-6-methylphenyl)-5-thiazolecarboxamide

A solution of copper (II) bromide (2.68 g, 12 mmol) in acetonitrile (50 mL) was purged with nitrogen and cooled to 0° C. t-Butyl nitrite (2 mL, 15 mmol) was added, followed by a solution of compound 315D (2.68 g, 10 mmol) in acetonitrile (50 mL), The mixture was stirred at rt overnight and concentrated in vacuo. The residue was dissolved in EtOAc, washed with satd. aq. NaHCO₃ solution and the precipitate was removed by filtration. The organic extract was dried (Na₂SO₄), filtered and concentrated. The residue was crystallized from EtOAc/ether/hexanes mixture to obtain the title compound (1.68 g, 51%) as a yellow solid.

B. N-(2-Chloro-6-methylphenyl)-2-[(4.6-dimethyl-2-pyridinyl)amino]-5-thiazolecarboxamide 95% Sodium hydride (15 mg) was added to a mixture of 319A (25 mg, 0.075 mmol) and 4,6-dimethyl-2-aminopyridine (37 mg, 0.302 mmol) in THF (1 mL). The mixture was heated to 60° C. overnight, cooled to rt and diluted with satd. aq. ammonium chloride solution. The mixture was extracted with EtOAc (2x). Organic extracts were combined, washed with water and dried (Na₂SO₄), filtered and concentrated. The residue was triturated with ether to obtain the title compound (17.5 mg, 63%) as a tan solid.

EXAMPLE 320

Preparation of N-(2-Chloro-6-methylphenyl)-2-[(4-ethyl-2-pyridinyl)amino]-5-thiazolecarboxamide

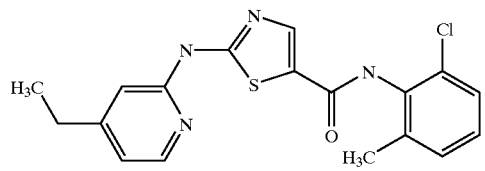

Compound 320 was prepared by an analogous method as that of 319B, except using 4-ethyl-2-aminopyridine to give the title compound 320.

EXAMPLE 321

Preparation of N-(2-Chloro-6-methylphenyl)-2-[(2,6-dimethyl-4-pyrimidinyl)amino]-5-thiazolecarboxamide

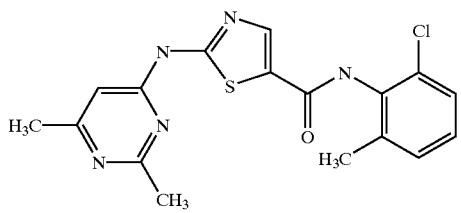

Compound 321 was prepared by an analogous method as that of 319B, except using 2,6-dimethyl-4-aminopyrimidine to give the title compound 321.

EXAMPLE 322

Preparation of N-(2-Chloro-6-methylphenyl)-2-(3-pyridazinylamino)-5-thiazolecarboxamide

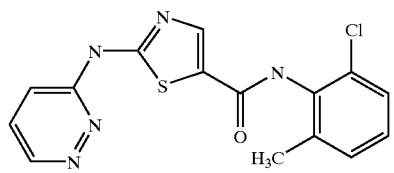

Compound 322 was prepared by an analogous method as that of 319B, except using 3-aminopyridazine to give the title compound 322.

EXAMPLES 323 TO 335

General Procedure

Compounds 323 to 335 were prepared following the procedure described below. Diisopropylethyl amine (60 µL, 0.34 mmol) was added to a mixture of amine 144 (31 mg, 0.11 mmol), appropriate carboxylic acid (0.13 mmol), 1-hydroxy-7-azabenzotriazole (19.5 mg, 0.14 mmol), and ethyl-3-(3-dimethylamino)-propyl carbodiimide hydrochloride (26.8 mg, 0.14 mmol) in THF (0.4 mL). The mixture was heated in a sealed tube under argon at 50° C. for 24 h. The reaction mixture was diluted with dichloromethane (4 mL) and washed with 1 N aq. HCl solution. The dichloromethane solution was passed through a Varian Mega Bond Elut SCX cation exchange column (prewashed with methanol and equilibrated with acetonitrile-methanol (4:1). The column was eluted sequentially with acetonitrile-methanol (4:1), methanol-2M methanolic ammonia (4:1). Fractions containing the product were combined and concentrated in vacuo. "HPLC Ret Time" is the HPLC retention time under the following conditions: YMC S5 ODS 4.6×50 mm Ballastic Column, 4 min gradient starting from 100% solvent A (10% MeOH, 90% $H_2O$, 0.2% $H_3PO_4$) to 100% solvent B (90% MeOH, 10% H2O, 0.2% H3PO4), flow rate 4 ml/min, λ=220 nM.

| EX. NO. | Compound Structure | Compound Name | HPLC Ret Time (min) |
|---|---|---|---|
| 323 | 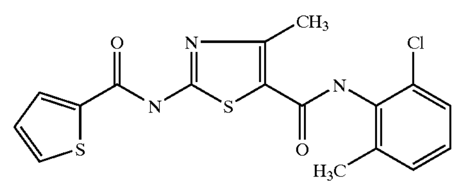 | N-(2-Chloro-6-methylphenyl)-4-methyl-2-[(2-thienyl-carbonyl)amino]-5-thiazolecarboxamide | 3.70 |
| 324 | 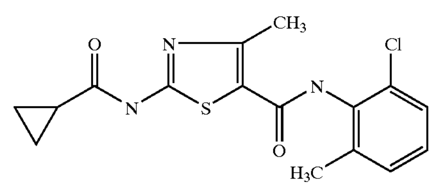 | N-(2-Chloro-6-methylphenyl)-2-[(cyclopropylcarbonyl)amino]-4-methyl-5-thiazolecarboxamide | 3.41 |
| 325 | 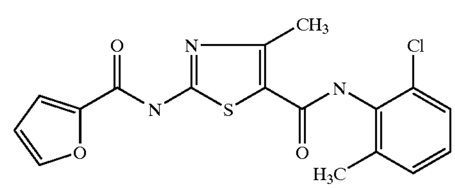 | N-(2-Chloro-6-methylphenyl)-4-methyl-2-[(2-furanyl-carbonyl)amino]-5-thiazolecarboxamide | 3.49 |
| 326 | 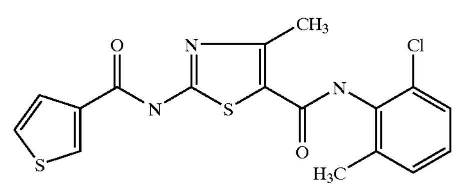 | N-(2-Chloro-6-methylphenyl)-4-methyl-2-[(3-thienylcarbonyl)amino]-5-thiazolecarboxamide | 3.71 |
| 327 | 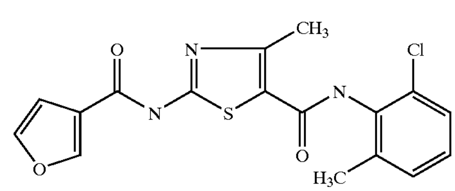 | N-(2-Chloro-6-methylphenyl)-4-methyl-2-[(3-furanylcarbonyl)amino]-5-thiazolecarboxamide | 3.57 |
| 328 | 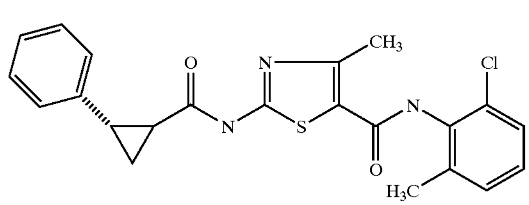 | trans-N-(2-Chloro-6-methylphenyl)-4-methyl-2-[[(2-phenylcyclopropyl)carbonyl]amino]-5-thiazolecarboxamide | 4.09 |

-continued

| EX. NO. | Compound Structure | Compound Name | HPLC Ret Time (min) |
|---|---|---|---|
| 329 | 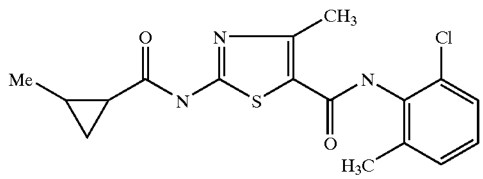 | N-(2-Chloro-6-methylphenyl)-4-methyl-2-[[(2-methylcyclopropyl)carbonyl]amino]-5-thiazolecarboxamide | 3.65 |
| 330 | 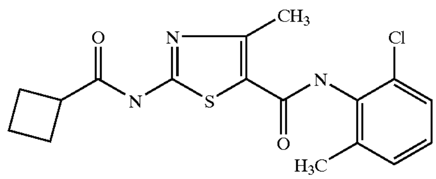 | N-(2-Chloro-6-methylphenyl)-2-[(cyclobutylcarbonyl)amino]-4-methyl-5-thiazolecarboxamide | 3.63 |
| 331 | 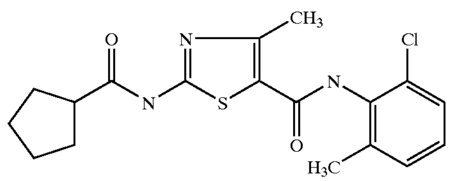 | N N(2-Chloro-6-methylphenyl)-2-[(cyclopentylcarbonyl)amino]-4-methyl-5-thiazolecarboxamide | 3.82 |
| 332 | 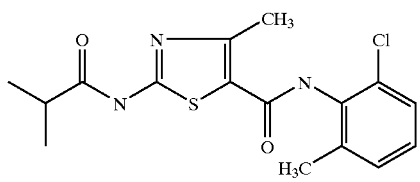 | N-(2-Chloro-6-methylphenyl)-4-methyl-2-[(2-methyl-1-oxopropyl)amino]-5-thiazolecarboxamide | 3.50 |
| 333 | 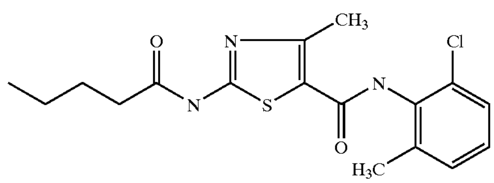 | N-(2-Chloro-6-methylphenyl)-4-methyl-2-[(1-oxopentyl)amino]-5-thiazolecarboxamide | 3.79 |
| 334 | 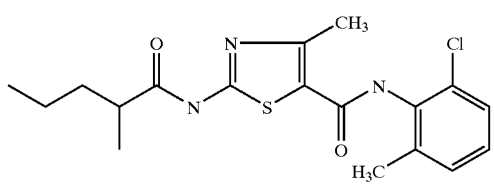 | N-(2-Chloro-6-methylphenyl)-4-methyl-2-[(2-methyl-1-oxopentyl)amino]-5-thiazolecarboxamide | 3.90 |
| 335 | 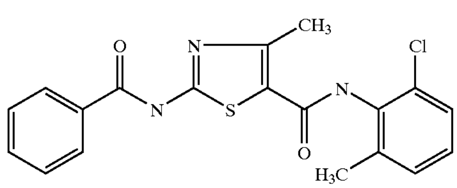 | 2-(Benzoylamino)-N-(2-chloro-6-methylphenyl)-4-methyl-5-thiazolecarboxamide | 3.79 |

EXAMPLES 336 TO 362

General Procedure

Compounds 336 to 362 were prepared by an analogous method as that of 323–335, except using 315D in place of 144. The crude products were purified by automatic preparative HPLC (conditions: YMC S5 ODS A 20×100 mm Column, 10 min gradient starting from 10% solvent B (90% MeOH, 10% H2O, 0.1% TFA) and 90% solvent A (10% MeOH, 90% H2O, 0.1% TFA) to 100% solvent B, flow rate 20 mL/min, λ=220 nM to obtain the title compounds 336–362.

"HPLC Ret Time" is the HPLC retention time under the following conditions: YMC S5 ODS 4.6×50 mm Ballastic Column, 4 min gradient starting from 100% solvent A (10% MeOH, 90% H2O, 0.2% H3PO4) to 100% solvent B (90% MeOH, 10% H2O, 0.2% H3PO4), flow rate 4 mL/min, λ=220 nM.

| EX. NO. | Compound Structure | Compound Name | HPLC Ret Time (min) |
|---|---|---|---|
| 336 | 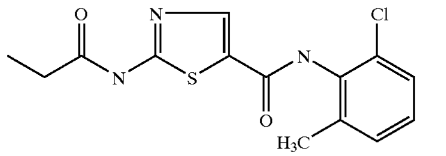 | N-(2-Chloro-6-methylphenyl)-2-[(1-oxopropyl)amino]-5-thiazolecarboxamide | 3.53 |
| 337 | 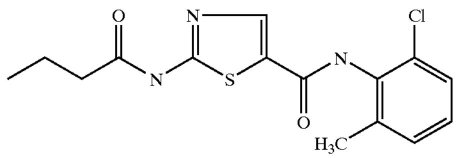 | N-(2-Chloro-6-methylphenyl)-2-[(1-oxopropyl)amino]-5-thiazolecarboxamide | 3.61 |
| 338 | 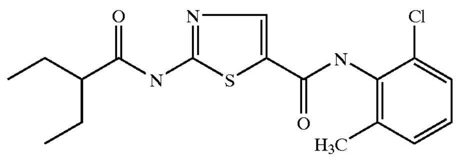 | N-(2-Chloro-6-methylphenyl)-2-[(2-ethyl-1-oxobutyl)amino]-5-thiazolecarboxamide | 3.54 |
| 339 | 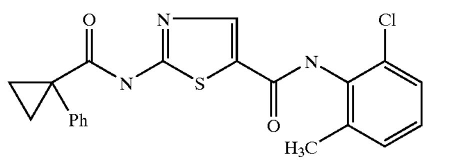 | N-(2-Chloro-6-methylphenyl)-2-[[(1-phenylcyclopropyl)carbonyl]amino]-5-thiazolecarboxamide | 3.86 |
| 340 | 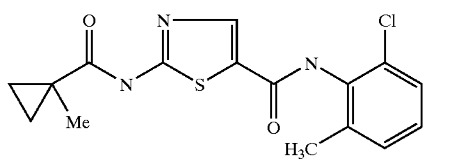 | N-(2-Chloro-6-methylphenyl)-2-[[(1-methylcyclopropyl)carbonyl]amino]-5-thiazolecarboxamide | 3.53 |
| 341 | 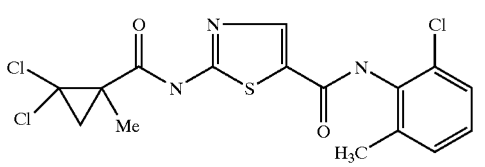 | N-(2-Chloro-6-methylphenyl)-2-[[(2,2-dichloro-1-methylcyclopropyl)carbonyl]amino]-5-thiazolecarboxamide | 3.53 |
| 342 | 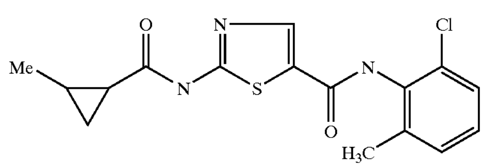 | N-(2-Chloro-6-methylphenyl)-2-[[(2-methylcyclopropyl)carbonyl]amino]-5-thiazolecarboxamide | 3.53 |
| 343 | 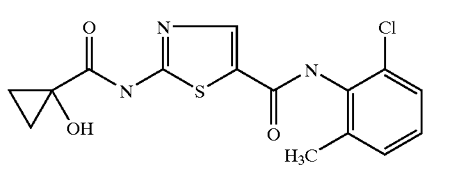 | N-(2-Chloro-6-methylphenyl)-2-[[(1-hydroxycyclopropyl)carbonyl]amino]-5-thiazolecarboxamide | 3.58 |
| 344 | 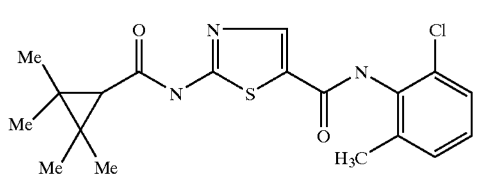 | N-(2-Chloro-6-methylphenyl)-2-[[(2,2,3,3-tetramethylcyclopropyl)carbonyl]amino]-5-thiazolecarboxamide | 3.69 |

-continued

| EX. NO. | Compound Structure | Compound Name | HPLC Ret Time (min) |
|---|---|---|---|
| 345 | 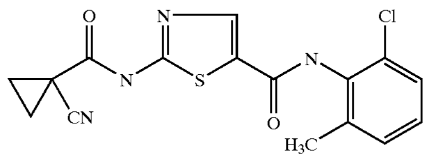 | N-(2-Chloro-6-methylphenyl)-2-[[(1-cyanocyclopropyl)-carbonyl]amino]-5-thiazolecarboxamide | 3.53 |
| 346 | 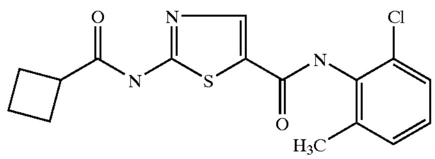 | N-(2-Chloro-6-methylphenyl)-2-[[(1-cyclobutylcarbonyl)-amino]-5-thiazolecarboxamide | 3.52 |
| 347 | 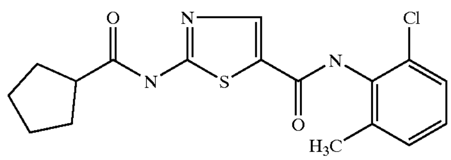 | N-(2-Chloro-6-methylphenyl)-2-[(cyclopentylcarbonyl)amino]-5-thiazolecarboxamide | 3.59 |
| 348 | 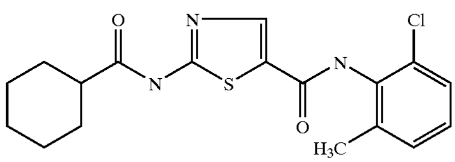 | N-(2-Chloro-6-methylphenyl)-2-[(cyclohexylcarbonyl)amino]-5-thiazolecarboxamide | 3.78 |
| 349 | 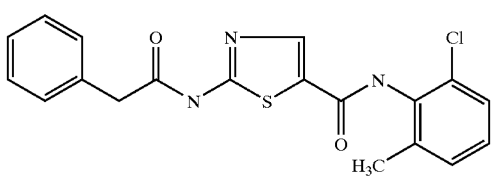 | N-(2-Chloro-6-methylphenyl)-2-[(phenylacetyl)amino]-5-thiazolecarboxamide | 3.62 |
| 350 | 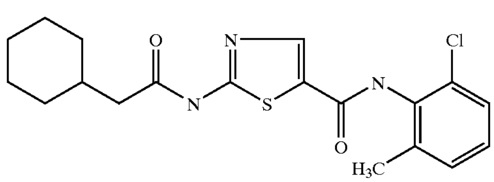 | N-(2-Chloro-6-methylphenyl)-2-[(cyclohexylcarbonyl)amino]-5-thiazolecarboxamide | 4.07 |
| 351 | 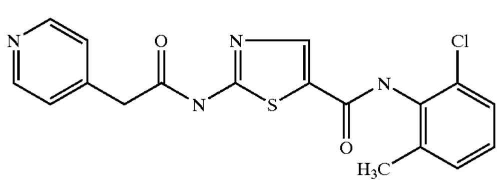 | N-(2-Chloro-6-methylphenyl)-2-[(4-pyridinylacetyl)amino]-5-thiazolecarboxamide | 3.75 |
| 352 | 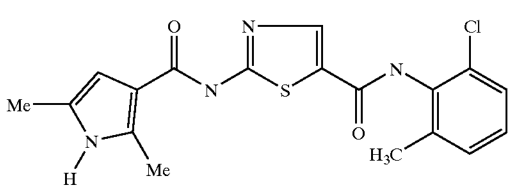 | N-(2-Chloro-6-methylphenyl)-2-[[(2,5-dimethyl-1H-pyrrol-3-yl)carbonyl]amino]-5-thiazolecarboxamide | 3.17 |

| EX. NO. | Compound Name | HPLC Ret Time (min) |
|---|---|---|
| 353 | N-(2-Chloro-6-methylphenyl)-2-[(2-pyridinylcarbonyl)amino]-5-thiazolecarboxamide | 3.07 |
| 354 | N-(2-Chloro-6-methylphenyl)-2-[(3-pyridinylcarbonyl)amino]-5-thiazolecarboxamide | 3.07 |
| 355 | N-(2-Chloro-6-methylphenyl)-2-[(4-pyridinylarbonyl)amino]-5-thiazolecarboxamide | 3.61 |
| 356 | N-(2-Chloro-6-methylphenyl)-2-[(3-thienylcarbonyl)amino]-5-thiazolecarboxamide | 3.60 |
| 357 | N-(2-Chloro-6-methylphenyl)-2-[(2-thienylcarbonyl)amino]-5-thiazolecarboxamide | 3.61 |
| 358 | N-(2-Chloro-6-methylphenyl)-2-[(2-furanylcarbonyl)amino]-5-thiazolecarboxamide | 3.61 |
| 359 | N-(2-Chloro-6-methylphenyl)-2-[(3-furanylcarbonyl)amino]-5-thiazolecarboxamide | 3.69 |
| 360 | trans-N-(2-Chloro-6-methylphenyl)-2-[[(2-phenylcyclopropyl)carbonyl)amino]-5-thiazolecarboxamide | 3.98 |
| 361 | N-(2-Chloro-6-methylphenyl)-2-[(2-methyl-1-oxopentyl)amino]-5-thiazolecarboxamide | 3.90 |

-continued

| EX. NO. | Compound Structure | Compound Name | HPLC Ret Time (min) |
|---|---|---|---|
| 362 | 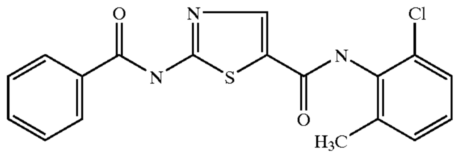 | 2-Benzoylamino-N-(2-chloro-6-methylphenyl)-5-thiazolecarboxamide | 3.61 |

EXAMPLE 363

Preparation of 2-[(Cyclopropylcarbonyl)amino]-N-(2,6-dimethylphenyl)-5-thiazolecarboxamide

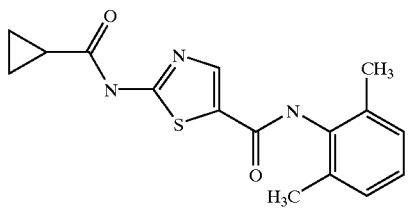

Compound 363 was prepared by an analogous method as that of 315, except using 2,6-dimethylaniline to give the title compound 363.

EXAMPLE 364

Preparation of 2-[(Cyclopropylcarbonyl)amino]-N-(2,4,6-trimethylphenyl)-5-thiazolecarboxamide

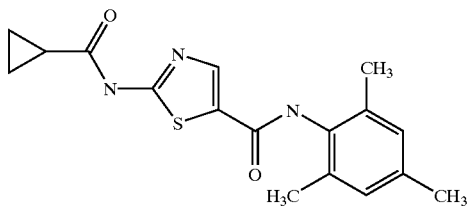

Compound 364 was prepared by an analogous method as that of 315, except using 2,4,6-trimethylaniline to give the title compound 364.

EXAMPLE 365

Preparation of N-(2-Chloro-4,6-dimethylphenyl)-2-[(cyclopropylcarbonyl)amino]-5-thiazolecarboxamide

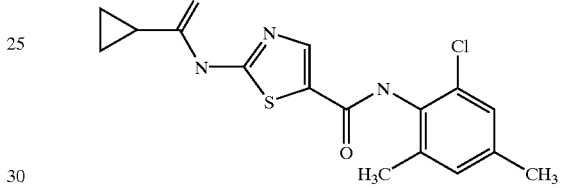

Compound 365 was prepared by an analogous method as that of 315, except using 2-chloro-4,6-dimethylaniline to give the title compound 365.

EXAMPLE 366

Preparation of [4-[2-Oxo-2-[(2,4,6-trimethylphenyl)amino]ethyl]-2-thiazolyl]carbamic acid 1,1-dimethylethyl ester

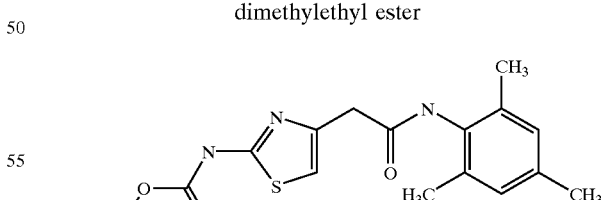

Compound 366 was prepared by an analogous method as that of 1 except, using 2-tert-butoxycarbonyloxyamino-thiazole-4-acetic acid to give the title compound 366 as a white solid.

EXAMPLE 367

Preparation of 2-Amino-N-(2,4,6-trimethylphenyl)-4-thiazoleacetamide

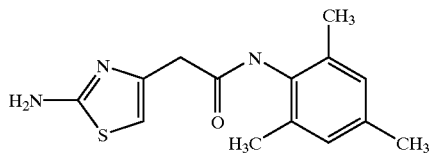

Compound 367 was prepared by an analogous method as that of 4, except using 365 to give the title compound 367 as a white solid.

EXAMPLE 368

Preparation of 2-Methyl-5-nitro-N-(2,4,6-trimethylphenyl)benzamide

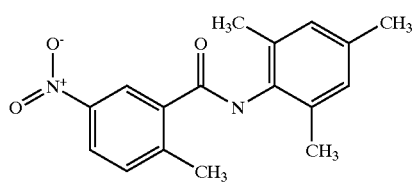

Compound 368 was prepared by an analogous method as that of 3, except using 2-methyl-5-nitrobenzoic acid to give the title compound 368 as a white solid.

EXAMPLE 369

Preparation of 5-Amino-2-methyl-N-(2,4,6-trimethylphenyl)benzamide

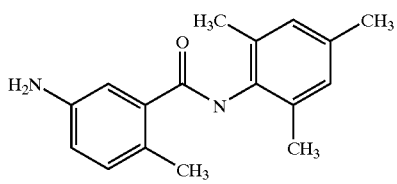

10% Palladium on charcoal (30 mg) was added to a stirred solution of 368 (149 mg, 0.5 mmol) in EtOAc (50 mL). The reaction flask was equipped with a hydrogen filled balloon via a three-way stopcock. Air inside the flask was evacuated under reduced pressure and the flask filled with hydrogen from the balloon. After 4 h, the catalyst was filtered, washed with EtOAc (5 mL, 5×). The filtrate was concentrated to obtain the title compound (133 mg, 99%) as a white solid.

EXAMPLE 370

Preparation of 2-Amino-5-chloro-N-(2,4,6-trimethylphenyl)-4-pyrimidinecarboxamide

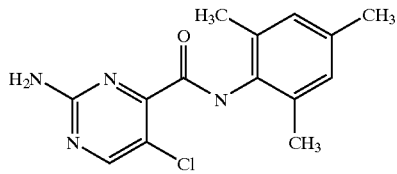

Compound 370 was prepared by an analogous method as that of 3, except using 2-amino-5-chloro-pyrimidine-4-carboxylic acid to give the title compound 370 as a white solid.

EXAMPLE 371

Preparation of [4-Methyl-5-[[(2,4,6-trimethylphenyl)amino]carbonyl]-2-oxazolyl]carbamic acid 1,1-dimethylethyl ester

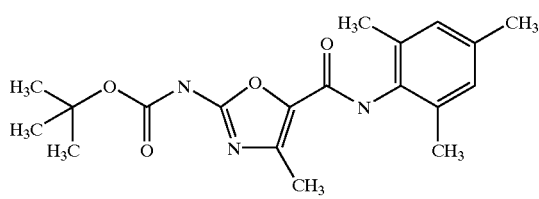

Compound 371 was prepared by an analogous method as that of 1, except using 2-tert-butoxycarbonyloxyamino-4-methyl-5-oxazolecarboxylic acid to give the title compound 371 as a light yellow foam.

EXAMPLE 372

Preparation of 2-Amino-4-(methyl)-N-(2,4,6-trimethylphenyl)-5-oxazolecarboxamide, trifluoroacetate (1:1)

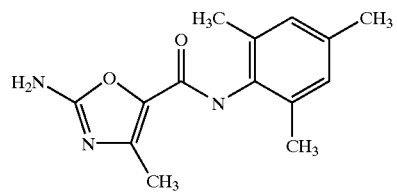

Compound 372 was prepared by an analogous method as that of 4, except using 369 to give the title compound 372 as a white solid.

EXAMPLE 373

Preparation of 2-Amino-N-(2,4,6-trimethylphenyl)-5-pyridinecarboxamide

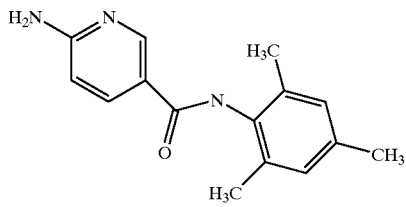

Compound 373 was prepared by an analogous method as that of 3, except using 6-aminonicotinic acid to give the title compound 373 as a white solid.

EXAMPLE 374

Preparation 3-Amino-N-(2,4,6-trimethylphenyl)-4-pyridinecarboxamide

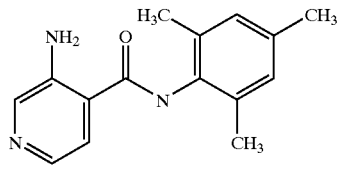

Compound 374 was prepared by an analogous method as that of 3, except using 3-amino-4-pyridinecarboxylic acid to give the title compound 374 as a white solid.

EXAMPLE 375

Preparation 2-Amino-4-methyl-N-(2,4,6-trimethylphenyl)-5-pyrimidinecarboxamide

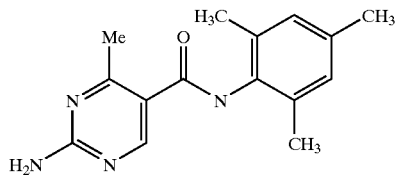

Compound 375 was prepared by an analogous method as that of 3, except using 2-amino-4-methyl-5-pyrimidinecarboxylic acid to give the title compound 375 as a white solid.

EXAMPLE 376

Preparation of N-(2-Chloro-6-methylphenyl)-2-[(4-methyl-2-pyridinyl)amino]-5-thiazolecarboxamide

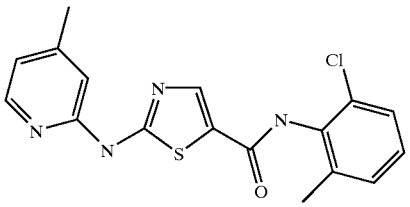

Compound 376 was prepared by an analogous method as that of 319B, except using 2-amino-4-methyl-pyridine to give the title compound 376 as an off-white solid.

EXAMPLE 377

Preparation of 2-[(6-Amino-2-pyridinyl)amino]-N-(2-chloro-6-methylphenyl)-5-thiazolecarboxamide

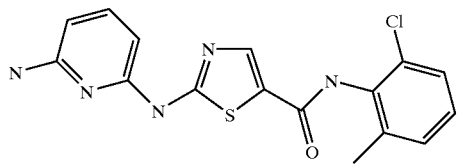

Compound 377 was prepared by an analogous method as that of 319B, except using 2,6-diaminopyridine to give the title compound 377 as a light brown solid solid.

EXAMPLE 378

Preparation of N-(2-Chloro-6-methylphenyl)-2-[(6-propyl-2-pyridinyl)amino]-5-thiazolecarboxamide

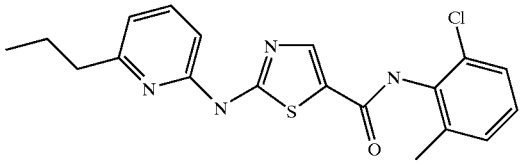

Compound 378 was prepared by an analogous method as that of 319B, except using 2-amino-6-propyl-pyridine to give the title compound 378 as an off-white solid.

EXAMPLE 379

Preparation of N-(2-Chloro-6-methylphenyl)-2-[(6-ethyl-4-pyrimidinyl)amino]-5-thiazolecarboxamide

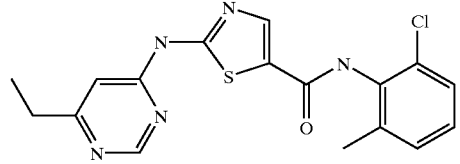

Compound 379 was prepared by an analogous method as that of 319B, except using 4-amino-6-ethyl-pyrimidine to give the title compound 379 as a white solid.

EXAMPLES 380 TO 409

General Procedure

Compounds 380 to 409 were prepared by an analogous method as that of 319B. For the following examples 380 to 527 "HPLC Ret Time" is the HPLC retention time under the following conditions: YMC S5 ODS 4.6×50 mm Ballastic Column, 4 min gradient starting from 100% solvent A (10% MeOH, 90% H₂O, 0.2% H₃PO₄) to 100% solvent B (90% MeOH, 10% H₂O, 0.2% H₃PO₄), flow rate 4 mL/min, λ=220 nM. Where used, "HPLC Ret Time 'B'" is the HPLC retention time under the following conditions: YMC S5 ODS 4.6×33 mm Turbo Column, 2 min gradient starting from 100% solvent A (10% MeOH, 90% H₂O, 0.1% TFA) to 100% solvent B (90% MeOH, 10% H₂O, 0.1% TFA) with 1 min at 100% solvent B, flow rate 4 mL/min, λ=220 nM.

| EX. NO. | Compound Structure | Compound Name | HPLC Ret Time (min) |
|---|---|---|---|
| 380 | 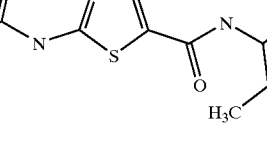 | 'N-(2-Chloro-6-methylphenyl)-2-(2-pyridinylamino)-5-thiazolecarboxamide | 3.337 |
| 381 | 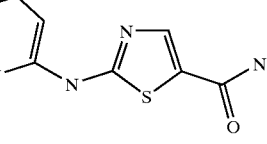 | 'N-(2-Chloro-6-methylphenyl)-2-[(6-methyl-2-pyridinyl)amino]-5-thiazolecarboxamide | 3.61 |
| 382 | 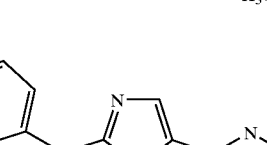 | 'N-(2-Chloro-6-methylphenyl)-2-[(5-methyl-2-pyridinyl)amino]-5-thiazolecarboxamide | 3.487 |
| 383 | 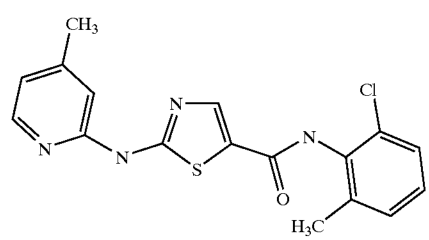 | 'N-(2-Chloro-6-methylphenyl)-2-[(4-methyl-2-pyridinyl)amino]-5-thiazolecarboxamide | 3.293 |
| 384 | 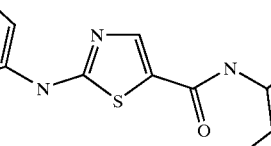 | 'N-(2-Chloro-6-methylphenyl)-2-[(3-methyl-2-pyridinyl)amino]-5-thiazolecarboxamide | 3.243 |
| 385 | 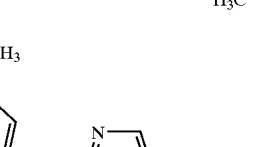 | '2-[(5-Bromo-3-methyl-2-pyridinyl)amino]-N-(2-chloro-6-methylphenyl)-5-thiazolecarboxamide | 4.17 |

-continued

| EX. NO. | Compound Structure | Compound Name | HPLC Ret Time (min) |
|---|---|---|---|
| 386 | 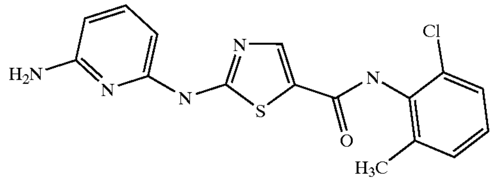 | '2-[(6-Amino-2-pyridinyl)amino]-N-(2-chloro-6-methylphenyl)-5-thiazolecarboxamide | 2.817 |
| 387 | 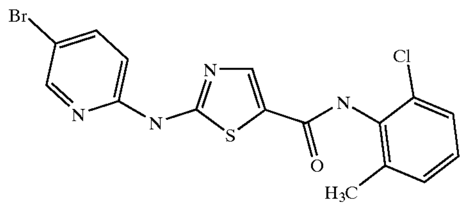 | '2-[(5-Bromo-2-pyridinyl)amino]-N-(2-chloro-6-methylphenyl)-5-thiazolecarboxamide | 4.023 |
| 388 | 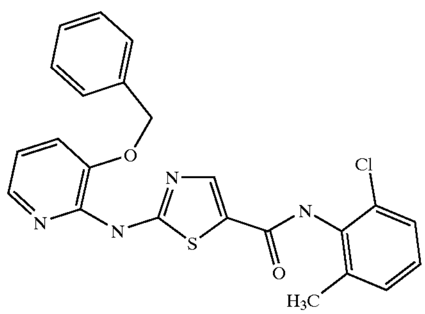 | 'N-(2-Chloro-6-methylphenyl)-2-[[3-(phenylmethoxy)-2-pyridinyl]amino]-5-thiazolecarboxamide | 4.143 |
| 389 | 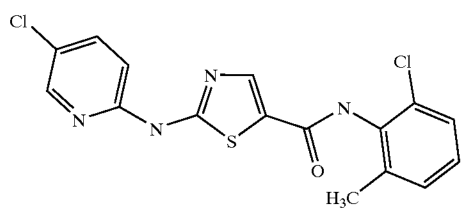 | 'N-(2-Chloro-6-methylphenyl)-2-[(5-chloro-2-pyridinyl)amino]-5-thiazolecarboxamide | 3.957 |
| 390 | 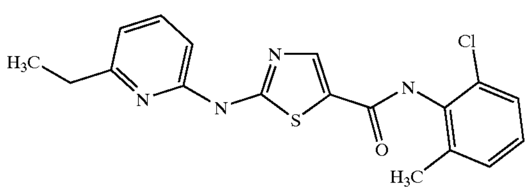 | 'N-(2-Chloro-6-methylphenyl)-2-[(6-ethyl-2-pyridinyl)amino]-5-thiazolecarboxamide | 3.867 |
| 391 | 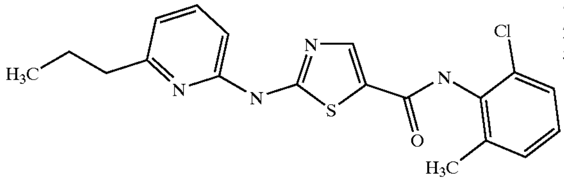 | 'N-(2-Chloro-6-methylphenyl)-2-[(6-propyl-2-pyridinyl)amino]-5-thiazolecarboxamide | 4.083 |
| 392 | 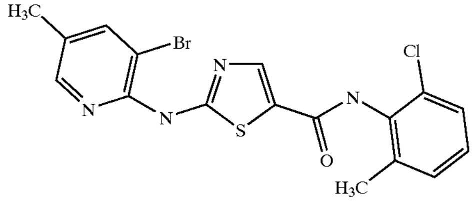 | '2-[(3-Bromo-5-methyl-2-pyridinyl)amino]-N-(2-chloro-6-methylphenyl)-5-thiazolecarboxamide | 4.077 |

-continued

| EX. NO. | Compound Structure | Compound Name | HPLC Ret Time (min) |
|---|---|---|---|
| 393 | 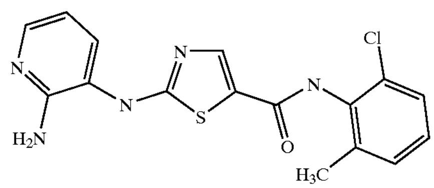 | '2-[(2-Amino-3-pyridinyl)amino]-N-(2-chloro-6-methylphenyl)-5-thiazolecarboxamide | 2.343 |
| 394 | 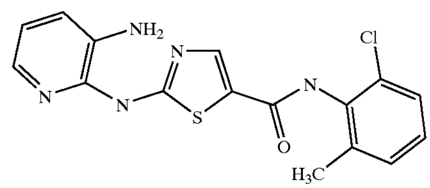 | '2-[(3-Amino-2-pyridinyl)amino]-N-(2-chloro-6-methylphenyl)-5-thiazolecarboxamide | 2.777 |
| 395 | 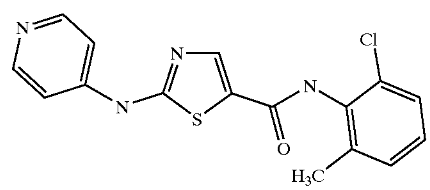 | 'N-(2-Chloro-6-methylphenyl)-2-(4-pyridinylamino)-5-thiazolecarboxamide | 2.493 |
| 396 | 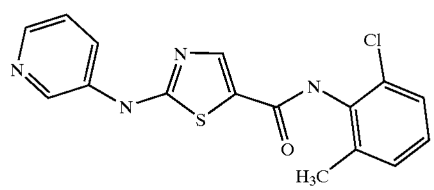 | 'N-(2-Chloro-6-methylphenyl)-2-(3-pyridinylamino)-5-thiazolecarboxamide | 2.47 |
| 397 | 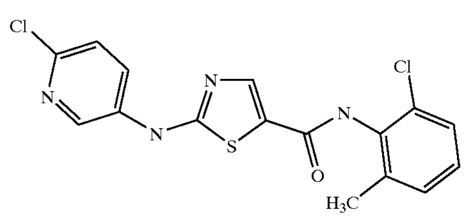 | 'N-(2-Chloro-6-methylphenyl)-2-[(6-chloro-3-pyridinyl)amino]-5-thiazolecarboxamide | 3.75 |
| 398 | 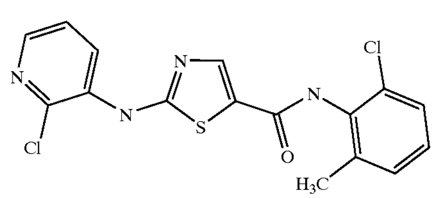 | 'N-(2-Chloro-6-methylphenyl)-2-[(2-chloro-3-pyridinyl)amino]-5-thiazolecarboxamide | 3.443 |
| 399 | 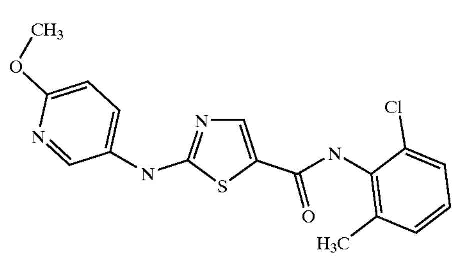 | 'N-(2-Chloro-6-methylphenyl)-2-[(6-methoxy-3-pyridinyl)amino]-5-thiazolecarboxamide | 3.517 |

-continued

| EX. NO. | Compound Structure | Compound Name | HPLC Ret Time (min) |
|---|---|---|---|
| 400 | 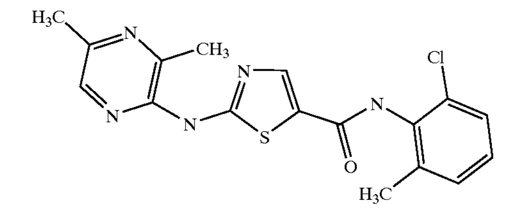 | 'N-(2-Chloro-6-methylphenyl)-2-[(3,5-dimethyl-2-pyrazinyl)amino]-5-thiazolecarboxamide | 3.583 |
| 401 | 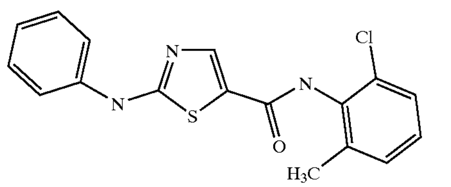 | 'N-(2-Chloro-6-methylphenyl)-2-(phenylamino)-5-thiazolecarboxamide | 3.697 |
| 402 | 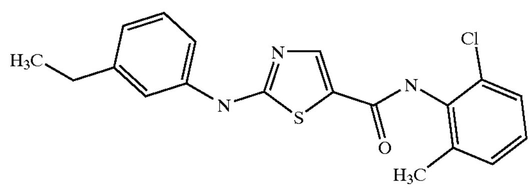 | 'N-(2-Chloro-6-methylphenyl)-2-[(3-ethylphenyl)amino]-5-thiazolecarboxamide | 4.107 |
| 403 | 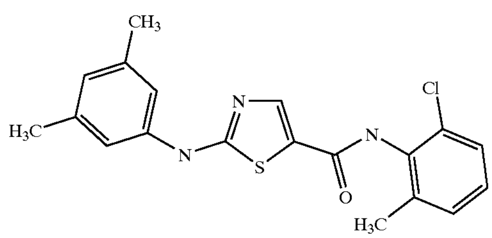 | 'N-(2-Chloro-6-methylphenyl)-2-[(3,5-dimethylphenyl)amino]-5-thiazolecarboxamide | 3.98 |
| 404 | 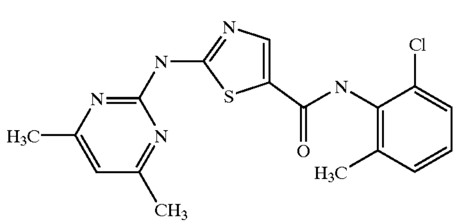 | 'N-(2-Chloro-6-methylphenyl)-2-[(4,6-dimethyl-2-pyrimidinyl)amino]-5-thiazolecarboxamide | 3.51 |
| 405 | 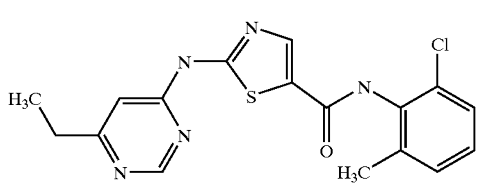 | 'N-(2-Chloro-6-methylphenyl)-2-[(6-ethyl-4-pyrimidinyl)amino]-5-thiazolecarboxamide | 2.943 |
| 406 | 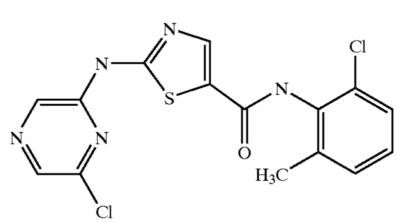 | 'N-(2-Chloro-6-methylphenyl)-2-[(6-chloro-2-pyrazinyl)amino]-5-thiazolecarboxamide | 3.763 |

-continued

| EX. NO. | Compound Structure | Compound Name | HPLC Ret Time (min) |
|---|---|---|---|
| 407 | 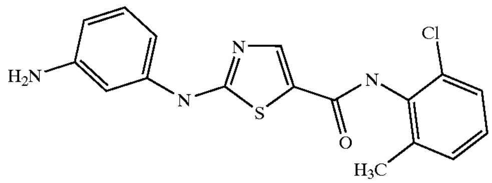 | '2-[(3-Aminophenyl)amino]-N-(2-chloro-6-methylphenyl)-5-thiazolecarboxamide | 2.633 |
| 408 | 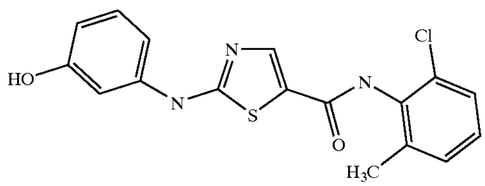 | 'N-(2-Chloro-6-methylphenyl)-2-[(3-hydroxyphenyl)amino]-5-thiazolecarboxamide | 3.337 |
| 409 | 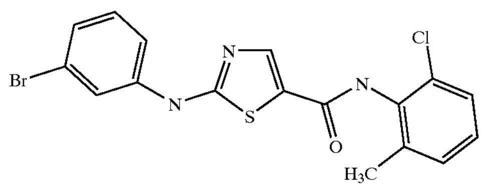 | '2-[(3-Bromophenyl)amino]-N-(2-chloro-6-methylphenyl)-5-thiazolecarboxamide | 4.12 |

EXAMPLE 410

Preparation of N-(2,6-Dimethylphenyl)-2-(phenylamino)-5-thiazolecarboxamide

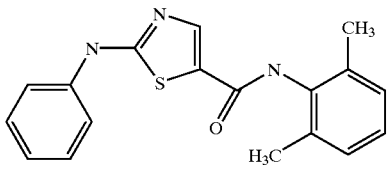

A. [5-[[(2,6-dimethylphenyl)amino]carbonyl]-2-thiazolyl] carbamic acid, 1,1-dimethylethyl ester Compound 410A was prepared by an analogous method as that of 315C, except using 2,6-dimethylaniline.

B. 2-Amino-N-(2,6-dimethylphenyl)-5-thiazolecarboxamide

Compound 410B was prepared by an analogous method as that of 315D, except using compound 410A.

C. Title Compound

The title compound was prepared by an analogous method as that of 319B, except using compound 410B and aniline.

HPLC Ret. Time 3.69 min.

EXAMPLES 411 TO 427

General Procedure

Compounds 411 to 427 were prepared by an analogous method as that of 319B.

| EX. NO. | Compound Structure | Compound Name | HPLC Ret Time (min) |
|---|---|---|---|
| 411 | 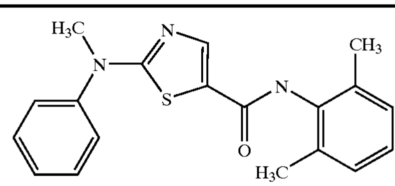 | 'N-(2,6-Dimethylphenyl)2-(methylphenylamino)-5-thiazolecarboxamide | 3.667 |
| 412 | 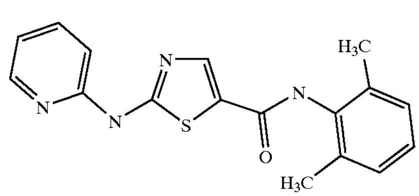 | 'N-(2,6-Dimethylphenyl)-2-(2-pyridinylamino)-5-thiazolecarboxamide | 3.297 |

-continued

| EX. NO. | Compound Structure | Compound Name | HPLC Ret Time (min) |
|---|---|---|---|
| 413 | 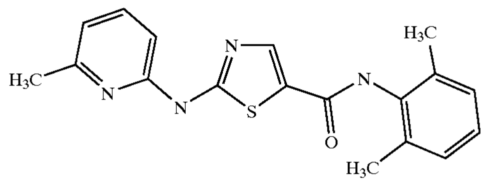 | 'N-(2,6-Dimethylphenyl)-2-[(6-methyl-2-pyridinyl)amino]-5-thiazolecarboxamide | 3.587 |
| 414 | 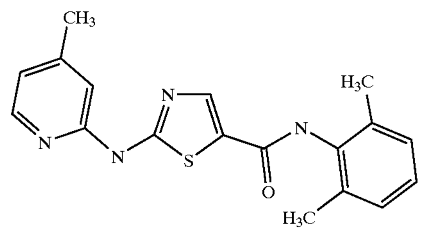 | 'N-(2,6-Dimethylphenyl)-2-[(4-methyl-2-pyridinyl)amino]-5-thiazolecarboxamide | 3.222 |
| 415 | 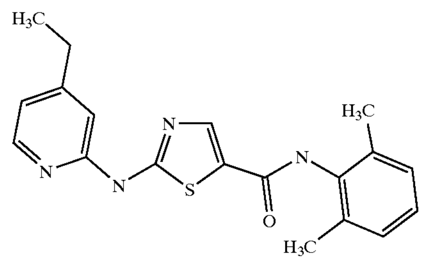 | 'N-(2,6-Dimethylphenyl)-2-[(4-ethyl-2-pyridinyl)amino]-5-thiazolecarboxamide | 3.54 |
| 416 | 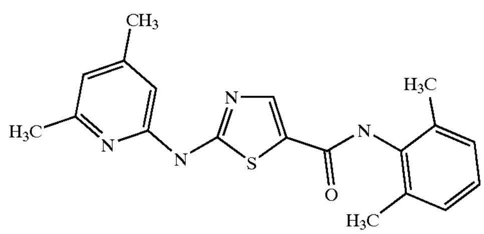 | 'N-(2,6-Dimethylphenyl)-2-[(4,6-dimethyl-2-pyridinyl)amino]-5-thiazolecarboxamide | 3.543 |
| 417 | 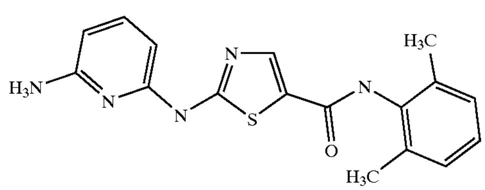 | '2-[(6-Amino-2-pyridinyl)amino]-N-(2,6-dimethylphenyl)-5-thiazolecarboxamide | 2.807 |
| 418 | 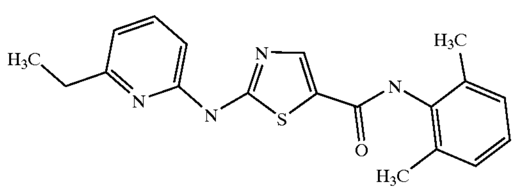 | 'N-(2,6-Dimethylphenyl)-2-[(6-ethyl-2-pyridinyl)amino]-5-thiazolecarboxamide | 3.847 |
| 419 | 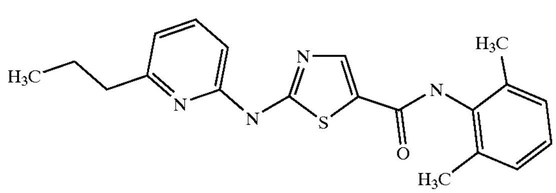 | 'N-(2,6-Dimethylphenyl)-2-[(6-propyl-2-pyridinyl)amino]-5-thiazolecarboxamide | 4.057 |

-continued

| EX. NO. | Compound Name | HPLC Ret Time (min) |
|---|---|---|
| 420 | '2-[(2-Amino-3-pyridinyl)amino]-N-(2,6-dimethylphenyl)-5-thiazolecarboxamide | 2.337 |
| 421 | '2-[(3-Amino-2-pyridinyl)amino]-N-(2,6-dimethylphenyl)-5-thiazolecarboxamide | 2.737 |
| 422 | '2-[(6-Amino-2-methyl-4-pyrimidinyl)amino]-N-(2,6-dimethylphenyl)-5-thiazolecarboxamide | 2.71 |
| 423 | 'N-(2,6-Dimethylphenyl)-2-[[6-(4-morpholinyl)-3-pyridazinyl]amino]-5-thiazolecarboxamide | 2.727 |
| 424 | '2-[(6-Chloro-3-pyridazinyl)amino]-N-(2,6-dimethylphenyl)-5-thiazolecarboxamide | 3.46 |
| 425 | 'N-(2,6-Dimethylphenyl)-2-(3-pyridazinylamino)-5-thiazolecarboxamide | 2.973 |
| 426 | '2-[(3-Aminophenyl)aminol]-N-(2,6-dimethylphenyl)-5-thiazolecarboxamide | 2.63 |

| EX. NO. | Compound Structure | Compound Name | HPLC Ret Time (min) |
|---|---|---|---|
| 427 | 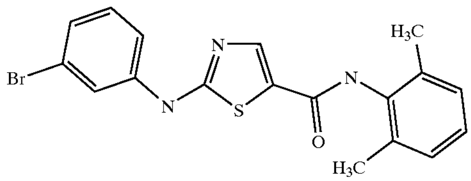 | '2-[(3-Bromophenyl)amino]-N-(2,6-dimethylphenyl)-5-thiazolecarboxamide | 4.143 |

EXAMPLE 428 reparation of '2-(2-Pyridinylamino)-N-(2,4,6-trimethylphenyl)-5-thiazolecarboxamide

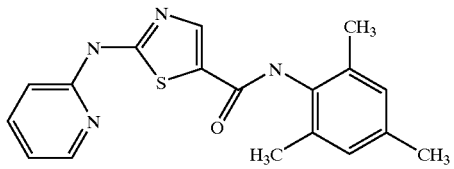

A. [5-[[(2,4,6-trimethylphenyl)amino]carbonyl]-2-thiazolyl]carbamic acid, 1,1-dimethylethyl ester Compound 428A was prepared by an analogous method as that of 315C, except using 2,4,6-trimethylaniline.

B. 2-Amino-N-(2,6-dimethylphenyl)-5-thiazolecarboxamide

Compound 428B was prepared by an analogous method as that of 315D, except using compound 428A.

C. Title Compound

The title compound was prepared by an analogous method as that of 319B, except using compound 428B and 2-aminopyridine. HPLC Ret. Time 3.66 min.

EXAMPLES 429 TO 443

General Procedure

Compounds 429 to 443 were prepared by an analogous method as that of 319B.

| EX. NO. | Compound Structure | Compound Name | HPLC Ret Time (min) |
|---|---|---|---|
| 429 | 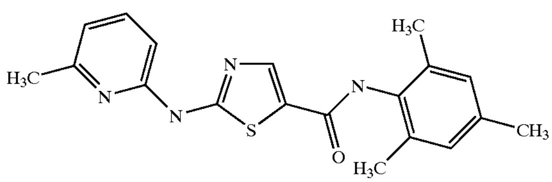 | '2-[(6-Methyl-2-pyridinyl)amino]-N-(2,4,6-trimethylphenyl)-5-thiazolecarboxamide | 3.903 |
| 430 | 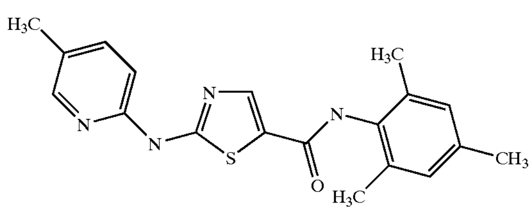 | '2-[(5-Methyl-2-pyridinyl)amino]-N-(2,4,6-trimethylphenyl)-5-thiazolecarboxamide | 3.8 |
| 431 | 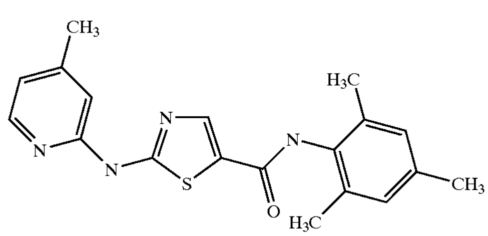 | '2-[(4-Methyl-2-pyridinyl)amino] N-(2,4,6-trimethylphenyl)-5-thiazolecarboxamide | 3.603 |

-continued

| EX. NO. | Compound Name | HPLC Ret Time (min) |
|---|---|---|
| 432 | '2-[(3-Methyl-2-pyridinyl)amino] N-(2,4,6-trimethylphenyl)-5-thiazolecarboxamide | 3.56 |
| 433 | '2-[(5-Bromo-2-pyridinyl)amino] N-(2,4,6-trimethylphenyl)-5-thiazolecarboxamide | 4.263 |
| 434 | '2-[(5-Chloro-2-pyridinyl)amino] N-(2,4,6-trimethylphenyl)-5-thiazolecarboxamide | 4.203 |
| 435 | '2-[(6-Methoxy-3-pyridinyl)amino] N-(2,4,6-trimethylphenyl)-5-thiazolecarboxamide | 3.8 |
| 436 | '2-[(4-Ethyl-2-pyridinyl)amino] N-(2,4,6-trimethylphenyl)-5-thiazolecarboxamide | 3.86 |
| 437 | '2-[(6-Ethyl-2-pyridinyl)amino] N-(2,4,6-trimethylphenyl)-5-thiazolecarboxamide | 4.127 |
| 438 | '2-[(6-Chloro-3-pyridinyl)amino] N-(2,4,6-trimethylphenyl)-5-thiazolecarboxamide | 4.017 |

| EX. NO. | Compound Structure | Compound Name | HPLC Ret Time (min) |
|---|---|---|---|
| 439 | 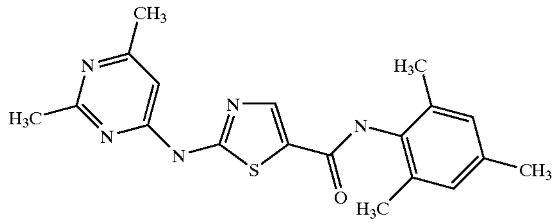 | '2-[(2,6-Methyl-4-pyridinyl)amino] N-(2,4,6-trimethylphenyl)-5-thiazolecarboxamide | 2.943 |
| 440 | 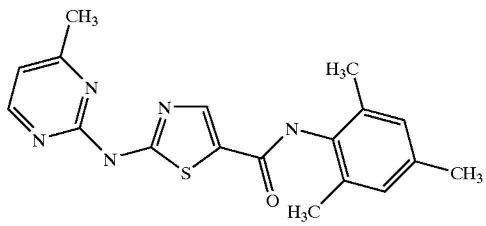 | '2-[(4-Methyl-2-pyridinyl)amino] N-(2,4,6-trimethylphenyl)-5-thiazolecarboxamide | 3.723 |
| 441 | 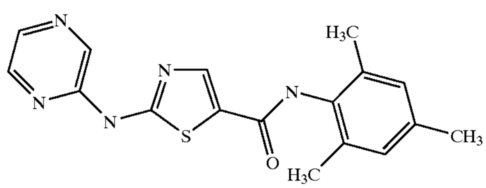 | '2-[(2-Pyrazinylamino)-N-(2,4,6-trimethylphenyl)-5-thiazolecarboxamide | 3.65 |
| 442 | 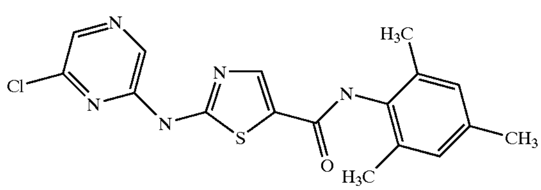 | '2-[(6-Chloro-2-pyridinyl)amino] N-(2,4,6-trimethylphenyl)-5-thiazolecarboxamide | 4.05 |
| 443 | 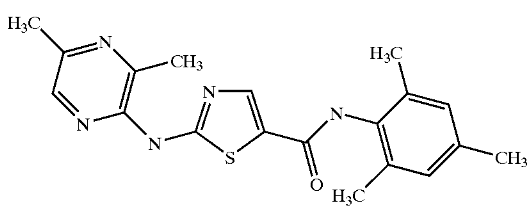 | '2-[(3,5-Dimethyl-2-pyridinyl)amino] N-(2,4,6-trimethylphenyl)-5-thiazolecarboxamide | 3.877 |

EXAMPLE 444

Preparation of 'N-(2-Chloro-6-methylphenyl)-2-[2-methyl-6-[[2-(4-morpholinyl)ethyl]amino]-4-pyrimidinyl]amino]-5-thiazolecarboxamide

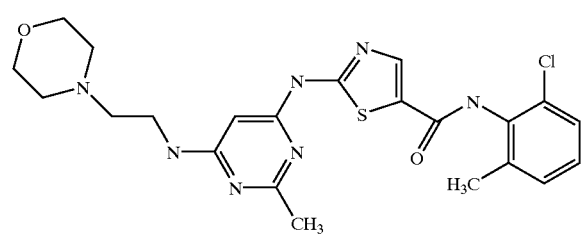

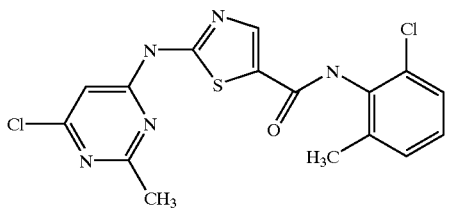

A

To a suspension of NaH (148 mg, 6.17 mmol) in THF (20 mL) was added a solution of compound 315D (551 mg, 2.06 mmol) in THF (10 mL) and stirred at RT for 0.5 h. A solution of 4,6-dichloro-2-methylpyrimidine (671.6 mg, 4.12 mmol) in THF (10 mL) and stirred at RT overnight. The reaction was quenched with acetic acid and the solvent removed in vacuo. Water and saturated NaHCO₃ were added to the residue and extracted with CH₂Cl₂. The organic layer was removed in vacuo and the crude material purified by column chromatography to give 444A (494 mg).

B. Title Compound

To compound 444A (30 mg) was added N-(2-aminoethyl)-morpholine (300 μL) and the mixture was heated at 80° C. for 2 h. Water was added to the reaction and the product was collected by filtration. HPLC Ret. Time 2.357 min.

EXAMPLES 445 TO 461

General Procedure

Compounds 445 to 461 were prepared by an analogous method as that of 444B by substituting the appropriate amine.

| EX. NO. | Compound Structure | Compound Name | HPLC Ret Time (min) |
|---|---|---|---|
| 445 | 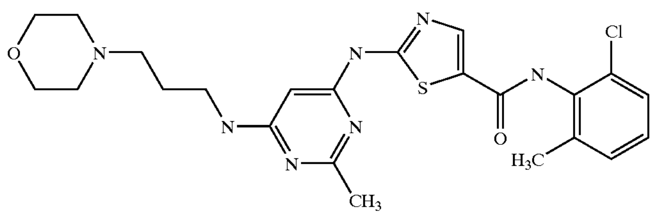 | 'N-(2-Chloro-6-methylphenyl)-2-[[2-methyl-6-[[3-(4-morpholinyl)propyl]amino]-4-pyrimidinyl]amino]-5-thiazolecarboxamide | 2.253 |
| 446 | 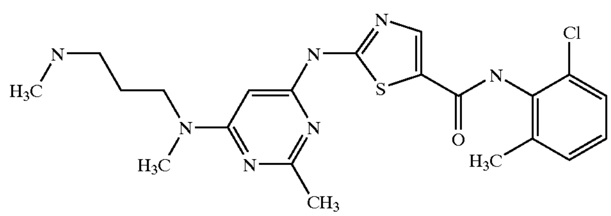 | 'N-(2-Chloro-6-methylphenyl)-2-[[2-methyl-6-[methyl[3-(methylamino)propyl]amino]-4-pyrimidinyl]amino]-5-thiazolecarboxamide | 2.493 |
| 447 | 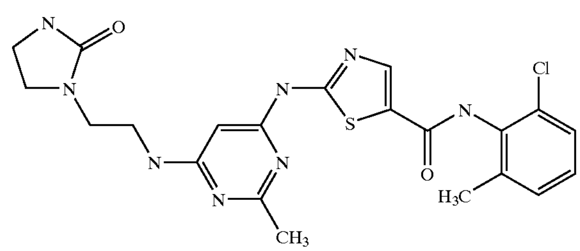 | 'N-(2-Chloro-6-methylphenyl)-2-[[2-methyl-6-[[2-(tetrahydro-2-oxo-1H-imidazol-1-yl)ethyl]-amino]-4-pyri-midinyl]amino]-5-thiazolecarboxamide | 2.71 |
| 448 | 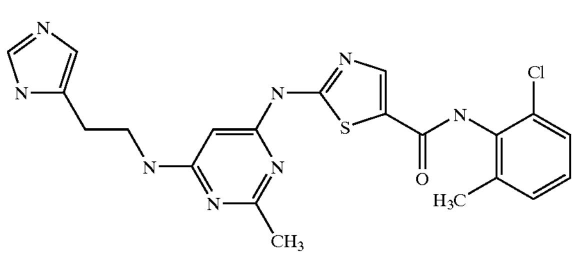 | 'N-(2-Chloro-6-methylphenyl)-2-[[2-methyl-6-[(2-1H-imidazol-4-ylethyl)amino]-4-pyrimidinyl[amino]-5-thiazolecarboxamide | 2.303 |
| 449 | 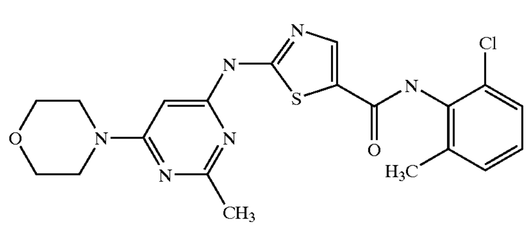 | 'N-(2-Chloro-6-methylphenyl)-2-[[2-methyl-6-(4-morpholinyl)-4-pyrimidinyl]amino]-5-thiazolecarboxamide | 3.337 |

-continued

| EX. NO. | Compound Structure | Compound Name | HPLC Ret Time (min) |
|---|---|---|---|
| 450 | 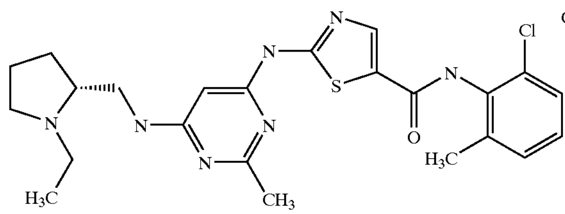 | 'N-(2-Chloro-6-methylphenyl)-2-[[6-[[[(2R)-1-ethyl-2-pyrrolidinyl]methyl]amino]-2-methyl-4-pyrimidinyl]amino]-5-thiazolecarboxamide | 2.703 |
| 451 | 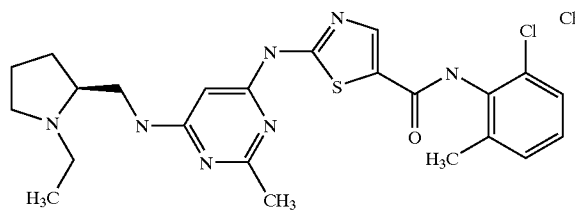 | 'N-(2-Chloro-6-methylphenyl)-2-[[6-[[[(2S)-1-ethyl-2-pyrrolidinyl]methyl]amino]-2-methyl-4-pyrimidinyl]amino]-5-thiazolecarboxamide | 2.717 |
| 452 | 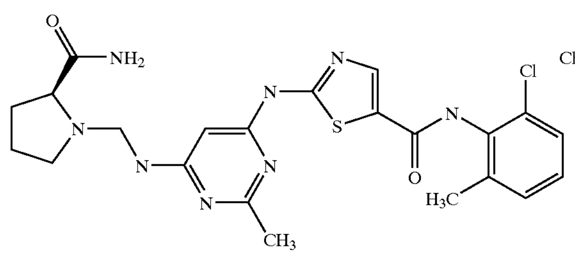 | '2-[[6-[(2S)-2-(Aminocarbonyl)-1-pyrrolidinyl]-2-methyl-4-pyrimidinyl]amino]-N-(2-chloro-6-methylphenyl)-5-thiazolecarboxamide | 2.81 |
| 453 | 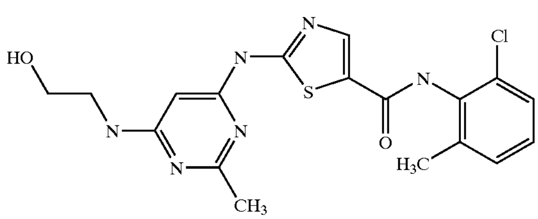 | 'N-(2-Chloro-6-methylphenyl)-2-[[6-[(2-hydroxyethyl)amino]-2-methyl-4-pyrimidinyl]amino]-5-thiazolecarboxamide | 2.677 |
| 454 | 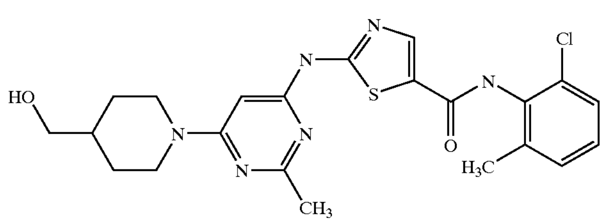 | 'N-(2-Chloro-6-methylphenyl)-2-[[6-[(4-hydroxymethyl)-1-piperidinyl]-2-methyl-4-pyrimidinyl]amino]-5-thiazolecarboxamide | 3.05 |
| 455 | 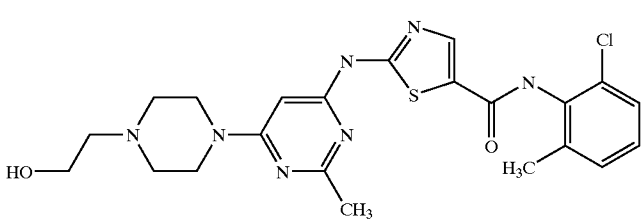 | 'N-(2-Chloro-6-methylphenyl)-2-[[6-[4-(2-hydroxyethyl)-1-piperazinyl]-2-methyl-4-pyrimidinyl]amino]-5-thiazolecarboxamide | 2.717 |

| EX. NO. | Compound Structure | Compound Name | HPLC Ret Time (min) |
|---|---|---|---|
| 456 | 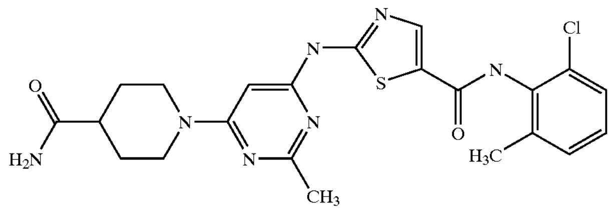 | '1-[6-[[5-[[(2-Chloro-6-methylphenyl)amino]carbonyl]-2-thiazolyl]amino]-2-methyl-4-pyrimidinyl]-4-piperidinecarboxamide | 2.863 |
| 457 | Chiral | 'N-(2-Chloro-6-methylphenyl)-2-[[2-methyl-6-[(3S)-3-methyl-1-piperazinyl]-4-pyrimidinyl]amino]-5-thiazolecarboxamide | 2.823 |
| 458 | 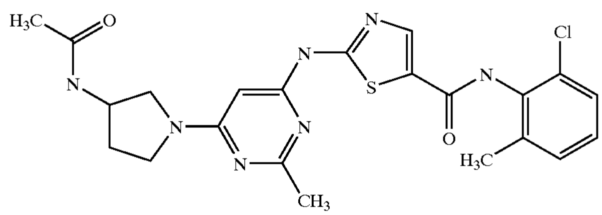 | '2-[[6-[3-(Acetylamino)-1-pyrrolindinyl]-2-methyl-4-pyrimidinyl]amino]-N-(2-chloro-6-methylphenyl)-5-thiazolecarboxamide | 2.78 |
| 459 | 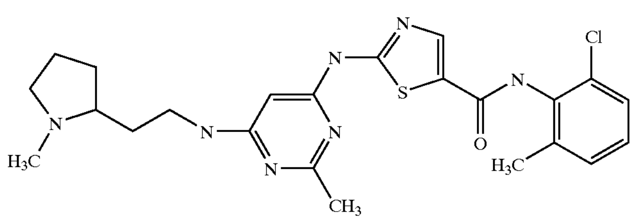 | 'N-(2-Chloro-6-methylphenyl)-2-[[6-[(1-methyl-2-pyrrolidinyl)ethyl]amino]-2-methyl-4-pyrimidinyl]amino]-5-thiazolecarboxamide | 2.383 |
| 460 | 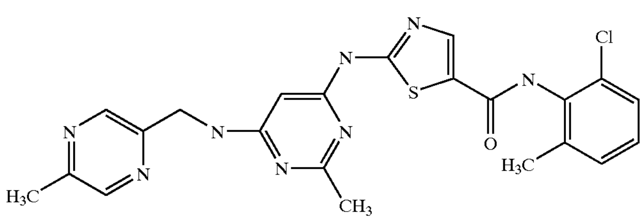 | 'N-(2-Chloro-6-methylphenyl)-2-[[2-methyl-6-[[5-methyl-2-pyrazinyl)methyl]amino]-4-pyrimidinyl]amino]-5-thiazolecarboxamide | 3.027 |
| 461 | 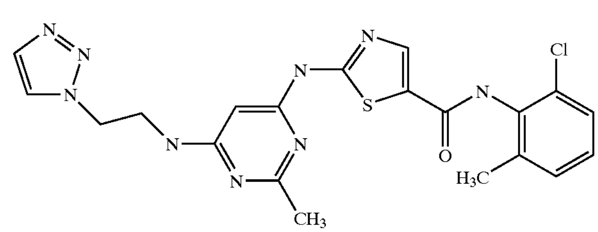 | 'N-(2-Chloro-6-methylphenyl)-2-[[2-methyl)-6-[[2-(1H-1,2,3-triazol-1-yl)ethyl]amino]-4-pyrimidinyl]amino]-5-thiazolecarboxamide | 2.78 |

EXAMPLE 462
Preparation of 'N-(2-Chloro-6-methylphenyl)-2-[[6-[[2-(4-morpholinyl)ethyl]amino]-4-pyrimidinyl]amino]-5-thiazolecarboxamide

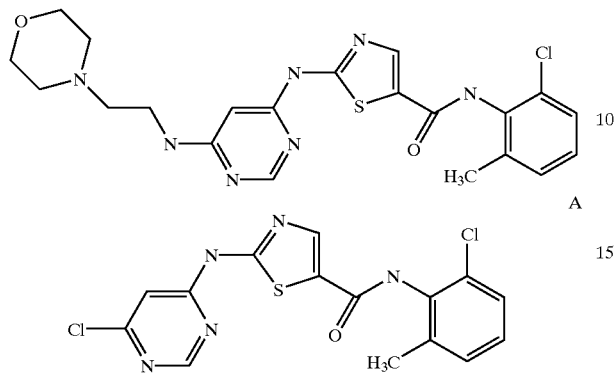

Compound 462A was prepared by an analogous method as that of 444A, except using 4,6-dichloropyrimidine.

B. Title Compound

The title compound was prepared by an analogous method as that of 444B, except using compound 462A in place of compound 444A. HPLC Ret. Time 2.553 min.

EXAMPLES 463 TO 472

General Procedure

Compounds 463 to 472 were prepared by an analogous method as that of 444B by substituting the appropriate amine. "HPLC Ret Time 'B'" is the HPLC retention time under the following conditions: YMC S5 ODS 4.6×33 mm Turbo Column, 2 min gradient starting from 100% solvent A (10% MeOH, 90% $H_2O$, 0.1% TFA) to 100% solvent B (90% MeOH, 10% $H_2O$, 0.1% TFA) with 1 min at 100% solvent B, flow rate 4 mL/min, λ=220 nM.

| EX. NO. | Compound Structure | Compound Name | HPLC Ret Time (min) |
|---|---|---|---|
| 463 | 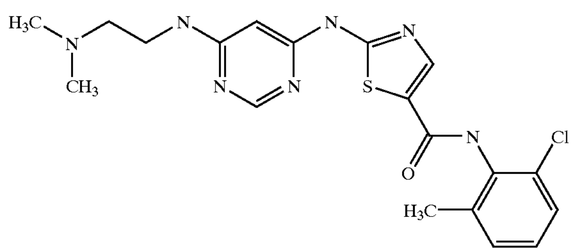 | 'N-(2-Chloro-6-methylphenyl)-2-[[6-[[2-(dimethyl-amino)-ethyl]amino]-4-pyrimidinyl]-amino]-5-thiazolecarboxamide | 2.527 |
| 464 | 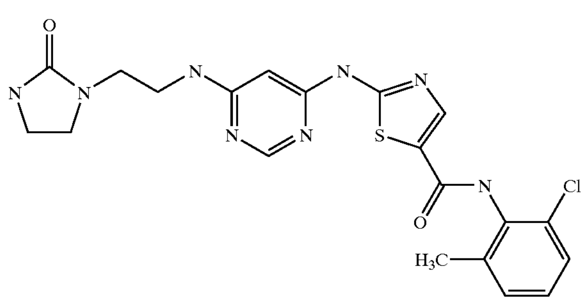 | 'N-(2-Chloro-6-methylphenyl)-2-[[6-[[2-(tetrahydro-2-oxo-1H-imidazol-1-yl)ethyl]amino]-4-pyrimidinyl]amino]-5-thiazolecarboxamide | 2.797 |
| 465 | 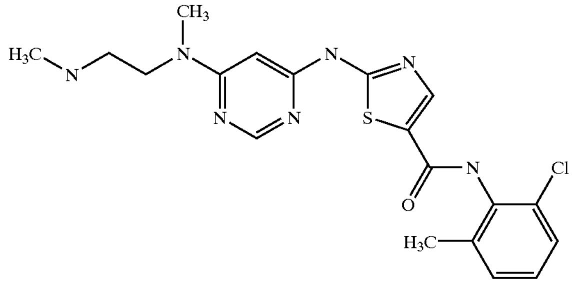 | 'N-(2-Chloro-6-methylphenyl)-2-[[6-[methyl[2-(methylamino)-ethyl]amino]-4-pyrimidinyl]-amino]-5-thiazolecarboxamide | 1.137 B |

-continued

| EX. NO. | Compound Structure | Compound Name | HPLC Ret Time (min) |
|---|---|---|---|
| 466 | 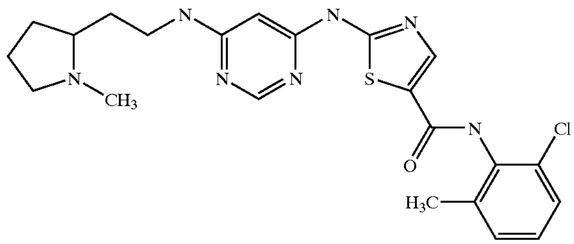 | 'N-(2-Chloro-6-methylphenyl)-2-[[6-[[2-(1-methyl-2-pyrrolidinyl)ethyl]amino]-4-pyrimidinyl]-amino]-5-thiazolecarboxamide | 1.113 B |
| 467 | 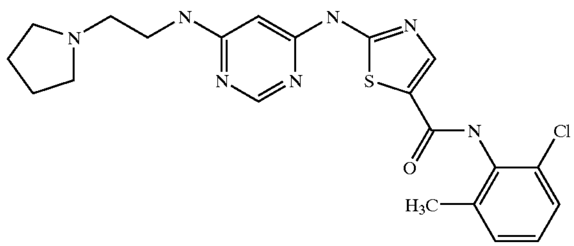 | 'N-(2-Chloro-6-methylphenyl)-2-[[6-[[2-(1-pyrrolidinyl)-ethyl]amino]-4-pyrimidinyl]-amino]-5-thiazolecarboxamide | 1.150 B |
| 468 | 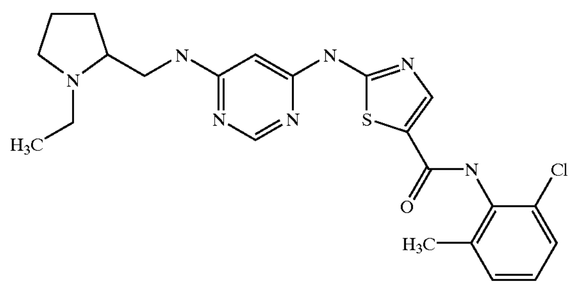 | 'N-(2-Chloro-6-methylphenyl)-2-[[6-[[(1-ethyl-2-pyrolidinyl)-methyl]amino]-4-pyrimi-dinyl]amino]-5-thiazolecarboxamide | 1.237 B |
| 469 | 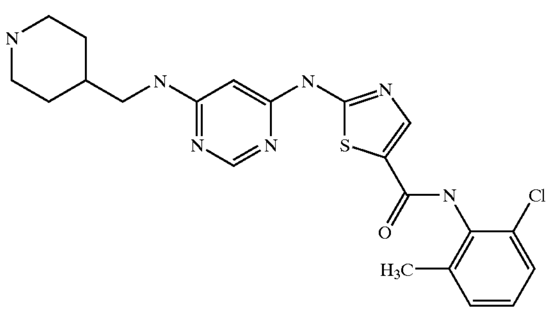 | 'N-(2-Chloro-6-methylphenyl)-2-[[6-[(4-piperidinyl-methyl)amino]-4-pyrimi-dinyl]amino]-5-thiazolecarboxamide | 1.160 B |
| 470 | 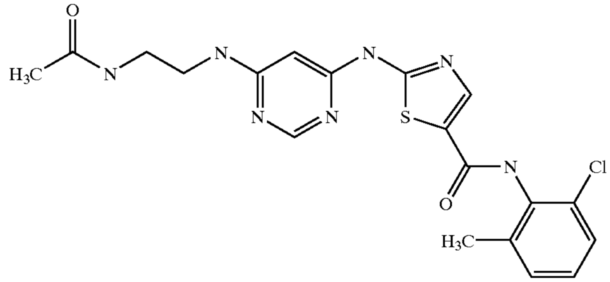 | '2-[[6-[[2-(Acetylamino)-ethyl]amino]-4-pyrimi-dinyl]amino]-N-(2-chloro-6-methylphenyl)-5-thiazolecarboxamide | 2.457 B |

-continued

| EX. NO. | Compound Structure | Compound Name | HPLC Ret Time (min) |
|---|---|---|---|
| 471 | 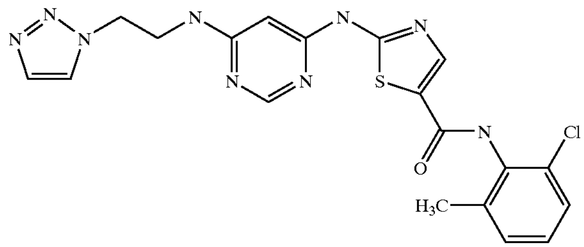 | 'N-(2-Chloro-6-methylphenyl)-2-[[6-[[2-(1H-1,2,3-triazol-1-yl)ethyl]amino]-4-pyrimidinyl]amino]-5-thiazolecarboxamide | 2.897 |
| 472 | 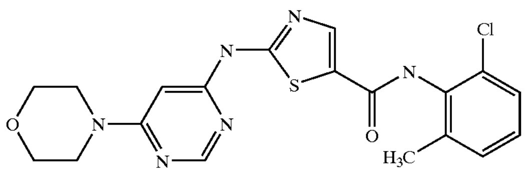 | 'N-(2-Chloro-6-methylphenyl)-2-[[6-(4-morpholinyl-4-pyrimidinyl]amino]-5-thiazolecarboxamide | 3.437 |

EXAMPLE 473

Preparation of 'N-(2-Chloro-6-methylphenyl)-2-[[6-[[2-(4-morpholinyl)ethyl]amino]-2-pyridinyl]amino]-5-thiazolecarboxamide

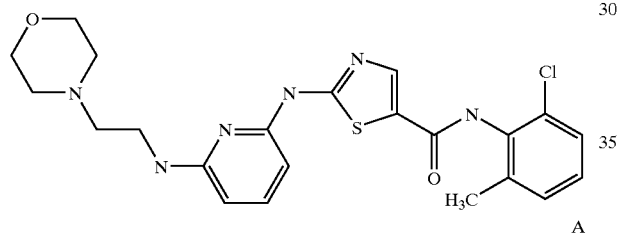

A

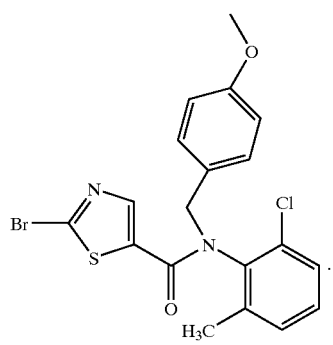

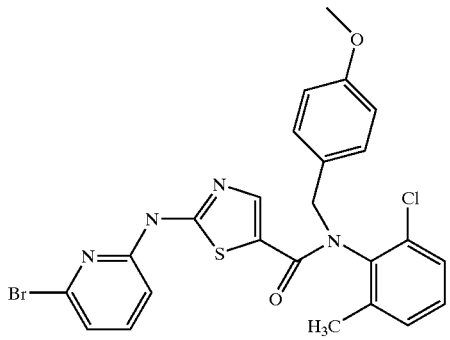

To a suspension of NaH (2.83 g, 118 mmol) in DMF (350 mL) cooled to 0° C. was added compound 319A (31 g, 93.5 mmol). The mixture was stirred for 45 min at 0° C. then Bu$_4$NI (6.9 g, 18.7 mmol) was added followed by addition of 4-methoxy benzylchloride (18 g, 115 mmol). The reaction was allowed to warm to RT. After stirring overnight at RT the reaction was quenched slowly with acetic acid then the solvent removed in vacuo. To the residue was added water and neutralized with saturated aqueous NaHCO$_3$. The mixture was extracted 3 times with EtOAc and the combined organic layers washed with water then washed with saturated NaCl solution. The EtOAc layer was concentrated in vacuo and the residue purified by column chromatography to give 473A (35 g).

To compound 473A (0.5 g, 1.1 mmol) dissolved in THF (50 mL) was slowly added NaH (0.13 g, 5.5 mmol) followed by 2-bromo-6-aminopyridine (0.76 g, 4.4 mmol). The reaction was heated to reflux for 2 h then cooled to RT and quenched with acetic acid. The solvent was removed in vacuo then water and hexane was added and stirred at RT. The solid precipitate was collected by filtration and washed with water and Et$_2$O to give 473B (0.48 g)

To compound 473B (0.48 g) dissolved in TFA (5 mL) was added anisole (2 mL) followed by triflic acid (1 mL). The reaction was stirred at RT for 3 h then was slowly added to a rapidly stirred mixture of ice, saturated NaHCO$_3$, Et$_2$O and CH$_{12}$Cl$_2$. The mixture was stirred cold for 1 h then the solid precipitate was collected by filtration and washed with water followed by Et$_2$O/CH$_2$Cl$_2$ mixture to give 473C (0.344 g). HPLC Ret. Time 3.85 min.

D. Title Compound

The title compound was prepared by an analogous method as that of 444B, except using compound 473C in place of compound 444A. HPLC Ret. Time 2.80 min.

EXAMPLES 474 TO 480

General Procedure

Compounds 474 to 480 were prepared by an analogous method as that of 473D by substituting the appropriate amine.

| EX. NO. | Compound Structure | Compound Name | HPLC Ret Time (min) |
|---|---|---|---|
| 474 | 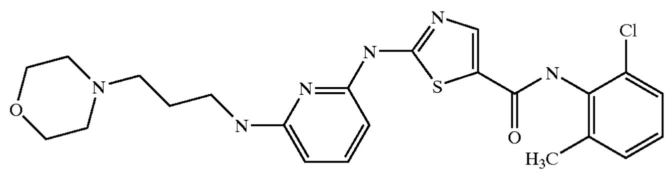 | 'N-(2-Chloro-6-methylphenyl)-2-[[6-[[3-(4-morpholinyl)-propyl]amino]-2-pyridinyl]-amino]-5-thiazolecarboxamide | 2.867 |
| 475 | 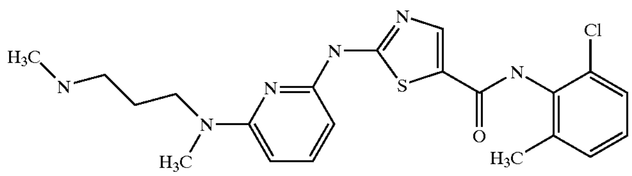 | 'N-(2-Chloro-6-methylphenyl)-2-[[6-[methyl[3-(methyl-amino)propyl]amino]-2-pyridinyl]amino]-5-thiazolecarboxamide | 3.067 |
| 476 | 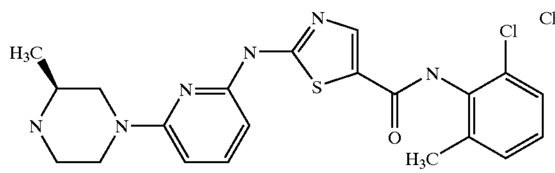 | 'N-(2-Chloro-6-methylphenyl)-2-[[6-[(3S)-3-methyl-1-piperazinyl]-2-pyridinyl]-amino]-5-thiazolecarboxamide | 2.827 |
| 477 | 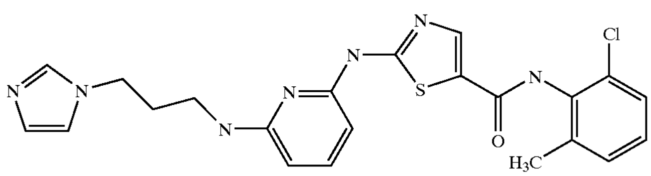 | 'N-(2-Chloro-6-methylphenyl)-2-[[6-[(3-1H-imidazol-1-ylpropyl)amino]-2-pyridinyl]-amino]-5-thiazolecarboxamide | 2.83 |
| 478 | 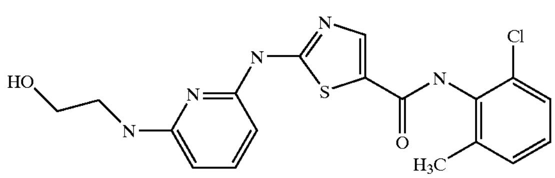 | 'N-(2-Chloro-6-methylphenyl)-2-[[6-[(2-hydroxyethyl)amino]-2-pyridinyl]amino]-5-thiazolecarboxamide | 3.077 |
| 479 | 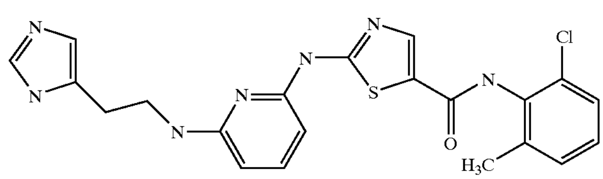 | 'N-(2-Chloro-6-methylphenyl)-2-[[6-[(2-1H-imidazol-1-ylethyl)amino]-2-pyridinyl]-amino]-5-thiazolecarboxamide | 2.903 |
| 480 | 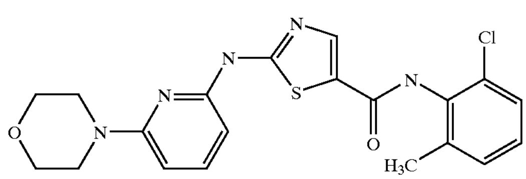 | 'N-(2-Chloro-6-methylphenyl)-2-[[6-(4-morpholinyl)-2-pyridinyl]amino]-5-thiazolecarboxamide | 3.727 |

EXAMPLE 481

Preparation of 'N-(2-Chloro-6-methylphenyl)-2-[[6-f[2-(4-morpholinyl)ethyl]amino]-2-pyrazinyl amino]-5-thiazolecarboxamide

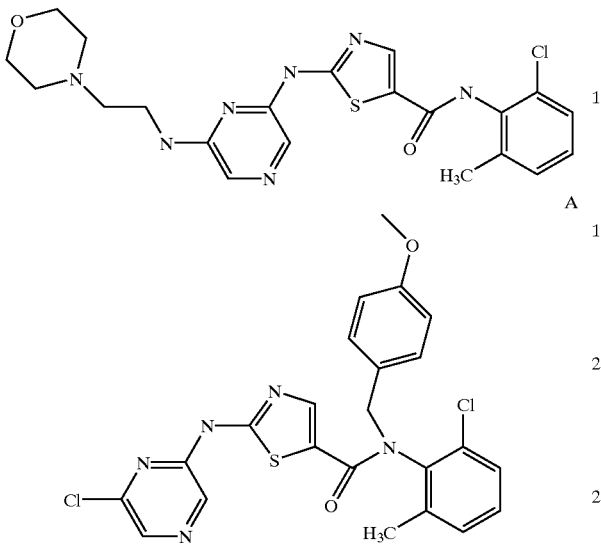

Compound 481A was prepared by an analogous method as that of 473B, except using compound 2-chloro-6-aminopyrazine in place of compound 2-bromo-6-aminopyridine.

B. (Alternate Synthesis for Compound 406)

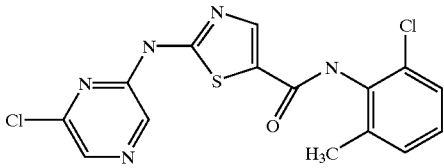

Compound 406 was prepared by an analogous method as that of 473C, except using compound 481A in place of compound 473B.

C. Title Compound

The title compound was prepared by an analogous method as that of 444B, except using compound 406 in place of compound 444A. HPLC Ret. Time 2.69 min.

EXAMPLES 482 TO 486

General Procedure

Compounds 482 to 486 were prepared by an analogous method as that of 481C by substituting the appropriate amine.

| EX. NO. | Compound Structure | Compound Name | HPLC Ret Time (min) |
|---|---|---|---|
| 482 | 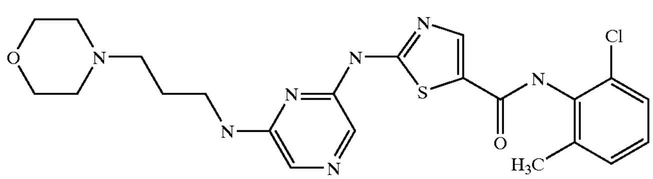 | 'N-(2-Chloro-6-methylphenyl)-2-[[6-[[3-(4-morpholinyl)-propyl]amino]-2-pyrazinyl]-amino]-5-thiazolecarboxamide | 2.783 |
| 483 | 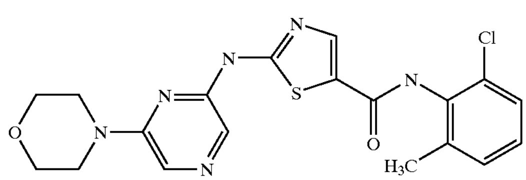 | 'N-(2-Chloro-6-methylphenyl)-2-[[6-(4-morpholinyl)-pyrazinyl]amino]-5-thiazolecarboxamide | 3.57 |
| 484 | 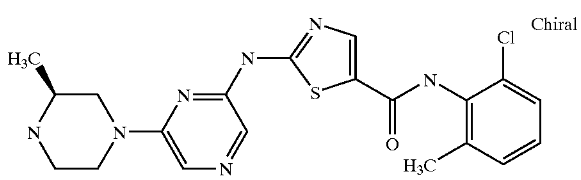 | 'N-(2-Chloro-6-methylphenyl)-2-[[6-[(3S)-3-methyl-1-piperazinyl]-2-pyrazinyl]-amino]-5-thiazolecarboxamide | 2.743 |
| 485 | 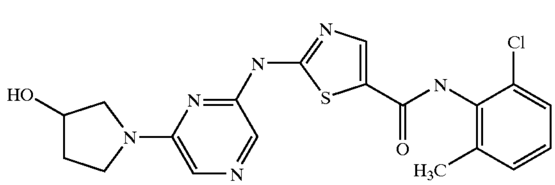 | 'N-(2-Chloro-6-methylphenyl)-2-[[6-(3-hydroxy-1-pyrrolidinyl)-2-pyrazinyl]-amino]-5-thiazolecarboxamide | 3.327 |

| EX. NO. | Compound Structure | Compound Name | HPLC Ret Time (min) |
|---|---|---|---|
| 486 | 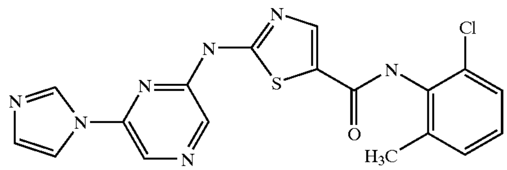 | 'N-(2-Chloro-6-methylphenyl)-2-[[6-(1H-imidazol-1-yl)-2-pyrazinyl]amino]-5-thiazolecarboxamide | 2.68 |

EXAMPLE 487

Preparation of 'N-(2-Chloro-6-methylphenyl)-2-[[6-(3-hydroxy-1-pyrrolidinyl)-3-pyridazinyl]amino]-5-thiazolecarboxamide

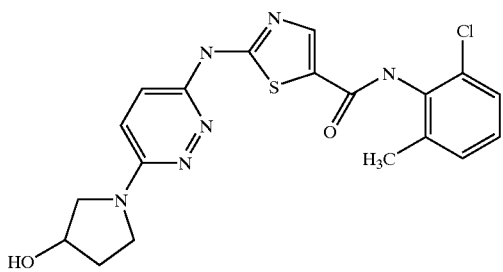

A

Compound 487A was prepared by an analogous method as that of 473B, except using compound 3-chloro-5-aminopyridazine in place of compound 2-bromo-6-aminopyridine.

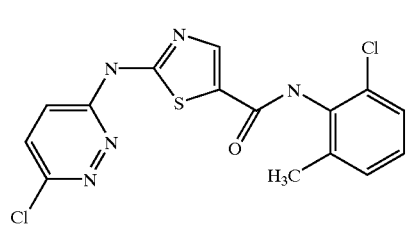

B

Compound 487B was prepared by an analogous method as that of 473C, except using compound 487A in place of compound 473B.

C. Title Compound

The title compound was prepared by an analogous method as that of 444B, except using compound 487B in place of compound 444A, and 3-hydroxypyrrolidine in place of N-(2-aminoethyl)-morpholine. HPLC Ret. Time 2.493 min.

EXAMPLE 488

Preparation of 'N-(2-Chloro-6-methylphenyl)-2-[[6-(1H-imidazol-1-yl)-3-pyridazinyl]amino]-5-thiazolecarboxamide

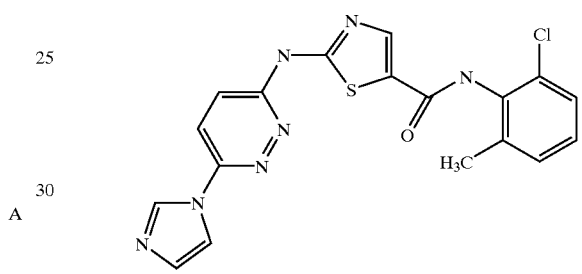

Compound 488 was prepared by an analogous method as that of 487C, except using imidazole in place of 3-hydroxypyrrolidine. HPLC Ret. Time 2.61 min.

EXAMPLE 489

Preparation of 'N-(2-Chloro-6-methylphenyl)-2-[3-(methylamino)-2-pyrazinyl]amino]-5-thiazolecarboxamide

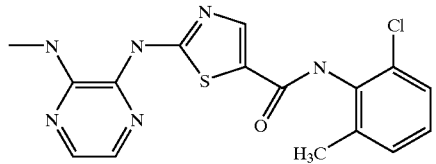

A

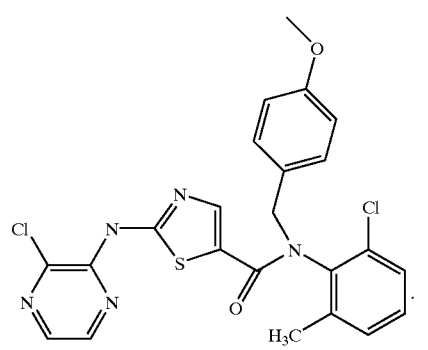

Compound 489A was prepared by an analogous method as that of 473B, except using compound 2-chloro-3-

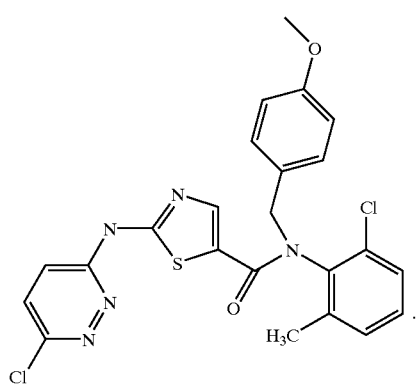

aminopyrazine in place of compound 2-bromo-6-aminopyridine.

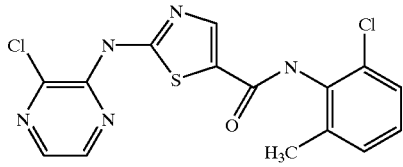

B

Compound 489B was prepared by an analogous method as that of 473C, except using compound 489A in place of compound 473B.

C. Title Compound

The title compound was prepared by an analogous method as that of 444B, except using compound 489B in place of compound 444A, and using methylamine in place of N-(2-aminoethyl)-morpholine. HPLC Ret. Time 2.81 in.

EXAMPLES 490 TO 494

General Procedure

Compounds 490 to 494 were prepared by an analogous method as that of 489C by substituting the appropriate amine.

| EX. NO. | Compound Structure | Compound Name | HPLC Ret Time (min) |
|---|---|---|---|
| 490 | 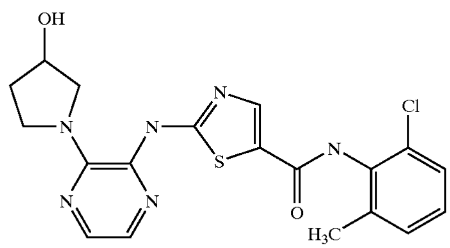 | 'N-(2-Chloro-6-methylphenyl)-2-[[3-(3-hydroxy-1-pyrrolidinyl)-2-pyrazinyl]amino]-5-thiazolecarboxamide | 2.82 |
| 491 | 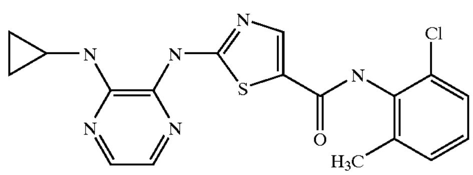 | 'N-(2-Chloro-6-methylphenyl)-2-[[3-(cyclopropylamino)-2-pyrazinyl]amino]-5-thiazolecarboxamide | 2.94 |
| 492 | 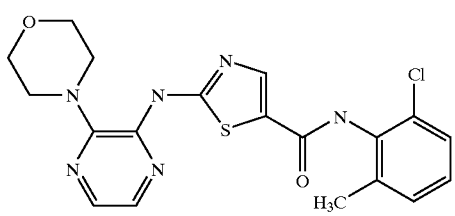 | 'N-(2-Chloro-6-methylphenyl)-2-[[3-(4-morpholinyl)-2-pyrazinyl]amino]-5-thiazolecarboxamide | 3.643 |
| 493 | 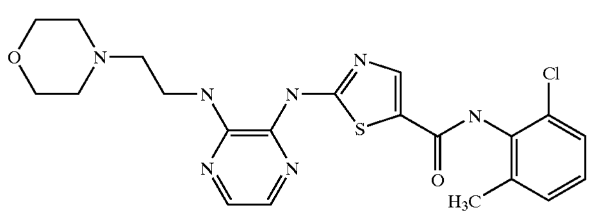 | 'N-(2-Chloro-6-methylphenyl)-2-[[3-[[2-(4-morpholinyl)ethyl]amino]-2-pyrazinyl]amino]-5-thiazolecarboxamide | 2.72 |
| 494 | 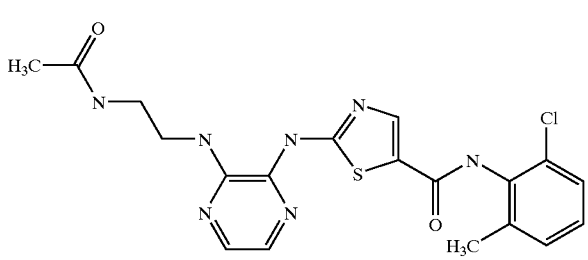 | '2-[[3-[[2-(Acetylamino)ethyl]amino]-2-pyrazinyl]amino]-N-(2-chloro-6-methylphenyl)-5-thiazolecarboxamide | 2.933 |

EXAMPLE 495

Preparation of 'N-(2-Chloro-6-methylphenyl)-2-(cyclohexylamino)-5-thiazolecarboxamide

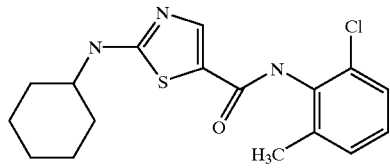

Compound 495 was prepared by an analogous method as that of 444B, except using compound 319A in place of compound 444A, and using cyclohexylamine in place of N-(2-aminoethyl)-morpholine. HPLC Ret. Time 3.547 min.

EXAMPLES 496 TO 500

General Procedure

Compounds 496 to 500 were prepared by an analogous method as that of 495 by substituting the appropriate amine.

| EX. NO. | Compound Structure | Compound Name | HPLC Ret. Time (min) |
|---|---|---|---|
| 496 | 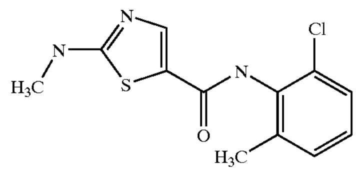 | 'N-(2-Chloro-6-methylphenyl)-2-(methylamino)-5-thiazolecarboxamide | 2.357 |
| 497 | 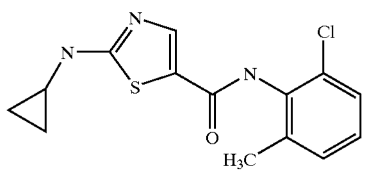 | 'N-(2-Chloro-6-methylphenlyl)-2-(cyclopropylamino)-5-thiazolecarboxamide | 2.887 |
| 498 | 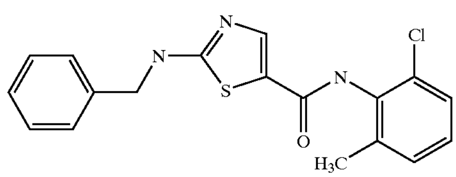 | 'N-(2-Chloro-6-methylphenyl)-2-[(phenylmethyl)amino]-5-thiazolecarboxamide | 3.500 |
| 499 | 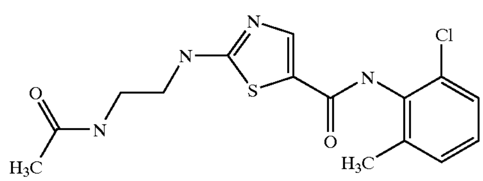 | '2-[[2-(Acetylamino)ethyl]amino]-N-(2-chloro-6-methylphenyl)-5-thiazolecarboxamide | 2.483 |
| 500 | Chiral | 'N-(2-Chloro-6-methylphenyl)-2-[[(1R)-1-(hydroxymethyl)-3-methylbutyl]amino]-5-thiazolecarboxamide | 3.407 |

EXAMPLE 501

Preparation of 'N-(2-Chloro-6-methylphenyl)-2-[[6-(methoxymethyl)-4-pyrimidinyl]amino]-5-thiazolecarboxamide

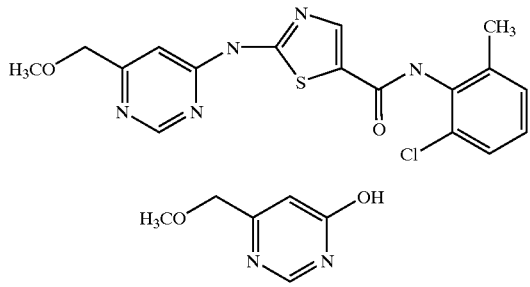

To the mixture of methyl 4-methoxyacetoacetate (14.6 g, 0.1 moL) and formami-dine hydrogen chloride salt (16.1 g, 0.2 mol.) in 70 mL of dry MeOH was added a 25% solution of sodium methoxide (70 mL, 0.3 mol.) in MeOH portionwise. A white precipitate was formed immediately. The reaction mixture was stirred at room temperature for 1.0 hr. Acetic acid (28.6 mL, 0.5 mol.) was added and the reaction mixture was concentrated in vacuo. Water was added to the residue and the mixture was supersaturated with NaCl and extracted with EtOAc (×5). Combined extracts were dried over anhydrous $Na_2SO_4$ and concentrated in vacuo to give 8.13 g of compound 501A as a yellow solid.

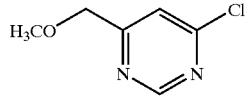

The mixture of compound 501A (5.3 g, 37.8 mmol.) and POCl (40 mL) was heated to reflux for 2.0 hrs. Concentration in vacuo and the residue was poured into a mixture of ice-$CH_2Cl_2$. The pH was adjusted to 6.5 to 7 using concentrated $NH_4OH$. The mixture was extracted with $CH_2Cl_2$ (×3) and combined extracts were dried over $Na_2SO_4$. Concentration in vacuo followed by flash chromatography ($CH_2Cl_2$-EtOAc: 9:1) on silica gel gave 5.33 g of compound 501B as a pale yellow oil.

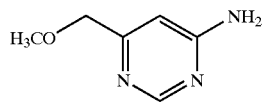

The mixture of compound 501B (3.2 g, 20 mmol.) and $NH_4OH$ (50 mL) was heated to 85.C in a pressure tube for 3.0 hrs. After cooled to room temperature, the reaction mixture was concentrated in vacuo and the residue was triturated with ether to give 2.81 g of compound 501C as a pale yellow solid.

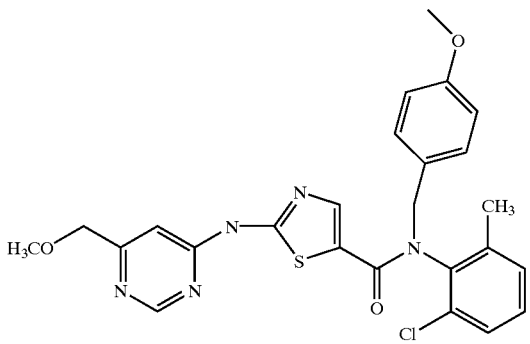

Compound 501D was prepared from compound 501C by a method analogous to that used for the preparation of compound 473B.

E Title Compound

The title compound was prepared from compound 501D by a method analogous to that used for the preparation of compound 473C. HPLC Retention time=3.25 min.

EXAMPLE 502

Preparation of 'N-(2-Chloro-6-methylphenyl)-2-[[6-(hydroxymethyl)-4-pyrimidinyl]amino]-5-thiazolecarboxamide

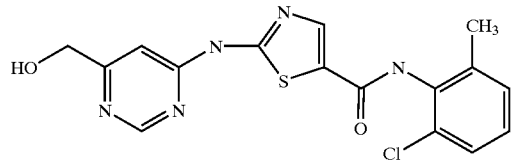

To a solution of compound 501 (56 mg, 0.144 mmol.) in dry $CH_{12}Cl_2$ (3.0 mL) cooled at 0.C was added neat BBr. (0.054 mL, 0.574 mmol.). The mixture was stirred for 1.0 hr at ambient temperature. MeOH was added slowly with care at 0.C and the resulting mixture was concentrated in vacuo. Water was added to the residue and pH was adjusted to 7 with Sat'd $NaHCO_3$. The white precipitate was collected by filtration, rinsed with water/ether and dried under high vacuum to give 52 mg of Compound 502 as an off-white solid. HPLC Retention time=2.84 min.

EXAMPLE 503

Preparation of 'N-(2-Chloro-6-methylphenyl)-2-[[6-(4-morpholinylmethyl)-4-pyrimidinyl]amino]-5-thiazolecarboxamide

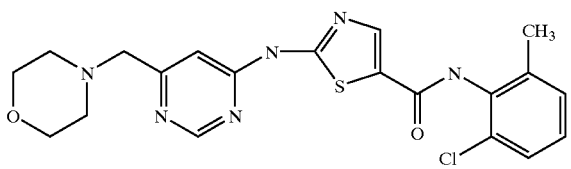

233

-continued

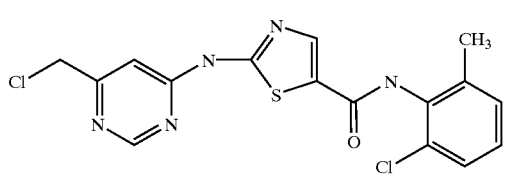
A

To a suspension of compound 502 (44.2 mg, 0.118 mmol.) in 0.5 mL of dry CH₂Cl₂ was added thionyl chloride (0.086 mL, 1.18 mmol.). The reaction mixture was stirred for 5.0 hrs. Concentration in vacuo and the residue was azeotropic evaporated with CH₂Cl₂ to give 56 mg of 503 as an yellow solid.

234

B Title Compound

The mixture of compound 503A (20 mg), morpholine (0.014 mL) and diisopropylethyl amine (0.09 mL) in 0.5 mL of dry dioxane was heated to 85.C for 4.0 hrs. Concentration in vacuo followed by flash chromatography (CH₂Cl₂-MeOH—NH₄OH: 95:5:0.5) on silica gel gave 15 mg of title compound as an off-white solid.

HPLC Retention time=2.52 min.

EXAMPLES 504 TO 513

General Procedure

Compounds 504 to 513 were prepared from 503A by a route analogous to that used for the preparation of 503. The compounds of these examples have the structure:

| EX. NO. | Compound Structure | Compound Name | HPLC Ret Time (min) |
|---|---|---|---|
| 504 | 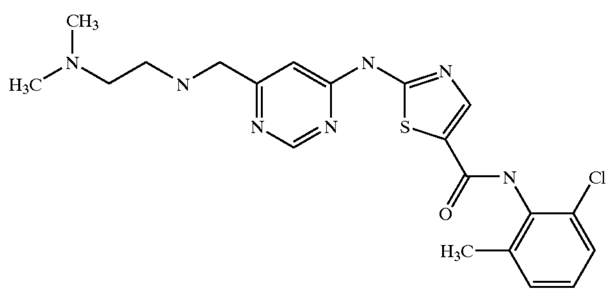 | 'N-(2-Chloro-6-methylphenyl)-2-{{6-{{{2-(dimethylamino)ethyl}amino}methyl}-4-pyrimidinyl}amino}-5-thiazolecarboxamide | 2.083 |
| 505 | 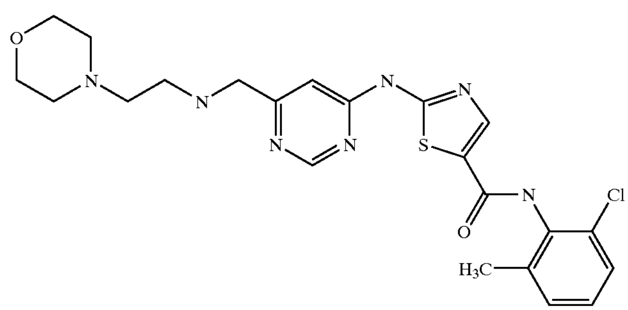 | 'N-(2-Chloro-6-methylphenyl)-2-{{6-{{{2-(4-morpholinyl)ethyl}amino}methyl}-4-pyrimidinyl}amino}-5-thiazolecarboxamide | 2.593 |
| 506 | 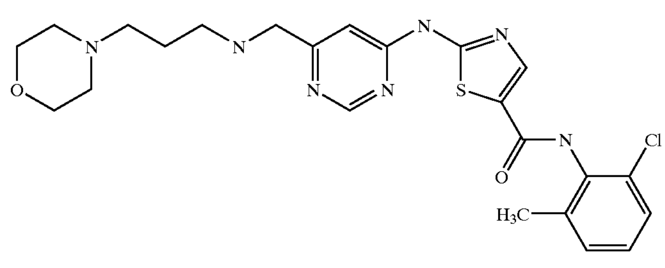 | 'N-(2-Chloro-6-methylphenyl)-2-{{6-{{{3-(4-morpholinyl)propyl}amino}methyl}-4-pyrimidinyl}amino}-5-thiazolecarboxamide | 2.163 |

-continued

| EX. NO. | Compound Name | HPLC Ret Time (min) |
|---|---|---|
| 507 | 'N-(2-Chloro-6-methylphenyl)-2-{{6-{{{3-(2-oxo-1-pyrrolidinyl)propyl}amino}methyl}-4-pyrimidinyl}amino}-5-thiazolecarboxamide | 2.693 |
| 508 | 'N-(2-Chloro-6-methylphenyl)-2-{{6-{{{(2-1H-imidazol-4-yl)ethyl)amino}methyl}-4-pyrimidinyl}amino}-5-thiazolecarboxamide | 2.143 |
| 509 | 'N-(2-Chloro-6-methylphenyl)-2-{{6-{{{(3-1H-imidazol-1-ylpropyl)amino}methyl}-4-pyrimidinyl}amino}-5-thiazolecarboxamide | 1.103 B |
| 510 | 'N-(2-Chloro-6-methylphenyl)-2-{{6-{{{2-(2-pyridinyl)ethyl}amino}methyl}-4-pyrimidinyl}amino}-5-thiazolecarboxamide | 1.113 B |
| 511 | 'N-(2-Chloro-6-methylphenyl)-2-{{6-{{{2-(3-pyridinyl)ethyl}amino}methyl}-4-pyrimidinyl}amino}-5-thiazolecarboxamide | 1.117 B |

-continued

| EX. NO. | Compound Structure | Compound Name | HPLC Ret Time (min) |
|---|---|---|---|
| 512 | 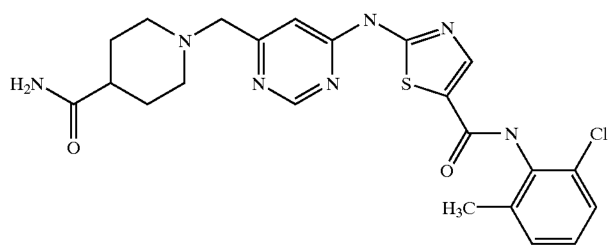 | '1-{{6-{{5-{{(2-Chloro-6-methylphenyl)amino}carbonyl}-2-thiazolyl}amino}-4-pyrimidinyl}methyl}-4-piperidinecarboxamide | 1.207 B |
| 513 | 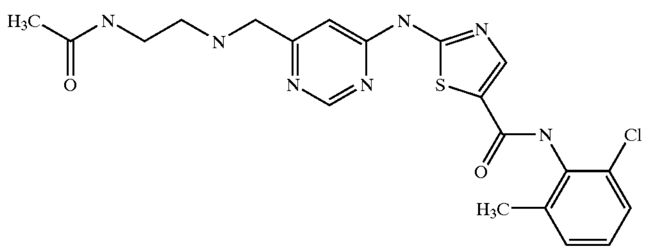 | '2-{{6-{{{2-(Acetylamino)ethyl}amino}methyl}-4-pyrimidinyl}amino}-N-(2-chloro-6-methylphenyl)-5-thiazolecarboxamide | 1.193 B |

EXAMPLE 514

Preparation of 'N-(2-Chloro-6-methylphenyl)-2-(2-naphthalenylamino)-5-thiazolecarboxamide

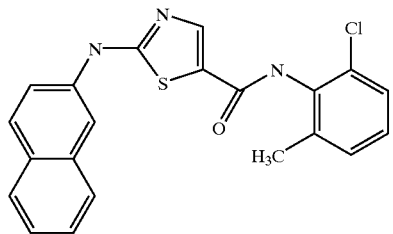

A

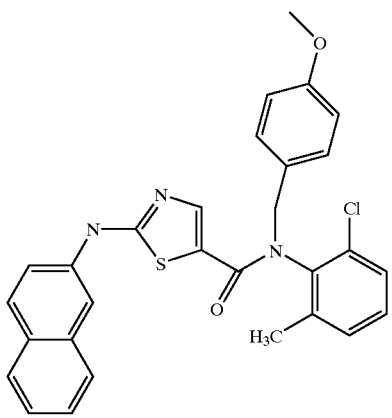

Compound 514A was prepared from 473A by an analogous method as that of 473B, except using 2-aminonapthaline in place of 2-bromo-6-aminopyridine.

B. Title Compound

The title compound was prepared by an analogous method as that of 473C, except using compound 514A in place of compound 473B. HPLC Ret. Time 4.11 min.

EXAMPLE 515

Preparation of 'N-(2-Chloro-6-methylphenyl)-2-(2-quinolinylamino)-5-thiazolecarboxamide

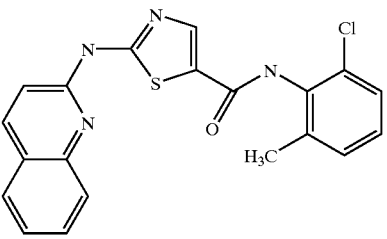

A

Compound 515A was prepared from 473A by an analogous method as that of 473B, except using 2-aminoquinoline in place of 2-bromo-6-aminopyridine.

B. Title Compound

The title compound was prepared by an analogous method as that of 473C, except using compound 515A in place of compound 473B. HPLC Ret. Time 3.94 min.

EXAMPLE 516

Preparation of 'N-(2-Chloro-6-methylphenyl)-2-(3-isoquinolinylamino)-5-thiazolecarboxamide

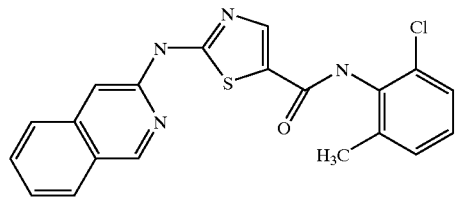

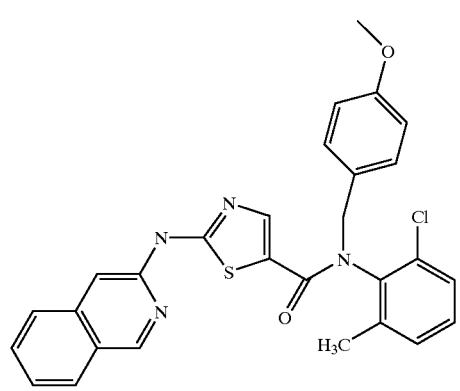

A

Compound 516A was prepared from 473A by an analogous method as that of 473B, except using 3-aminoisoquinoline in place of 2-bromo-6-aminopyridine.

B. Title Compound

The title compound was prepared by an analogous method as that of 473C, except using compound 516A in place of compound 473B. HPLC Ret. Time 3.94 min.

EXAMPLE 517

Preparation of 'N-(2-Chloro-6-methylphenyl)-2-(2-quinoxalinylamino)-5-thiazolecarboxamide

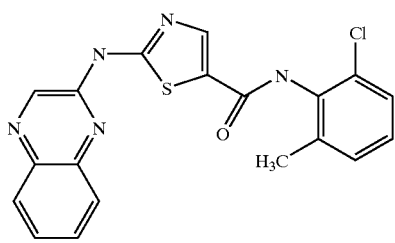

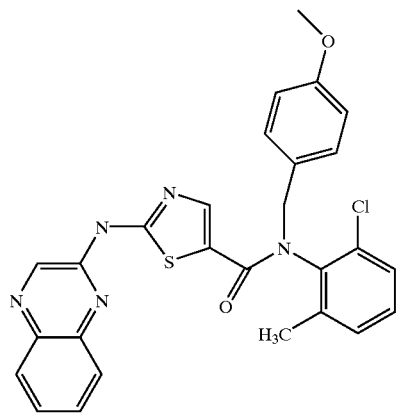

A

Compound 517A was prepared from 473A by an analogous method as that of 473B, except using 2-aminoquinoxaline in place of 2-bromo-6-aminopyridine.

B. Title Compound

The title compound was prepared by an analogous method as that of 473C, except using compound 517A in place of compound 473B. HPLC Ret. Time 3.927 min.

EXAMPLE 518

Preparation of 'N-(2-Chloro-6-methylphenyl)-4-methyl-2-[[2-methyl-6-(4-morpholinyl)-4-pyrimidinyl]amino]-5-thiazolecarboxamide

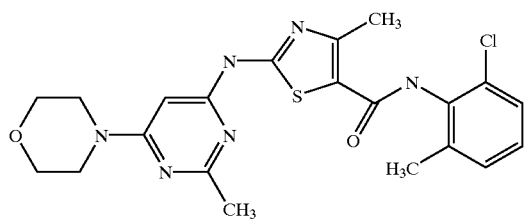

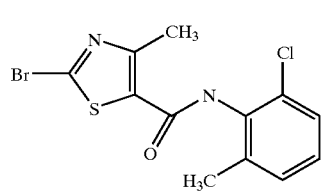

A

Compound 518A was prepared from 144 by an analogous method as that of 319A.

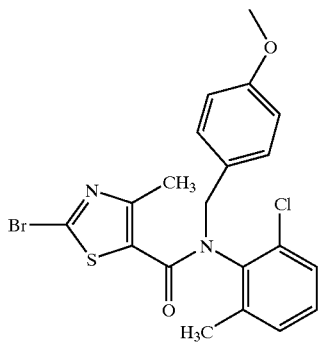

B

Compound 518B was prepared by an analogous method as that of 473A, except using 518A in place of 319A.

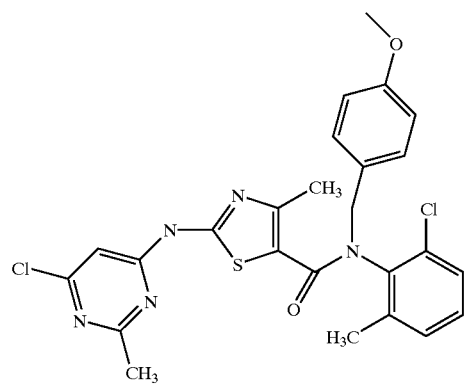

C

Compound 518C was prepared by an analogous method as that of 473B, except using 518B in place of 473A, and 4-amino-6-chloro-2-methylpyrimidine in place of 2-amino-6-bromopyridine.

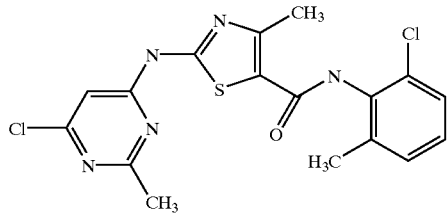

D

Compound 518D was prepared by an analogous method as that of 473C, except using 518C in place of 473B.

E. Title Compound

The title compound was prepared by an analogous method as that of 444B, except using compound 518D in place of compound 444A, and morpholine in place of N-(2-aminoethyl)-morpholine. HPLC Ret. Time 3.397 min.

EXAMPLE 519

Preparation of 'N-(2-Chloro-6-methylphenyl)-4-methyl-2-[[2-methyl-6-[[2-(4-morpholinyl)ethyl]amino]-4-pyrimidinyl]amino]-5-thiazolecarboxamide

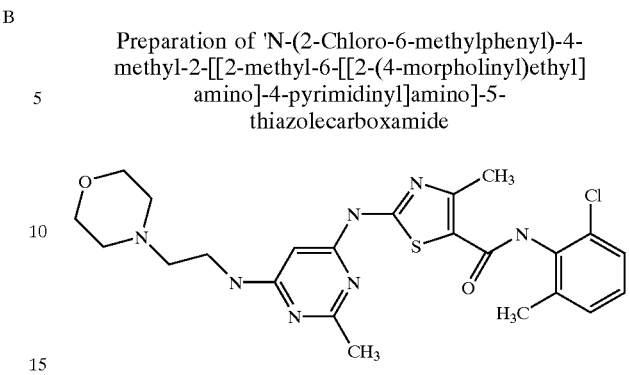

Compound 519 was prepared by an analogous method as that of 518E, except using N-(2-aminoethyl)-morpholine in place of morpholine. HPLC Ret. Time 2.493 min.

EXAMPLE 520

Alternative preparation of compound 321

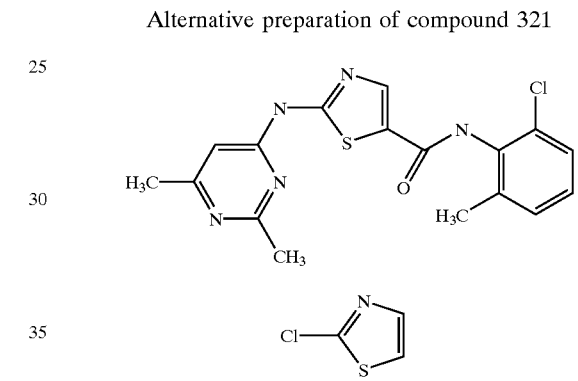

A

Compound 520A was prepared from 2-aminothiazole according to the procedure described in UK Patent Application GB 2323595A.

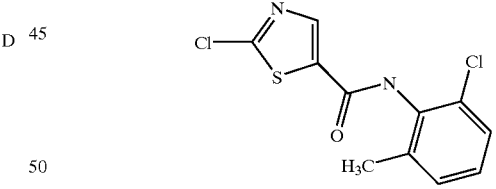

B

To a solution of compound 520A (480 mg, 4.0 mmol.) in dry THF (10 mL) cooled at −78.C was added a 2.5M solution of n-BuLi (1.68 mL, 4.2 mmol.) in hexane dropwise via a syringe while kept the internal temperature below −75.C. Upon completion of addition, a beige suspension was obtained. The reaction mixture was stirred for 15 min at −78.C. A solution of 2-chloro-6-methyl phenyl isocyanate (0.6 mL, 4.4 mmol.) in 5 mL of dry THF was added and the reaction mixture was stirred for an additional 2.0 hrs at −78.C. Saturated aq. NH$_4$Cl solution (10 mL) was added, the mixture was partitioned between EtOAc-water and extracted with EtOAc (×2). The combined extracts were dried over Na$_2$SO$_4$ and concentration in vacuo to give, after recrystallization from EtOAc-hexane, 0.99 g of title compound as a pale yellow crystalline material.

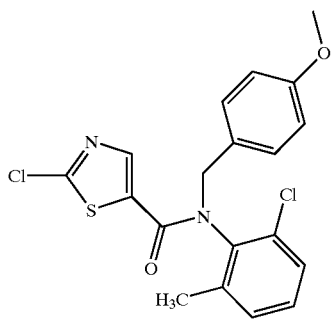

Compound 520C was prepared by a method analogous to that used for the preparation of compound 473A, using 520B in place of 319A.

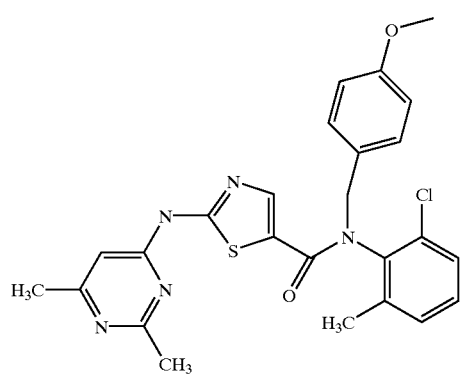

Compound 520D was prepared from compound 520C by a method analogous to that used for the preparation of compound 473B.

E. Title Compound

Compound 321 was prepared by a method analogous to that used for the preparation of compound 473C.

EXAMPLE 521

Preparation of '2-[(2,6-Dimethyl-4-pyrimidinyl) amino]-N-phenyl-5-thiazolecarboxamide

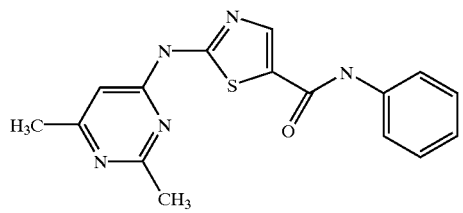

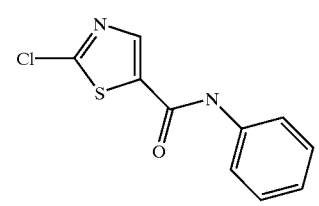

Compound 521A was prepared by an analogous method as that of 520B, except using phenylisocyanate in place of 2-chloro-6-methylphenylisocyanate.

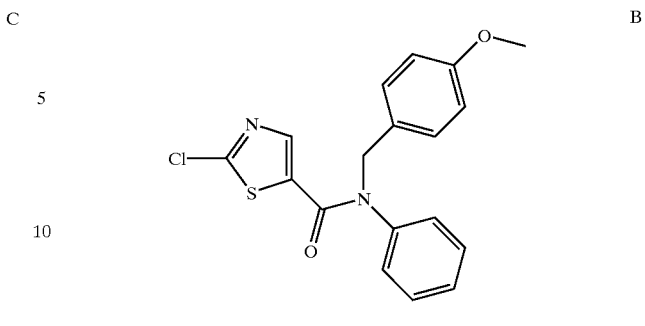

Compound 521B was prepared by a method analogous to that used for the preparation of compound 473A, using 521A in place of 319A.

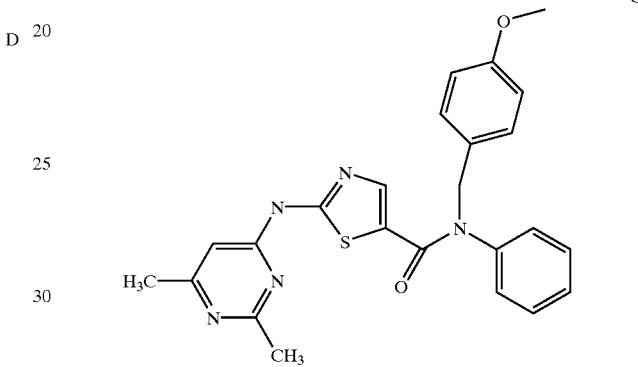

Compound 521C was prepared from compound 521B by a method analogous to that used for the preparation of compound 473B.

D Title Compound

The title compound was prepared by a method analogous to that used for the preparation of compound 473C. HPLC Ret. Time 1.3 min method B

EXAMPLE 522

Preparation of '2-[(2.6-Dimethyl-4-pyrimidinyl) methylamino]-N-(2-methylphenyl)-5-thiazolecarboxamide

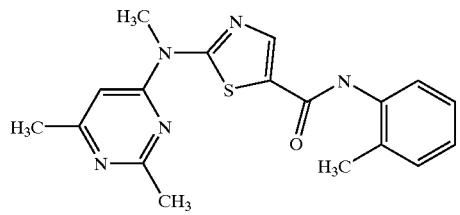

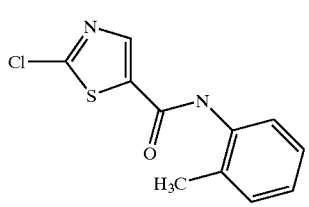

Compound 522A was prepared by an analogous method as that of 520B, except using 2-methylphenylisocyanate in place of 2-chloro-6-methylphenylisocyanate.

B

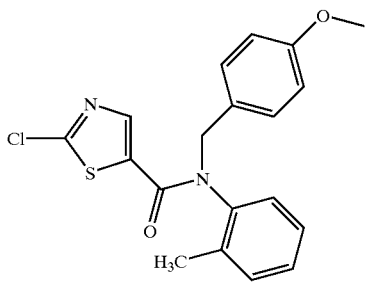

Compound 522B was prepared by a method analogous to that used for the preparation of compound 473A, using 522A in place of 319A.

C

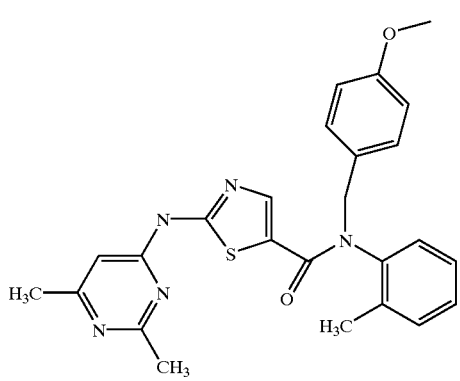

Compound 522C was prepared from compound 522B by a method analogous to that used for the preparation of compound 473B.

D

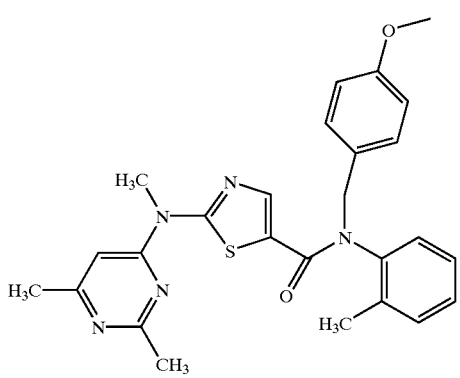

Sodium hydride (60% in oil; 40 mg; 1 mmol) was added to a solution of compound 522C (280 mg; 0.61 mmol) in 2 ml of DMF at room temp. After stirring 30 minutes, iodomethane (0.2 ml; 3 mmol) was added and the reaction was stirred 4 hr. After the reaction mixture was partitioned between ethyl acetate (50 ml) and water (50 ml), the organic layer was washed with water (2×50 ml) and brine (50 ml). Drying (MgSO$_4$) and concentration afforded an oil that was chromatographed on a 2.5×15 cm silica gel column using 50–75% ethyl acetate/hexane. The pure fractions were concentrated and the residue was crystalized from ethyl acetate/hexane to afford 100 mg of 522D as a light yellow solid.

E Title Compound

The title compound was prepared by a method analogous to that used for the preparation of compound 473C. HPLC Ret. Time 1.21 min method B

EXAMPLE 523

Preparation of '2-[(2,6-Dimethyl-4-pyrimidinyl)amino]-N-(2-methylphenyl)-5-thiazolecarboxamide

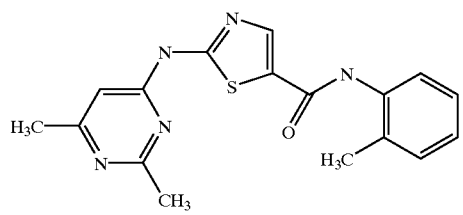

Compound 523 was prepared by a method analogous to that used for the preparation of compound 473C, except using compound 522C in place of 473B. HPLC Ret. Time 1.24 min method B

EXAMPLE 524

Preparation of 'N-(3,5-Dimethoxyphenyl)-2-[(2,6-dimethyl-4-pyrimidinyl)amino]-5-thiazolecarboxamide

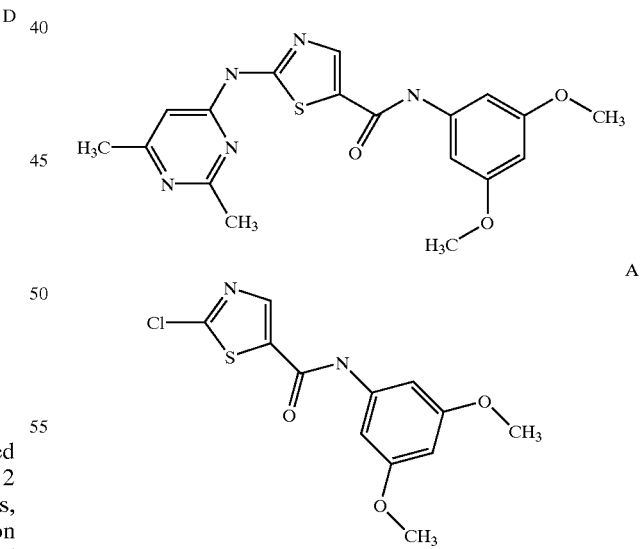

A

Compound 524A was prepared by an analogous method as that of 520B, except using 3,5-dimethoxyphenylisocyanate in place of 2-chloro-6-methylphenylisocyanate.

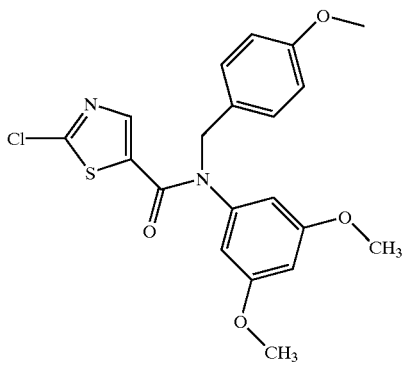

Compound 524B was prepared by a method analogous to that used for the preparation of compound 473A, using 524A in place of 319A.

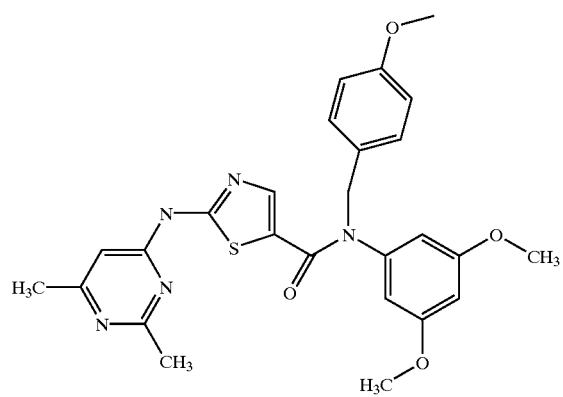

Compound 524C was prepared from compound 524B by a method analogous to that used for the preparation of compound 473B.

D Title Compound

The title compound was prepared by a method analogous to that used for the preparation of compound 473C, except using compound 524C in place of compound 473B HPLC Ret. Time 1.28 min method B

EXAMPLE 525

Preparation of 'N-[2,6-Bis(1-methylethyl)phenyl]-2-[(2,6-dimethyl-4-pyrimidinyl)amino]-5-thiazolecarboxamide

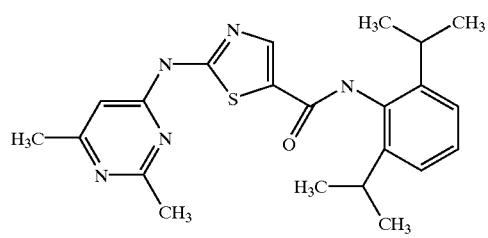

-continued

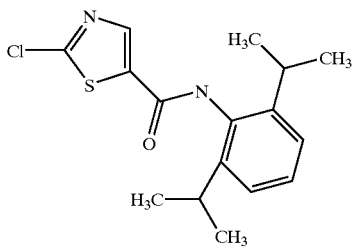

Compound 525A was prepared by an analogous method as that of 520B, except using 2,2-diisopropylphenylisocyanate in place of 2-chloro-6-methylphenylisocyanate.

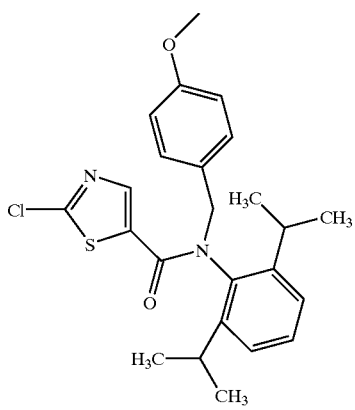

Compound 525B was prepared by a method analogous to that used for the preparation of compound 473A, using 525A in place of 319A.

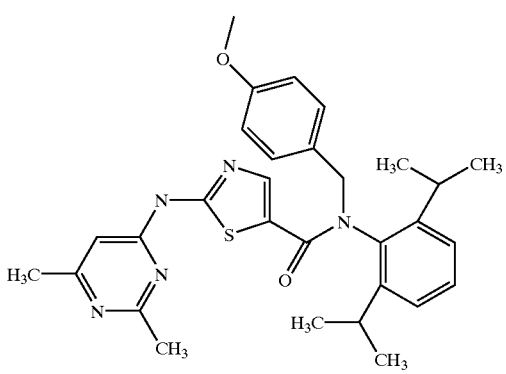

Compound 525C was prepared from compound 525B by a method analogous to that used for the preparation of compound 473B.

D Title Compound

The title compound was prepared by a method analogous to that used for the preparation of compound 473C, except using compound 525C in place of compound 473B. HPLC Ret. Time 1.6 min method B

EXAMPLE 526

Preparation of 'N-(2-Chloro-6-methylphenyl)-2-[(2,6-dimethyl-4-pyrimidinyl)methylamino]-5-thiazolecarboxamide

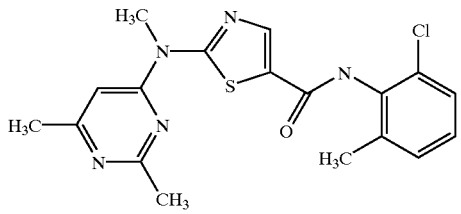

A mixture of compound 321 (110 mg; 0.29 mmol), potassium carbonate (138 mg; 1 mmol) and iodomethane (0.06 ml; 1 mmol) in DMF was stirred 2 hr at room temperature. After the reaction mixture was partitioned between ethyl acetate (25 ml) and water (25 ml), the organic layer was washed with water (2×25 ml) and brine (25 ml). Drying (MgSO$_4$) and concentration afforded an oil that was chromatographed on a 2.5×15 cm silica gel column using 1–4% MeOH/CH$_2$Cl$_2$ and the fractions containing compound 526 were collected to give 20 mg of product. HPLC Ret. Time 1.3 min method B.

EXAMPLE 527

Preparation of 'N-(2-Chloro-6-methylphenyl)-2-[(2,6-dimethyl-4-pyrimidinyl)amino]-N-methyl-5-thiazolecarboxamide

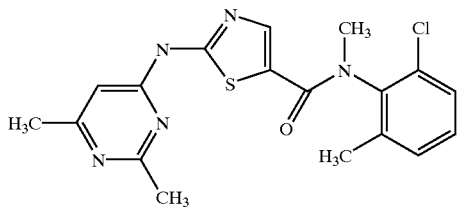

Compound 527 was prepared by a method analogous to that used for the preparation of compound 526, except the fractions containing compound 527 were collected to give 60 mg of product. HPLC Ret. Time 1.23 min method B

EXAMPLE 528

Preparation of 2-Bromo-N-, N-(2-chloro-6-methylphenyl)-(4-methoxybenzyl)-5-thiazolecarboxamide

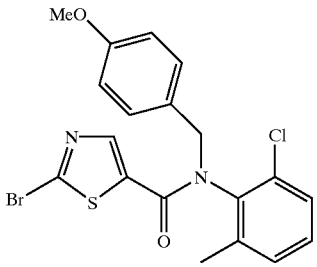

To a cooled (0° C.) THF solution of 2-chloro-6-methyl aniline (2.86 mL, 23.3 mmol, 1.10 equiv) was added dropwise a 1.0 M solution of lithium bis(trimethylsilyl)amide (42.2 mL, 42.2 mmol, 2.00 equiv) via syringe. The homogeneous solution was allowed to stir for 5 minutes, and then a THF solution of ethyl 2-bromo-5-thiazolecarboxylate (5.00 g, 21.1 mmol, 1.00 equiv, prepared in a manner analogous to compound 319A) was added via cannula. The solution was allowed to stir for 15 minutes until TLC analysis showed no remaining starting material. To the reaction was then added 4-methoxybenzyl chloride (7.15 mL, 52.7 mmol, 2.5 equiv), followed by a catalytic amount of tetrabutylammonium iodide (1.56 g, 4.22 mmol, 0.20 equiv). The homogeneous mixture was allowed to stir overnight at ambient temperature and then concentrated in vacuo. The residue was partitioned between ethyl acetate and water, and the organic extracts were washed with brine and dried over Na$_2$SO$_4$. After filtration and removal of solvent, the product was purified by flash chromatography (10–20% ethyl acetate in hexanes) to afford the title compound as a tan solid (47%).

EXAMPLE 529

Preparation of N-,N-(2-Chloro-6-methylphenyl)-(4-methoxybenzyl)-2-[(6-bromo-2-pyridinyl)amino]-5-thiazolecarboxamide

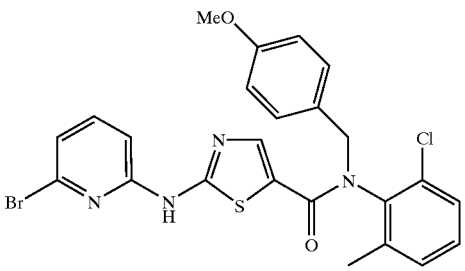

Compound 529 was prepared in an analogous manner to 319B, except using 528 and 6-bromo-2-aminopyridine as the reactants.

EXAMPLE 530

Preparation of N-(2-Chloro-6-methylphenyl)-2-[(6-bromo-2-pyridinyl)amino]-5-thiazolecarboxamide

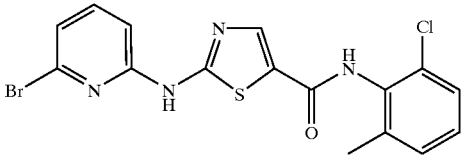

Compound 529 (0.500 g, 0.919 mmol, 1.00 equiv) was dissolved in 5 mL trifluoroacetic acid and charged at ambient temperature with 2 mL anisole followed by 1 mL trifluoromethanesulfonic acid. The dark red homogeneous solution was allowed to stir overnight, and then quenched by carefully pouring the solution into an ice/sodium bicarbonate mixture. A white solid was filtered off and washed sequentially with water, 1:1 hexane/ether, and ether to afford the title compound (41%).

EXAMPLES 531–538

General Procedure

Compounds 531 to 538 were prepared to the general procedure described below. A 1-dram vial was charged with 530 and excess amine and heated to 90° C. overnight. The residue was then purified by reverse phase HPLC to afford the pure compound. For the following examples 531 to 555 "HPLC Ret Time" is the HPLC retention time under the following conditions: YMC ODS-A C18 S7 3.0×50 mm, 2 min gradient starting from 100% solvent A (10% MeOH, 90% H$_2$O, 0.1% TFA) to 100% solvent B (90% MeOH, 10% H$_2$O, 0.1% TFA), flow rate 5 mL/min, λ=220 nM.

| EX. NO. | Compound Structure | Compound Name | HPLC Ret time (min) |
|---|---|---|---|
| 531 | 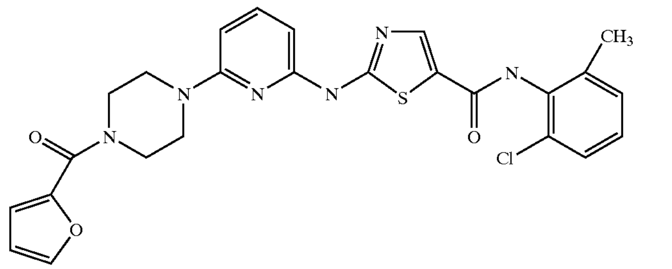 | 'N-(2-Chloro-6-methylphenyl)-2-[[6-[4-(2-furanylcarbonyl)-1-piperazinyl]-2-pyridinyl]amino]-5-thiazolecarboxamide | 1.56 |
| 532 | 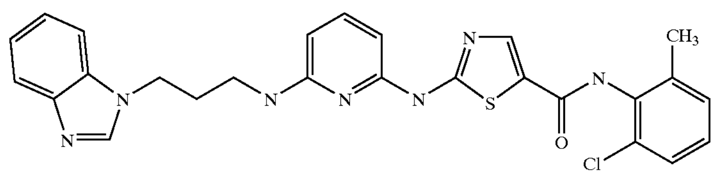 | '2-[[6-[[3-(1H-Benzimidazol-1-yl)propyl]amino]-2-pyridinyl]amino]-N-(2-chloro-6-methylphenyl)-5-thiazolecarboxamide | 1.41 |
| 533 | 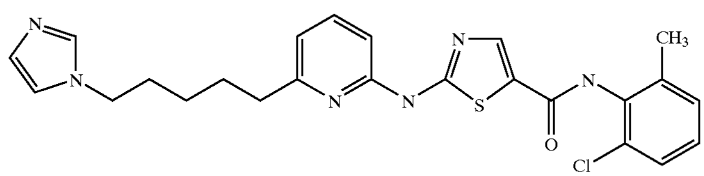 | 'N-(2-Chloro-6-methylphenyl)-2-[[6-[[4-(1H-imidazol-1-yl)butyl]amino]-2-pyridinyl]amino]-5-thiazolecarboxamide | 1.24 |
| 534 | 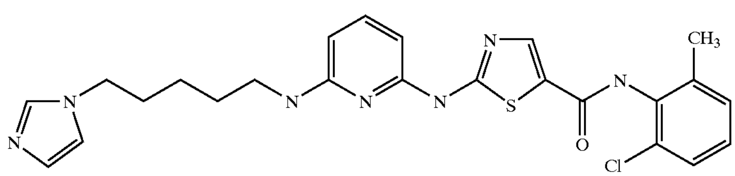 | 'N-(2-Chloro-6-methylphenyl)-2-[[6-[[5-(1H-imidazol-1-yl)pentyl]amino]-2-pyridinyl]amino]-5-thiazolecarboxamide | 1.25 |
| 535 | 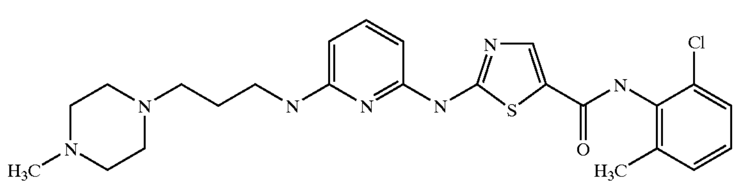 | 'N-(2-Chloro-6-methylphenyl)-2-[[6-[[3-(4-methyl-1-piperazinyl)propyl]amino]-2-pyridinyl]amino]-5-thiazolecarboxamide | |
| 536 | 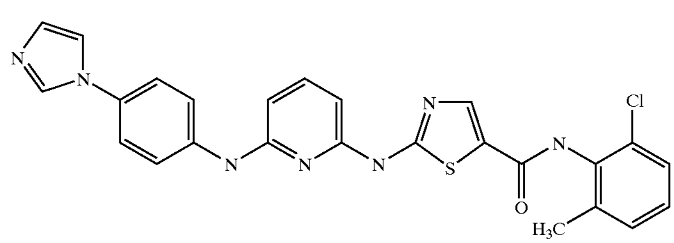 | 'N-(2-Chloro-6-methylphenyl)-2-[[6-[[4-(1H-imidazol-1-yl)phenyl]amino]-2-pyridin]amino]-5-thiazolecarboxamide | 1.29 |
| 537 | 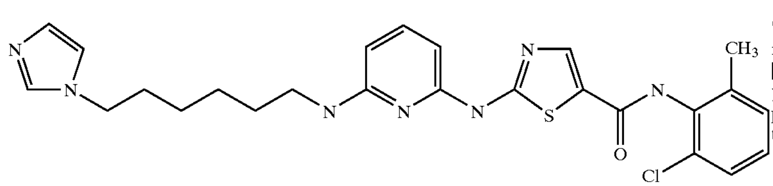 | 'N-(2-Chloro-6-methylphenyl)-2-[[6-[[6-(1H-imidazol-1-yl)hexyl]amino]-2-pyridinyl]amino]-5-thiazolecarboxamide | 1.27 |

| EX. NO. | Compound Structure | Compound Name | HPLC Ret time (min) |
|---|---|---|---|
| 538 | 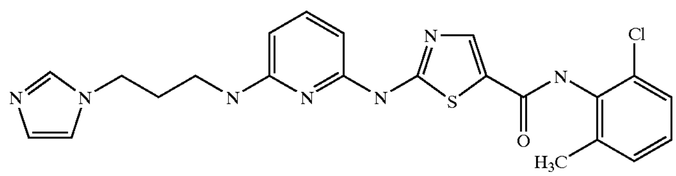 | 'N-(2-Chloro-6-methylphenyl)-2-[[6-[(3-1H-imidazol-1-ylpropyl)amino]-2-pyridinyl]amino]-5-thiazolecarboxamide | 1.24 |

EXAMPLE 539

Preparation of Ethyl-2-[(6-bromo-2-pyridinyl)amino]-5-thiazolecarboxylate

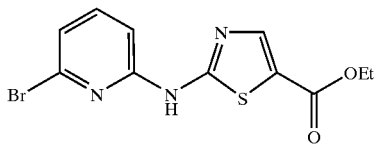

Compound 539 was prepared in an analogous manner to 319B, except using ethyl 2-bromo-5-thiazolecarboxylate and 6-bromo-2-aminopyridine as the reactants.

EXAMPLES 540–550

General Procedure

Compounds 540 to 550 were prepared according to the general procedure described below. Compound 539 was condensed with the appropriate aniline according to the procedure for example 528 to afford the afford the corresponding N-(4-methoxybenzyl)amide. The intermediate bromopyridine was then reacted with N-(3-aminopropyl)-imidazole according to the procedure for examples 531 to 538 to afford the corresponding diaminopyridine. Removal of the 4-methoxybenzyl group according to the procedure described for example 530 followed by purification by reverse phase preparative HPLC afforded compounds 540 to 550.

| EX. NO. | Compound Structure | Compound Name | HPLC Ret time (min) |
|---|---|---|---|
| 540 | 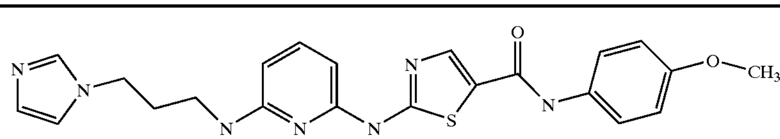 | '2-[[6-[[3-(1H-Imidazol-1-yl)propyl]amino]-2-pyridinyl]amino]-N-(4-methoxyphenyl)-5-thiazolecarboxamide | 1.12 |
| 541 | 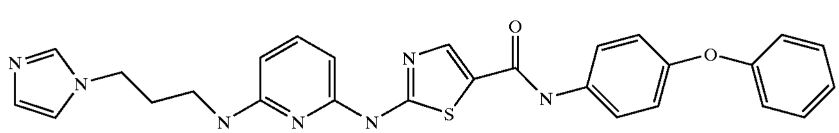 | '2-[[6-[[3-(1H-Imidazol-1-yl)propyl]amino]-2-pyridinyl]amino]-N-(4-phenoxyphenyl)-5-thiazolecarboxamide | 1.48 |
| 542 | 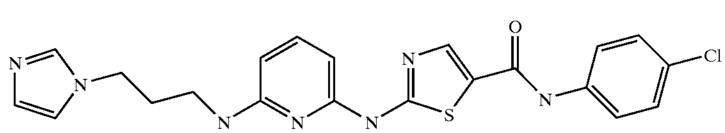 | 'N-(4-Chlorophenyl)-2-[[6-[[3-(1H-imidazol-1-yl)propyl]amino]-2-pyridinyl]amino]-5-thiazolecarboxamide | 1.31 |
| 543 | 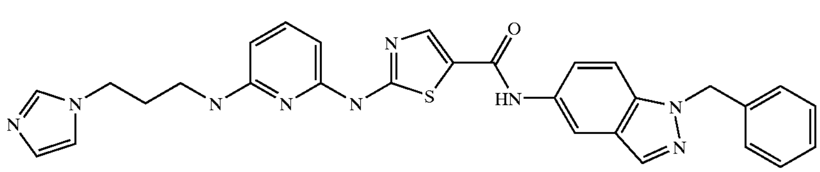 | '2-[[6-[[3-(1H-Imidazol-1-yl)propyl]amino]-2-pyridinyl]amino]-N-]1-(phenylmethyl)-1H-indazol-5-yl]-5-thiazolecarboxamide | 1.34 |

-continued

| EX. NO. | Compound Structure | Compound Name | HPLC Ret time (min) |
|---|---|---|---|
| 544 | 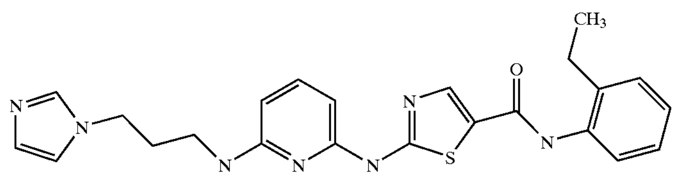 | 'N-(2-Ethylphenyl)-2-[[6-[[3-(1H-imidazol-1-yl)propyl]amino]-2-pyridinyl]amino]-5-thiazolecarboxamide | 1.18 |
| 545 | 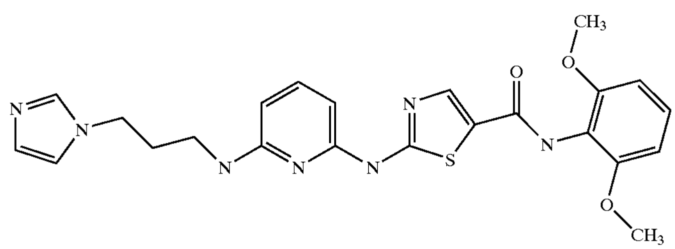 | 'N-(2,6-Dimethoxyphenyl)-2-[[6-[[3-(1H-imidazol-1-yl)propyl]amino]-2-pyridinyl]amino]-5-thiazolecarboxamide | 1.11 |
| 546 | 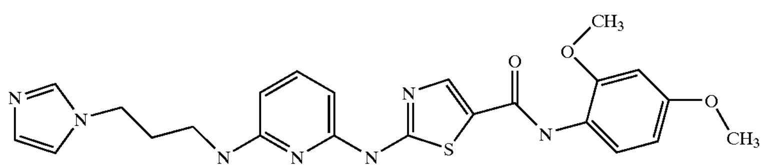 | 'N-(2,4-Dimethoxyphenyl)-2-[[6-[[3-(1H-imidazol-1-yl)propyl]amino]-2-pyridinyl]amino]-5-thiazolecarboxamide | 1.06 |
| 547 | 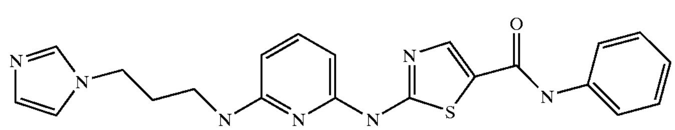 | '2-[[6-[[3-(1H-Imidazol-1-yl)propyl]amino]-2-pyridinyl]amino]-N-phenyl-5-thiazolecarboxamide | 1.06 |
| 548 | 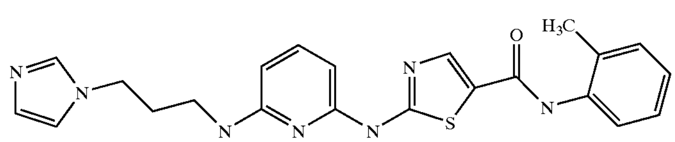 | '2-[[6-[[3-(1H-Imidazol-1-yl)propyl]amino]-2-pyridinyl]amino]-N-(2-methylphenyl)-5-thiazolecarboxamide | 1.11 |
| 549 | 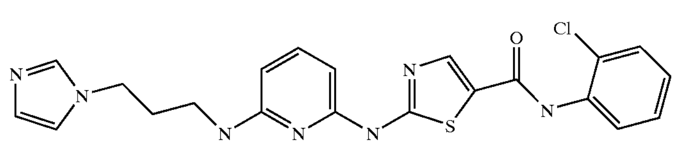 | 'N-(2-Chlorophenyl)-2-[[6-[[3-(1H-imidazol-1-yl)propyl]amino]-2-pyridinyl]amino]-5-thiazolecarboxamide | 1.16 |
| 550 | 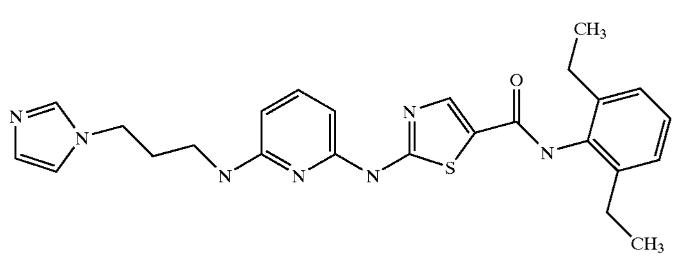 | 'N-(2,6-Diethylphenyl)-2-[[6-[[3-(1H-imidazol-1-yl)propyl]amino]-2-pyridinyl]amino]-5-thiazolecarboxamide | 1.29 |

EXAMPLE 551

Preparation of Ethyl-2-[(6-bromo-2-pyridinyl)amino]-4-methyl-5-thiazolecarboxylate

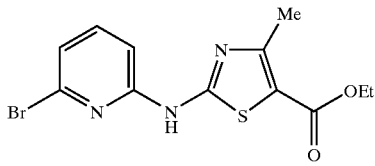

Compound 551 was prepared in an analogous manner to 319B, except using ethyl 2-bromo-4-methyl-5-thiazolecarboxylate and 6-bromo-2-aminopyridine as the reactants.

EXAMPLES 552 AND 553

Compounds 552 and 553 were prepared using a similar procedure described for the preparation of compounds 540 to 550, except using compound 551 as the starting material.

EXAMPLE 555

Preparation of 'N-(2-Chloro-6-methylphenyl)-2-[[5-[[3-(1H-imidazol-1-yl)propyl]amino]-2-nitrophenyl amino]-5-thiazolecarboxamide

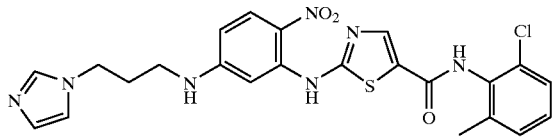

A solution of 2,4-difluoronitrobenzene (0.400 mL, 3.65 mmol, 1.00 equiv) in acetonitrile was charged with $K_2CO_3$ (0.605 g, 4.38 mmol, 1.20 equiv) followed by ethyl-2-amino-5-thiazolecarboxylate (0.628 g, 3.65 mmol, 1.00 equiv) as a solid. The heterogeneous mixture was sealed and heated to 120° C. overnight. The solution was filtered and

| EX. NO. | Compound Structure | Compound Name | HPLC Ret time (min) |
|---|---|---|---|
| 552 | 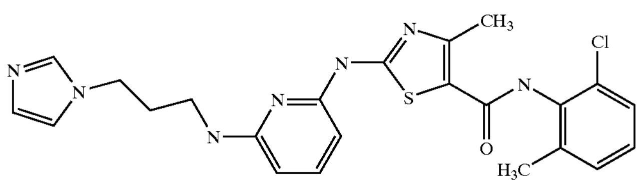 | 'N-(2-Chloro-6-methylphenyl)-2-[[6-[[3-(1H-imidazol-1-yl)propyl]amino]-2-pyridinyl]amino]-4-methyl-5-thiazolecarboxamide | 1.19 |
| 553 | 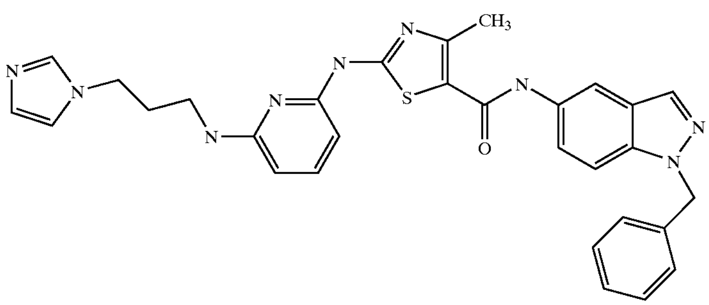 | '2-[[6-[[3-(1H-Imidazol-1-yl)propyl]amino]-2-pyridinyl]amino]-4-methyl-N-]1-(phenylmethyl)-1H-indazol-5-yl]-5-thiazolecarboxamide | 1.35 |

EXAMPLE 554

Preparation of 'N-(2-Chloro-6-methylphenyl)-2-[[3-[[3-(1H-imidazol-1-yl)propyl]amino]phenyl]amino]-5-thiazolecarboxamide

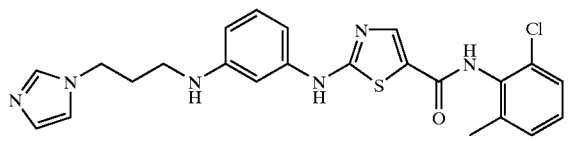

A solution of 528 (0.127 g, 0.281 mmol, 1.00 equiv) and 3-[N-,N-(tert-butoxycarbonyl)-(3-aminopropyl)-imidazoyl]-1,3-phenylenediamine (0.178 g, 0.563 mmol, 2.00 equiv) in 0.200 mL DMSO was heated at 120° C. in a sealed vial overnight. Purification by reverse phase preparative HPLC followed by deprotection according to the procedure for compound 530 afforded the title compound.

then concentrated in vacuo. Purification by flash chromatography afforded ethyl-2-[(3-fluoro-6-nitro-1-phenyl)amino]-5-thiazolecarboxylate as a yellow solid (9%). This intermediate was coupled with 2-chloro-6-methyl aniline according to the procedure for compound 528 to afford N-(2-Chloro-6-methylphenyl)-2-[3-(fluoro-6-nitro-1-phenyl)amino]-5-thiazolecarboxamide (21%). The title compound was synthesized by reacting this intermediate with excess N-(3-aminopropyl)-imidazole at 80° C. followed by purification by reverse phase preparative HPLC.

EXAMPLES 556–566

General Procedure:

Compounds 556 to 566 were prepared according to the general procedure described below. A mixture of 2-bromo-N-[2-chloro-6-methylphenyl]-5-thiazolecarboxamide 319A, an aniline (1 eq), 1.0 N aqueous HCl (0.5 eq) in n-BuOH was heated overnight at 120° C. in a sealed vial. This was diluted with methanol and the product was isolated by preparative HPLC (YMC S5 ODS 30×100 mm column eluted with a gradient comprised of two solvent mixtures (mixture A: 10% MeOH, 90% water, and 0.1% TFA; mixture B: 90% MeOH, 10% water, and 0.1% TFA). For anilines substituted with a carboxylic acid group, the reaction mixture was treated with 1 N aqueous NaOH (5 eq) overnight before final purification of the product by HPLC. "HPLC Ret Time" is the HPLC retention time under the following conditions: YMC S5 OSD 4.6×30 mm (for 556 to 560) or YMC S7 ODS 3×50 mm column (for 561 to 566), 2 min gradient starting from 100% solvent A (10% MeOH, 90% $H_2O$, 0.1% TFA) to 100% solvent B (90% MeOH, 10% $H_2O$, 0.1% TFA), flow rate 5 mL/min, λ=220 nM.

| EX. NO. | Compound Structure | Compound Name | HPLC Ret time (min) |
|---|---|---|---|
| 556 | 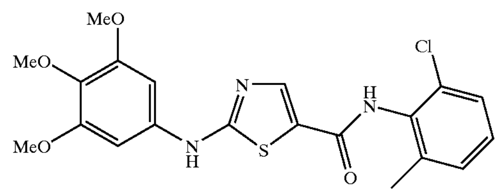 | N-(2-Chloro-6-methylphenyl)-2-[(3,4,5-trimethoxyphenyl)amino]-5-thiazolecarboxamide | 1.63 |
| 557 | 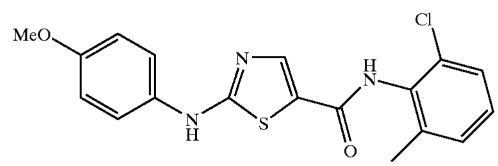 | N-(2-Chloro-6-methylphenyl)-2-[(4-methoxyphenyl)amino]-5-thiazolecarboxamide | 1.63 |
| 558 | 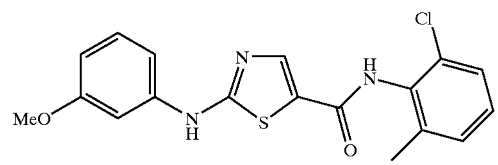 | N-(2-Chloro-6-methylphenyl)-2-[(3-methoxyphenyl)amino]-5-thiazolecarboxamide | 1.70 |
| 559 | 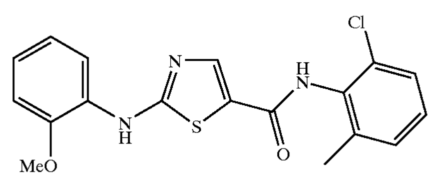 | N-(2-Chloro-6-methylphenyl)-2-[(2-methoxyphenyl)amino]-5-thiazolecarboxamide | 1.65 |
| 560 | 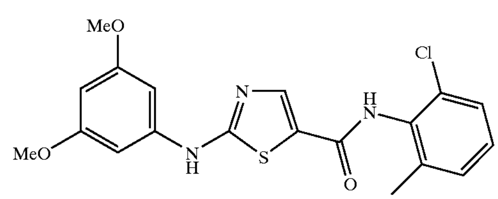 | N-(2-Chloro-6-methylphenyl)-2-[(3,5-dimethoxyphenyl)-amino]-5-thiazolecarboxamide | 1.55 |
| 561 | 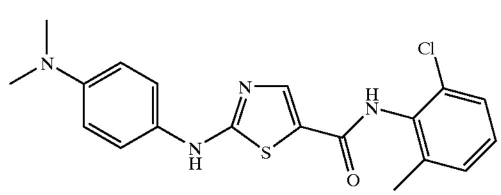 | N-(2-Chloro-6-methylphenyl)-2-[[4-(dimethylamino)-phenyl]amino]-5-thiazolecarboxamide | 1.25 |
| 562 | 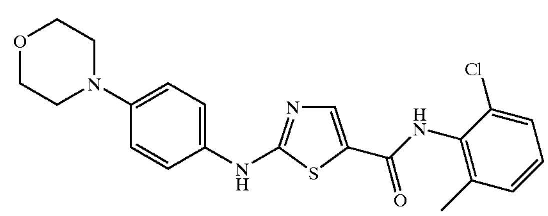 | N-(2-Chloro-6-methylphenyl)-2-[[4-(4-morpholinyl)phenyl]amino]-5-thiazolecarboxamide | 1.24 |

| EX. NO. | Compound Structure | Compound Name | HPLC Ret time (min) |
|---|---|---|---|
| 563 | 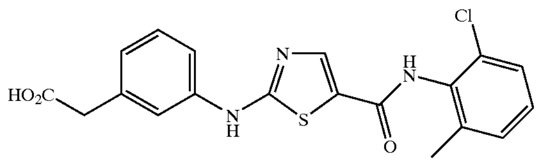 | N-(2-Chloro-6-methylphenyl)-2-[[3-(carboxymethyl)-phenyl]amino]-5-thiazolecarboxamide | 1.36 |
| 564 | 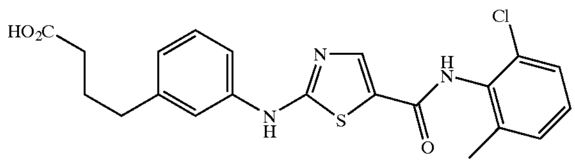 | N-(2-Chloro-6-methylphenyl)-2-[[3-(3-carboxypropyl)-phenyl]amino]-5-thiazolecarboxamide | 1.48 |
| 565 | 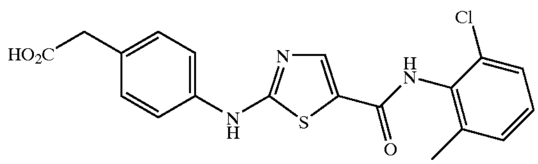 | N-(2-Chloro-6-methylphenyl)-2-[[4-(carboxymethyl)phenyl]amino]-5-thiazolecarboxamide | 1.35 |
| 566 | 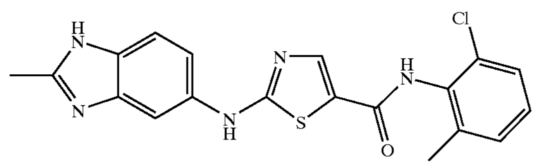 | N-(2-Chloro-6-methylphenyl)-2-[(2-methyl-1H-benzimidazol-5-yl)amino]-5-thiazolecarboxamide | 1.27 |

EXAMPLE 567

N-(2-Chloro-6-methylphenyl)-2-[[1-[3-(1H-imidazol-1-yl)propyl]-1H-benzimidazol-4-yl]amino]-5-thiazolecarboxamide

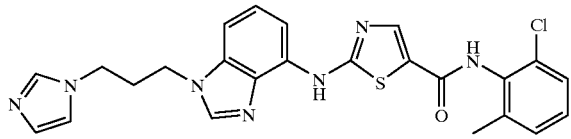

A mixture of 1-bromo-3-chloropropane (10 mL, 0.10 mmole), imidazole (6.81 gm, 0.10 mmole) in ethanolic NaOEt (41.3 mL, 21 wt %, 1.1 mmole) was heated at reflux for 1 hr. After cooling to RT, this was filtered and the filter cake was washed with EtOH. The solvent was removed from the filtrate to afford crude 3-chloro-1-(imidazo-1-yl)-propane as an oil. A portion of the crude chloride (1.07 gm, 7.40 mmole) was added to a mixture of 4-nitro-benzimidazole (1.09 gm, 6.66 mmole) and NaH (293 mg, 60% in oil, 8.14 mmole) in DMF (15 mL). After being heated at 60° C. overnight and then 75° C. for 3 hr, the solvent was removed. The residue was partitioned between water and a mixture of 10% MeOH in DCM. The organic phase was separated, dried (Na$_2$SO$_4$) and the solvents removed. Radial chromatography (4 mm silica gel plate that was eluted with a step gradient of DCM containing 2, 3, 4, . . . 10% MeOH) afforded the major product, 1-[3-imidazo-1-ylpropyl]-4-nitro-benzimidazole as a solid (513 mg, 28%). A mixture of this material (250 mg) and 10% palladium on charcoal (200 mg) in EtOH (10 mL) under a hydrogen atmosphere (balloon) was vigorously stirred for 1 hr. Removal of the catalyst by filtration and the solvent under reduced pressure left the crude 4-amino-1-[3-imidazo-1-ylpropyl]-benzimidazole as a solid. A portion of this material (46 mg, 0.191 mmole) was added to a mixture of 319A (63 mg, 1.0 eq), an aqueous solution of HCl (0.24 mL, 1.0 M, 1.25 eq) and n-BuOH (1 mL). This was heated in a sealed vial at 120° C. for 44 hr. After cooling to RT, 567 (HPLC retention time (YMC ODS S5 4.6×30 mm): 1.20 min) was isolated by preparative HPLC.

EXAMPLE 568

N-(2-Chloro-6-methylphenyl)-2-[[1-[2-(1H-imidazol-1-yl)ethyl]-1H-indazol-6-yl]amino]-5-thiazolecarboxamide

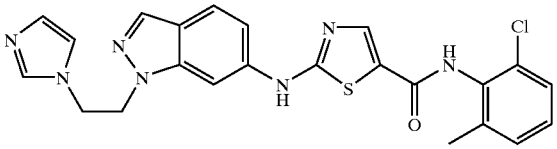

A mixture of 1-bromo-2-chloroethane (4.6 mL, 0.055 mole), imidazole (3.40 gm, 0.050 mole) in ethanolic NaOEt (19 mL, 21 wt %, 1 eq) was heated at reflux for 2 hr. After cooling to RT, the reaction was filtered and the filter cake was washed with EtOH. The solvent was removed from the filtrate to afford crude 2-chloro-1-(imidazo-1-yl)-ethane. A portion of the crude chloride (2.24 gm, 17.2 mmole) was added to a mixture of 6-nitro-indazole (1.63 gm, 10.0 mmole), K$_2$CO$_3$ (1.50 mg, 1.1 eq), and KI (1.70 gm, 1.1 eq) in DMF (15 mL). After being heated at 70° C. overnight and then 90° C. for 4 hr, the solvent was removed. The residue was partitioned between water and a mixture of 5% MeOH in DCM. The organic phase was separated, dried (Na$_2$SO$_4$) and the solvents removed. Radial chromatography (4 mm silica gel plate that was eluted with a step gradient of DCM containing 0, 1, 2% MeOH) afforded 659 mg of 1-[2-imidazo-1-ylethyl]-6-nitro-indazole and 450 mg of the isomeric 2-[2-imidazo-1-ylethyl]-6-nitro-indazole. A mixture of 1-[2-imidazo-1-ylethyl]-6-nitro-indazole (650 mg) and 10% palladium on charcoal (600 mg) in EtOH (10 mL) under a hydrogen atmosphere (balloon) was vigorously stirred overnight. Removal of the catalyst by filtration and the solvent under reduced pressure left the crude 6-amino-1-[2-imidazo-1-ylethyl]-indazole as a solid. A portion of this material (68.1 mg, 1.5 eq) was added to a mixture of 556 (99.3 mg, 0.300 mmole), an aqueous solution of HCl (0.45 mL, 1.0 M, 1.5 eq) and n-BuOH (1.5 mL). This was heated in a sealed vial at 120° C. for 44 hr. After cooling to RT, 568 (HPLC retention time (YMC ODS S7 3×50 mm): 1.31 min) was isolated by preparative HPLC.

EXAMPLE 569

N-(2-Chloro-6-methylphenyl)-2-[2-[2-(1H-imidazol-1-yl)ethyl]-2H-indazol-6-yl]amino]-5-thiazolecarboxamide

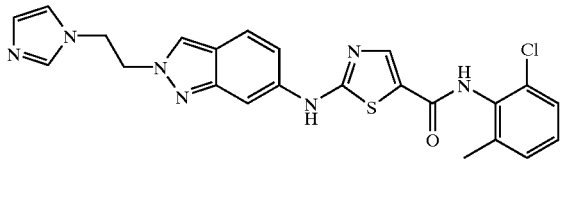

Beginning with the isomeric 2-[2-imidazo-1-ylethyl]-6-nitro-indazole, 569 (HPLC retention time (YMC ODS S7 3×50 mm): 1.28 min) was prepared in the same manner as 568.

EXAMPLE 570

N-(2-Chloro-6-methylphenyl)-2-[(1-methyl-1H-benzimidazol-6-yl)amino]-5-thiazolecarboxamide

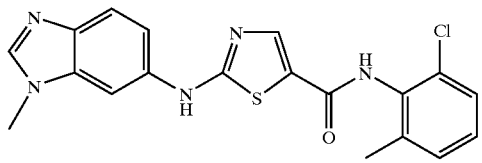

and

EXAMPLE 571

N-(2-Chloro-6-methylphenyl)-2-[(1-methyl-1H-benzimidazol-5-yl)amino]-5-thiazolecarboxamide

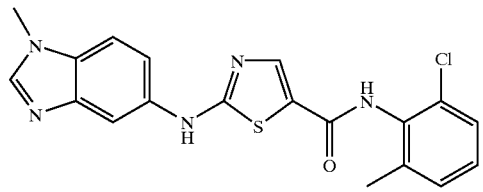

Beginning with 5-nitrobenzimidazole and methyl iodide, 570 (HPLC retention time (YMC ODS S7 3×50 mm): 1.23 min) and 571 (HPLC retention time (YMC ODS S7 3×50 mm): 1.23 min) were prepared in the same manner as compounds 557 and 558.

EXAMPLE 572

N-(2-Chloro-6-methylphenyl)-2-[[2-[[3-(1H-imidazol-1-yl)propyl]amino]-1H-benzimidazol-5-yl]amino]-5-thiazolecarboxamide

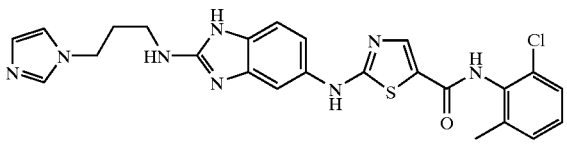

A mixture of 2-chloro-5-nitro-benzimidazole (985 mg, 5.0 mmole) and 1-(3-aminopropyl)-imidazole (1.8 mL, 3 eq) in toluene (15 mL) was heated at reflux for 5 hr. The reaction was partitioned between EtOAc and brine to give a precipitate that was collected by filtration. Flash chromatography of this material (silica gel; stepwise gradient elution with mixtures of DCM containing 1, 2, 3, . . . 10% MeOH) afforded 2-[3-[imidazo-1-yl]-propylamino]-5-nitro-benzimidazole (550 mg) as a solid. This material was combined with 10% Pd on charcoal (500 mg), suspended in EtOH, and stirred under a hydrogen atmosphere (balloon) overnight. Removal of the catalyst by filtration and the solvent under reduced pressure left the crude 5-amino-2-[3-imidazo-1-ylpropylamino]-benzimidazole as a solid. A portion of this material (77 mg, 0.30 mmole) was added to a mixture of 319A (99 mg, 1.0 eq), an aqueous solution of HCl (0.60 mL, 1.0 M, 2 eq) and n-BuOH (1.5 mL). This was heated in a sealed vial at 120° C. for 20 hr. After cooling to RT, 572 (HPLC retention time (YMC ODS S7 3×50 mm): 1.20 min) was isolated by preparative HPLC.

EXAMPLE 573

N-(2-Chloro-6-methylphenyl)-2-[[2-(4-morpholinylmethyl)-1H-benzimidazol-5-yl]amino]-5-thiazolecarboxamide

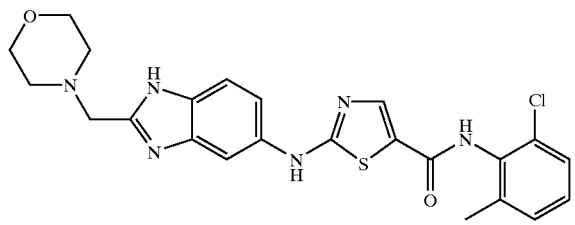

A mixture of 3,4-diamino-nitrobenzene (15.3 g, 0.10 mole) and chloroacetic acid (14.18 gm, 1.5 eq) in 5.0 N aqueous HCl (80 mL) was heated at reflux for 1 hr. After cooling to RT, the reaction was filtered through celite and the filtrate was stored at 0° C. for 2 days. The crystals that formed, were collected and recrystallized from a mixture of EtOH and water to give 7.2 gm of the hydrogen chloride salt of 2-chloromethyl-5-nitro-benzimidazole. A portion of this salt (528 mg, 2.13 mmole) and morpholine (1.31 mL, 7 eq) in toluene (15 mL) were heated at reflux for 4 hr. After cooling to RT, the reaction was filtered and the filter cake was washed with toluene. The solvent was removed from the filtrate to leave the crude 2-[N-morpholinylmethyl]-5-nitro-benzimidazole as an oil. A portion of this material (657 mg) and 10% palladium on charcoal (650 mg) in EtOH (10 mL) was stirred overnight under a hydrogen atmosphere (balloon). Removal of the catalyst by filtration and the solvent left the crude 5-amino-2-[N-morpholinylmethyl]-benzimidazole as an oil. A portion of this material was coupled with 556 as described for 570 to afford 573 (HPLC retention time (YMC ODS S7 3×50 mm): 0.92 min).

EXAMPLE 574

N-(2-Chloro-6-methylphenyl)-2-[[2-(1H-imidazol-1-ylmethyl)-1H-benzimidazol-5-yl]amino]-5-thiazolecarboxamide

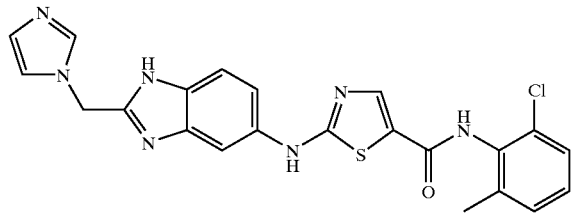

Beginning with imidazole and 2-chloromethyl-5-nitro-benzimidazole compound 574 (HPLC retention time (YMC ODS S7 3×50 mm): 1.17 min) was prepared in the same manner as compounds 570.

EXAMPLE 575

N-(2-Chloro-6-methylphenyl)-2-[[3-[[5-(1H-imidazol-1-yl)-2-pyridinyl]amino]phenyl]amino]-5-thiazolecarboxamide

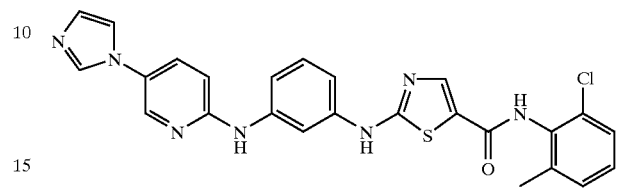

A mixture of 3-nitroaniline (2.91 gm, 21.1 mmole) and 2,5-dibromopyridine (5.0 gm, 1 eq) was heated at 185° C. for 1 hr. After cooling to RT, the solid was broken up and treated with a mixture of saturated aq. NaHCO$_3$ and 10% MeOH in DCM. The suspended solid was collected by filtration and washed with a little 10% MeOH in DCM and then water to leave, after drying, 3.72 gm of crude N-[5-bromo-pyridin-2-yl]-5-nitroaniline. A portion of this material (500 mg, 1.70 mmole) was combined with imidazole (116 mg, 1 eq), CuI (81 mg, 0.25 eq), and K$_2$CO$_3$ (235 mg, 1 eq) in DMF (2 mL) and the mixture was heated at 130° C. for 2 days. After cooling to RT, the solvent was removed and the residue was partitioned between water and a mixture of 20% MeOH in DCM. The organic phase was removed, dried (Na$_2$SO$_4$), and the solvents removed to leave the crude N-[5-imidazo-1-yl]-pyridin-2-yl]-5-nitroaniline as a solid. This was taken and treated with 10% palladium on charcoal (650.mg) in EtOH under a hydrogen atmosphere for 1.5 hr. Removal of the catalyst and then the solvent left the crude N-[5-imidazo-1-yl]-pyridin-2-yl]-5-aminoaniline. It was purified by radial chromatography (4 mm silica gel plate that was eluted with a step gradient of DCM containing 1, 2, 3, . . . 6% MeOH). The aniline was then coupled with 319A as described for 570 to afford 575 (HPLC retention time (YMC ODS S5 4.6×30 mm): 1.42 min).

EXAMPLE 576

N-(2-Chloro-6-methylphenyl)-2-[[3-[3-(1H-imidazol-1-yl)propoxy]phenyl]amino]-5-thiazolecarboxamide

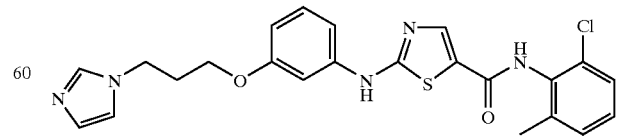

and

EXAMPLE 577

N-(2-Chloro-6-methylphenyl)-2-[[4-[3-(1H-imidazol-1-yl)propoxy]phenyl]amino]-5-thiazolecarboxamide

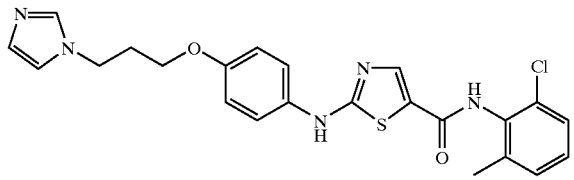

A suspension of 3-nitrophenol (837 mg, 6.02 mmole), 1-chloro-3-[imidazo-1-yl]-propane (871 mg, 1 eq), $K_2CO_3$ (3.3 gm, 4 eq) and NaI (1.0 gm, 1.1 eq) in DMF was heated at 120° C. for 6 hr. After cooling to RT, the reaction was filtered and the filter cake was washed with DMF. The solvent was removed from the filtrate and the residue was chromatographed (radial chromatography; 4 mm silica gel plate that was eluted with a step gradient of DCM containing 0, 1, 2.5, 5, 7.5% MeOH) to afford 400 mg of 3-[3-imidazo-1-ylpropyloxy]]-nitrobenzene. This was treated with 10% palladium on charcoal (400 mg) in EtOH under a hydrogen atmosphere for 4 hr. Removal of the catalyst and the solvent left 3-[3-imidazo-1-ylpropyloxy]]-aniline was then coupled with 319A as described for 570 to afford 576 (HPLC retention time (YMC ODS S5 4.6×30 mm): 1.33 min).

Beginning with 4-nitrophenol and 1-chloro-3-[imidazo-1-yl]-propane 577 (HPLC retention time (YMC ODS S5 4.6×30 mm): 1.42 min) was prepared in a similar manner as 576.

EXAMPLE 578

N-(2-Chloro-6-methylphenyl)-2-[[4-[2-(1H-imidazol-1-yl)ethoxy]-3-methoxyphenyl]amino]-5-thiazolecarboxamide

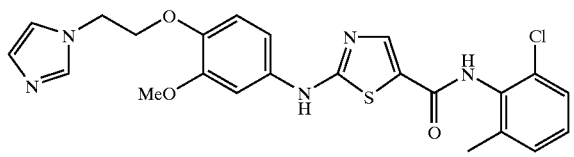

Beginning with 2-methoxy-4-nitrophenol and 1-chloro-3-[imidazo-1-yl]-ethane, 578 (HPLC retention time (YMC ODS S5 4.6×30 mm): 1.35 min) was prepared in a similar manner as 576.

EXAMPLE 579

N-(2-Chloro-6-methylphenyl)-2-[[3-[[[3-(1H-imidazol-1-yl)propyl]amino]sulfonyl]phenyl]amino]-5-thiazolecarboxamide

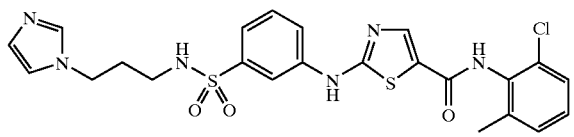

and

EXAMPLE 580

N-(2-Chloro-6-methylphenyl)-2-[[4-[[[3-(1H-imidazol-1-yl)propyl]amino]sulfonyl]phenyl]amino]-5-thiazolecarboxamide

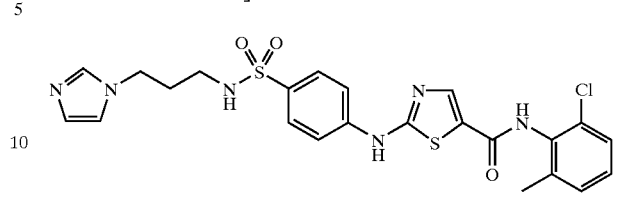

3-Imidazo-1-yl-propylamine (2.04 mL, 2.5 eq) was added to a solution of 3-nitro-benzenesulfonyl chloride (1.5 gm, 6.77 mmole) in THF (20 mL) at RT. After 1 hr, the solvent was removed and the residue was partitioned between water and a mixture of 10% MeOH in DCM. The organic phase was separated, washed with water and dried (Na2SO$_4$). The crude N-[3-[imidazo-1-yl]-propyl]-3-nitro-benzenesulfonamide was treated with 10% palladium on charcoal (2 gm) in THF (60 mL) under a hydrogen atmosphere overnight. Removal of the catalyst and then the solvent left crude 3-amino-N-[3-[imidazo-1-yl]-propyl]-benzenesulfonamide which was then coupled with 319A as described for 570 to afford 579 (HPLC retention time (YMC ODS S7 3×50 mm): 1.22 min). Beginning with 4-nitro-benzenesulfonyl chloride and 3-[imidazo-1-yl]-propylamine, 580 (HPLC retention time (YMC ODS S7 3×50 mm): 1.21 min) was prepared in a similar manner as 579.

What is claimed is:
1. A compound of formula I or salt thereof

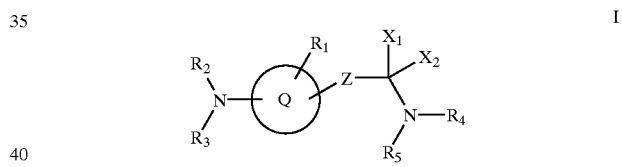

where

Q is thiazole optionally substituted with $R_1$;

Z is a single bond;

$X_1$ and $X_2$ together form =O;

$R_1$ is (1) hydrogen or $R_6$, where $R_6$ is alkyl, alkenyl, alkynyl, cycloalkyl, cycloalkylalkyl, cycloalkenyl, cycloalkenylalkyl, aryl, or aralkyl, each of which is unsubstituted or substituted with $Z_1$, $Z_2$ and one or more groups $Z_3$;

(2) —OH or —OR$_6$;

(3) —SH or —SR$_6$;

(4) —C(O)$_2$H, —C(O)$_q$R$_6$, or —O—C(O)$_q$R$_6$, where q is 1 or 2;

(5) —SO$_3$H or —S(O)$_q$R$_6$;

(6) halo;

(7) cyano;

(8) nitro;

(9) -Z$_4$-NR$_7$R$_8$;

(10) -Z$_4$-N(R$_9$)-Z$_5$-NR$_{10}$R$_{11}$;

(11) -Z$_4$-N(R$_{12}$)-Z$_5$-R$_6$;

(12) —P(O)(OR$_6$)$_2$;

$R_2$ is hydrogen, $R_6$, -Z$_4$-R$_6$ or -Z$_{13}$-NR$_7$R$_8$;

$R_3$ is -Z$_4$-R$_6$ where Z$_4$ is —SO$_2$-, —C(O)—, or —C(O)O—;

$R_4$ and $R_5$
(1) are each independently hydrogen or $R_6$;
(2) $-Z_4-N(R_9)-Z_5-NR_{10}R_{11}$;
(3) $—N(R_9)Z_4R_6$; or
(4) together with the nitrogen atom to which they are attached complete a 3- to 8-membered saturated or unsaturated heterocyclic ring which is unsubstituted or substituted with $Z_1$, $Z_2$ and $Z_3$, which heterocyclic ring may optionally have fused to it a benzene ring itself unsubstituted or substituted with $Z_1$, $Z_2$ and $Z_3$;

$R_7$, $R_8$, $R_9$, $R_{10}$, $R_{11}$ and $R_{12}$
(1) are each independently hydrogen or $R_6$;
(2) $R_7$ and $R_8$ may together be alkylene, alkenylene or heteroalkyl, completing a 3- to 8-membered saturated or unsaturated ring with the nitrogen atom to which they are attached, which ring is unsubstituted or substituted with $Z_1$, $Z_2$ and $Z_3$; or
(3) any two of $R_9$, $R_{10}$ and $R_{11}$ may together be alkylene or alkenylene completing a 3- to 8-membered saturated or unsaturated ring together with the nitrogen atoms to which they are attached, which ring is unsubstituted or substituted with $Z_1$, $Z_2$ and $Z_3$;

$R_{13}$ is
(1) cyano;
(2) nitro;
(3) $—NH_2$;
(4) —NHOalkyl;
(5) —OH;
(6) —NHOaryl;
(7) —NHCOOalkyl;
(8) —NHCOOaryl;
(9) $—NHSO_2$alkyl;
(10) $—NHSO_2$aryl;
(11) aryl;
(12) heteroaryl;
(13) —Oalkyl; or
(14) —Oaryl;

$R_{14}$ is
(1) $—NO_2$;
(2) —COOalkyl; or
(3) —COOaryl;

$R_{15}$ is
(1) hydrogen;
(2) alkyl;
(3) aryl;
(4) arylalkyl; or
(5) cycloalkyl;

$Z_1$, $Z_2$ and $Z_3$ are each independently
(1) hydrogen or $Z_6$, where $Z_6$ is (i) alkyl, alkenyl, alkynyl, cycloalkyl, cycloalkylalkyl, cycloalkenyl, cycloalkenylalkyl, aryl, aralkyl, alkylaryl, cycloalkylaryl, heterocyclo, or heterocycloalkyl; (ii) a group (i) which is itself substituted by one or more of the same or different groups (i); or (iii) a group (i) or (ii) which is substituted by one or more of the following groups (2) to (16) of the definition of $Z_1$, $Z_2$ and $Z_3$;
(2) —OH or $—OZ_6$;
(3) —SH or $—SZ_6$;
(4) $—C(O)_qH$, $—C(O)_qZ_6$, or $—O—C(O)_qZ_6$;
(5) $—SO_3H$, $—S(O)_qZ_6$; or $S(O)_qN(Z_9)Z_6$;
(6) halo;
(7) cyano;
(8) nitro;
(9) $-Z_4-NZ_7Z_8$;
(10) $-Z_4-N(Z_9)-Z_5-NZ_7Z_8$;
(11) $-Z_4-N(Z_{10})-Z_5-Z_6$;
(12) $-Z_4-N(Z_{10})-Z_5-H$;
(13) oxo;
(14) $—O—C(O)-Z_6$;
(15) any two of $Z_1$, $Z_2$, and $Z_3$ may together be alkylene or alkenylene completing a 3- to 8-membered saturated or unsaturated ring together with the atoms to which they are attached; or
(16) any two of $Z_1$, $Z_2$, and $Z_3$ may together be $—O—(CH_2)_r—O—$, where r is 1 to 5, completing a 4- to 8-membered ring together with the atoms to which they are attached;

$Z_4$ and $Z_5$ are each independently
(1) a single bond;
(2) $-Z_{11}-S(O)_q-Z_{12}-$;
(3) $-Z_{11}-C(O)-Z_{12}-$;
(4) $-Z_{11}-C(S)-Z_{12}-$;
(5) $-Z_{11}-O-Z_{12}-$;
(6) $-Z_{11}-S-Z_{12}-$;
(7) $-Z_{11}-O—C(O)-Z_{12}-$; or
(8) $-Z_{11}-C(O)—O-Z_{12}-$;

$Z_7$, $Z_8$, $Z_9$ and $Z_{10}$
(1) are each independently hydrogen or $Z_6$;
(2) $Z_7$ and $Z_8$, or $Z_6$ and $Z_{10}$, may together be alkylene or alkenylene, completing a 3- to 8-membered saturated or unsaturated ring together with the atoms to which they are attached, which ring is unsubstituted or substituted with $Z_1$, $Z_2$ and $Z_3$; or
(3) $Z_7$ or $Z_8$, together with $Z_9$, may be alkylene or alkenylene completing a 3- to 8-membered saturated or unsaturated ring together with the nitrogen atoms to which they are attached, which ring is unsubstituted or substituted with $Z_1$, $Z_2$ and $Z_3$;

$Z_{11}$ and $Z_{12}$ are each independently
(1) a single bond;
(2) alkylene;
(3) alkenylene; or
(4) alkynylene; and $Z_{13}$ is
(1) a single bond;
(2) $-Z_{11}-S(O)_q-Z_{12}-$;
(3) $-Z_{11}-C(O)-Z_{12}-$;
(4) $-Z_{11}-C(S)-Z_{12}-$;
(5) $-Z_{11}-O-Z_{12}-$;
(6) $-Z_{11}-S-Z_{12}-$;
(7) $-Z_{11}-O—C(O)-Z_{12}-$;
(8) $-Z_{11}-C(O)—O-Z_{12}-$;
(9) $—C(NR_{13})—$;
(10) $—C(CHR_{14})—$; or
(11) $—C(C(R_{14})_2)-$ provided said compound is other than a compound of formula (i)

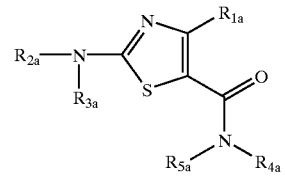

(i)

where
$R_{1a}$ is alkyl or $—C(O)NHNH_2$;
$R_{2a}$ and $R_{3a}$ are independently hydrogen, alkyl, —C(O)-(alk); and $R_{4a}$ is hydrogen and $R_{5a}$ is aryl, alkyl-substituted aryl, halo-substituted aryl, aralkyl, cycloalkyl or amino;

Or $R_{4a}$ is alkyl and $R_{5a}$ is alkyl or aryl;

Or $R_{4a}$ and $R_{5a}$ together with the nitrogen atom to which they are bonded together from morpholino.

2. A compound of claim 1 wherein $R_1$ is hydrogen, halo, alkyl, aryl, alkoxy, alkoxycarbonyl, or aryloxycarbonyl.

3. A compound of claim 2 wherein $R_1$ is hydrogen.

4. A compound of claim 2 wherein $R_2$ is hydrogen.

5. A compound of claim 2 wherein $R_4$ is hydrogen.

6. A compound of claim 2 wherein $R_5$ is an aryl group which is substituted with $Z_1$, $Z_2$ and one or more groups $Z_3$.

7. A compound of claim 2 wherein $R_1$ is hydrogen or alkyl, $R_2$ and $R_4$ are independently hydrogen or alkyl, and $R_5$ is aryl which is unsubstituted or substituted with $Z_1$, $Z_2$ and one or more groups $Z_3$.

8. A compound of claim 7 wherein $R_5$ is aryl which is unsubstituted or independently substituted with one or more alkyl or halo.

9. A compound of formula II or salt thereof

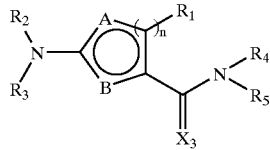

(II)

where n is 1;

$X_3$ is oxygen;

A is nitrogen;

B is sulfur $R_1$ is
  (1) hydrogen or $R_6$, where $R_6$ is alkyl, alkenyl, alkynyl, cycloalkyl, cycloalkylalkyl, cycloalkenyl, cycloalkenylalkyl, aryl, or aralkyl, each of which is unsubstituted or substituted with $Z_1$, $Z_2$ and one or more groups $Z_3$;
  (2) —OH or —OR$_6$;
  (3) —SH or —SR$_6$;
  (4) —C(O)$_2$H, —C(O)$_q$R$_6$, or —OC(O)$_q$R$_6$, where q is 1 or 2;
  (5) —SO$_3$H or —S(O)$_q$R$_6$;
  (6) halo;
  (7) cyano;
  (8) nitro;
  (9) -Z$_4$-NR$_7$R$_8$;
  (10) -Z$_4$-N(R$_9$)-Z$_5$-NR$_{10}$R$_{11}$;
  (11) -Z$_4$-N(R$_{12}$)-Z$_5$-R$_6$;
  (12) —P(O)(OR$_6$)$_2$;

$R_2$ is hydrogen, $R_6$, -Z$_4$-R$_6$ or -Z$_{13}$-NR$_7$R$_8$;

$R_3$ is -Z$_4$-R$_6$ where $Z_4$ is —SO$_2$-, —C(O)—, or —C(O)O—;

$R_4$ and $R_5$
  (1) are each independently hydrogen or $R_6$;
  (2) -Z$_4$-N(R$_9$)-Z$_5$-NR$_{10}$R$_{11}$;
  (3) —N(R$_9$)Z$_4$R$_6$; or
  (4) together with the nitrogen atom to which they are attached complete a 3- to 8-membered saturated or unsaturated heterocyclic ring which is unsubstituted or substituted with $Z_1$, $Z_2$ and $Z_3$, which heterocyclic ring may optionally have fused to it a benzene ring itself unsubstituted or substituted with $Z_1$, $Z_2$ and $Z_3$;

$R_7$, $R_8$, $R_9$, $R_{10}$, $R_{11}$ and $R_{12}$
  (1) are each independently hydrogen or $R_6$;
  (2) $R_7$ and $R_8$ may together be alkylene, alkenylene or heteroalkyl, completing a 3- to 8-membered saturated or unsaturated ring with the nitrogen atom to which they are attached, which ring is unsubstituted or substituted with $Z_1$, $Z_2$ and $Z_3$; or
  (3) any two of $R_9$, $R_{10}$ and $R_{11}$ may together be alkylene or alkenylene completing a 3- to 8-membered saturated or unsaturated ring together with the nitrogen atoms to which they are attached, which ring is unsubstituted or substituted with $Z_1$, $Z_2$ and $Z_3$;

$R_{13}$ is
  (1) cyano,
  (2) nitro;
  (3) —NH$_2$;
  (4) —NHOalkyl;
  (5) —OH;
  (6) —NHOaryl;
  (7) —NHCOOalkyl;
  (8) —NHCOOaryl;
  (9) —NHSO$_2$alkyl;
  (10) —NHSO$_2$aryl;
  (11) aryl;
  (12) heteroaryl;
  (13) —Oalkyl; or
  (14) —Oaryl;

$R_{14}$ is
  (1) —NO$_2$;
  (2) —COOalkyl; or
  (3) —COOaryl;

$R_{15}$ is
  (1) hydrogen;
  (2) alkyl;
  (3) aryl;
  (4) arylalkyl; or
  (5) cycloalkyl;

$Z_1$, $Z_2$ and $Z_3$ are each independently
  (1) hydrogen or $Z_6$, where $Z_6$ is (i) alkyl, alkenyl, alkynyl, cycloalkyl, cycloalkylalkyl, cycloalkenyl, cycloalkenylalkyl, aryl, aralkyl, alkylaryl, cycloalkylaryl, heterocyclo, or heterocycloalkyl, (ii) a group (i) which is itself substituted by one or more of the same or different groups (i); or (iii) a group (i) or (ii) which is substituted by one or more of the following groups (2) to (16) of the definition of $Z_2$, $Z_2$ and $Z_3$;
  (2) —OH or —OZ$_6$;
  (3) —SH or —SZ$_6$;
  (4) —C(O)$_q$H, —C(O)$_q$Z$_6$, or —O—C(O)$_q$Z$_6$;
  (5) —SO$_3$H, —S(O)$_q$Z$_6$; or S(O)$_q$N(Z$_9$)Z$_6$;
  (6) halo;
  (7) cyano;
  (8) nitro;
  (9) -Z$_4$—NZ$_7$Z$_8$;
  (10) -Z$_4$-N(Z$_9$)-Z$_5$-NZ$_7$Z$_8$;
  (11) -Z$_4$-N(Z$_{10}$)-Z$_5$-Z$_6$;
  (12) -Z$_6$-N(Z$_{10}$)-Z$_5$-H;
  (13) oxo;
  (14) —O—C(O)-Z$_6$;
  (15) any two of $Z_1$, $Z_2$, and $Z_3$ may together be alkylene or alkenylene completing a 3- to 8-membered saturated or unsaturated ring together with the atoms to which they are attached; or
  (16) any two of $Z_1$, $Z_2$, and $Z_3$ may together be —O—(CH2)$_r$—O— where r is 1 to 5, completing a 4-to 8-membered ring together with the atoms to which they are attached;

$Z_4$ and $Z_5$ are each independently
(1) a single bond;
(2) -$Z_{11}$-S(O)$_q$-$Z_{12}$-;
(3) -$Z_{11}$-C(O)-$Z_{12}$-;
(4) -$Z_{11}$-C(S)-$Z_{12}$-;
(5) -$Z_{11}$-O-$Z_{12}$-;
(6) -$Z_{11}$-S-$Z_{12}$-;
(7) -$Z_{11}$-O—C(O)-$Z_{12}$-; or
(8) -$Z_{11}$-C(O)—O-$Z_{12}$-;

$Z_7$, $Z_8$, $Z_9$ and $Z_{10}$
(1) are each independently hydrogen or $Z_6$;
(2) $Z_7$ and $Z_8$, or $Z_6$ and $Z_{10}$, may together be alkylene or alkenylene, completing a 3- to 8-membered saturated or unsaturated ring together with the atoms to which they are attached, which ring is unsubstituted or substituted with $Z_1$, $Z_2$ and $Z_3$; or
(3) $Z_7$ or $Z_8$, together with $Z_9$, may be alkylene or alkenylene completing a 3- to 8-membered saturated or unsaturated ring together with the nitrogen atoms to which they are attached, which ring is unsubstituted or substituted with $Z_1$, $Z_2$ and $Z_3$;

$Z_{11}$ and $Z_{12}$ are each independently
(1) a single bond;
(2) alkylene;
(3) alkenylene; or
(4) alkynylene; and $Z_{13}$ is
(1) a single bond;
(2) -$Z_{11}$-S(O)$_q$-$Z_{12}$-;
(3) -$Z_{11}$-C(O)-$Z_{12}$-;
(4) -$Z_{11}$-C(S)-$Z_{12}$-;
(5) -$Z_{11}$-O-$Z_{12}$-;
(6) -$Z_{11}$-S-$Z_{12}$-;
(7) -$Z_{11}$-O—C(O)-$Z_{12}$-;
(8) -$Z_{11}$-C(O)—O-$Z_{12}$-;
(9) —C(NR$_{13}$)—;
(10) —C(CHR$_{14}$)—; or
(11) —C(C(R$_{14}$)$_2$)—, provided said compound is other than a compound of formula (i)

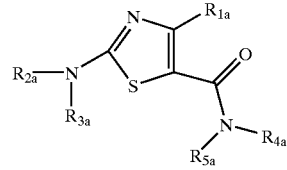

(i)

where $R_{1a}$ is alkyl or —C(O)NHNH$_2$;

$R_{2a}$ and $R_{3a}$ are independently hydrogen, alkyl, —C(O)-(alk); and $R_{4a}$ is hydrogen and $R_{5a}$ is aryl, alkyl-substituted aryl, halo-substituted aryl, aralkyl, cycloalkyl or amino;

Or $R_{4a}$ is alkyl and $R_{5a}$ is alkyl or aryl;

Or $R_{4a}$ and $R_{5a}$ together with the nitrogen atom to which they are bonded together from morpholino.

10. A compound of claim 9 wherein $R_1$ is hydrogen or alkyl, $R_2$ and $R_4$ are independently hydrogen or alkyl, and $R_5$ is aryl which is unsubstituted or substituted with $Z_1$, $Z_2$ and one or more groups $Z_3$.

11. A compound of claim 10 wherein $R_5$ is axyl which is unsubstituted or independently substituted with one or more alkyl or halo.

* * * * *

UNITED STATES PATENT AND TRADEMARK OFFICE
CERTIFICATE OF CORRECTION

PATENT NO.       : 6,979,694 B2                                   Page 1 of 1
APPLICATION NO. : 10/378372
DATED            : December 27, 2005
INVENTOR(S)      : Jagabandhu Das et al.

It is certified that error appears in the above-identified patent and that said Letters Patent is hereby corrected as shown below:

In column 272, line 59, delete "(12) $-Z_6-N(Z_{10})-Z_5-H$;" and insert
-- (12) $-Z_4-N(Z_{10})-Z_5-H$; --.

In column 272, line 67, delete "(CH2)" and insert -- $(CH_2)$ --.

In column 274, line 32, delete "axyl" and insert -- aryl --.

Signed and Sealed this

Ninth Day of January, 2007

JON W. DUDAS
*Director of the United States Patent and Trademark Office*